(12) United States Patent
Kim et al.

(10) Patent No.: US 12,409,171 B2
(45) Date of Patent: Sep. 9, 2025

(54) PHARMACEUTICALLY ACTIVE PYRAZOLO-PYRIDONE MODULATORS OF DCN1/2-MEDIATED CULLIN NEDDYLATION

(71) Applicants: UNIVERSITY OF KENTUCKY RESEARCH FOUNDATION, Lexington, KY (US); MEMORIAL SLOAN-KETTERING CANCER CENTER, New York, NY (US); St. Jude Children's Research Hospital, Inc., Memphis, TN (US)

(72) Inventors: Hoshin Kim, Lexington, KY (US); Rodney Kiplin Guy, Lexington, KY (US); Jared T. Hammill, Lexington, KY (US); Daniel Charles Scott, Marion, KY (US); Brenda Arlene Schulman, Martinsried (DE); Bhuvanesh Singh, Old Westbury, NY (US)

(73) Assignees: University of Kentucky Research Foundation, Lexington, KY (US); Memorial Sloan-Kettering Cancer Center, New York, NY (US); St. Jude Children's Research Hospital, Inc., Memphis, TN (US)

( * ) Notice: Subject to any disclaimer, the term of this patent is extended or adjusted under 35 U.S.C. 154(b) by 743 days.

(21) Appl. No.: 17/618,952

(22) PCT Filed: Jun. 22, 2020

(86) PCT No.: PCT/US2020/038998
§ 371 (c)(1),
(2) Date: Dec. 14, 2021

(87) PCT Pub. No.: WO2020/257790
PCT Pub. Date: Dec. 24, 2020

(65) Prior Publication Data
US 2022/0280488 A1    Sep. 8, 2022

Related U.S. Application Data

(60) Provisional application No. 62/864,331, filed on Jun. 20, 2019.

(51) Int. Cl.
*A61K 31/437* (2006.01)

(52) U.S. Cl.
CPC ................... *A61K 31/437* (2013.01)

(58) Field of Classification Search
CPC .................................................. A61K 31/437
See application file for complete search history.

(56) References Cited

U.S. PATENT DOCUMENTS

| | | | |
|---|---|---|---|
| 7,115,634 B2 | 10/2006 | Thurieau et al. | |
| 2004/0006081 A1 | 1/2004 | Burrows et al. | |
| 2014/0057938 A1* | 2/2014 | Dounay et al. ...... | C07D 471/04 514/303 |

FOREIGN PATENT DOCUMENTS

| | | | |
|---|---|---|---|
| CN | 103189378 A | 7/2013 | |
| CN | 107271687 | 10/2017 | |
| WO | WO-99/07672 | 2/1999 | |
| WO | WO-01/44191 A1 | 6/2001 | |
| WO | WO-02/24649 A1 | 3/2002 | |
| WO | WO-03/007888 A2 | 1/2003 | |
| WO | WO-03/070242 | 8/2003 | |
| WO | WO-2004/009549 A2 | 1/2004 | |
| WO | WO-2011/060396 | 5/2011 | |
| WO | WO-2015/054555 A1 | 4/2015 | |
| WO | WO-2017/049295 | 3/2017 | |
| WO | WO 2017/049295 A1 * | 3/2017 | ............ A61K 31/17 |
| WO | WO-2020/257790 | 12/2020 | |

OTHER PUBLICATIONS

Jae Wook Lee and Philip L. Fuchs. Reduction of Azides to Primary Amines in Substrates Bearing Labile Ester Functionality. Synthesis of a PEG-Solubilized, "Y"-Shaped Iminodiacetic Acid Reagent for Preparation of Folate-Tethered Drugs. 1999, Organic Lett., 1: 179-181 (Year: 1999).*
Aher, et al., "3D-QSAR studies of substituted 1-(3, 3-diphenylpropyl)-piperidinyl amides and ureas as CCR5 receptor antagonists," J. Mol. Model, vol. 13, pp. 519-529 (Feb. 16, 2007).
Archibald, et al., "Antihypertensive Ureidopiperidines," J. Med. Chem., vol. 23, pp. 857-861 (1980).
Burrows, et al., "Modulators of the human CCR5 receptor. Part 1: Discovery and initial SAR of 1-(3,3-diphenylpropyl)-piperidinyl amides and ureas," Bioorg. & Med. Chem. Lett., vol. 15, pp. 25-28 (Nov. 6, 2004).
CAS Registry No. 898183-92-1; STN Entry Date Aug. 3, 2006; Urea, N'-(4-chlorophenyl)-N-(3-methylbutyl)-N-[1-(1-methylethyl)-4-piperidinyl]-.
CAS Registry No. 898206-60-5; STN Entry Date Aug. 3, 2006; Urea, N'-(3,4-dichlorophenyl)-N-(2-methoxyethyl)-N-[1-(1-methylethyl)-4-piperidinyl]-.
CAS Registry No. 898206-72-9; STN Entry Date Aug. 3, 2006; Urea, N'-(3,4-dimethylphenyl)-N-(3-methylbutyl)-N-[1-(1-methylethyl)-4-piperidinyl]-.

(Continued)

*Primary Examiner* — Scarlett Y Goon
*Assistant Examiner* — Samantha Lynn Schachermeyer
(74) *Attorney, Agent, or Firm* — Foley & Lardner LLP

(57) ABSTRACT

A DCN1/2-mediated cullin neddylation modulator; a method for treating disorders associated with dysfunctional DCN1 and/or UBC12, Alzheimer's disease, other neurodegenerative diseases, bacterial infections, or viral infections; and a method for treating cancers are provided. The DCN1/2-mediated cullin neddylation modulator includes a compound according to Formula I disclosed herein. The methods include administering to a mammal a therapeutically effective amount of a compound according to Formula I. Also provided herein is a pharmaceutical composition including a therapeutically effective amount of a compound according to Formula I, or a pharmaceutically acceptable salt thereof, and a pharmaceutically acceptable carrier.

20 Claims, 25 Drawing Sheets

(56) References Cited

OTHER PUBLICATIONS

CAS Registry No. 909663-27-0; STN Entry Date Oct. 5, 2006; Urea, N-(2-methoxyethyl)-N-[1-[2-(2-thienyl)ethyl]-4-piperidinyl]-N'-[3-(trifluoromethyl)phenyl]-.
CAS Registry No. 909663-30-5; STN Entry Date Oct. 5, 2006; Urea, N'-(3-fluorophenyl)-N-(2-methoxyethyl)-N-[1-[2-(2-thienyl)ethyl]-4-piperidinyl]-.
CAS Registry No. 909664-01-3; STN Entry Date Oct. 5, 2006; Urea, N'-(3-fluorophenyl)-N-(2-methoxyethyl)-N-[1-[2-(2-pyridinyl)ethyl]-4-piperidinyl]-.
CAS Registry No. 909665-71-0; STN Entry Date Oct. 5, 2006; Urea, N-[1-[2-(4-chlorophenyl) ethyl]-4-piperidinyl]-N-(2-methoxyethyl)-N'-[3-(trifluoromethyl)phenyl]-.
CAS Registry No. 909684-72-6; STN Entry Date Oct. 5, 2006; Urea, N-(2-methoxyethyl)-N-[1-(4-pyridinylmethyl)-4-piperidinyl]-N'-[3-(trifluoromethyl)phenyl]-.
CAS Registry No. 909684-75-9; STN Entry Date Oct. 5, 2006; Urea, N'-(3-fluorophenyl)-N-(2-methoxyethyl)-N-[1-(4-pyridinylmethyl)-4-piperidinyl]-.
CAS Registry No. 909689-50-5; STN Entry Date Oct. 5, 2006; Urea, N-[1-[2-(4-chlorophenyl)ethyl]-4-piperidinyl]-N'-(3-fluorophenyl)-N-(2-methoxyethyl)-.
CAS Registry No. 909689-68-5; STN Entry Date Oct. 5, 2006; Urea, N'-(3-fluorophenyl)-N-(2-methoxyethyl)-N-[1-(3-phenylpropyl)-4-piperidinyl]-.
CAS Registry No. 909695-29-0; STN Entry Date Oct. 5, 2006; Urea, N-(2-methoxyethyl)-N-[1-(3-phenylpropyl)-4-piperidinyl]-N'-[3-(trifluoromethyl)phenyl]-.
Devegowda et al., "Novel 6-N-arylcarboxamidopyrazolo[4,3-d]pyrimidin-7-one derivatives as potential anti-cancer agents", Bioorganic & Medicinal Chemistry Letters, 2010, vol. 20, pp. 1630-1633.
Duan, et al., "Discovery of novel pyridyl carboxamides as potent CCR5 antagonists and optimization of their pharmacokinetic profile in rats," Bioorg. Med. Chem. Lett., 21, pp. 6470-6475 (2011).
Hammill, J.T., et al., "Discovery of an Orally Bioavailable Inhibitor of Defective in Cullin Neddylation 1 (DCN1)-Mediated Cullin Neddylation," J. Med. Chem., 61:2694-2706 (2018) (13 pages).
Hammill, J.T., et al., "Piperidinyl Ureas Chemically Control Defective in Cullin Neddylation 1 (DCN1)-Mediated Cullin Neddylation," J. Med. Chem., 61:2680-2693 (2018) (14 pages).
International Search Report and Written Opinion on PCT PCT/US2020/038998 dated Oct. 5, 2020 (13 pages).
Ito et al., Cancer Science, 94(1), 3-8 (2003).
Kim et al., "Discovery of Novel Pyrazolo-Pyridone DCN1 Inhibitors Controlling Cullin Neddylation", J. Med. Chem., 2019, vol. 62, pp. 8429-8442.
Leonard, et al., "Comparative QSAR modeling of CCR5 receptor binding affinity of substituted 1-(3,3-diphenylpropyl)-piperidinyl amides and ureas," Bioorg. & Med. Chem. Lett., vol. 16, pp. 4467-4474 (Jun. 27, 2006).
Lolicato et al., Nature Chemical Biology, vol. 10, No. 8, Jun. 2014, pp. 457-462 Supplementary Information.
Mahobia, et al., "3D QSAR analysis of some piperidinyl amide and ureas as CCR5 antagonist," Journal of Pharmacy Research, vol. 5, Issue 9, pp. 4706-4709 (Sep. 2012).
Mouhibi, et al., "Using multiple linear regression and artificial neural network techniques for predicting CCR5 binding affinity of substituted 1-(3, 3-diphenylpropyl)-piperidinyl amides and ureas," Journal of Medicinal Chemistry, vol. 3, pp. 7-15 (Mar. 2013).
Raffa et al., "Pyrazolo[3,4-d]pyrimidine Derivatives as COX-2 Selective Inhibitors: Synthesis and Molecular Modelling Studies", Arch. Pharm. Chem. Life Sci., 2009, vol. 342, pp. 321-326.
Scott, D.C., et al., "Blocking an N-terminal acetylation-dependent protein interaction inhibits an E3 ligase," Nature Chem. Biol., doi:10.1038/nchembio.2386 (2017) (12 pages).
Shahlaei, et al., "QSAR analysis of some 1-(3, 3-diphenylpropyl)-piperidinyl amides and ureas as CCR5 inhibitors using genetic algorithm-least square support vector machine," Med. Chem. Res., vol. 22, pp. 4384-4400 (Jan. 10, 2013).
Shin Kim, H., et al., "Discovery of Novel Pyrazolo-pyridone DCN1 Inhibitors Controlling Cullin Neddylation," J. Med. Chem., 62:8429-8442 (2019) (14 pages).
Shin Kim, H., et al., "Improvement of Oral Bioavailability of Pyrazolo-Pyridone Inhibitors of the Interaction of DCN1/2 and UBE2M," J. Med. Chem., 64:5850-5862 (2021) (13 pages).
STN Registry database entry for CAS RN 898206-78-5, entry date Aug. 3, 2006, Accessed Oct. 10, 2018.
STN Registry entry for CAS RN 1171707-20-2; entered STN Registry database Aug. 2, 2009.
Watson et al., "Development of CXCR3 antagonists. Part 2: Identification of 2-amino(4-piperidinyl)azoles as potent CXCR3 antagonists," Bioorganic & Medicinal Chemistry Letters, 2007, vol. 17, No. 24, pp. 6806-6810.
Yuan, et al., "Prediction of CCR5 receptor binding affinity of substituted 1-(3, 3-diphenylpropyl)-piperidinyl amides and ureas based on the heuristic method, support vector machine and projection pursuit regression," European Journal of Medicinal Chemistry, vol. 44, pp. 25-34 (2009).
Carling et al., "1-(3-Cyanobenzylpiperidin-4-yl)-5-methyl-4-phenyl-1,3-dihydroimidazol-2-one: A Selective High-Affinity Antagonist for the Human Dopamine D4 Receptor with Excellent Selectivity over Ion Channels", Journal of Medicinal Chemistry, 42, pp. 2706-2715, Jul. 15, 1999.
Foreign Office Action other than Search Report on MX Appl. Ser. No. MX/a/2021/016133 dated Jan. 28, 2025 (4, pages).

\* cited by examiner

¹³C-NMR of Compound 141

PHARMACEUTICALLY ACTIVE PYRAZOLO-PYRIDONE MODULATORS OF DCN1/2-MEDIATED CULLIN NEDDYLATION

RELATED APPLICATIONS

This application is a U.S. National Stage Application under 35 U.S.C. § 371 of International Patent Application No. PCT/US2020/038998, filed on Jun. 22, 2020, which claims the benefit of U.S. Provisional Application Ser. No. 62/864,331, filed Jun. 20, 2019, the entire disclosures of each of which are incorporated herein by reference.

TECHNICAL FIELD

The present disclosure is directed to modulators of DCN1/2-mediated cullin neddylation and methods of use thereof. In particular, the disclosure is directed to pharmaceutically active pyrazolo-pyridone modulators of DCN1/2-mediated cullin neddylation and methods of use thereof.

BACKGROUND

Neural precursor cell expressed developmentally down-regulated protein 8 (NEDD8) is a ubiquitin-like protein (UBL) that is post-translationally appended to eukaryotic proteins in a process termed neddylation. A three-step enzymatic cascade carries out neddylation. The first step is the ATP-dependent formation of an E1-NEDD8 thioester intermediate. Next, the NEDD8 is transferred by a transthioesterification reaction from the E1 to a Cys on the E2. E3s then join the E2-NEDD8 complex and recruit specific target proteins. The E3 complex then catalyzes the formation of an isopeptide bond connecting NEDD8's C-terminus to the γ-amino group of a lysine side-chain on the target protein.

The cullin family of ubiquitination E3s are the most well-characterized substrates of neddylation. Upon neddylation, the cullins constellate the cullin-RING E3 UB ligase family (CRLs), which has approximately 300 members. The CRLs regulate diverse biological processes including cell cycle, signal transduction, DNA replication, and viral modulation. CRL dysfunction is implicated in a number of human diseases, including cancer. Drug discovery efforts targeting the CRLs and the associated proteasomal protein degradation machinery have been extensive and continue to grow. The neddylation pathway has been successfully targeted by MLN4924 (Pevonedistat), an inhibitor of NEDD8's E1 enzyme, that completely blocks NEDD8 ligation to substrates. MLN4924 is currently being tested in oncology clinical trials. An inhibitor of the COP9 signalosome, responsible for de-neddylation of the CRLs, has been reported and also displays anti-tumor activity.

Additionally, the discovery of inhibitors of defective in cullin neddylation 1 (DCN1) mediated neddylation has been reported. DCN1 is also known as DCUN1D1, DCNL1, or Squamous Cell Carcinoma-related Oncogene (SCCRO), although the term "DCN1" is used hereafter. Humans express five isoforms of DCNs. In vitro, the five DCNs can cooperate with RBX1 to promote NEDD8 ligation from UBE2M or UBE2F to CULs 1-5, or with RBX2 to promote NEDD8 ligation from UBE2F to CULs 1-5. In mammals, the genetic redundancy is currently unclear although DCN1 is clearly not essential. Only DCN1 is broadly expressed across all tissues. DCN1 and DCN2 share >80% sequence homology (100% conservation in UBE2M binding pocket) and are the only isoforms expressed in both the cytosol and nucleus. DCN3, 4, and 5 share less than 35% sequence homology with DCN1 and appear to have more distinct tissue and cellular distributions. The high sequence homology, overlapping expression patterns, and similar subcellular distributions suggest that DCN1 and 2 may be redundant, while DCNs 3, 4, and 5 likely possess unique roles.

DCN1 is the most well characterized isoform due to its common amplification as part of a large 3q26.3 amplicon in squamous cell carcinomas (SCC) and other tumors. DCN1 amplification in SCC negatively correlates with cause-specific survival suggesting that targeting DCN1 may be of clinical utility. Although other important cancer gene(s) may be present within the amplicon, several studies have demonstrated that DCN1 plays a critical role in tumor progression and metastasis, and drives selection for 3q amplification in SCC. Recently, DCN1 has been reported to have a driving role in prostate cancer and depletion of DCN1 in LNCaP cells significantly reduced their proliferation, migration, and invasion capability. Similar results have been reported in cervical cancers. DCN1's emerging roles in these diseases suggest it may present a new oncology drug discovery target.

DCN1 acts as a co-E3 together with RBX1 to stimulate the transfer of NEDD8 from its E2 (UBE2M) to the cullin proteins. DCN1's activation of the NEDD8 pathway requires binding to UBE2M. This interaction is driven by binding of UBE2M's N-terminal acetyl-methionine and immediately proximal amino acid side chains to a ≈350 Å$^3$ hydrophobic pocket on DCN1. This interaction is controlled in a switch-like way by the N-terminal acetylation of UBE2M with the equilibrium dissociation constant for the N-terminally acetylated protein being 100-fold more potent relative to the non-acetylated protein. With this understanding, peptide based inhibitors of the DCN1-UBE2M interaction were also recently reported, as was a series of N-benzyl piperidines that bind the UBE2M pocket on DCN1 has recently been reported. While this series of compounds, represented by NAcM-OPT (FIG. 1), were the first reported small molecule inhibitors of DCN1, they suffered several limitations: 1) they do not access the N-acetyl pocket that controls the binding of the native substrate; 2) they possess only one stereocenter, thus lacking 3-dimensional character affording access to the available sub-pockets within the binding pocket, and 3) they have a moderate murine half-life that requires relatively high and frequent dosing to maintain relevant concentrations in mouse models.

Accordingly, there remains a need for effective DCN1 inhibitors.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a DCN1/2-mediated cullin neddylation modulator comprising a compound according to Formula I.

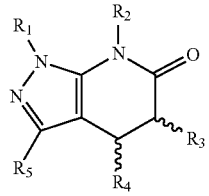

I wherein each of $R_1$, $R_2$, and $R_4$ are independently selected from alkyl, haloalkyl, heteroalkyl, cycloalkyl, heterocycloalkyl, alkenyl, alkynyl, acyl, aryl, heteroaryl, haloaryl, alkyl ester, alkyl carboxylic acid, alkyl amide, or cyanomethyl; wherein $R_3$ is selected from —NHC(=O)—$R_6$, —NHC(=O)—NH—$R_6$, —NHSO$_2$—$R_6$, —C(=O)—NH—$R_6$, or —CH$_2$C(=O)—$R_6$; wherein $R_4$ is selected from alkyl, acyl, aryl, or heteroaryl; wherein $R_5$ is selected from alkyl, cycloalkyl, heterocycloalkyl, aryl, heteroaryl, carboxylic acid, nitrile, or —(CH$_2$)$_n$—X—$R_7$; wherein $R_6$ is selected from alkyl, alkenyl, acyl, aryl, or heteroaryl; wherein $R_7$ is selected from H, alkyl, haloalkyl, heteroalkyl, cycloalkyl, heterocycle, heterocycloalkyl, alkenyl, alkynyl, acyl, aryl, heteroaryl, alkyl ester, alkyl carboxylic acid, alkyl amide, or cyanomethyl; wherein X is selected from O, N, S, or Linker; wherein Linker is selected from —(OCH$_2$CH$_2$)$_n$— (PEG), alkyl linker, or aminoalkyl linker; and wherein n is between 0 and 20. In some embodiments, $R_1$, $R_2$, and $R_4$ are not the same. In some embodiments, at least two of $R_1$, $R_2$, and $R_4$ are the same. In some embodiments, each of $R_1$, $R_2$, and $R_4$ are the same. In some embodiments, $R_1$ is an aryl. In some embodiments, $R_2$ is an alkyl. In some embodiments, $R_4$ is a haloaryl. In some embodiments, $R_3$ and $R_4$ comprise a cis geometry. In some embodiments, $R_1$ is an aryl and $R_4$ is a haloaryl. In some embodiments, $R_1$ is an aryl, $R_2$ is an alkyl, and $R_4$ is a haloaryl.

In some embodiments, $R_5$ is —(CH$_2$)$_n$—X—$R_7$. In some embodiments, the modulator according to Formula I includes a compound according to Formula II:

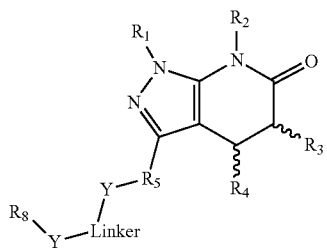

II wherein each Y is independently selected from CH$_2$, N, O, or S; and wherein $R_8$ is selected from a functional group for biorthogonal reactions, Biotin, JQ1, or E3 ligand. In some embodiments, $R_3$ and $R_4$ comprise a cis geometry. In some embodiments, $R_1$ is an aryl. In some embodiments, $R_2$ is an alkyl. In some embodiments, $R_4$ is a haloaryl. In some embodiments, $R_1$ is an aryl, $R_2$ is an alkyl, and $R_4$ is a haloaryl.

Also provided herein, in some embodiments, is a pharmaceutical composition including a therapeutically effective amount of a compound according to Formula I, or a pharmaceutically acceptable salt thereof, and a pharmaceutically acceptable carrier.

Further provided herein, in some embodiments, is a method for treating disorders associated with dysfunctional DCN1 and/or UBC12, Alzheimer's disease, other neurodegenerative diseases, bacterial infections, or viral infections, the method including the step of administering to a mammal a therapeutically effective amount of a compound according to Formula I.

Still further provided herein, in some embodiments, is a method for treating cancers, the method comprising the step of administering to a mammal a therapeutically effective amount of a compound according to Formula I.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein.

¹H-NMR of compound 80. (E) ¹H-NMR of compound 141. (F) ¹³C-NMR of compound 141. (G) HMBC of compound 141.

Figure 10:
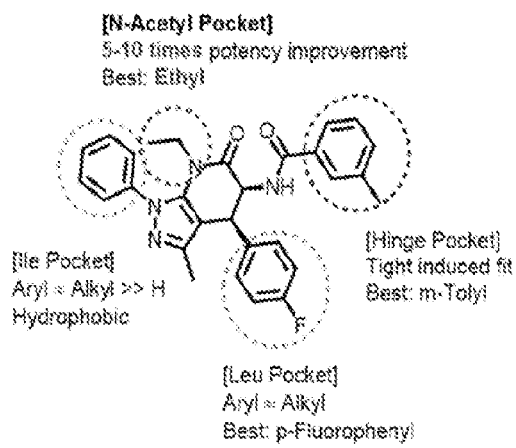
Figure 10:
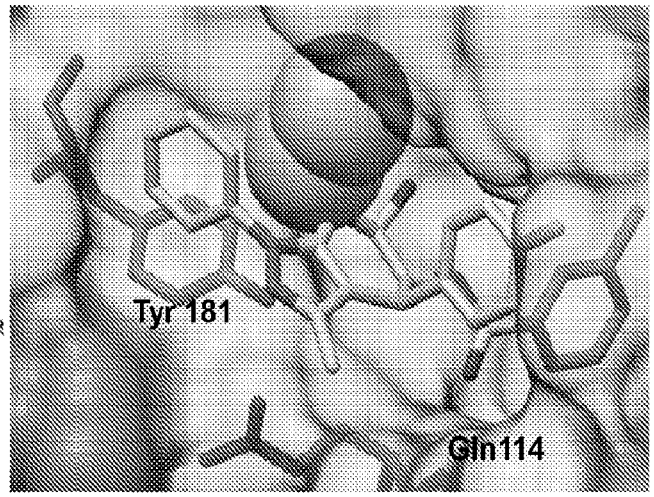

FIG. 10 shows images illustrating interaction of compound 27 with DCN1. Left: SAR summary compound 27. Right: X-ray crystal structure of compound 27(yellow): DCN1(gray) (PDB YYY). The ethyl substituent is represented as space filling spheres to highlight the key driver of potency. Hashed orange line represents the 2.6 Å hydrogen-bonding interaction between the compound's hinge amide and backbone amide of DCN1 Gln114. DCN1 Tyr181 is shown as sticks to highlight the hydrophobic interaction and potential electrostatic interaction.

Figure 11:
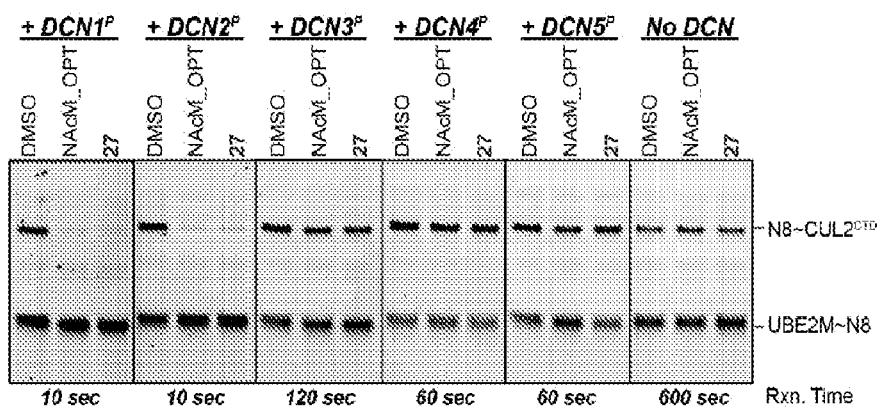

FIG. 11 shows an image illustrating the DCN isoform selectivity of compound 27 and the known DCN1/2 selective inhibitor NAcM-OPT (positive control). Pulse-chase assay monitoring transfer of NEDD8 from UBE2M to CUL2 in the presence of 10 µM inhibitor or DMSO as tested against all five of the DCN family members.

Figure 12:
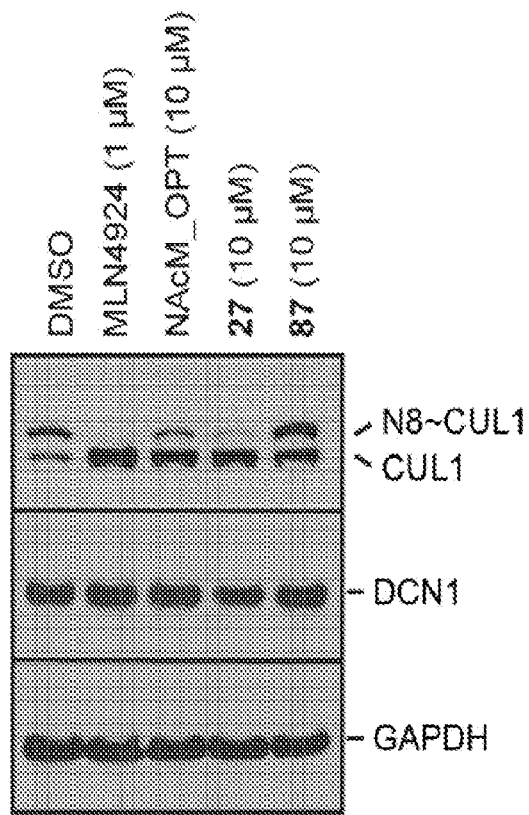

FIG. 12 shows an image illustrating western blot for inhibition of cellular neddylation at 24 hours by DMSO, MLN4924 (positive control, 1 µM), NAcM-OPT (10 µM), and compound 27 (10 µM).

Figure 13:
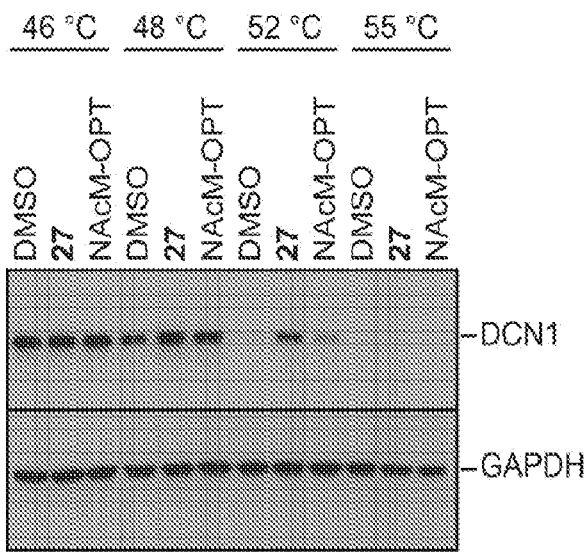

FIG. 13 shows an image illustrating enhancement of DCN1 thermal stability by compounds 27 and NAcM-OPT (positive control) but not by DMSO (negative control). HCC95 cells were treated with either DMSO or 10 µM of the indicated compound for 1 h, heated at the indicated temperature for 3 minutes, lysed, and blotted with the indicated antibodies.

Figure 14:
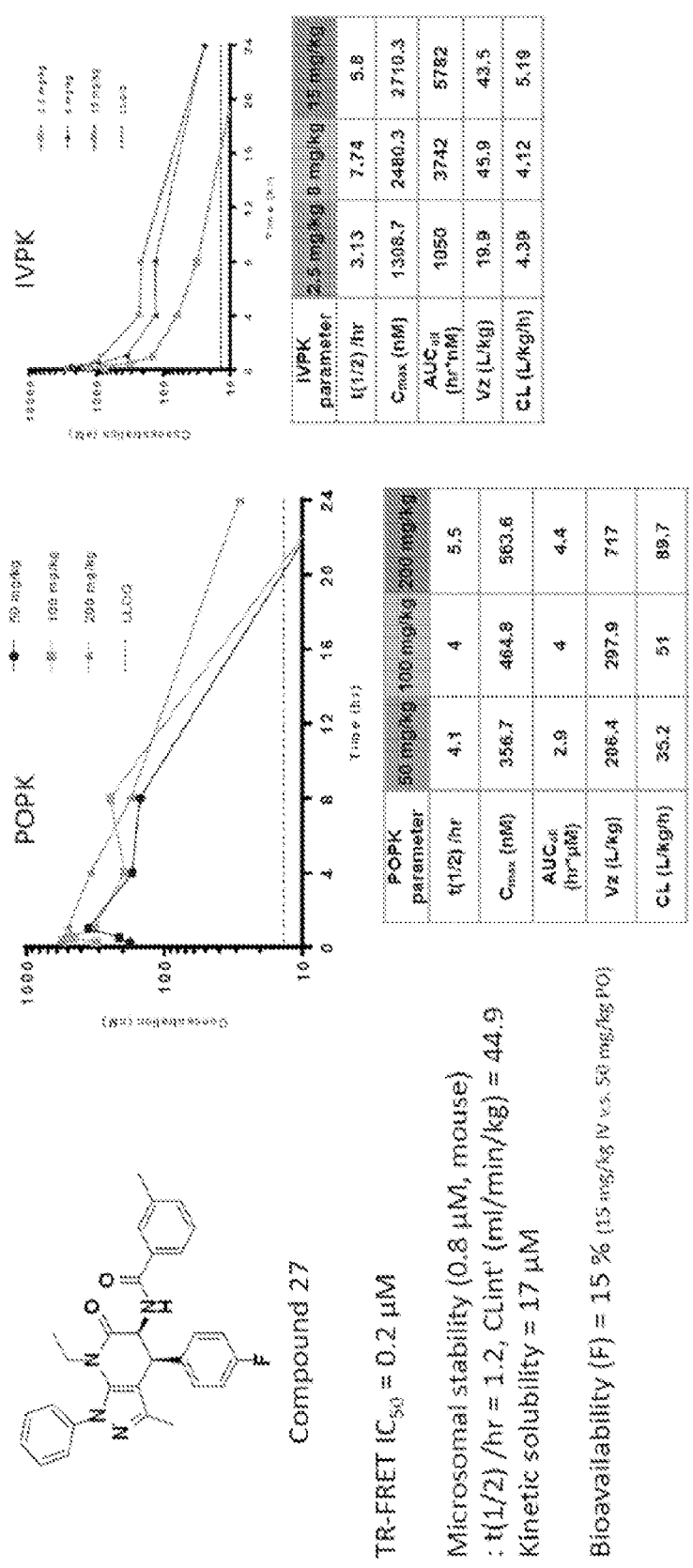

FIG. 14 shows graphs and images illustrating PK data of compound 27 (RG-0007413).

Figure 15:
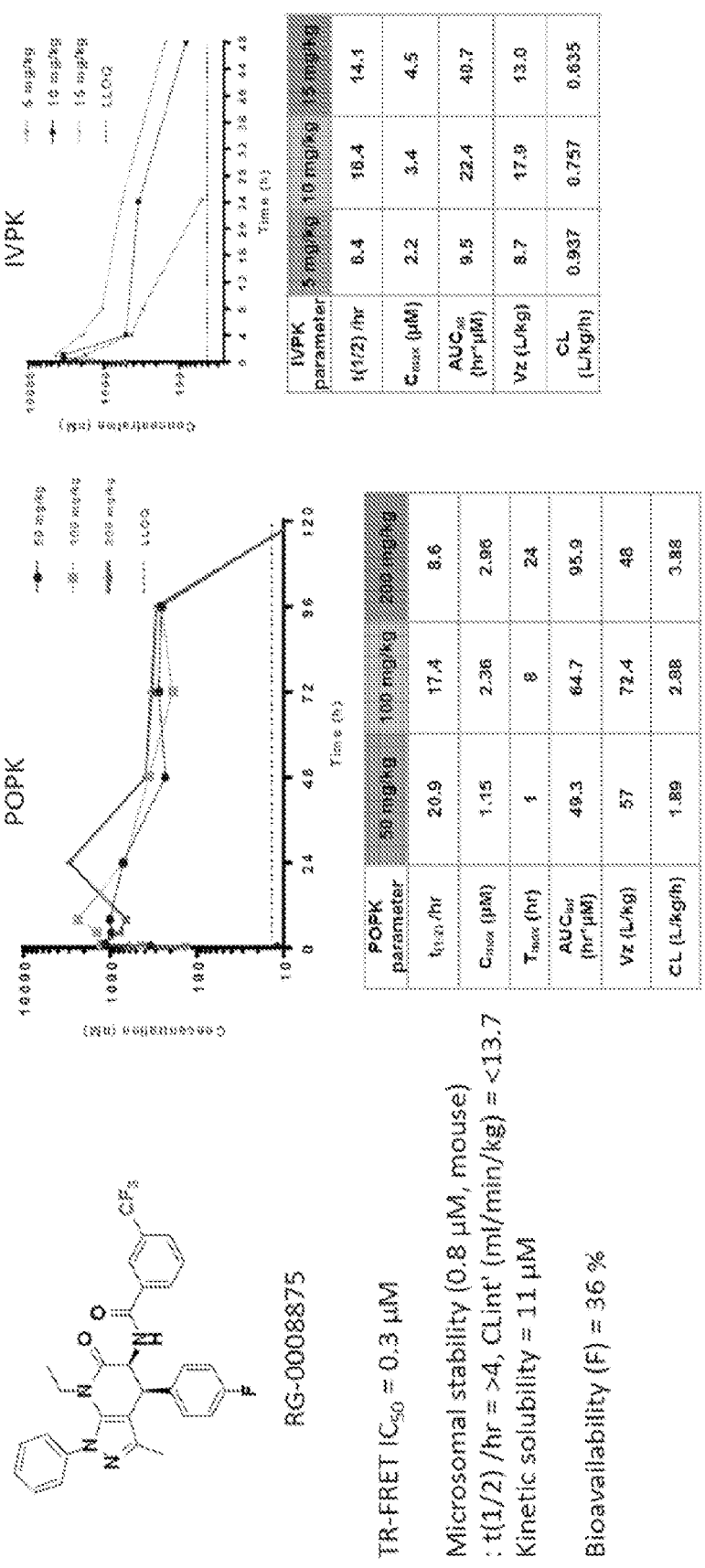

FIG. 15 shows graphs and images illustrating PK data of compound 174 (RG-0008875).

Figure 16:
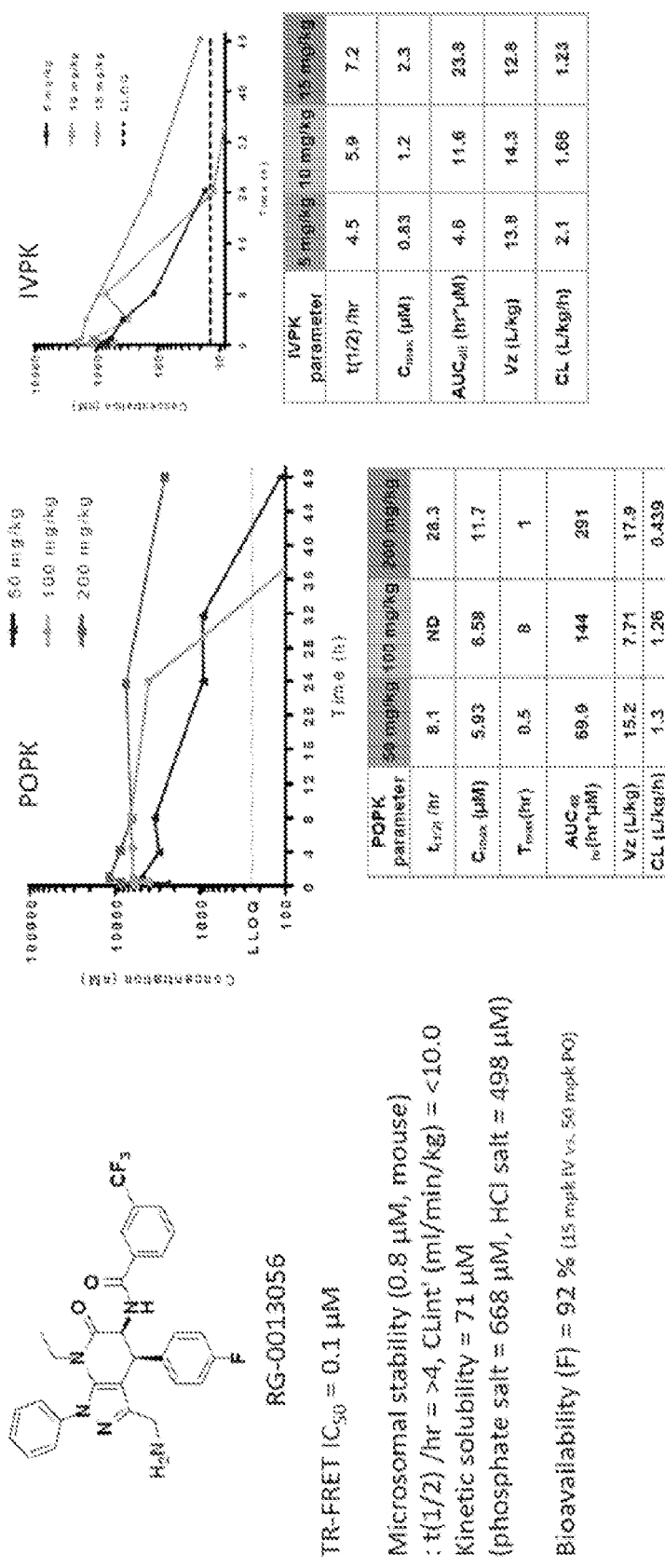

FIG. 16 shows graphs and images illustrating PK data of compound 175 (RG-0013056).

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

Definitions

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "semisynthetic" refers to aurones bearing the skeleton found in aurone natural products as well as functional groups and/or additional rings not found in aurone natural products.

All combinations of method or process steps as used herein can be performed in any order, unless otherwise specified or clearly implied to the contrary by the context in which the referenced combination is made.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, nonhuman primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders, e.g., a neurodegenerative disease or disease of uncontrolled cellular proliferation, associated with DCN1-UBC12 interaction prior to the administering step. In some aspects of the disclosed method, the subject has been diagnosed with a need for inhibition of DCN1-mediated cullin-RING ligase activity prior to the administering step. In some aspects of the disclosed method, the subject has been diagnosed with a disorder of uncontrolled cellular proliferation, e.g., a cancer, prior to the administering step. In some aspects of the disclosed method, the subject has been diagnosed with a neurodegenerative disorder prior to the administering step. In some aspects of the disclosed method, the subject has been identified with a disorder treatable by inhibiting the DCN1-UBC12 interaction prior to the administering step. In some aspects of the disclosed method, the subject has been identified with a disorder treatable by inhibiting DCN1-mediated cullin-RING ligase activity prior to the administering step. In some aspects of the disclosed method, the subject has been identified with a bacterial or viral infection prior to the administering step. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by inhibiting the DCN1-UBC12 interaction" means having been subjected to a physical examination by a person of skill, for example, a physician, and found to have a condition that can be diagnosed or treated by a compound or composition that can inhibit the DCN1-UBC12 interaction. As a further example, "diagnosed with a need for inhibiting the DCN1-UBC12 interaction" refers to having been subjected to a physical examination by a person of skill, for example, a physician, and found to have a condition characterized by a DCN1-UBC12 interaction dysfunction. Such a diagnosis can be in reference to a disorder, such as a neurodegenerative disease, and the like, as discussed herein. For example, the term "diagnosed with a need for treatment of a disorder of uncontrolled cellular proliferation" refers to having been subjected to a physical examination by a person of skill, for example, a physician, and found to have a condition of uncontrolled cellular proliferation, e.g., a cancer, that can be treated by various therapeutic agents or methods, including, but not limited to, the disclosed compounds and/or products of the disclosed methods of making. For example, "diagnosed with a need for treatment of one or more disorders of uncontrolled cellular proliferation associated with a DCN1-UBC12 interaction dysfunction" means having been subjected to a physical examination by a person of skill, for example, a physician, and found to have one or more disorders of uncontrolled cellular proliferation, e.g., a cancer, associated with a DCN1-UBC12 interaction dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a DCN1-UBC12 interaction dysfunction) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target protein(s) (e.g., the DCN1-UBC12 proteins), or other biological entity together in such a manner that the compound can affect the activity of the target, either directly; e.g., by interacting with the target protein(s) itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "IC$_{50}$" is intended to refer to the concentration of a substance (e.g., a compound or a drug) that is required for 50% inhibition of a biological process, or component of a process, including a protein, subunit, organelle, ribonucleoprotein, etc. For example, IC$_{50}$ refers to the half maximal (50%) inhibitory concentration (IC) of a substance as determined in a suitable assay. For example, an IC$_{50}$ for inhibiting DCN1-UBC12 interaction can be determined in an in vitro assay system.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, propyl, isopropyl, butyl, isobutyl, s-butyl, i-butyl, pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group is acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_n$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (teri-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula C(O)OH.

The term "ester" as used herein is represented by the formula $OC(O)A^1$ or $C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $—(A^1O(O)C-A^2-C(O)O)_a—$ or $—(A^1O(O)C-A^2-OC(O))_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $—(A^1O-A^2O)_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, 1,2-oxazol-4-yl, 1,2-oxazol-5-yl, 1,3-oxazolyl, 1,2,4-oxadiazol-5-yl, 1,2,3-triazolyl, 1,3-thiazol-4-yl, pyridinyl, and pyrimidin-5-yl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "tricyclic heterocycle" or "bicyclic heterocyclyl," as used herein refers to a ring system in which at least one of the ring members is other than carbon. Bicyclic heterocyclyl encompasses ring systems an aromatic ring is fused with another aromatic ring, or an aromatic ring is fused with a non-aromatic ring. Bicyclic heterocyclyl encompasses ring systems a benzene ring is fused to a 5- or a 6-membered ring containing 1, 2 or 3 ring heteroatoms or a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term 'heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" as used herein is represented by the formula OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula $—N_3$.

The term "nitro" as used herein is represented by the formula $—NO_2$.

The term "nitrile" as used herein is represented by the formula $—CN$.

The term "silyl" as used herein is represented by the formula $—SiA^1A^2A^3$, where $A^1$, $A^2$ and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. It is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter relates to modulators of DCN1/2-mediated cullin neddylation and methods of use thereof. In some embodiments, the modulator include inhibitors. In some embodiments, the inhibitors contain a pyrazolo-pyridone core. In some embodiments, the modulators include a general pyrazolo-pyridone structure according to Formula I below:

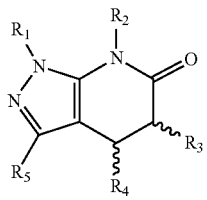

I

Where each of $R_1$, $R_2$, and $R_4$ independently includes alkyl, haloalkyl, heteroalkyl, cycloalkyl, heterocycloalkyl, alkenyl, alkynyl, acyl, aryl, heteroaryl, haloaryl, alkyl ester, alkyl carboxylic acid, alkyl amide, or cyanomethyl; $R_3$ includes —NHC(=O)—$R_6$, —NHC(=O)—NH—$R_6$, —NHSO$_2$—$R_6$, —C(=O)—NH—$R_6$, or —CH$_2$C(=O)—$R_6$; $R_5$ includes H, alkyl, cycloalkyl, heterocycloalkyl, aryl, heteroaryl, carboxylic acid, nitrile, or —(CH$_2$)$_n$—X—$R_7$; $R_6$ includes alkyl, alkenyl, acyl, aryl, or heteroaryl; $R_7$ includes H, heterocycle, alkyl, haloalkyl, heteroalkyl, cycloalkyl, heterocycloalkyl, alkenyl, alkynyl, acyl, aryl, heteroaryl, alkyl ester, alkyl carboxylic acid, alkyl amide, cyanomethyl, or —Y—Z—Y—$R_8$; $R_8$ includes H, a functional group for biorthogonal reactions, Biotin, JQ1, or E3 ligand; X includes O, N, S, a bond, or a combination thereof, each Y independently includes CH$_2$, N, O, S, a bond, or a combination thereof, Z includes a linker, such as, but not limited to, polyethylene glycol (PEG; —(OCH$_2$CH$_2$)$_n$—), alkyl linker, aminoalkyl linker, or other suitable linker; and each n is independently between 0 and 20. Suitable functional groups include, but are not limited to, azide, allyl, cyclooctynes (e.g., OCT, DIBAC, DIBO), nitrile oxide, nitrile imine, diazo, oxanoborandiene, boronic acid, tetrazine. Suitable E3 ligands include, but are not limited to, Cereblon ligand or VHL ligand. In some embodiments, $R_1$ and $R_2$ together form a ring with the nitrogen atoms to which they are bound.

In some embodiments, $R_1$, $R_2$, and $R_4$ are all different. For example, in one embodiment, $R_1$ is an aryl, $R_2$ is an alkyl, and $R_4$ is a haloaryl. In some embodiments, at least two of $R_1$, $R_2$, and $R_4$ are the same. For example, in one embodiment, $R_1$ and $R_2$ are alkyl and $R_4$ is a haloalkyl. In some embodiments, each of $R_1$, $R_2$, and $R_4$ is the same. For example, in one embodiment, each of $R_1$, $R_2$, and $R_4$ is an alkyl.

In some embodiments, at least one of $R_1$, $R_2$, and $R_4$ is an alkyl and the remaining variable groups include any substituent as disclosed herein. In some embodiments, at least one of $R_1$, $R_2$, and $R_4$ is a haloalkyl and the remaining variable groups include any substituent as disclosed herein. In some embodiments, at least one of $R_1$, $R_2$, and $R_4$ is a heteroalkyl and the remaining variable groups include any substituent as disclosed herein. In some embodiments, at least one of $R_1$, $R_2$, and $R_4$ is a cycloalkyl and the remaining variable groups include any substituent as disclosed herein. In some embodiments, at least one of $R_1$, $R_2$, and $R_4$ is a heterocycloalkyl and the remaining variable groups include any substituent as disclosed herein. In some embodiments, at least one of $R_1$, $R_2$, and $R_4$ is a alkenyl and the remaining variable groups include any substituent as disclosed herein. In some embodiments, at least one of $R_1$, $R_2$, and $R_4$ is a acyl and the remaining variable groups include any substituent as disclosed herein. In some embodiments, at least one of $R_1$, $R_2$, and $R_4$ is a aryl and the remaining variable groups include any substituent as disclosed herein. In some embodiments, at least one of $R_1$, $R_2$, and $R_4$ is a heteroaryl and the remaining variable groups include any substituent as disclosed herein. In some embodiments, at least one of $R_1$, $R_2$, and $R_4$ is a haloaryl and the remaining variable groups include any substituent as disclosed herein. In some embodiments, at least one of $R_1$, $R_2$, and $R_4$ is a alkyl ester and the remaining variable groups include any substituent as disclosed herein. In some embodiments, at least one of $R_1$, $R_2$, and $R_4$ is a alkyl carboxylic acid and the remaining variable groups include any substituent as disclosed herein. In some embodiments, at least one of $R_1$, $R_2$, and $R_4$ is a alkyl amid and the remaining variable groups include any substituent as disclosed herein. In some embodiments, at least one of $R_1$, $R_2$, and $R_4$ is a cyanomethyl and the remaining variable groups include any substituent as disclosed herein.

In some embodiments, $R_1$ is an alkyl and the remaining variable groups include any substituent as disclosed herein. In some embodiments, $R_1$ is a haloalkyl and the remaining variable groups include any substituent as disclosed herein. In some embodiments, $R_1$ is a heteroalkyl and the remaining variable groups include any substituent as disclosed herein. In some embodiments, $R_1$ is a cycloalkyl and the remaining variable groups include any substituent as disclosed herein. In some embodiments, $R_1$ is a heterocycloalkyl and the remaining variable groups include any substituent as disclosed herein. In some embodiments, $R_1$ is a alkenyl and the remaining variable groups include any substituent as disclosed herein. In some embodiments, $R_1$ is a acyl and the remaining variable groups include any substituent as disclosed herein. In some embodiments, $R_1$ is a aryl and the remaining variable groups include any substituent as disclosed herein. In some embodiments, $R_1$ is a heteroaryl and the remaining variable groups include any substituent as disclosed herein. In some embodiments, $R_1$ is a haloaryl and the remaining variable groups include any substituent as disclosed herein. In some embodiments, $R_1$ is a alkyl ester and the remaining variable groups include any substituent as disclosed herein. In some embodiments, $R_1$ is a alkyl carboxylic acid and the remaining variable groups include any substituent as disclosed herein. In some embodiments, $R_1$ is a alkyl amid and the remaining variable groups include any substituent as disclosed herein. In some embodiments, $R_1$ is a cyanomethyl and the remaining variable groups include any substituent as disclosed herein. In some embodiments, $R_1$ and $R_2$ together form a ring with the nitrogen atoms to which they are bound, and $R_3$ through $R_5$ include any substituent as disclosed herein.

In some embodiments, $R_2$ is an alkyl and the remaining variable groups include any substituent as disclosed herein. In some embodiments, $R_2$ is a haloalkyl and the remaining variable groups include any substituent as disclosed herein. In some embodiments, $R_2$ is a heteroalkyl and the remaining variable groups include any substituent as disclosed herein. In some embodiments, $R_2$ is a cycloalkyl and the remaining variable groups include any substituent as disclosed herein. In some embodiments, $R_2$ is a heterocycloalkyl and the remaining variable groups include any substituent as disclosed herein. In some embodiments, $R_2$ is a alkenyl and the remaining variable groups include any substituent as disclosed herein. In some embodiments, $R_2$ is a acyl and the remaining variable groups include any substituent as disclosed herein. In some embodiments, $R_2$ is a aryl and the remaining variable groups include any substituent as disclosed herein. In some embodiments, $R_2$ is a heteroaryl and the remaining variable groups include any substituent as disclosed herein. In some embodiments, $R_2$ is a haloaryl and the remaining variable groups include any substituent as disclosed herein. In some embodiments, $R_2$ is a alkyl ester and the remaining variable groups include any substituent as disclosed herein. In some embodiments, $R_2$ is a alkyl carboxylic acid and the remaining variable groups include any substituent as disclosed herein. In some embodiments, $R_2$ is a alkyl amid and the remaining variable groups include any substituent as disclosed herein. In some embodiments, $R_2$ is a cyanomethyl and the remaining variable groups include any substituent as disclosed herein. In some embodiments, $R_1$ and $R_2$ together form a ring with the nitrogen atoms to which they are bound, and $R_3$ through $R_5$ include any substituent as disclosed herein.

In some embodiments, $R_4$ is an alkyl and the remaining variable groups include any substituent as disclosed herein. In some embodiments, $R_4$ is a haloalkyl and the remaining variable groups include any substituent as disclosed herein. In some embodiments, $R_4$ is a heteroalkyl and the remaining variable groups include any substituent as disclosed herein. In some embodiments, $R_4$ is a cycloalkyl and the remaining variable groups include any substituent as disclosed herein. In some embodiments, $R_4$ is a heterocycloalkyl and the remaining variable groups include any substituent as disclosed herein. In some embodiments, $R_4$ is a alkenyl and the remaining variable groups include any substituent as disclosed herein. In some embodiments, $R_4$ is a acyl and the remaining variable groups include any substituent as disclosed herein. In some embodiments, $R_4$ is a aryl and the remaining variable groups include any substituent as disclosed herein. In some embodiments, $R_4$ is a heteroaryl and the remaining variable groups include any substituent as disclosed herein. In some embodiments, $R_4$ is a haloaryl and the remaining variable groups include any substituent as disclosed herein. In some embodiments, $R_4$ is a alkyl ester and the remaining variable groups include any substituent as disclosed herein. In some embodiments, $R_4$ is a alkyl carboxylic acid and the remaining variable groups include any substituent as disclosed herein. In some embodiments, $R_4$ is a alkyl amid and the remaining variable groups include any substituent as disclosed herein. In some embodiments, $R_4$ is a cyanomethyl and the remaining variable groups include any substituent as disclosed herein.

In some embodiments, two of $R_1$, $R_2$, and $R_4$ (i.e., $R_1$ and $R_2$, $R_1$ and $R_4$, or $R_2$ and $R_4$) are an alkyl and the remaining variable groups include any substituent as disclosed herein. In some embodiments, two of $R_1$, $R_2$, and $R_4$ are a haloalkyl and the remaining variable groups include any substituent as disclosed herein. In some embodiments, two of $R_1$, $R_2$, and $R_4$ are a heteroalkyl and the remaining variable groups include any substituent as disclosed herein. In some embodiments, two of $R_1$, $R_2$, and $R_4$ are a cycloalkyl and the remaining variable groups include any substituent as disclosed herein. In some embodiments, two of $R_1$, $R_2$, and $R_4$ are a heterocycloalkyl and the remaining variable groups include any substituent as disclosed herein. In some embodiments, two of $R_1$, $R_2$, and $R_4$ are a alkenyl and the remaining variable groups include any substituent as disclosed herein. In some embodiments, two of $R_1$, $R_2$, and $R_4$ are a acyl and the remaining variable groups include any substituent as disclosed herein. In some embodiments, two of $R_1$, $R_2$, and $R_4$ are a aryl and the remaining variable groups include any substituent as disclosed herein. In some embodiments, two of $R_1$, $R_2$, and $R_4$ are a heteroaryl and the remaining variable groups include any substituent as disclosed herein. In some embodiments, two of $R_1$, $R_2$, and $R_4$ are a alkyl ester and the remaining variable groups include any substituent as disclosed herein. In some embodiments, two of $R_1$, $R_2$, and $R_4$ are a alkyl carboxylic acid and the remaining variable groups include any substituent as disclosed herein. In some embodiments, two of $R_1$, $R_2$, and $R_4$ are a alkyl amid and the remaining variable groups include any substituent as disclosed herein. In some embodiments, two of $R_1$, $R_2$, and $R_4$ are a cyanomethyl and the remaining variable groups include any substituent as disclosed herein.

In some embodiments, each of $R_1$, $R_2$, and $R_4$ is an alkyl and the remaining variable groups include any substituent as disclosed herein. In some embodiments, each of $R_1$, $R_2$, and $R_4$ is a haloalkyl and the remaining variable groups include any substituent as disclosed herein. In some embodiments, each of $R_1$, $R_2$, and $R_4$ is a heteroalkyl and the remaining variable groups include any substituent as disclosed herein. In some embodiments, each of $R_1$, $R_2$, and $R_4$ is a cycloalkyl and the remaining variable groups include any substituent as disclosed herein. In some embodiments, each of $R_1$, $R_2$, and $R_4$ is a heterocycloalkyl and the remaining variable groups include any substituent as disclosed herein. In some embodiments, each of $R_1$, $R_2$, and $R_4$ is a alkenyl and the remaining variable groups include any substituent as disclosed herein. In some embodiments, each of $R_1$, $R_2$, and $R_4$ is a acyl and the remaining variable groups include any substituent as disclosed herein. In some embodiments, each of $R_1$, $R_2$, and $R_4$ is a aryl and the remaining variable groups include any substituent as disclosed herein. In some embodiments, each of $R_1$, $R_2$, and $R_4$ is a heteroaryl and the remaining variable groups include any substituent as disclosed herein. In some embodiments, each of $R_1$, $R_2$, and $R_4$ is a alkyl ester and the remaining variable groups include any substituent as disclosed herein. In some embodiments, each of $R_1$, $R_2$, and $R_4$ is a alkyl carboxylic acid and the remaining variable groups include any substituent as disclosed herein. In some embodiments, each of $R_1$, $R_2$, and $R_4$ is a alkyl amid and the remaining variable groups include any substituent as disclosed herein. In some embodiments, each of $R_1$, $R_2$, and $R_4$ is a cyanomethyl and the remaining variable groups include any substituent as disclosed herein.

In some embodiments, $R_3$ is —NHC(=O)—$R_6$, $R_6$ is alkyl, and the remaining variable groups include any substituent as disclosed herein. In some embodiments, $R_3$ is —NHC(=O)—$R_6$, $R_6$ is alkenyl, and the remaining variable groups include any substituent as disclosed herein. In some embodiments, $R_3$ is —NHC(=O)—$R_6$, $R_6$ is acyl, and the remaining variable groups include any substituent as disclosed herein. In some embodiments, $R_3$ is —NHC(=O)—$R_6$, $R_6$ is aryl, and the remaining variable groups include any substituent as disclosed herein. In some embodiments, $R_3$ is —NHC(=O)—$R_6$, $R_6$ is heteroaryl, and the remaining variable groups include any substituent as disclosed herein. In some embodiments, $R_3$ is —NHC(=O)—NH—$R_6$, $R_6$ is alkyl, and the remaining variable groups include any substituent as disclosed herein. In some embodiments, $R_3$ is —NHC(=O)—NH—$R_6$, $R_6$ is alkenyl, and the remaining variable groups include any substituent as disclosed herein. In some embodiments, $R_3$ is —NHC(=O)—NH—$R_6$, $R_6$ is acyl, and the remaining variable groups include any substituent as disclosed herein. In some embodiments, $R_3$ is —NHC(=O)—NH—$R_6$, $R_6$ is aryl, and the remaining variable groups include any substituent as disclosed herein. In some embodiments, $R_3$ is —NHC(=O)—NH—$R_6$, $R_6$ is heteroaryl, and the remaining variable groups include any substituent as disclosed herein. In some embodiments, $R_3$ is —NHSO$_2$—$R_6$, $R_6$ is alkyl, and the remaining variable groups include any substituent as disclosed herein. In some embodiments, $R_3$ is —NHSO$_2$—$R_6$, $R_6$ is alkenyl, and the remaining variable groups include any substituent as disclosed herein. In some embodiments, $R_3$ is —NHSO$_2$—$R_6$, $R_6$ is acyl, and the remaining variable groups include any substituent as disclosed herein. In some embodiments, $R_3$ is —NHSO$_2$—$R_6$, $R_6$ is aryl, and the remaining variable groups include any substituent as disclosed herein. In some embodiments, $R_3$ is —NHSO$_2$—$R_6$, $R_6$ is heteroaryl, and the remaining variable groups include any substituent as disclosed herein. In some embodiments, $R_3$ is —C(=O)—NH—$R_6$, $R_6$ is alkyl, and the remaining variable groups include any substituent as disclosed herein. In some embodiments, $R_3$ is —C(=O)—NH—$R_6$, $R_6$ is alkenyl, and the remaining variable groups include any substituent as disclosed herein. In some embodiments, $R_3$ is —C(=O)—NH—$R_6$, $R_6$ is acyl, and the remaining variable groups include any substituent as disclosed herein. In some embodiments, $R_3$ is —C(=O)—NH—$R_6$, $R_6$ is aryl, and the remaining variable groups include any substituent as disclosed herein. In some embodiments, $R_3$ is —C(=O)—NH—$R_6$, $R_6$ is heteroaryl, and the remaining variable groups include any substituent as disclosed herein. In some embodiments, $R_3$ is —CH$_2$C(=O)—$R_6$, $R_6$ is alkyl, and the remaining variable groups include any substituent as disclosed herein. In some embodiments, $R_3$ is —CH$_2$C(=O)—$R_6$, $R_6$ is alkenyl, and the remaining variable groups include any substituent as disclosed herein. In some embodiments, $R_3$ is —CH$_2$C(=O)—$R_6$, $R_6$ is acyl, and the remaining variable groups include any substituent as disclosed herein. In some embodiments, $R_3$ is —CH$_2$C(=O)—$R_6$, $R_6$ is aryl, and the remaining variable groups include any substituent as disclosed herein. In some embodiments, $R_3$ is —CH$_2$C(=O)—$R_6$, $R_6$ is heteroaryl, and the remaining variable groups include any substituent as disclosed herein.

In some embodiments, $R_5$ is H and the remaining variable groups include any substituent as disclosed herein. In some embodiments, $R_5$ is alkyl and the remaining variable groups include any substituent as disclosed herein. In some embodiments, $R_5$ is cycloalkyl and the remaining variable groups include any substituent as disclosed herein. In some embodiments, $R_5$ is heterocycloalkyl and the remaining variable groups include any substituent as disclosed herein. In some embodiments, $R_5$ is aryl and the remaining variable groups include any substituent as disclosed herein. In some embodiments, $R_5$ is heteroaryl and the remaining variable groups include any substituent as disclosed herein. In some embodiments, $R_5$ is carboxylic acid and the remaining variable groups include any substituent as disclosed herein. In some embodiments, $R_5$ is nitrile and the remaining variable groups include any substituent as disclosed herein. In some embodiments, $R_5$ is —(CH$_2$)$_n$—X—$R_7$ and the remaining variable groups include any substituent as disclosed herein.

In some embodiments, where $R_5$ is —(CH$_2$)$_n$—X—$R_7$, X is O and the remaining variable groups include any substituent discussed herein. In some embodiments, where $R_5$ is —(CH$_2$)$_n$—X—$R_7$, X is O, $R_7$ is H, and the remaining variable groups include any substituent discussed herein. In some embodiments, where $R_5$ is —(CH$_2$)$_n$—X—$R_7$, X is O, $R_7$ is heterocycle, and the remaining variable groups include any substituent discussed herein. In some embodiments, where $R_5$ is —(CH$_2$)$_n$—X—$R_7$, X is O, $R_7$ is alkyl, and the remaining variable groups include any substituent discussed herein. In some embodiments, where $R_5$ is —(CH$_2$)$_n$—X—$R_7$, X is O, $R_7$ is haloalkyl, and the remaining variable groups include any substituent discussed herein. In some embodiments, where $R_5$ is —(CH$_2$)$_n$—X—$R_7$, X is O, $R_7$ is heteroalkyl, and the remaining variable groups include any substituent discussed herein. In some embodiments, where $R_5$ is —(CH$_2$)$_n$—X—$R_7$, X is O, $R_7$ is cycloalkyl, and the remaining variable groups include any substituent discussed herein. In some embodiments, where $R_5$ is —(CH$_2$)$_n$—X—$R_7$, X is O, $R_7$ is heterocycloalkyl, and the remaining variable groups include any substituent discussed herein. In some embodiments, where $R_5$ is —(CH$_2$)$_n$—X—$R_7$, X is O, $R_7$ is alkenyl, and the remaining variable groups include any substituent discussed herein. In some embodiments, where $R_5$ is —(CH$_2$)$_n$—X—$R_7$, X is O, $R_7$ is alkynyl, and the remaining variable groups include any substituent discussed herein. In some embodiments, where $R_5$ is —(CH$_2$)$_n$—X—$R_7$, X is O, $R_7$ is acyl, and the remaining variable groups include any substituent discussed herein. In some embodiments, where $R_5$ is —(CH$_2$)$_n$—X—$R_7$, X is O, $R_7$ is aryl, and the remaining variable groups include any substituent discussed herein. In some embodiments, where $R_5$ is —(CH$_2$)$_n$—X—$R_7$, X is O, $R_7$ is heteroaryl, and the remaining variable groups include any substituent discussed herein. In some embodiments, where $R_5$ is —(CH$_2$)$_n$—X—$R_7$, X is O, $R_7$ is alkyl ester, and the remaining variable groups include any substituent discussed herein. In some embodiments, where $R_5$ is —(CH$_2$)$_n$—X—$R_7$, X is O, $R_7$ is alkyl carboxylic acid, and the remaining variable groups include any substituent discussed herein. In some embodiments, where $R_5$ is —(CH$_2$)$_n$—X—$R_7$, X is O, $R_7$ is alkyl amide, and the remaining variable groups include any substituent discussed herein. In some embodiments, where $R_5$ is —(CH$_2$)$_n$—X—$R_7$, X is O, $R_7$ is cyanomethyl, and the remaining variable groups include any substituent discussed herein. In some embodiments, where $R_5$ is —(CH$_2$)$_n$—X—$R_7$, X is O, $R_7$ is —Y—Z—Y—$R_8$, and the remaining variable groups include any substituent discussed herein.

In some embodiments, where $R_5$ is —(CH$_2$)$_n$—X—$R_7$, X is N and the remaining variable groups include any substituent discussed herein. In some embodiments, where $R_5$ is —(CH$_2$)$_n$—X—$R_7$, X is N, $R_7$ is H, and the remaining variable groups include any substituent discussed herein. In some embodiments, where $R_5$ is —(CH$_2$)$_n$—X—$R_7$, X is N, $R_7$ is heterocycle, and the remaining variable groups include any substituent discussed herein. In some embodiments, where $R_5$ is —(CH$_2$)$_n$—X—$R_7$, X is N, $R_7$ is alkyl, and the remaining variable groups include any substituent discussed herein. In some embodiments, where $R_5$ is —$(CH_2)_n$—X—$R_7$, X is N, $R_7$ is haloalkyl, and the remaining variable groups include any substituent discussed herein. In some embodiments, where $R_5$ is —$(CH_2)_n$—X—$R_7$, X is N, $R_7$ is heteroalkyl, and the remaining variable groups include any substituent discussed herein. In some embodiments, where $R_5$ is —$(CH_2)_n$—X—$R_7$, X is N, $R_7$ is cycloalkyl, and the remaining variable groups include any substituent discussed herein. In some embodiments, where $R_5$ is —$(CH_2)_n$—X—$R_7$, X is N, $R_7$ is heterocycloalkyl, and the remaining variable groups include any substituent discussed herein. In some embodiments, where $R_5$ is —$(CH_2)_n$—X—$R_7$, X is N, $R_7$ is alkenyl, and the remaining variable groups include any substituent discussed herein. In some embodiments, where $R_5$ is —$(CH_2)_n$—X—$R_7$, X is N, $R_7$ is alkynyl, and the remaining variable groups include any substituent discussed herein. In some embodiments, where $R_5$ is —$(CH_2)_n$—X—$R_7$, X is N, $R_7$ is acyl, and the remaining variable groups include any substituent discussed herein. In some embodiments, where $R_5$ is —$(CH_2)_n$—X—$R_7$, X is N, $R_7$ is aryl, and the remaining variable groups include any substituent discussed herein. In some embodiments, where $R_5$ is —$(CH_2)_n$—X—$R_7$, X is N, $R_7$ is heteroaryl, and the remaining variable groups include any substituent discussed herein. In some embodiments, where $R_5$ is —$(CH_2)_n$—X—$R_7$, X is N, $R_7$ is alkyl ester, and the remaining variable groups include any substituent discussed herein. In some embodiments, where $R_5$ is —$(CH_2)_n$—X—$R_7$, X is N, $R_7$ is alkyl carboxylic acid, and the remaining variable groups include any substituent discussed herein. In some embodiments, where $R_5$ is —$(CH_2)_n$—X—$R_7$, X is N, $R_7$ is alkyl amide, and the remaining variable groups include any substituent discussed herein. In some embodiments, where $R_5$ is —$(CH_2)_n$—X—$R_7$, X is N, $R_7$ is cyanomethyl, and the remaining variable groups include any substituent discussed herein. In some embodiments, where $R_5$ is —$(CH_2)_n$—X—$R_7$, X is N, $R_7$ is —Y—Z—Y—$R_8$, and the remaining variable groups include any substituent discussed herein.

In some embodiments, where $R_5$ is —$(CH_2)_n$—X—$R_7$, X is S and the remaining variable groups include any substituent discussed herein. In some embodiments, where $R_5$ is —$(CH_2)_n$—X—$R_7$, X is S, $R_7$ is H, and the remaining variable groups include any substituent discussed herein. In some embodiments, where $R_5$ is —$(CH_2)_n$—X—$R_7$, X is S, $R_7$ is heterocycle, and the remaining variable groups include any substituent discussed herein. In some embodiments, where $R_5$ is —$(CH_2)_n$—X—$R_7$, X is S, $R_7$ is alkyl, and the remaining variable groups include any substituent discussed herein. In some embodiments, where $R_5$ is —$(CH_2)_n$—X—$R_7$, X is S, $R_7$ is haloalkyl, and the remaining variable groups include any substituent discussed herein. In some embodiments, where $R_5$ is —$(CH_2)_n$—X—$R_7$, X is S, $R_7$ is heteroalkyl, and the remaining variable groups include any substituent discussed herein. In some embodiments, where $R_5$ is —$(CH_2)_n$—X—$R_7$, X is S, $R_7$ is cycloalkyl, and the remaining variable groups include any substituent discussed herein. In some embodiments, where $R_5$ is —$(CH_2)_n$—X—$R_7$, X is S, $R_7$ is heterocycloalkyl, and the remaining variable groups include any substituent discussed herein. In some embodiments, where $R_5$ is —$(CH_2)_n$—X—$R_7$, X is S, $R_7$ is alkenyl, and the remaining variable groups include any substituent discussed herein. In some embodiments, where $R_5$ is —$(CH_2)_n$—X—$R_7$, X is S, $R_7$ is alkynyl, and the remaining variable groups include any substituent discussed herein. In some embodiments, where $R_5$ is —$(CH_2)_n$—X—$R_7$, X is S, $R_7$ is acyl, and the remaining variable groups include any substituent discussed herein. In some embodiments, where $R_5$ is —$(CH_2)_n$—X—$R_7$, X is S, $R_7$ is aryl, and the remaining variable groups include any substituent discussed herein. In some embodiments, where $R_5$ is —$(CH_2)_n$—X—$R_7$, X is S, $R_7$ is heteroaryl, and the remaining variable groups include any substituent discussed herein. In some embodiments, where $R_5$ is —$(CH_2)_n$—X—$R_7$, X is S, $R_7$ is alkyl ester, and the remaining variable groups include any substituent discussed herein. In some embodiments, where $R_5$ is —$(CH_2)_n$—X—$R_7$, X is S, $R_7$ is alkyl carboxylic acid, and the remaining variable groups include any substituent discussed herein. In some embodiments, where $R_5$ is —$(CH_2)_n$—X—$R_7$, X is S, $R_7$ is alkyl amide, and the remaining variable groups include any substituent discussed herein. In some embodiments, where $R_5$ is —$(CH_2)_n$—X—$R_7$, X is S, $R_7$ is cyanomethyl, and the remaining variable groups include any substituent discussed herein. In some embodiments, where $R_5$ is —$(CH_2)_n$—X—$R_7$, X is S, $R_7$ is —Y—Z—Y—$R_8$, and the remaining variable groups include any substituent discussed herein.

In some embodiments, where $R_5$ is —$(CH_2)_n$—X—$R_7$, X is a bond and the remaining variable groups include any substituent discussed herein. In some embodiments, where $R_5$ is —$(CH_2)_n$—X—$R_7$, X is a bond, $R_7$ is H, and the remaining variable groups include any substituent discussed herein. In some embodiments, where $R_5$ is —$(CH_2)_n$—X—$R_7$, X is a bond, $R_7$ is heterocycle, and the remaining variable groups include any substituent discussed herein. In some embodiments, where $R_5$ is —$(CH_2)_n$—X—$R_7$, X is a bond, $R_7$ is alkyl, and the remaining variable groups include any substituent discussed herein. In some embodiments, where $R_5$ is —$(CH_2)_n$—X—$R_7$, X is a bond, $R_7$ is haloalkyl, and the remaining variable groups include any substituent discussed herein. In some embodiments, where $R_5$ is —$(CH_2)_n$—X—$R_7$, X is a bond, $R_7$ is heteroalkyl, and the remaining variable groups include any substituent discussed herein. In some embodiments, where $R_5$ is —$(CH_2)_n$—X—$R_7$, X is a bond, $R_7$ is cycloalkyl, and the remaining variable groups include any substituent discussed herein. In some embodiments, where $R_5$ is —$(CH_2)_n$—X—$R_7$, X is a bond, $R_7$ is heterocycloalkyl, and the remaining variable groups include any substituent discussed herein. In some embodiments, where $R_5$ is —$(CH_2)_n$—X—$R_7$, X is a bond, $R_7$ is alkenyl, and the remaining variable groups include any substituent discussed herein. In some embodiments, where $R_5$ is —$(CH_2)_n$—X—$R_7$, X is a bond, $R_7$ is alkynyl, and the remaining variable groups include any substituent discussed herein. In some embodiments, where $R_5$ is —$(CH_2)_n$—X—$R_7$, X is a bond, $R_7$ is acyl, and the remaining variable groups include any substituent discussed herein. In some embodiments, where $R_5$ is —$(CH_2)_n$—X—$R_7$, X is a bond, $R_7$ is aryl, and the remaining variable groups include any substituent discussed herein. In some embodiments, where $R_5$ is —$(CH_2)_n$—X—$R_7$, X is a bond, $R_7$ is heteroaryl, and the remaining variable groups include any substituent discussed herein. In some embodiments, where $R_5$ is —$(CH_2)_n$—X—$R_7$, X is a bond, $R_7$ is alkyl ester, and the remaining variable groups include any substituent discussed herein. In some embodiments, where $R_5$ is —$(CH_2)_n$—X—$R_7$, X is a bond, $R_7$ is alkyl carboxylic acid, and the remaining variable groups include any substituent discussed herein. In some embodiments, where $R_5$ is —$(CH_2)_n$—X—$R_7$, X is a bond, $R_7$ is alkyl amide, and the remaining variable groups include any substituent discussed herein. In some embodiments, where $R_5$ is —$(CH_2)_n$—X—$R_7$, X is a bond, $R_7$ is cyanomethyl, and the remaining variable groups include any substituent discussed herein. In some embodiments, where $R_5$ is —$(CH_2)_n$—X—$R_7$, X is a bond, $R_7$ is —Y—Z—Y—$R_8$, and the remaining variable groups include any substituent discussed herein.

In some embodiments, where $R_5$ is —$(CH_2)_n$—X—$R_7$, X is a combination of one or more of O, N, S, and a bond, and the remaining variable groups include any substituent discussed herein. In some embodiments, where $R_5$ is —$(CH_2)_n$—X—$R_7$, X is a combination of one or more of O, N, S, and a bond, $R_7$ is H, and the remaining variable groups include any substituent discussed herein. In some embodiments, where $R_5$ is —$(CH_2)_n$—X—$R_7$, X is a combination of one or more of O, N, S, and a bond, $R_7$ is heterocycle, and the remaining variable groups include any substituent discussed herein. In some embodiments, where $R_5$ is —$(CH_2)_n$—X—$R_7$, X is a combination of one or more of O, N, S, and a bond, $R_7$ is alkyl, and the remaining variable groups include any substituent discussed herein. In some embodiments, where $R_5$ is —$(CH_2)_n$—X—$R_7$, X is a combination of one or more of O, N, S, and a bond, $R_7$ is haloalkyl, and the remaining variable groups include any substituent discussed herein. In some embodiments, where $R_5$ is —$(CH_2)_n$—X—$R_7$, X is a combination of one or more of O, N, S, and a bond, $R_7$ is heteroalkyl, and the remaining variable groups include any substituent discussed herein. In some embodiments, where $R_5$ is —$(CH_2)_n$—X—$R_7$, X is a combination of one or more of O, N, S, and a bond, $R_7$ is cycloalkyl, and the remaining variable groups include any substituent discussed herein. In some embodiments, where $R_5$ is —$(CH_2)_n$—X—$R_7$, X is a combination of one or more of O, N, S, and a bond, $R_7$ is heterocycloalkyl, and the remaining variable groups include any substituent discussed herein. In some embodiments, where $R_5$ is —$(CH_2)_n$—X—$R_7$, X is a combination of one or more of O, N, S, and a bond, $R_7$ is alkenyl, and the remaining variable groups include any substituent discussed herein. In some embodiments, where $R_5$ is —$(CH_2)_n$—X—$R_7$, X is a combination of one or more of O, N, S, and a bond, $R_7$ is alkynyl, and the remaining variable groups include any substituent discussed herein. In some embodiments, where $R_5$ is —$(CH_2)_n$—X—$R_7$, X is a combination of one or more of O, N, S, and a bond, $R_7$ is acyl, and the remaining variable groups include any substituent discussed herein. In some embodiments, where $R_5$ is —$(CH_2)_n$—X—$R_7$, X is a combination of one or more of O, N, S, and a bond, $R_7$ is aryl, and the remaining variable groups include any substituent discussed herein. In some embodiments, where $R_5$ is —$(CH_2)_n$—X—$R_7$, X is a combination of one or more of O, N, S, and a bond, $R_7$ is heteroaryl, and the remaining variable groups include any substituent discussed herein. In some embodiments, where $R_5$ is —$(CH_2)_n$—X—$R_7$, X is a combination of one or more of O, N, S, and a bond, $R_7$ is alkyl ester, and the remaining variable groups include any substituent discussed herein. In some embodiments, where $R_5$ is —$(CH_2)_n$—X—$R_7$, X is a combination of one or more of O, N, S, and a bond, $R_7$ is alkyl carboxylic acid, and the remaining variable groups include any substituent discussed herein. In some embodiments, where $R_5$ is —$(CH_2)_n$—X—$R_7$, X is a combination of one or more of O, N, S, and a bond, $R_7$ is alkyl amide, and the remaining variable groups include any substituent discussed herein. In some embodiments, where $R_5$ is —$(CH_2)_n$—X—$R_7$, X is a combination of one or more of O, N, S, and a bond, $R_7$ is cyanomethyl, and the remaining variable groups include any substituent discussed herein. In some embodiments, where $R_5$ is —$(CH_2)_n$—X—$R_7$, X is a combination of one or more of O, N, S, and a bond, $R_7$ is —Y—Z—Y—$R_8$, and the remaining variable groups include any substituent discussed herein.

In some embodiments, where $R_5$ is —$(CH_2)_n$—X—$R_7$ and $R_7$ is —Y—Z—Y—$R_8$, one Y is $CH_2$, the other Y is N, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is O, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is S, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is a bond, and the remaining variable groups include any substituent discussed herein. In some embodiments, where $R_5$ is —$(CH_2)_n$—X—$R_7$ and $R_7$ is —Y—Z—Y—$R_8$, both Y are $CH_2$ and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is O, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is S, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is a bond, and the remaining variable groups include any substituent discussed herein. In some embodiments, where $R_5$ is —$(CH_2)_n$—X—$R_7$ and $R_7$ is —Y—Z—Y—$R_8$, both Y are N and the remaining variable groups include any substituent discussed herein. In some embodiments, where $R_5$ is —$(CH_2)_n$—X—$R_7$ and $R_7$ is —Y—Z—Y—$R_8$, one Y is O, the other Y is S, and the remaining variable groups include any substituent discussed herein. In some embodiments, where $R_5$ is —$(CH_2)_n$—X—$R_7$ and $R_7$ is —Y—Z—Y—$R_8$, one Y is O, the other Y is a bond, and the remaining variable groups include any substituent discussed herein. In some embodiments, where $R_5$ is —$(CH_2)_n$—X—$R_7$ and $R_7$ is —Y—Z—Y—$R_8$, both Y are O and the remaining variable groups include any substituent discussed herein. In some embodiments, where $R_5$ is —$(CH_2)_n$—X—$R_7$ and $R_7$ is —Y—Z—Y—$R_8$, one Y is S, the other Y is a bond, and the remaining variable groups include any substituent discussed herein. In some embodiments, where $R_5$ is —$(CH_2)_n$—X—$R_7$ and $R_7$ is —Y—Z—Y—$R_8$, both Y are S and the remaining variable groups include any substituent discussed herein. In some embodiments, where $R_5$ is —$(CH_2)_n$—X—$R_7$ and $R_7$ is —Y—Z—Y—$R_8$, both Y are a bond and the remaining variable groups include any substituent discussed herein.

In some embodiments, where $R_5$ is —$(CH_2)_n$—X—$R_7$ and $R_7$ is —Y—Z—Y—$R_8$, Z is polyethylene glycol and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is N, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is O, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is S, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is a bond, Z is polyethylene glycol, and the remaining variable groups include any substituent discussed herein. In some embodiments, where $R_5$ is —$(CH_2)_n$—X—

$R_7$ and $R_7$ is —Y—Z—Y—$R_8$, both Y are $CH_2$, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is O, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is S, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is a bond, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, both Y are N, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, one Y is O, the other Y is S, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, one Y is O, the other Y is a bond, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, both Y are O, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, one Y is S, the other Y is a bond, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, both Y are S, Z is polyethylene glycol, and the remaining variable groups include any substituent discussed herein. In some embodiments, where $R_5$ is —$(CH_2)_n$—X—$R_7$ and $R_7$ is —Y—Z—Y—$R_8$, both Y are a bond, Z is polyethylene glycol, and the remaining variable groups include any substituent discussed herein.

In some embodiments, where $R_5$ is —$(CH_2)_n$—X—$R_7$ and $R_7$ is —Y—Z—Y—$R_8$, Z is an alkyl linker and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is N, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is O, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is S, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is a bond, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, both Y are $CH_2$, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is O, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is S, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is a bond, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, both Y are N, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, one Y is O, the other Y is S, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, one Y is O, the other Y is a bond, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, both Y are O, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, one Y is S, the other Y is a bond, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, both Y are S, Z is an alkyl linker, and the remaining variable groups include any substituent discussed herein. In some embodiments, where $R_5$ is —$(CH_2)_n$—X—$R_7$ and $R_7$ is —Y—Z—Y—$R_8$, both Y are a bond, Z is an alkyl linker, and the remaining variable groups include any substituent discussed herein.

In some embodiments, where $R_5$ is —$(CH_2)_n$—X—$R_7$ and $R_7$ is —Y—Z—Y—$R_8$, Z is an aminoalkyl linker and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is N, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is O, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is S, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, one Y is $CH_2$, the other Y is a bond, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, both Y are $CH_2$, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is O, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is S, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, one Y is N, the other Y is a bond, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, both Y are N, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, one Y is O, the other Y is S, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, one Y is O, the other Y is a bond, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, both Y are O, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, one Y is S, the other Y is a bond, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, both Y are S, Z is an aminoalkyl linker, and the remaining variable groups include any substituent discussed herein. In some embodiments, where $R_5$ is —$(CH_2)_n$—X—$R_7$ and $R_7$ is —Y—Z—Y—$R_8$, both Y are a bond, Z is aminoalkyl linker, and the remaining variable groups include any substituent discussed herein.

In some embodiments, where $R_5$ is —$(CH_2)_n$—X—$R_7$ and $R_7$ is —Y—Z—Y—$R_8$, $R_8$ is H and the remaining variable groups include any substituent discussed herein. In some embodiments, where $R_5$ is —$(CH_2)_n$—X—$R_7$ and $R_7$ is —Y—Z—Y—$R_8$, $R_8$ is a functional group for biorthogonal reactions and the remaining variable groups include any substituent discussed herein. In some embodiments, where $R_5$ is —$(CH_2)_n$—X—$R_7$ and $R_7$ is —Y—Z—Y—$R_8$, $R_8$ is biotin and the remaining variable groups include any substituent discussed herein. In some embodiments, where $R_5$ is —$(CH_2)_n$—X—$R_7$ and $R_7$ is —Y—Z—Y—$R_8$, $R_8$ is JQ1 and the remaining variable groups include any substituent discussed herein. In some embodiments, where $R_5$ is —$(CH_2)_n$—X—$R_7$ and $R_7$ is —Y—Z—Y—$R_8$, $R_8$ is E3 and the remaining variable groups include any substituent discussed herein.

In some embodiments, the modulators include a general structure according to Formula II below:

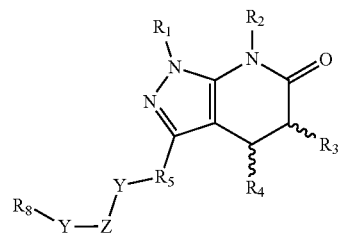

Where $R_1$, $R_2$, $R_3$, $R_4$, $R_6$, $R_8$, X, Y, Z, and n are as defined above for Formula I, and $R_5$ includes —$(CH_2)_n$—X. As will be appreciated by those skilled in the art, the general structure of Formula II corresponds to the general structure of Formula I where $R_5$ is —$(CH_2)_n$—X—$R_7$ and $R_7$ is Y—Z—Y—$R_8$.

As will also be appreciated by those skilled in the art, any group in Formula I and/or II including "n" number of repeat units will be absent when n equals 0. For example, in one embodiment, when n equals 0, the —$(CH_2)_n$—X—$R_7$ group of $R_5$ becomes —X—$R_7$. As will further be appreciated by those skilled in the art, when both X and Y are a bond, they form a single bond between Z and —$(CH_2)_n$ or, when n equals 0, the pyrazole of the general structure. As will still further be appreciated by those skilled in the art, all combinations of variable groups, whether separately disclosed or not, are individually and explicitly contemplated herein. For example, even though a specific combination of substituents at $R_1$-$R_5$ may not be separately stated, such a combination is nevertheless explicitly contemplated herein.

Examples of compounds according to Formula I include, but are not limited to, one or more of the compounds shown in TABLE 1 below.

TABLE 1

| Molecule Name | Structure | DCN1_TRFRET Mean EC50 (uM) | IUPAC Name |
|---|---|---|---|
| RG-0005655 | 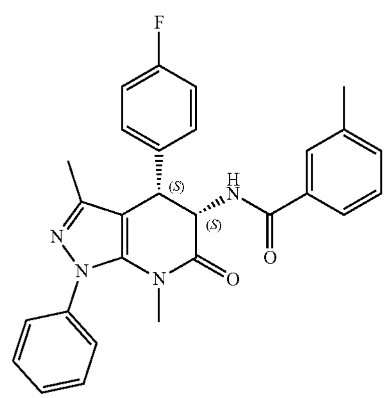 | 0.446 ± 0.0681 (n = 12) | N-[(4S,5S)-4-(4-fluorophenyl)-3,7-dimethyl-6-oxo-1-phenyl-1H,4H,5H,6H,7H-pyrazolo[3,4-b]pyridin-5-yl]-3-methylbenzamide |

TABLE 1-continued

| Molecule Name | Structure | DCN1_TRFRET Mean EC50 (uM) | IUPAC Name |
|---|---|---|---|
| RG-0005656 | 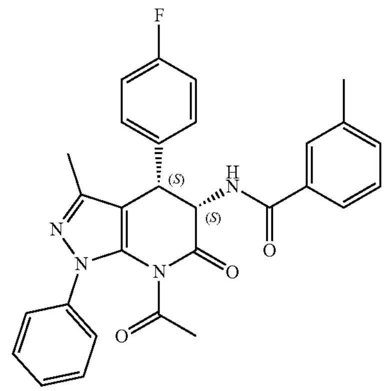 | 5.64 ± 0.827 (n = 6) | N-[(4S,5S)-7-acetyl-4-(4-fluorophenyl)-3-methyl-6-oxo-1-phenyl-1H,4H,5H,6H,7H-pyrazolo[3,4-b]pyridin-5-yl]-3-methylbenzamide |
| RG-0005665 | 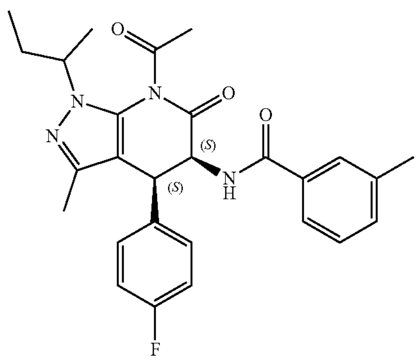 | 5.31 ± 0.85 (n = 6) | N-[(4S,5S)-7-acetyl-1-(butan-2-yl)-4-(4-fluorophenyl)-3-methyl-6-oxo-1H,4H,5H,6H,7H-pyrazolo[3,4-b]pyridin-5-yl]-3-methylbenzamide |
| RG-0007411 | 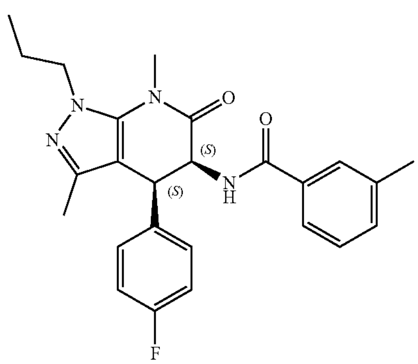 | 0.585 ± 0.106 (n = 6) | N-[(4S,5S)-4-(4-fluorophenyl)-3,7-dimethyl-6-oxo-1-propyl-1H,4H,5H,6H,7H-pyrazolo[3,4-b]pyridin-5-yl]-3-methylbenzamide |
| RG-0007412 | 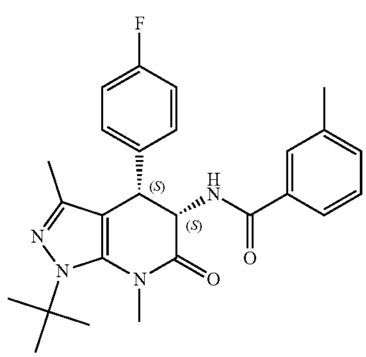 | 2.34 ± 0.745 (n = 6) | N-[(4S,5S)-1-tert-butyl-4-(4-fluorophenyl)-3,7-dimethyl-6-oxo-1H,4H,5H,6H,7H-pyrazolo[3,4-b]pyridin-5-yl]-3-methylbenzamide |

TABLE 1-continued

| Molecule Name | Structure | DCN1_TRFRET Mean EC50 (uM) | IUPAC Name |
|---|---|---|---|
| RG-0007413 | 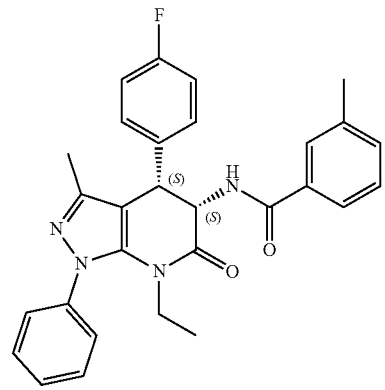 | 0.198 ± 0.0352 (n = 12) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-methylbenzamide |
| RG-0007415 | 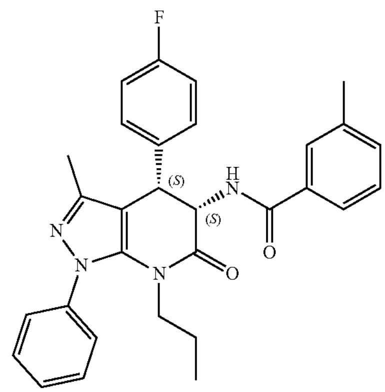 | 1.04 ± 0.204 (n = 6) | N-[(4S,5S)-4-(4-fluorophenyl)-3-methyl-6-oxo-1-phenyl-7-propyl-1H,4H,5H,6H,7H-pyrazolo[3,4-b]pyridin-5-yl]-3-methylbenzamide |
| RG-0008665 | 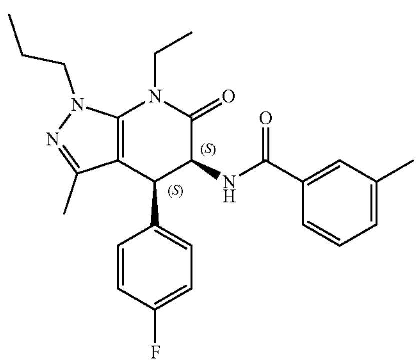 | 0.244 ± 0.0208 (n = 6) | N-[(4S,5S)-7-ethyl-4-(4-fluorophenyl)-3-methyl-6-oxo-1-propyl-1H,4H,5H,6H,7H-pyrazolo[3,4-b]pyridin-5-yl]-3-methylbenzamide |
| RG-0008666 | 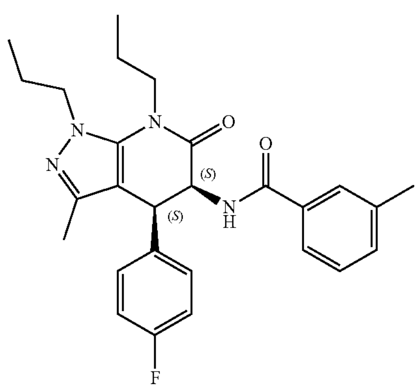 | 1.17 ± 0.0993 (n = 6) | N-[(4S,5S)-4-(4-fluorophenyl)-3-methyl-6-oxo-1,7-dipropyl-1H,4H,5H,6H,7H-pyrazolo[3,4-b]pyridin-5-yl]-3-methylbenzamide |

TABLE 1-continued

| Molecule Name | Structure | DCN1_TRFRET Mean EC50 (uM) | IUPAC Name |
|---|---|---|---|
| RG-0008670 | 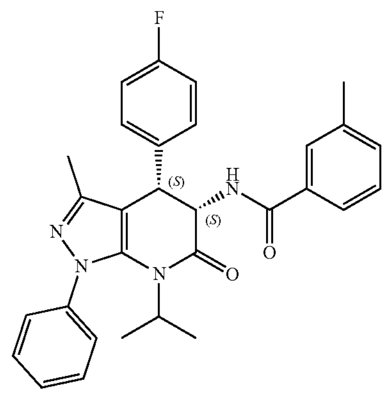 | 4.14 ± 0.765 (n = 6) | N-[(4S,5S)-4-(4-fluorophenyl)-3-methyl-6-oxo-1-phenyl-7-(propan-2-yl)-1H,4H,5H,6H,7H-pyrazolo[3,4-b]pyridin-5-yl]-3-methylbenzamide |
| RG-0008677 | 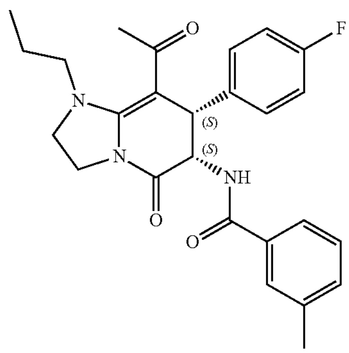 | ±5.79 (n = 1.99) | N-[(6S,7S)-8-acetyl-7-(4-fluorophenyl)-5-oxo-1-propyl-1H,2H,3H,5H,6H,7H-imidazo[1,2-a]pyridin-6-yl]-3-methylbenzamide |
| RG-0008682 | 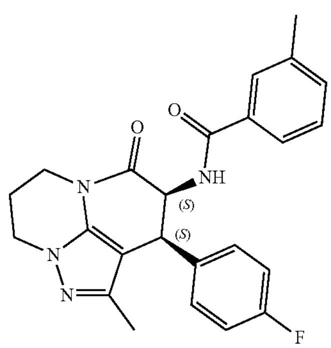 | ±12.3 (n = 2.33) | N-[(5S,6S)-5-(4-fluorophenyl)-3-methyl-7-oxo-1,2,8-triazatricyclo[6.3.1.0$^{4,12}$]dodeca-2,4(12)-dien-6-yl]-3-methylbenzamide |
| RG-0008859 | 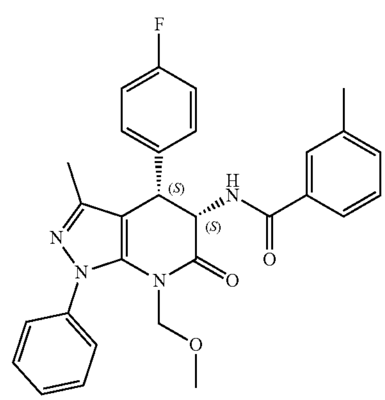 | 0.491 ± 0.0255 (n = 6) | N-[(4S,5S)-4-(4-fluorophenyl)-7-(methoxymethyl)-3-methyl-6-oxo-1-phenyl-1H,4H,5H,6H,7H-pyrazolo[3,4-b]pyridin-5-yl]-3-methylbenzamide |

TABLE 1-continued

| Molecule Name | Structure | DCN1_TRFRET Mean EC50 (uM) | IUPAC Name |
|---|---|---|---|
| RG-0008860 | 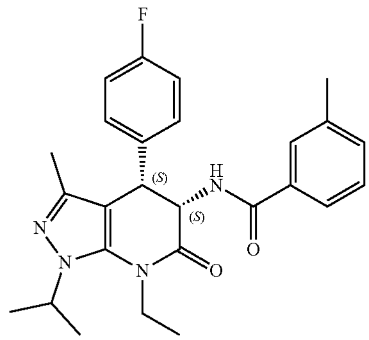 | 0.467 ± 0.028 (n = 6) | N-[(4S,5S)-7-ethyl-4-(4-fluorophenyl)-3-methyl-6-oxo-1-(propan-2-yl)-1H,4H,5H,6H,7H-pyrazolo[3,4-b]pyridin-5-yl]-3-methylbenzamide |
| RG-0008861 | 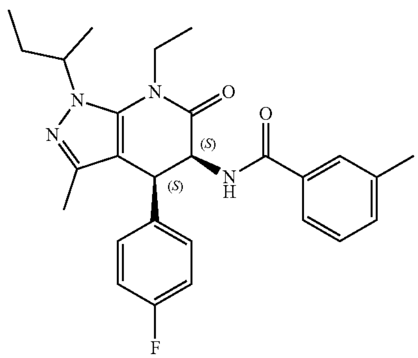 | 0.827 ± 0.371 (n = 12) | N-[(4S,5S)-1-(butan-2-yl)-7-ethyl-4-(4-fluorophenyl)-3-methyl-6-oxo-1H,4H,5H,6H,7H-pyrazolo[3,4-b]pyridin-5-yl]-3-methylbenzamide |
| RG-0008866 | 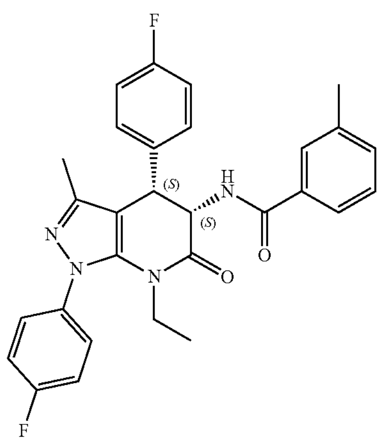 | 0.489 ± 0.0185 (n = 6) | N-[(4S,5S)-7-ethyl-1,4-bis(4-fluorophenyl)-3-methyl-6-oxo-1H,4H,5H,6H,7H-pyrazolo[3,4-b]pyridin-5-yl]-3-methylbenzamide |
| RG-0008867 | 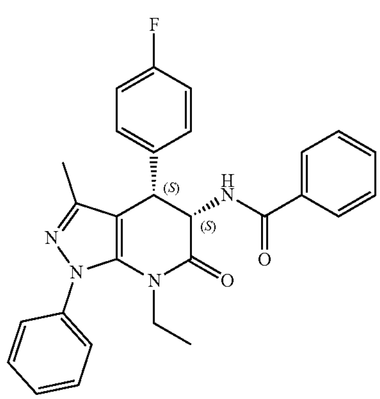 | 1.32 ± 0.083 (n = 6) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]benzamide |

TABLE 1-continued

| Molecule Name | Structure | DCN1_TRFRET Mean EC50 (uM) | IUPAC Name |
|---|---|---|---|
| RG-0008869 | 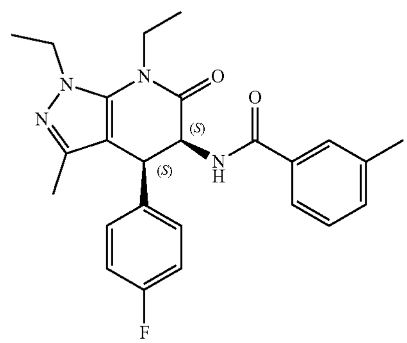 | 0.384 ± 0.0306 (n = 6) | N-[(4S,5S)-1,7-diethyl-4-(4-fluorophenyl)-3-methyl-6-oxo-1H,4H,5H,6H,7H-pyrazolo[3,4-b]pyridin-5-yl]-3-methylbenzamide |
| RG-0008870 | 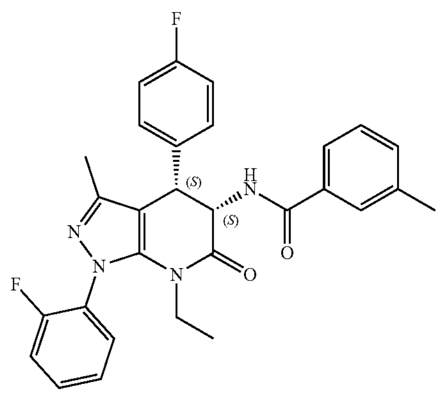 | 0.187 ± 0.00573 (n = 6) | N-[(4S,5S)-7-ethyl-1-(2-fluorophenyl)-4-(4-fluorophenyl)-3-methyl-6-oxo-1H,4H,5H,6H,7H-pyrazolo[3,4-b]pyridin-5-yl]-3-methylbenzamide |
| RG-0008871 | 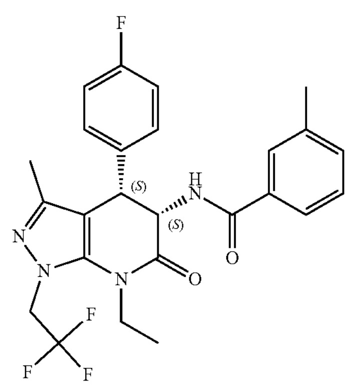 | 0.729 ± 0.0901 (n = 6) | N-[(4S,5S)-7-ethyl-4-(4-fluorophenyl)-3-methyl-6-oxo-1-(2,2,2-trifluoroethyl)-1H,4H,5H,6H,7H-pyrazolo[3,4-b]pyridin-5-yl]-3-methylbenzamide |
| RG-0008872 | 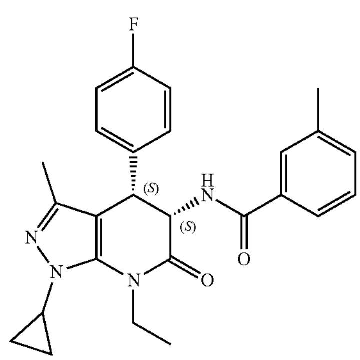 | 0.19 ± 0.0356 (n = 6) | N-[(4S,5S)-1-cyclopropyl-7-ethyl-4-(4-fluorophenyl)-3-methyl-6-oxo-1H,4H,5H,6H,7H-pyrazolo[3,4-b]pyridin-5-yl]-3-methylbenzamide |

TABLE 1-continued

| Molecule Name | Structure | DCN1_TRFRET Mean EC50 (uM) | IUPAC Name |
|---|---|---|---|
| RG-0008875 | 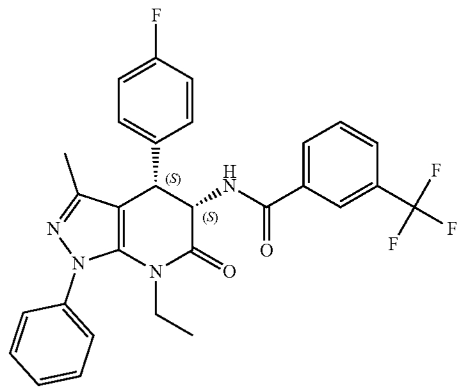 | 0.325 ± 0.0265 (n = 13) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-(trifluoromethyl)benzamide |
| RG-0008876 | 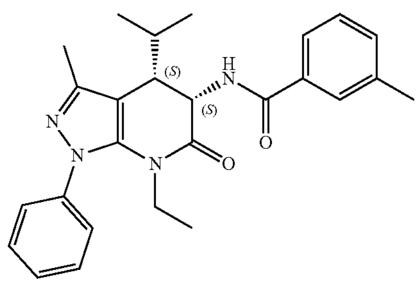 | 1.75 ± 0.165 (n = 5) | N-[(4S,5S)-7-ethyl-3-methyl-6-oxo-1-phenyl-4-(propan-2-yl)-1H,4H,5H,6H,7H-pyrazolo[3,4-b]pyridin-5-yl]-3-methylbenzamide |
| RG-0008877 | 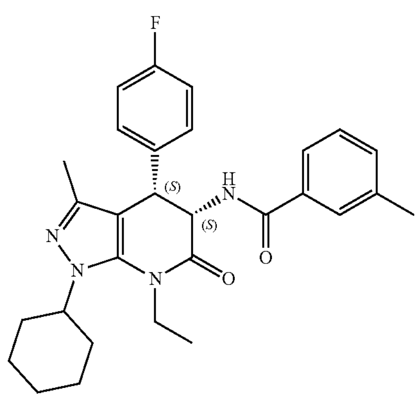 | 0.835 ± 0.0348 (n = 5) | N-[(4S,5S)-1-cyclohexyl-7-ethyl-4-(4-fluorophenyl)-3-methyl-6-oxo-1H,4H,5H,6H,7H-pyrazolo[3,4-b]pyridin-5-yl]-3-methylbenzamide |
| RG-0008878 | 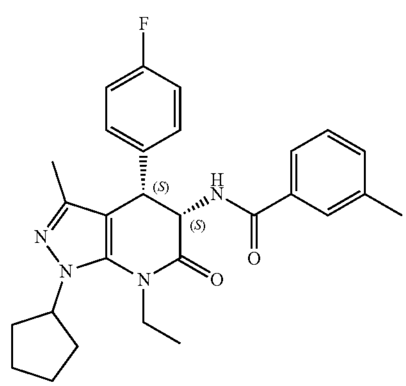 | 0.77 ± 0.0761 (n = 5) | N-[(4S,5S)-1-cyclopentyl-7-ethyl-4-(4-fluorophenyl)-3-methyl-6-oxo-1H,4H,5H,6H,7H-pyrazolo[3,4-b]pyridin-5-yl]-3-methylbenzamide |

TABLE 1-continued

| Molecule Name | Structure | DCN1_TRFRET Mean EC50 (uM) | IUPAC Name |
|---|---|---|---|
| RG-0008879 | 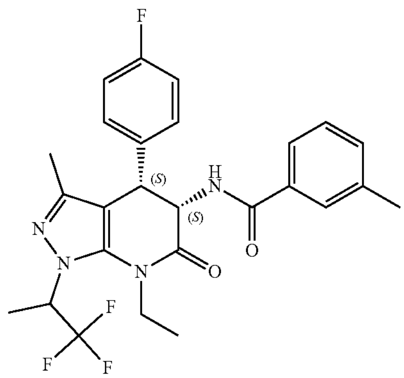 | 7.26 ± 1.09 (n = 5) | N-[(4S,5S)-7-ethyl-4-(4-fluorophenyl)-3-methyl-6-oxo-1-(1,1,1-trifluoropropan-2-yl)-1H,4H,5H,6H,7H-pyrazolo[3,4-b]pyridin-5-yl]-3-methylbenzamide |
| RG-0008880 | 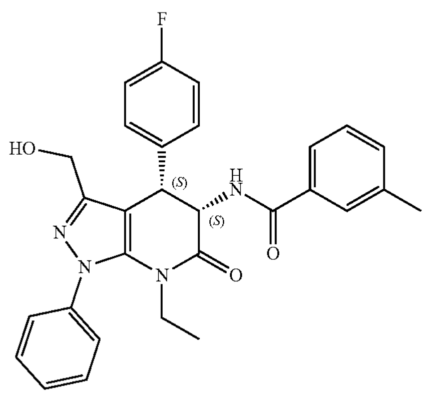 | 0.173 ± 0.0297 (n = 9) | N-[(4S,5S)-7-ethyl-4-(4-fluorophenyl)-3-(hydroxymethyl)-6-oxo-1-phenyl-1H,4H,5H,6H,7H-pyrazolo[3,4-b]pyridin-5-yl]-3-methylbenzamide |
| RG-0008885 | 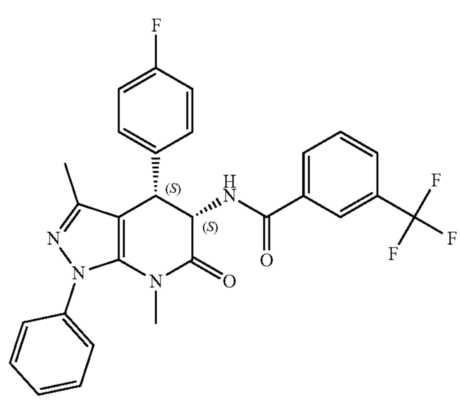 | 0.943 ± 0.0863 (n = 5) | N-[(4S,5S)-4-(4-fluorophenyl)-3,7-dimethyl-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0008886 | 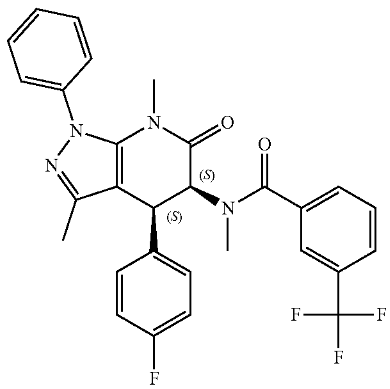 | >36.5 ± 0 (n = 5) | N-[(4S,5S)-4-(4-fluorophenyl)-3,7-dimethyl-6-oxo-1-phenyl-1H,4H,5H,6H,7H-pyrazolo[3,4-b]pyridin-5-yl]-N-methyl-3-(trifluoromethyl)benzamide |
| RG-0009505 | 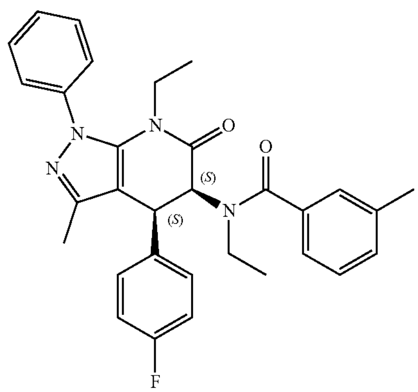 | 2.62 ± 0.404 (n = 4) | N-ethyl-N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-methylbenzamide |
| RG-0009506 | 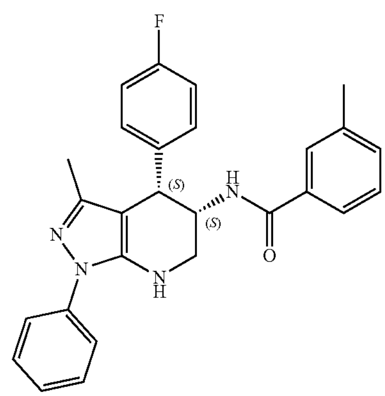 | ±>36.5 (n = 0) | N-[(4S,5S)-4-(4-fluorophenyl)-3-methyl-1-phenyl-1H,4H,5H,6H,7H-pyrazolo[3,4-b]pyridin-5-yl]-3-methylbenzamide |

TABLE 1-continued

| Molecule Name | Structure | DCN1_TRFRET Mean EC50 (uM) | IUPAC Name |
|---|---|---|---|
| RG-0009507 | 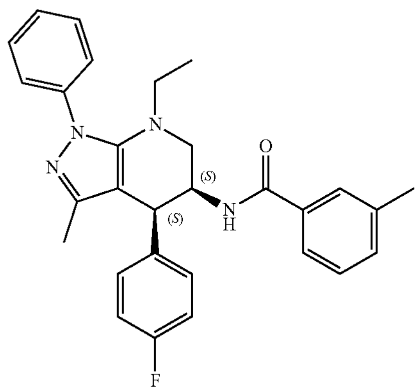 | ±>36.5 (n = 0) | N-[(4S,5S)-7-ethyl-4-(4-fluorophenyl)-3-methyl-1-phenyl-1H,4H,5H,6H,7H-pyrazolo[3,4-b]pyridin-5-yl]-3-methylbenzamide |
| RG-0009508 | 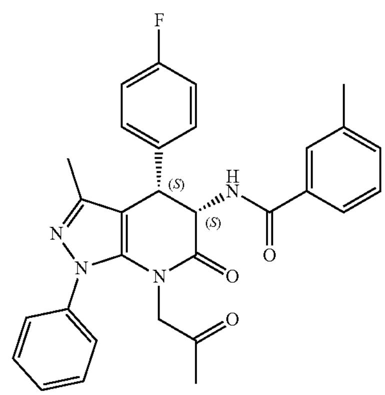 | 7.05 ± 1.67 (n = 8) | N-[(4S,5S)-4-(4-fluorophenyl)-3-methyl-6-oxo-7-(2-oxopropyl)-1-phenyl-1H,4H,5H,6H,7H-pyrazolo[3,4-b]pyridin-5-yl]-3-methylbenzamide |
| RG-0009509 | 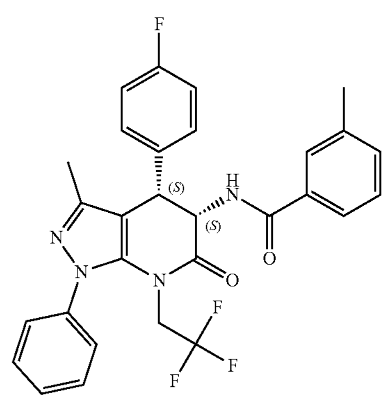 | 7 ± 1.71 (n = 8) | N-[(4S,5S)-4-(4-fluorophenyl)-3-methyl-6-oxo-1-phenyl-7-(2,2,2-trifluoroethyl)-1H,4H,5H,6H,7H-pyrazolo[3,4-b]pyridin-5-yl]-3-methylbenzamide |

TABLE 1-continued

| Molecule Name | Structure | DCN1_TRFRET Mean EC50 (uM) | IUPAC Name |
| --- | --- | --- | --- |
| RG-0009512 | 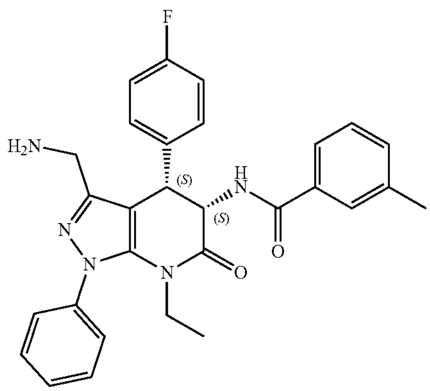 | 0.171 ± 0.0179 (n = 8) | N-[(4S,5S)-3-(aminomethyl)-7-ethyl-4-(4-fluorophenyl)-6-oxo-1-phenyl-1H,4H,5H,6H,7H-pyrazolo[3,4-b]pyridin-5-yl]-3-methylbenzamide |
| RG-0009513 | 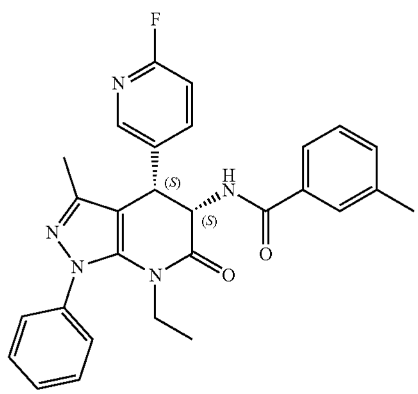 | 0.255 ± 0.0282 (n = 8) | N-[(4S,5S)-7-ethyl-4-(6-fluoropyridin-3-yl)-3-methyl-6-oxo-1-phenyl-1H,4H,5H,6H,7H-pyrazolo[3,4-b]pyridin-5-yl]-3-methylbenzamide |
| RG-0009514 | 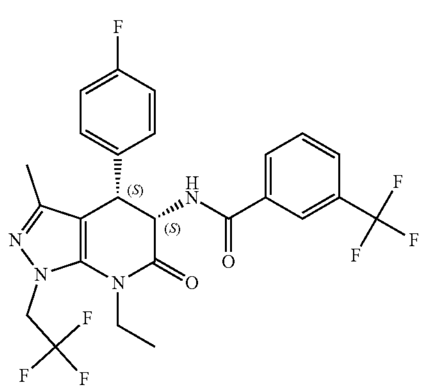 | 2.43 ± 0.253 (n = 4) | N-[(4S,5S)-7-ethyl-4-(4-fluorophenyl)-3-methyl-6-oxo-1-(2,2,2-trifluoroethyl)-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0009515 | 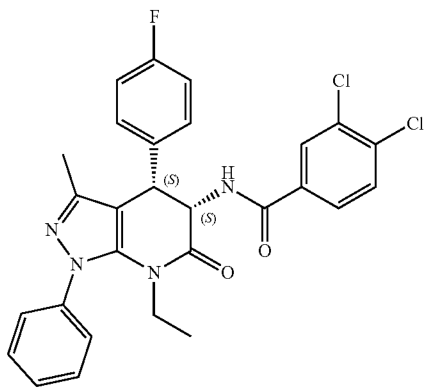 | 3.23 ± 0.371 (n = 4) | 3,4-dichloro-N-[(4S,5S)-7-ethyl-4-(4-fluorophenyl)-3-methyl-6-oxo-1-phenyl-1H,4H,5H,6H,7H-pyrazolo[3,4-b]pyridin-5-yl]benzamide |
| RG-0009516 | 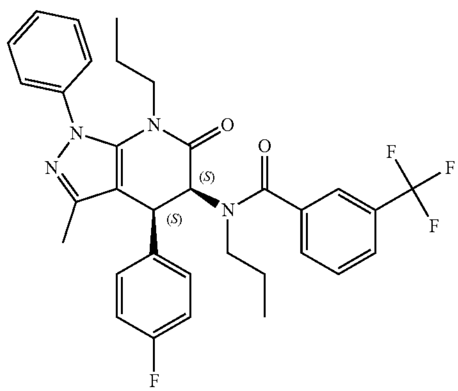 | >36.5 ± 0 (n = 4) | N-[(4S,5S)-4-(4-fluorophenyl)-3-methyl-6-oxo-1-phenyl-7-propyl-1H,4H,5H,6H,7H-pyrazolo[3,4-b]pyridin-5-yl]-N-propyl-3-(trifluoromethyl)benzamide |
| RG-0009518 | 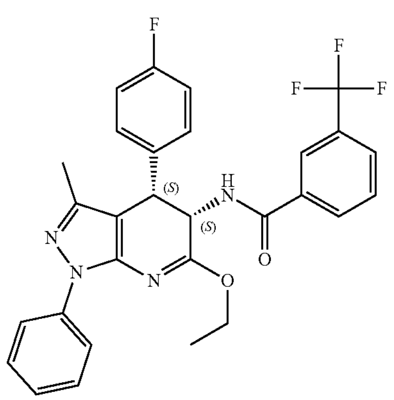 | ±>36.5 (n = 0) | N-[(4S,5S)-6-ethoxy-4-(4-fluorophenyl)-3-methyl-1-phenyl-1H,4H,5H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0013047 | 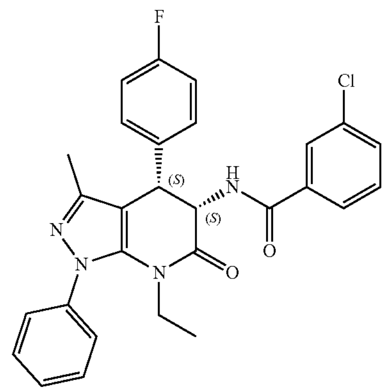 | 0.644 ± 0.0354 (n = 3) | 3-chloro-N-[(4S,5S)-7-ethyl-4-(4-fluorophenyl)-3-methyl-6-oxo-1-phenyl-1H,4H,5H,6H,7H-pyrazolo[3,4-b]pyridin-5-yl]benzamide |
| RG-0013048 | 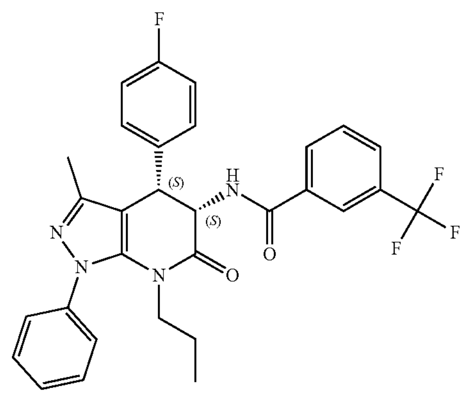 | 1.93 ± 0.0742 (n = 3) | N-[(4S,5S)-4-(4-fluorophenyl)-3-methyl-6-oxo-1-phenyl-7-propyl-1H,4H,5H,6H,7H-pyrazolo[3,4-b]pyridin-5-yl]-3-(trifluoromethyl)benzamide |
| RG-0013049 | 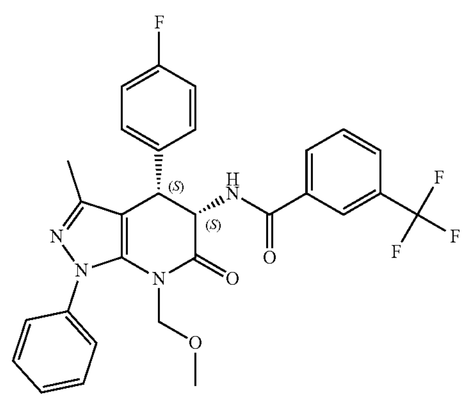 | 1.19 ± 0.113 (n = 3) | N-[(4S,5S)-4-(4-fluorophenyl)-7-(methoxymethyl)-3-methyl-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0013050 | 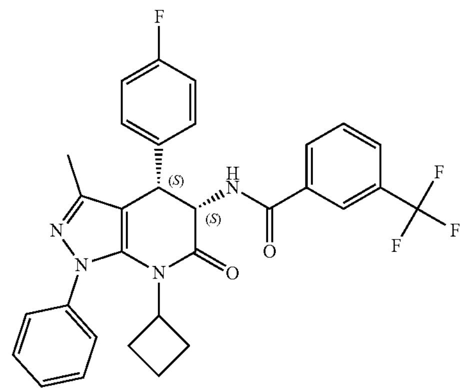 | 2.58 ± 0.247 (n = 3) | N-[(4S,5S)-7-cyclobutyl-4-(4-fluorophenyl)-3-methyl-6-oxo-1-phenyl-1H,4H,5H,6H,7H-pyrazolo[3,4-b]pyridin-5-yl]-3-(trifluoromethyl)benzamide |
| RG-0013052 | 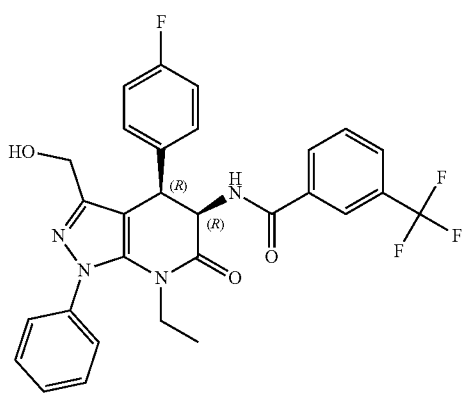 | 0.173 ± 0.00273 (n = 3) | N-[(4R,5R)-7-ethyl-4-(4-fluorophenyl)-3-(hydroxymethyl)-6-oxo-1-phenyl-1H,4H,5H,6H,7H-pyrazolo[3,4-b]pyridin-5-yl]-3-(trifluoromethyl)benzamide |
| RG-0013053 | 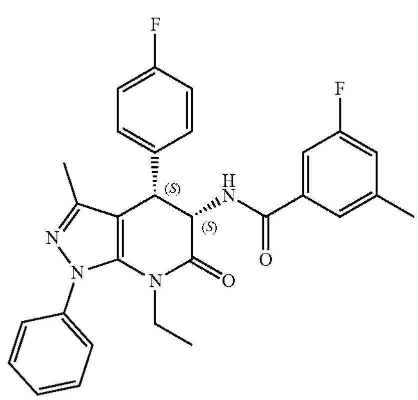 | 2.33 ± 0.105 (n = 3) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-fluoro-5-methylbenzamide |

TABLE 1-continued

| Molecule Name | Structure | DCN1_TRFRET Mean EC50 (uM) | IUPAC Name |
|---|---|---|---|
| RG-0013054 | 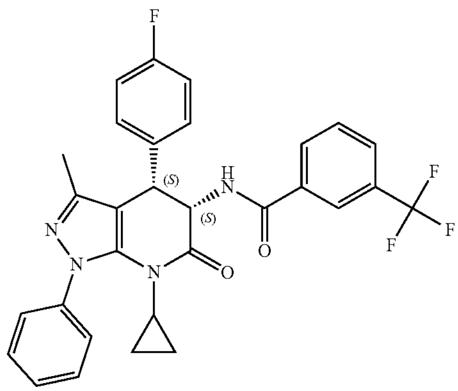 | 1.23 ± 0.112 (n = 8) | N-[(4S,5S)-7-cyclopropyl-4-(4-fluorophenyl)-3-methyl-6-oxo-1-phenyl-1H,4H,5H,6H,7H-pyrazolo[3,4-b]pyridin-5-yl]-3-(trifluoromethyl)benzamide |
| RG-0013055 | 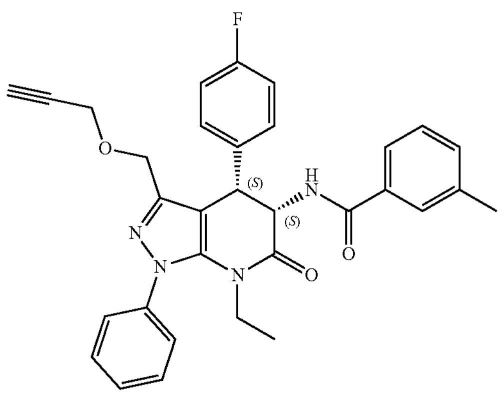 | 0.168 ± 0.0081 (n = 8) | N-[(4S,5S)-7-ethyl-4-(4-fluorophenyl)-6-oxo-1-phenyl-3-[(prop-2-yn-1-yloxy)methyl]-1H,4H,5H,6H,7H-pyrazolo[3,4-b]pyridin-5-yl]-3-methylbenzamide |
| RG-0013056 | 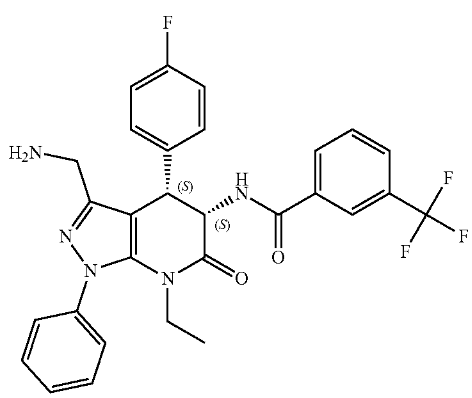 | 0.103 ± 0.0278 (n = 25) | N-[(4S,5S)-3-(aminomethyl)-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0013060 | 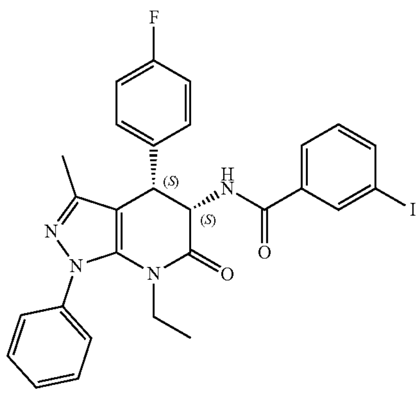 | 0.461 ± 0.0294 (n = 8) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-iodobenzamide |
| RG-0013061 | 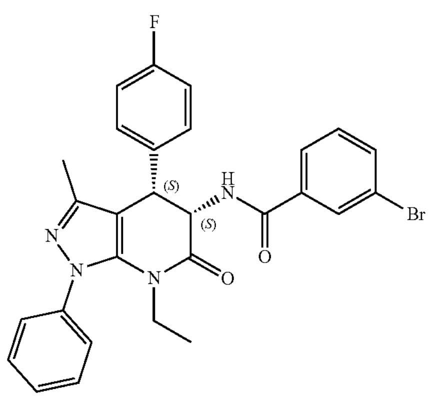 | 0.485 ± 0.0411 (n = 8) | 3-bromo-N-[(4S,5S)-7-ethyl-4-(4-fluorophenyl)-3-methyl-6-oxo-1-phenyl-1H,4H,5H,6H,7H-pyrazolo[3,4-b]pyridin-5-yl]benzamide |
| RG-0013062 | 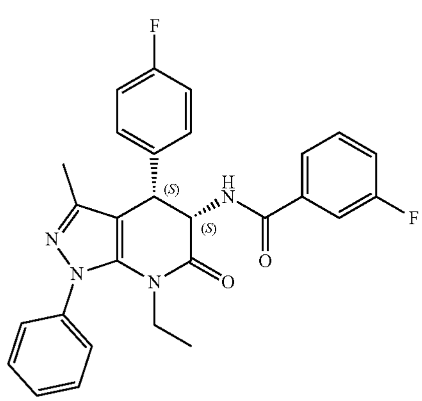 | 1.81 ± 0.153 (n = 3) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-fluorobenzamide |

TABLE 1-continued

| Molecule Name | Structure | DCN1_TRFRET Mean EC50 (uM) | IUPAC Name |
|---|---|---|---|
| RG-0013063 | 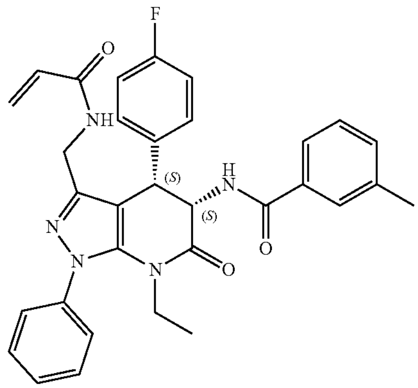 | 0.0968 ± 0.00721 (n = 3) | N-[(4S,5S)-7-ethyl-4-(4-fluorophenyl)-6-oxo-1-phenyl-3-[(prop-2-enamido)methyl]-1H,4H,5H,6H,7H-pyrazolo[3,4-b]pyridin-5-yl]-3-methylbenzamide |
| RG-0013806 | 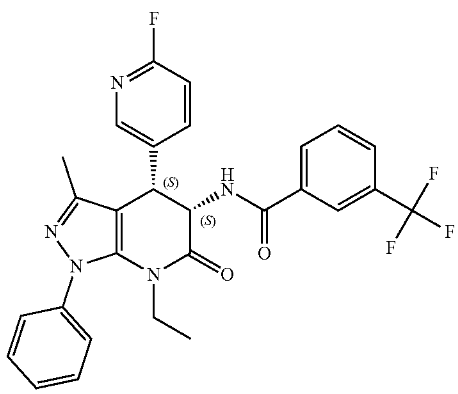 | 0.237 ± 0.0324 (n = 5) | N-[(4S,5S)-7-ethyl-4-(6-fluoropyridin-3-yl)-3-methyl-6-oxo-1-phenyl-1H,4H,5H,6H,7H-pyrazolo[3,4-b]pyridin-5-yl]-3-(trifluoromethyl)benzamide |
| RG-0013807 | 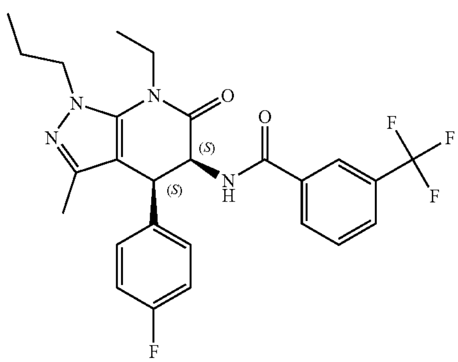 | 0.538 ± 0.0504 (n = 5) | N-[(4S,5S)-7-ethyl-4-(4-fluorophenyl)-3-methyl-6-oxo-1-propyl-1H,4H,5H,6H,7H-pyrazolo[3,4-b]pyridin-5-yl]-3-(trifluoromethyl)benzamide |
| RG-0013808 | 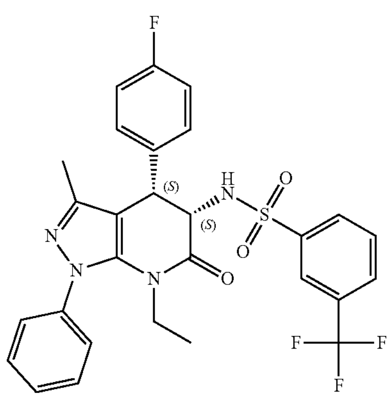 | >36.5 ± 0 (n = 5) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-(trifluoromethyl)benzene-1-sulfonamide |

TABLE 1-continued

| Molecule Name | Structure | DCN1_TRFRET Mean EC50 (uM) | IUPAC Name |
|---|---|---|---|
| RG-0013809 | 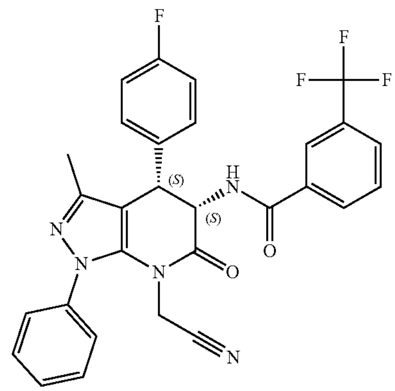 | >28.2 ± 8.08 (n = 5) | N-[(4S,5S)-7-(cyanomethyl)-4-(4-fluorophenyl)-3-methyl-6-oxo-1-phenyl-1H,4H,5H,6H,7H-pyrazolo[3,4-b]pyridin-5-yl]-3-(trifluoromethyl)benzamide |
| RG-0013837 | 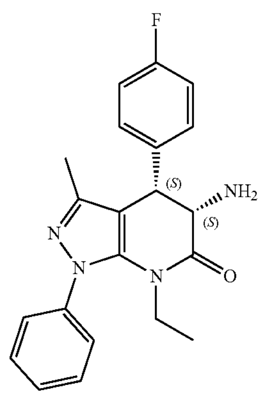 | >36.5 ± 0 (n = 4) | (4S,5S)-5-amino-7-ethyl-4-(4-fluorophenyl)-3-methyl-1-phenyl-1H,4H,5H,6H,7H-pyrazolo[3,4-b]pyridin-6-one |
| RG-0013838 | 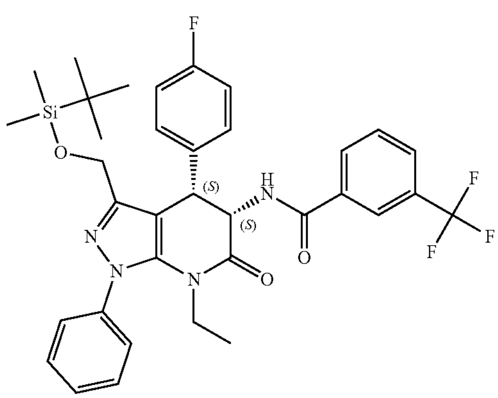 | 4.13 ± 0.316 (n = 4) | N-[(4S,5S)-3-{[(tert-butyldimethylsilyl)oxy]methyl}-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0013839 | 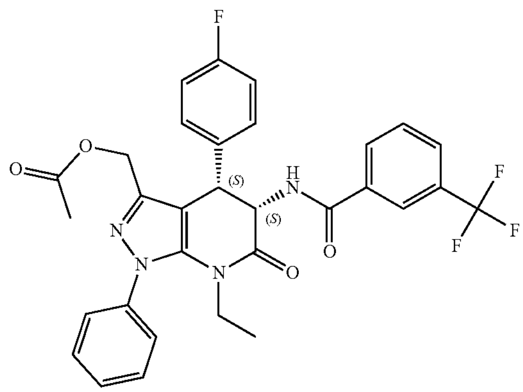 | 0.116 ± 0.0132 (n = 4) | [(4S,5S)-7-ethyl-4-(4-fluorophenyl)-6-oxo-1-phenyl-5-[3-(trifluoromethyl)benzamido]-1H,4H,5H,6H,7H-pyrazolo[3,4-b]pyridin-3-yl]methyl acetate |
| RG-0013840 | 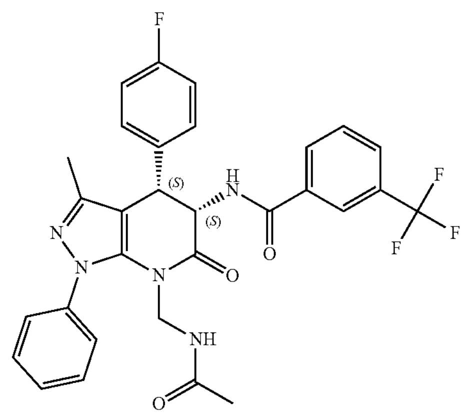 | >36.5 ± 0 (n = 4) | N-[(4S,5S)-7-(acetamidomethyl)-4-(4-fluorophenyl)-3-methyl-6-oxo-1-phenyl-1H,4H,5H,6H,7H-pyrazolo[3,4-b]pyridin-5-yl]-3-(trifluoromethyl)benzamide |
| RG-0013841 | 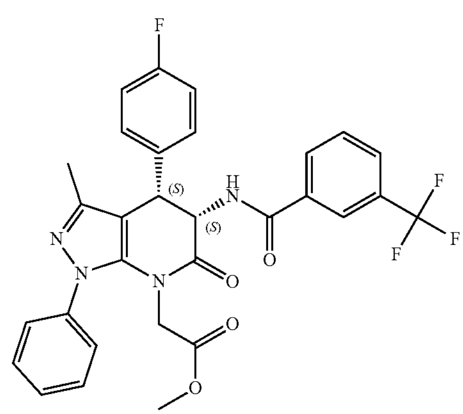 | 5.54 ± 1.08 (n = 4) | methyl 2-[(4S,5S)-4-(4-fluorophenyl)-3-methyl-6-oxo-1-phenyl-5-[3-(trifluoromethyl)benzamido]-1H,4H,5H,6H,7H-pyrazolo[3,4-b]pyridin-7-yl]acetate |

TABLE 1-continued

| Molecule Name | Structure | DCN1_TRFRET Mean EC50 (uM) | IUPAC Name |
|---|---|---|---|
| RG-0013842 | 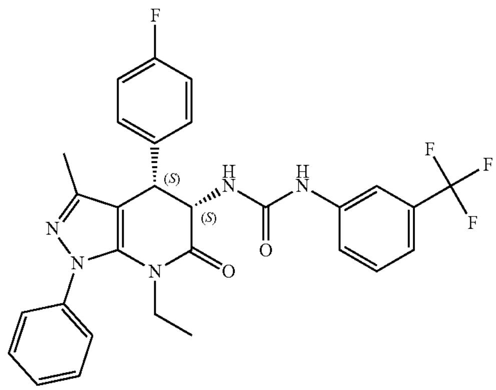 | >36.5 ± 0 (n = 4) | 3-[(4S,5S)-7-ethyl-4-(4-fluorophenyl)-3-methyl-6-oxo-1-phenyl-1H,4H,5H,6H,7H-pyrazolo[3,4-b]pyridin-5-yl]-1-[3-(trifluoromethyl)phenyl]urea |
| RG-0013843 | (A) | 0.0969 ± 0.0125 (n = 4) | N-[(4S,5S)-3-(aminomethyl)-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |
| RG-0013844 | 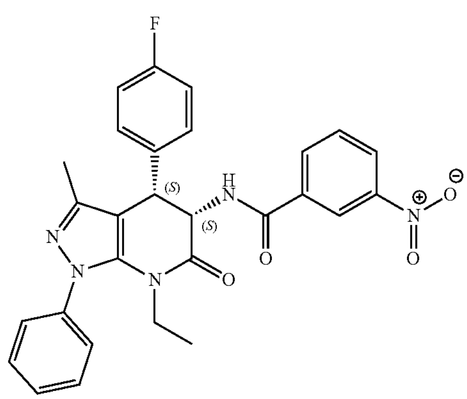 | 1.98 ± 0.134 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-nitrobenzamide |

TABLE 1-continued

| Molecule Name | Structure | DCN1_TRFRET Mean EC50 (uM) | IUPAC Name |
|---|---|---|---|
| RG-0013845 | 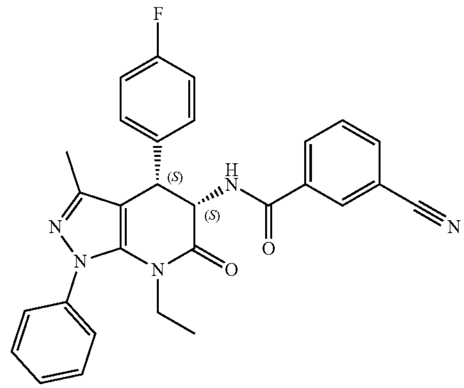 | 2.17 ± 0.244 (n = 4) | 3-cyano-N-[(4S,5S)-7-ethyl-4-(4-fluorophenyl)-3-methyl-6-oxo-1-phenyl-1H,4H,5H,6H,7H-pyrazolo[3,4-b]pyridin-5-yl]benzamide |
| RG-0013847 | 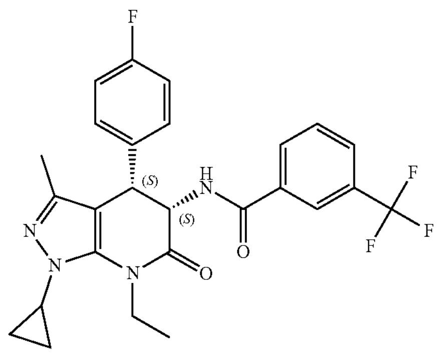 | 0.506 ± 0.0696 (n = 4) | N-[(4S,5S)-1-cyclopropyl-7-ethyl-4-(4-fluorophenyl)-3-methyl-6-oxo-1H,4H,5H,6H,7H-pyrazolo[3,4-b]pyridin-5-yl]-3-(trifluoromethyl)benzamide |
| RG-0013848 | 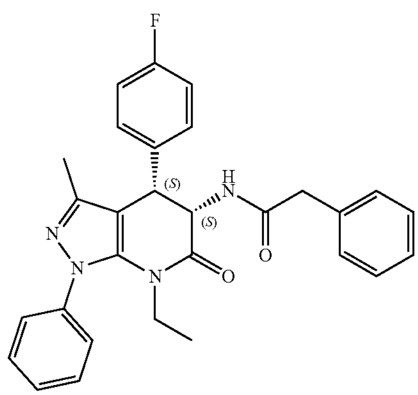 | >36.5 ± 0 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-2-phenylacetamide |
| RG-0013976 | 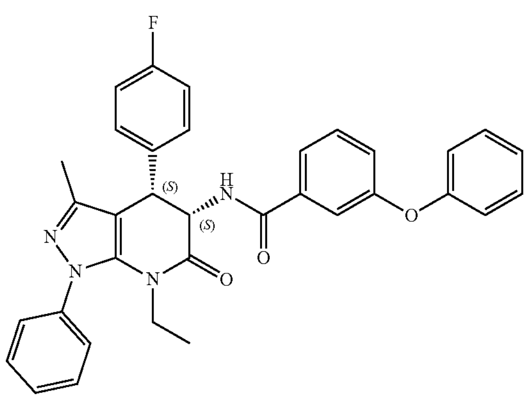 | 5.93 ± 0.606 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-phenoxybenzamide |

TABLE 1-continued

| Molecule Name | Structure | DCN1_TRFRET Mean EC50 (uM) | IUPAC Name |
|---|---|---|---|
| RG-0013977 | 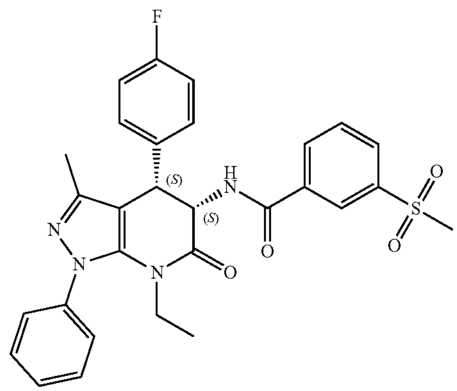 | >36.5 ± 0 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-methanesulfonylbenzamide |
| RG-0013978 | 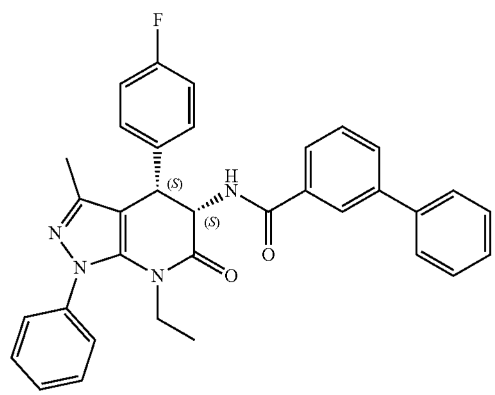 | 1.31 ± 0.0973 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-[1,1'-biphenyl]-3-carboxamide |
| RG-0013979 | 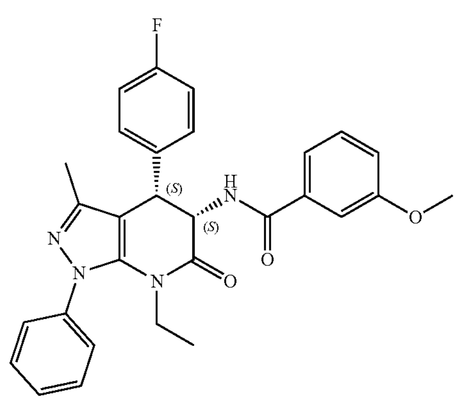 | 0.629 ± 0.0648 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-methoxybenzamide |

TABLE 1-continued

| Molecule Name | Structure | DCN1_TRFRET Mean EC50 (uM) | IUPAC Name |
|---|---|---|---|
| RG-0013980 | 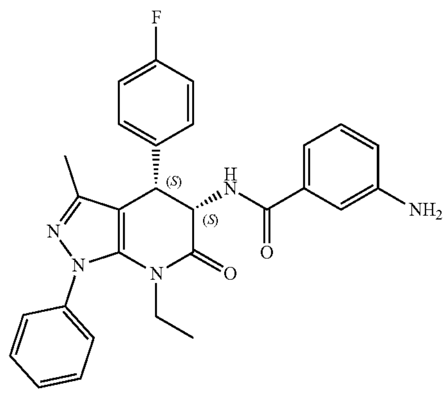 | 4.32 ± 0.288 (n = 4) | 3-amino-N-[(4S,5S)-7-ethyl-4-(4-fluorophenyl)-3-methyl-6-oxo-1-phenyl-1H,4H,5H,6H,7H-pyrazolo[3,4-b]pyridin-5-yl]benzamide |
| RG-0013981 | 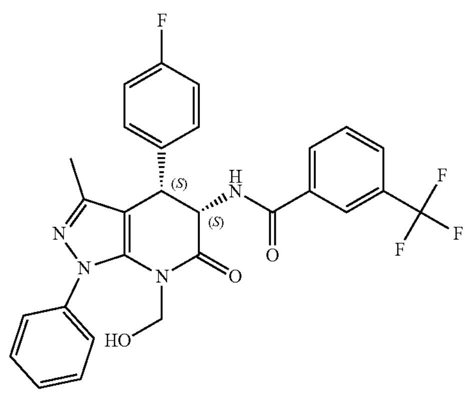 | >36.5 ± 0 (n = 4) | N-[(4S,5S)-4-(4-fluorophenyl)-7-(hydroxymethyl)-3-methyl-6-oxo-1-phenyl-1H,4H,5H,6H,7H-pyrazolo[3,4-b]pyridin-5-yl]-3-(trifluoromethyl)benzamide |
| RG-0013985 | 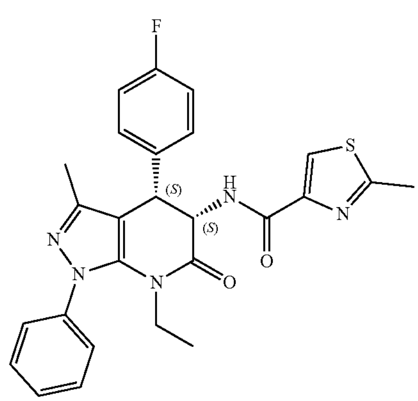 | 0.517 ± 0.0807 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-2-methyl-1,3-thiazole-4-carboxamide |

TABLE 1-continued

| Molecule Name | Structure | DCN1_TRFRET Mean EC50 (uM) | IUPAC Name |
|---|---|---|---|
| RG-0013986 | 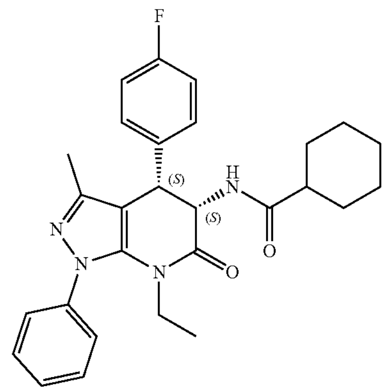 | >36.5 ± 0 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]cyclohexanecarboxamide |
| RG-0013987 | 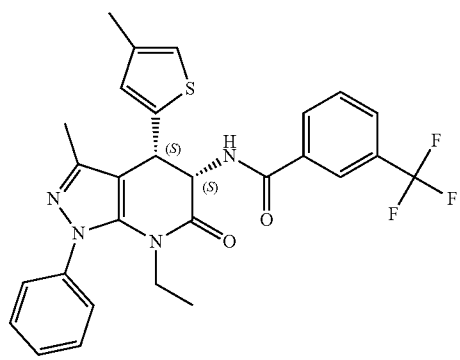 | 3.1 ± 0.559 (n = 4) | N-[(4S,5S)-7-ethyl-3-methyl-4-(4-methylthiophen-2-yl)-6-oxo-1-phenyl-1H,4H,5H,6H,7H-pyrazolo[3,4-b]pyridin-5-yl]-3-(trifluoromethyl)benzamide |
| RG-0013988 | 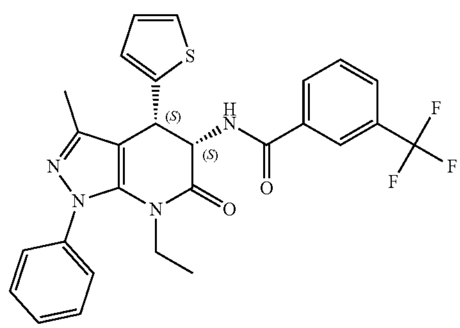 | 1.33 ± 0.0507 (n = 4) | N-[(4S,5S)-7-ethyl-3-methyl-6-oxo-1-phenyl-4-(thiophen-2-yl)-1H,4H,5H,6H,7H-pyrazolo[3,4-b]pyridin-5-yl]-3-(trifluoromethyl)benzamide |
| RG-0013990 | 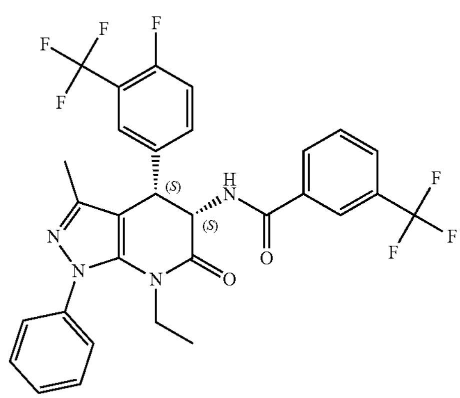 | 4.81 ± 0.152 (n = 4) | N-[(4S,5S)-7-ethyl-4-[4-fluoro-3-(trifluoromethyl)phenyl]-3-methyl-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0013991 | 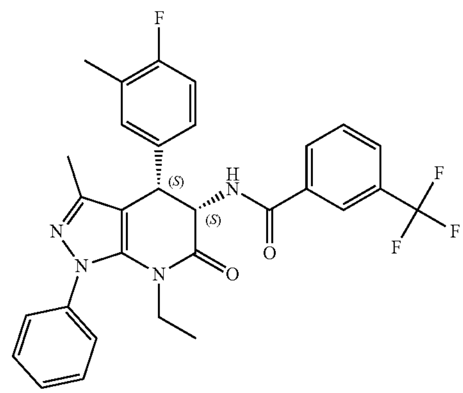 | 1.27 ± 0.0967 (n = 4) | N-[(4S,5S)-7-ethyl-4-(4-fluoro-3-methylphenyl)-3-methyl-6-oxo-1-phenyl-1H,4H,5H,6H,7H-pyrazolo[3,4-b]pyridin-5-yl]-3-(trifluoromethyl)benzamide |
| RG-0013992 | 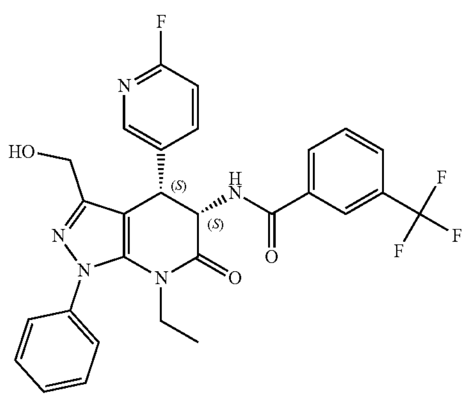 | 0.157 ± 0.0192 (n = 4) | N-[(4S,5S)-7-ethyl-4-(6-fluoropyridin-3-yl)-3-(hydroxymethyl)-6-oxo-1-phenyl-1H,4H,5H,6H,7H-pyrazolo[3,4-b]pyridin-5-yl]-3-(trifluoromethyl)benzamide |
| RG-0013995 | 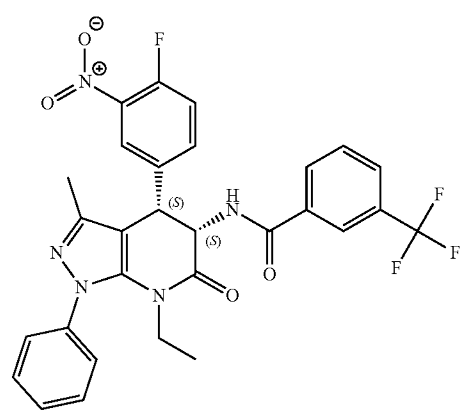 | 0.308 ± 0.0649 (n = 4) | N-[(4S,5S)-7-ethyl-4-(4-fluoro-3-nitrophenyl)-3-methyl-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0013996 | 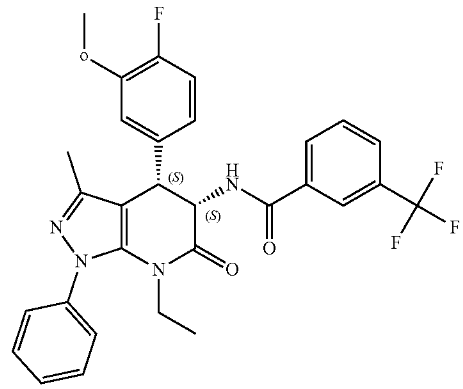 | 1.27 ± 0.047 (n = 4) | N-[(4S,5S)-7-ethyl-4-(4-fluoro-3-methoxyphenyl)-3-methyl-6-oxo-1-phenyl-1H,4H,5H,6H,7H-pyrazolo[3,4-b]pyridin-5-yl]-3-(trifluoromethyl)benzamide |
| RG-0013997 | 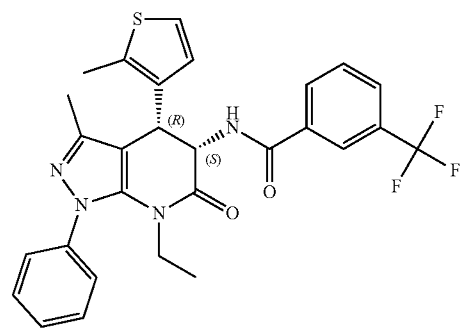 | 0.547 ± 0.0249 (n = 4) | N-[(4R,5S)-7-ethyl-3-methyl-4-(2-methylthiophen-3-yl)-6-oxo-1-phenyl-1H,4H,5H,6H,7H-pyrazolo[3,4-b]pyridin-5-yl]-3-(trifluoromethyl)benzamide |
| RG-0014000 | 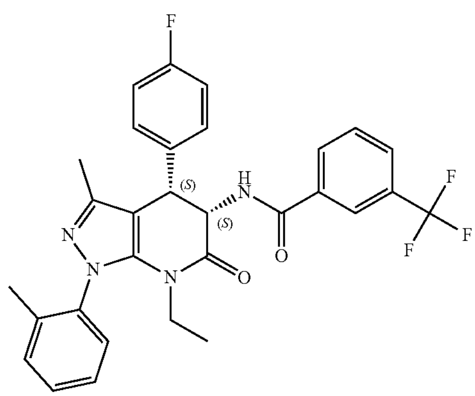 | 0.511 ± 0.0257 (n = 4) | N-[(4S,5S)-7-ethyl-4-(4-fluorophenyl)-3-methyl-1-(2-methylphenyl)-6-oxo-1H,4H,5H,6H,7H-pyrazolo[3,4-b]pyridin-5-yl]-3-(trifluoromethyl)benzamide |
| RG-0014001 | 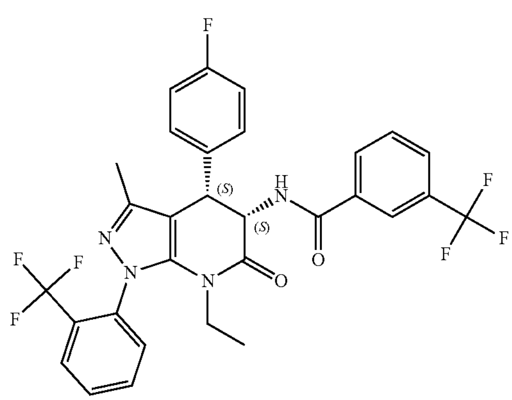 | 1.92 ± 0.131 (n = 4) | N-[(4S,5S)-7-ethyl-4-(4-fluorophenyl)-3-methyl-6-oxo-1-[2-(trifluoromethyl)phenyl]-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0014004 | 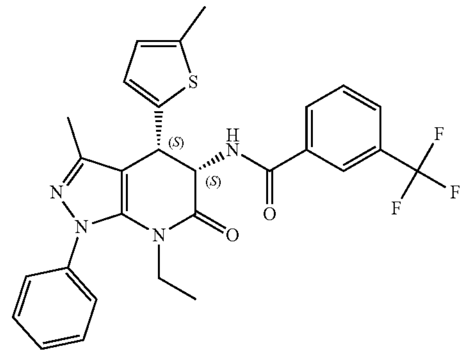 | 1.41 ± 0.0159 (n = 4) | N-[(4S,5S)-7-ethyl-3-methyl-4-(5-methylthiophen-2-yl)-6-oxo-1-phenyl-1H,4H,5H,6H,7H-pyrazolo[3,4-b]pyridin-5-yl]-3-(trifluoromethyl)benzamide |
| RG-0014005 | 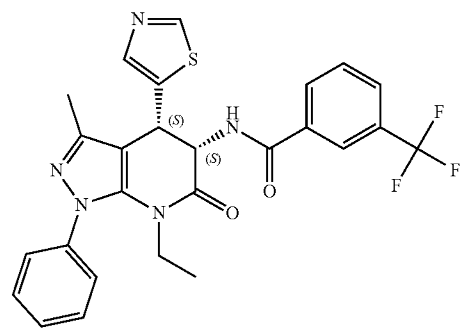 | 1.92 ± 0.0752 (n = 4) | N-[(4S,5S)-7-ethyl-3-methyl-6-oxo-1-phenyl-4-(1,3-thiazol-5-yl)-1H,4H,5H,6H,7H-pyrazolo[3,4-b]pyridin-5-yl]-3-(trifluoromethyl)benzamide |
| RG-0014006 | 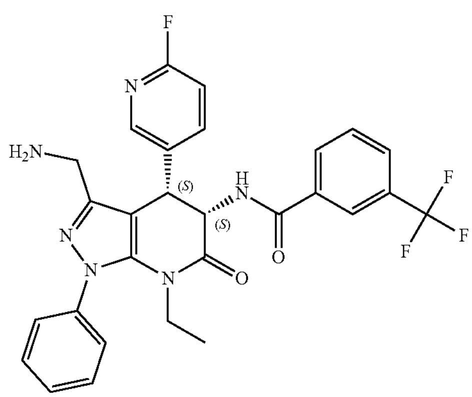 | 0.135 ± 0.007 (n = 4) | N-[(4S,5S)-3-(aminomethyl)-7-ethyl-4-(6-fluoropyridin-3-yl)-6-oxo-1-phenyl-1H,4H,5H,6H,7H-pyrazolo[3,4-b]pyridin-5-yl]-3-(trifluoromethyl)benzamide |
| RG-0014007 | 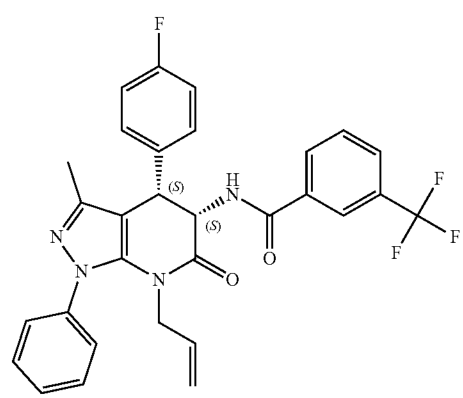 | 1.55 ± 0.157 (n = 4) | N-[(4S,5S)-4-(4-fluorophenyl)-3-methyl-6-oxo-1-phenyl-7-(prop-2-en-1-yl)-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0014035 | 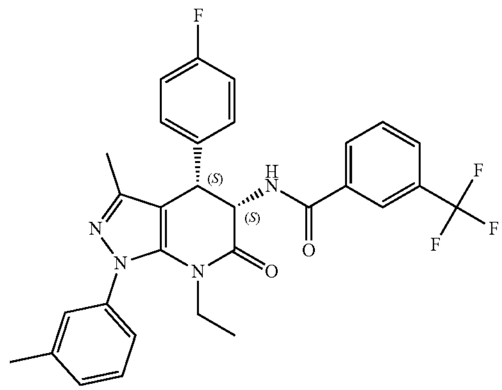 | 0.388 ± 0.0385 (n = 3) | N-[(4S,5S)-7-ethyl-4-(4-fluorophenyl)-3-methyl-1-(3-methylphenyl)-6-oxo-1H,4H,5H,6H,7H-pyrazolo[3,4-b]pyridin-5-yl]-3-(trifluoromethyl)benzamide |
| RG-0014036 | 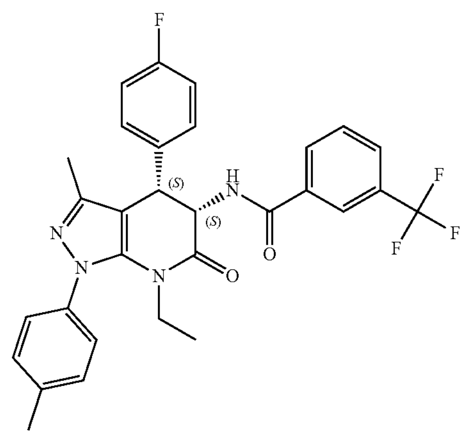 | 3.21 ± 0.156 (n = 3) | N-[(4S,5S)-7-ethyl-4-(4-fluorophenyl)-3-methyl-1-(4-methylphenyl)-6-oxo-1H,4H,5H,6H,7H-pyrazolo[3,4-b]pyridin-5-yl]-3-(trifluoromethyl)benzamide |
| RG-0014038 | 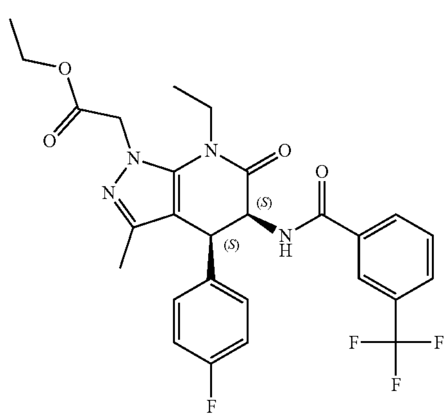 | 3.53 ± 0.458 (n = 3) | ethyl 2-[(4S,5S)-7-ethyl-4-(4-fluorophenyl)-3-methyl-6-oxo-5-[3-(trifluoromethyl)benzamido]-1H,4H,5H,6H,7H-pyrazolo[3,4-b]pyridin-1-yl]acetate |

TABLE 1-continued

| Molecule Name | Structure | DCN1_TRFRET Mean EC50 (uM) | IUPAC Name |
|---|---|---|---|
| RG-0014039 | 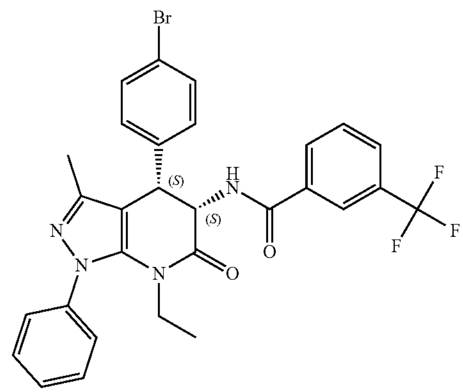 | 0.964 ± 0.0606 (n = 3) | N-[(4S,5S)-4-(4-bromophenyl)-7-ethyl-3-methyl-6-oxo-1-phenyl-1H,4H,5H,6H,7H-pyrazolo[3,4-b]pyridin-5-yl]-3-(trifluoromethyl)benzamide |
| RG-0014042 | 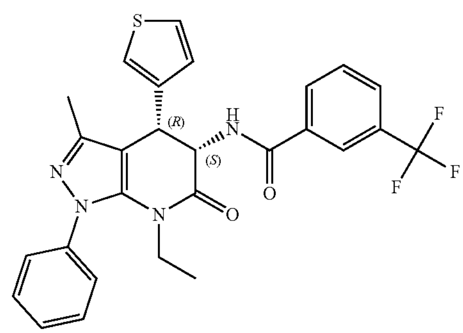 | 0.703 ± 0.0236 (n = 3) | N-[(4R,5S)-7-ethyl-3-methyl-6-oxo-1-phenyl-4-(thiophen-3-yl)-1H,4H,5H,6H,7H-pyrazolo[3,4-b]pyridin-5-yl]-3-(trifluoromethyl)benzamide |
| RG-0014043 | 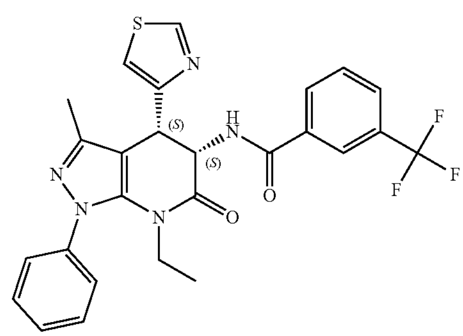 | 1.98 ± 0.0201 (n = 3) | N-[(4S,5S)-7-ethyl-3-methyl-6-oxo-1-phenyl-4-(1,3-thiazol-4-yl)-1H,4H,5H,6H,7H-pyrazolo[3,4-b]pyridin-5-yl]-3-(trifluoromethyl)benzamide |
| RG-0014044 | 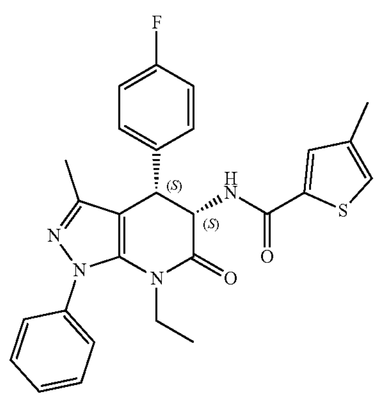 | 0.785 ± 0.0796 (n = 3) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-4-methylthiophene-2-carboxamide |

TABLE 1-continued

| Molecule Name | Structure | DCN1_TRFRET Mean EC50 (uM) | IUPAC Name |
|---|---|---|---|
| RG-0014047 | 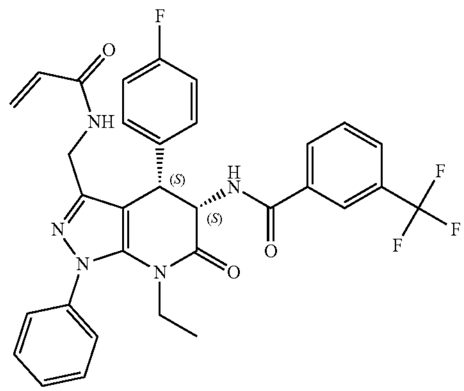 | 0.0953 ± 0.00467 (n = 3) | N-[(4S,5S)-7-ethyl-4-(4-fluorophenyl)-6-oxo-1-phenyl-3-[(prop-2-enamido)methyl]-1H,4H,5H,6H,7H-pyrazolo[3,4-b]pyridin-5-yl]-3-(trifluoromethyl)benzamide |
| RG-0014048 | 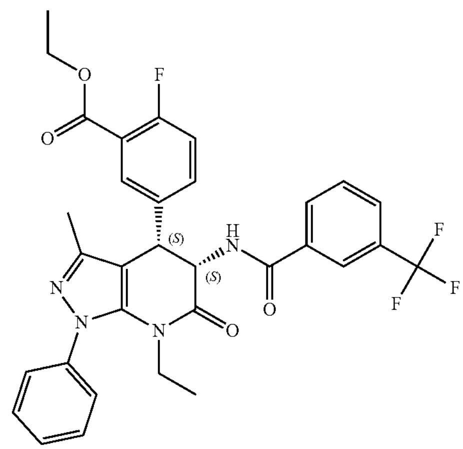 | >36.5 ± 0 (n = 3) | ethyl 5-[(4S,5S)-7-ethyl-3-methyl-6-oxo-1-phenyl-5-[3-(trifluoromethyl)benzamido]-1H,4H,5H,6H,7H-pyrazolo[3,4-b]pyridin-4-yl]-2-fluorobenzoate |
| RG-0014050 | 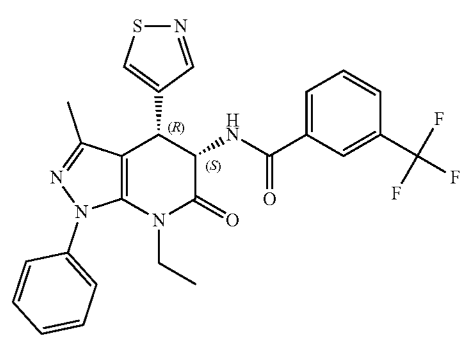 | 0.401 ± 0.0156 (n = 3) | N-[(4R,5S)-7-ethyl-3-methyl-6-oxo-1-phenyl-4-(1,2-thiazol-4-yl)-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0014051 | 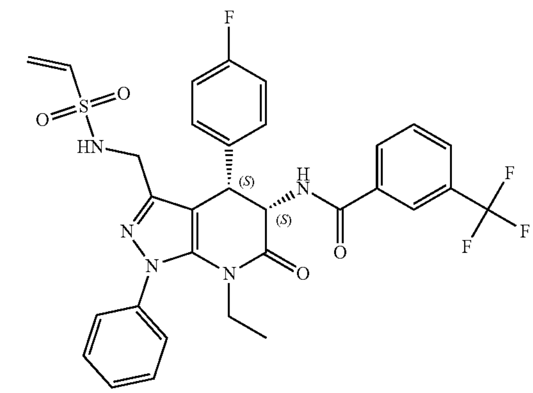 | 0.0715 ± 0.00443 (n = 3) | N-[(4S,5S)-3-(ethenesulfonamidomethyl)-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |
| RG-0014052 | 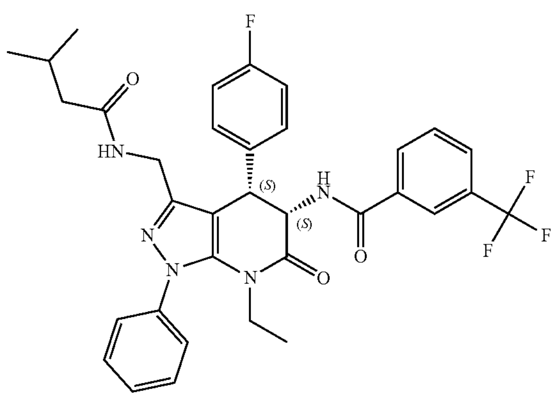 | 0.114 ± 0.00867 (n = 3) | N-[(4S,5S)-7-ethyl-4-(4-fluorophenyl)-3-[(3-methylbutanamido)methyl]-6-oxo-1-phenyl-1H,4H,5H,6H,7H-pyrazolo[3,4-b]pyridin-5-yl]-3-(trifluoromethyl)benzamide |
| RG-0014053 | 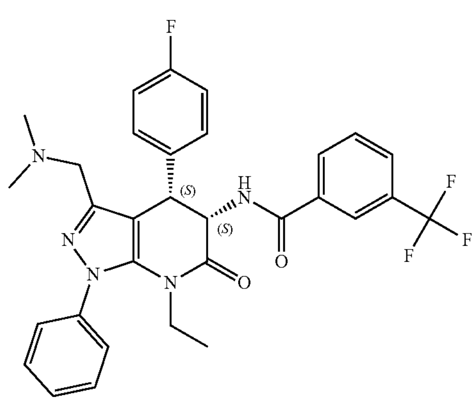 | 0.0907 ± 0.00438 (n = 3) | N-[(4S,5S)-3-[(dimethylamino)methyl]-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0014054 | 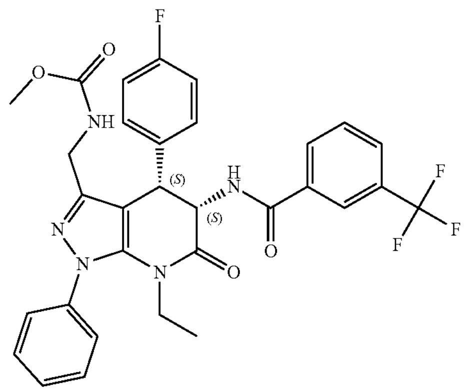 | 0.114 ± 0.00473 (n = 3) | methyl N-{[(4S,5S)-7-ethyl-4-(4-fluorophenyl)-6-oxo-1-phenyl-5-[3-(trifluoromethyl)benzamido]-1H,4H,5H,6H,7H-pyrazolo[3,4-b]pyridin-3-yl]methyl}carbamate |
| RG-0014055 | 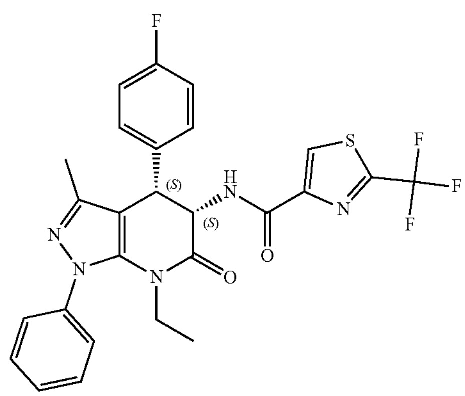 | 0.685 ± 0.108 (n = 3) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-2-(trifluoromethyl)-1,3-thiazole-4-carboxamide |
| RG-0014056 | 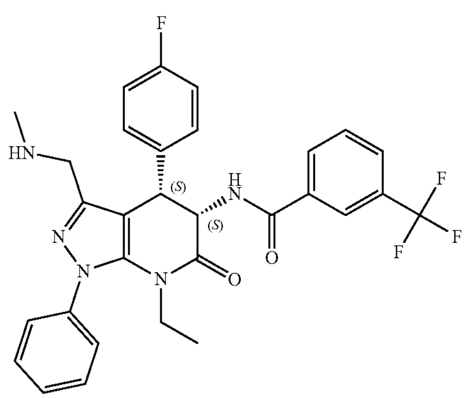 | 0.118 ± 0.00903 (n = 3) | N-[(4S,5S)-7-ethyl-4-(4-fluorophenyl)-3-[(methylamino)methyl]-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0014057 | 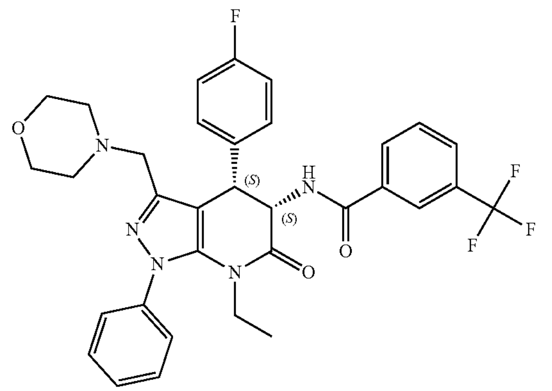 | 0.0969 ± 0.00757 (n = 3) | N-[(4S,5S)-7-ethyl-4-(4-fluorophenyl)-3-[(morpholin-4-yl)methyl]-6-oxo-1-phenyl-1H,4H,5H,6H,7H-pyrazolo[3,4-b]pyridin-5-yl]-3-(trifluoromethyl)benzamide |
| RG-0014058 | 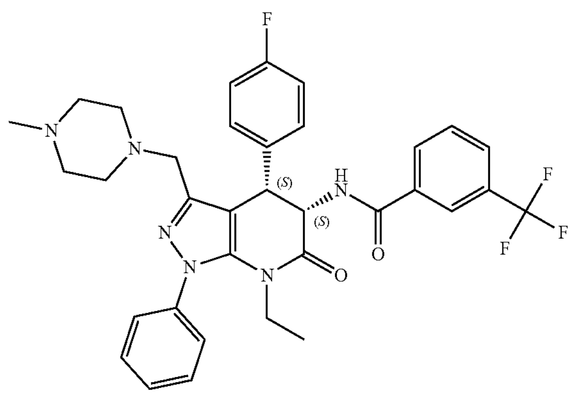 | 0.0676 ± 0.00449 (n = 3) | N-[(4S,5S)-7-ethyl-4-(4-fluorophenyl)-3-[(4-methylpiperazin-1-yl)methyl]-6-oxo-1-phenyl-1H,4H,5H,6H,7H-pyrazolo[3,4-b]pyridin-5-yl]-3-(trifluoromethyl)benzamide |
| RG-0014059 | 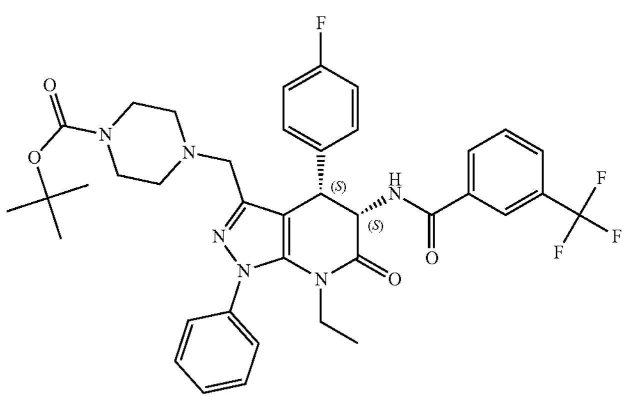 | 0.231 ± 0.0165 (n = 3) | tert-butyl 4-{[(4S,5S)-7-ethyl-4-(4-fluorophenyl)-6-oxo-1-phenyl-5-[3-(trifluoromethyl)benzamido]-1H,4H,5H,6H,7H-pyrazolo[3,4-b]pyridin-3-yl]methyl}piperazine-1-carboxylate |

TABLE 1-continued

| Molecule Name | Structure | DCN1_TRFRET Mean EC50 (uM) | IUPAC Name |
|---|---|---|---|
| RG-0014060 | 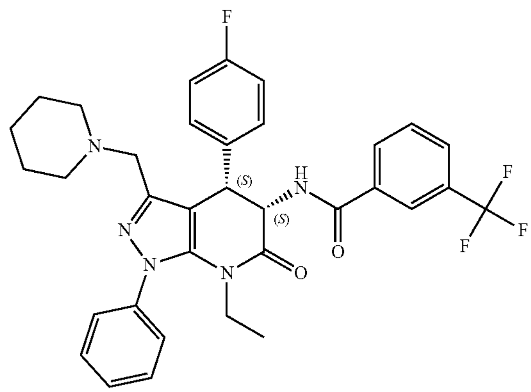 | 0.066 ± 0.00557 (n = 3) | N-[(4S,5S)-7-ethyl-4-(4-fluorophenyl)-6-oxo-1-phenyl-3-[(piperidin-1-yl)methyl]-1H,4H,5H,6H,7H-pyrazolo[3,4-b]pyridin-5-yl]-3-(trifluoromethyl)benzamide |
| RG-0014061 | 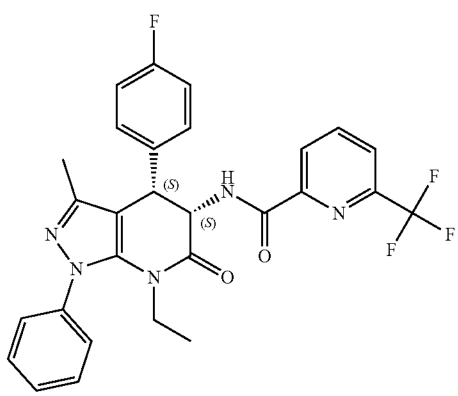 | 1.11 ± 0.13 (n = 3) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-6-(trifluoromethyl)pyridine-2-carboxamide |
| RG-0014062 | 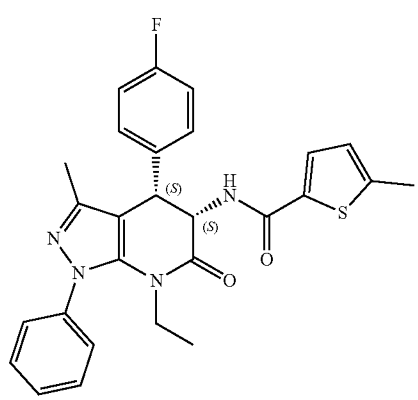 | 2.34 ± 0.0772 (n = 3) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-5-methylthiophene-2-carboxamide |

TABLE 1-continued

| Molecule Name | Structure | DCN1_TRFRET Mean EC50 (uM) | IUPAC Name |
|---|---|---|---|
| RG-0014063 | 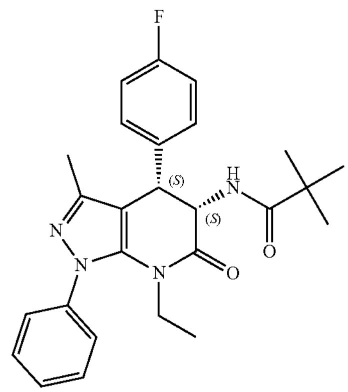 | >36.5 ± 0 (n = 3) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-2,2-dimethylpropanamide |
| RG-0014139 | 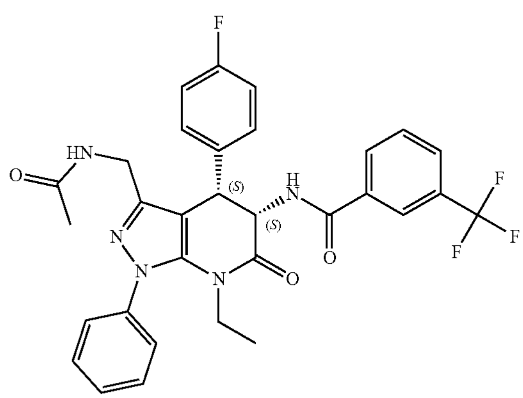 | 0.087 ± 0.0208 (n = 4) | N-[(4S,5S)-3-(acetamidomethyl)-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |
| RG-0014140 | 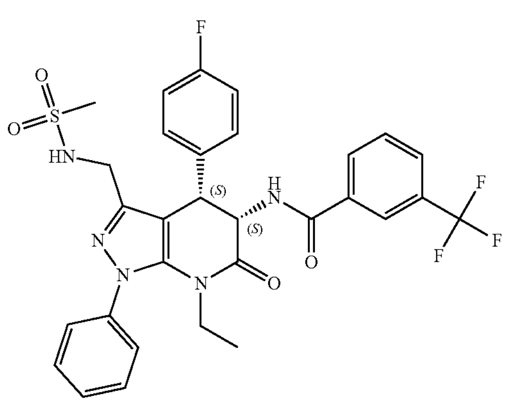 | 0.0947 ± 0.0197 (n = 4) | N-[(4S,5S)-7-ethyl-4-(4-fluorophenyl)-3-(methanesulfonamidomethyl)-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0014141 | 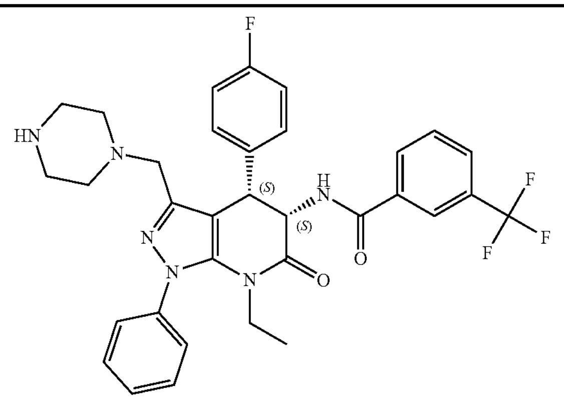 | 0.141 ± 0.00756 (n = 4) | N-[(4S,5S)-7-ethyl-4-(4-fluorophenyl)-6-oxo-1-phenyl-3-[(piperazin-1-yl)methyl]-1H,4H,5H,6H,7H-pyrazolo[3,4-b]pyridin-5-yl]-3-(trifluoromethyl)benzamide |
| RG-0014142 | 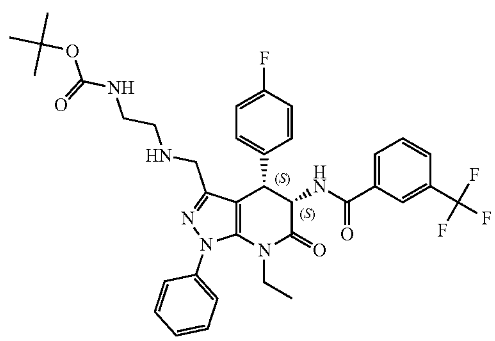 | 0.116 ± 0.0175 (n = 4) | tert-butyl N-[2-({[(4S,5S)-7-ethyl-4-(4-fluorophenyl)-6-oxo-1-phenyl-5-[3-(trifluoromethyl)benzamido]-1H,4H,5H,6H,7H-pyrazolo[3,4-b]pyridin-3-yl]methyl}amino)ethyl]carbamate |
| RG-0014143 | 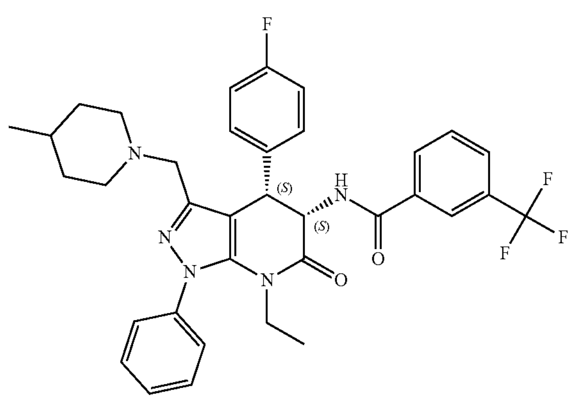 | 0.0827 ± 0.00769 (n = 4) | N-[(4S,5S)-7-ethyl-4-(4-fluorophenyl)-3-[(4-methylpiperidin-1-yl)methyl]-6-oxo-1-phenyl-1H,4H,5H,6H,7H-pyrazolo[3,4-b]pyridin-5-yl]-3-(trifluoromethyl)benzamide |
| RG-0014144 | 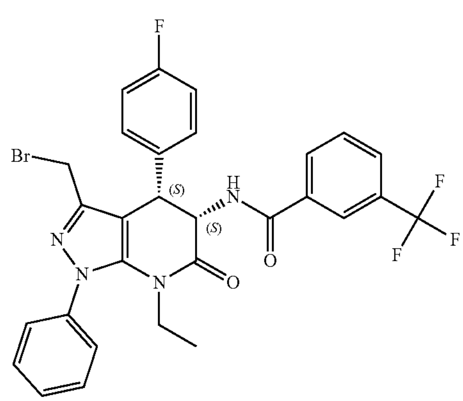 | 0.186 ± 0.0326 (n = 4) | N-[(4S,5S)-3-(bromomethyl)-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0014145 | 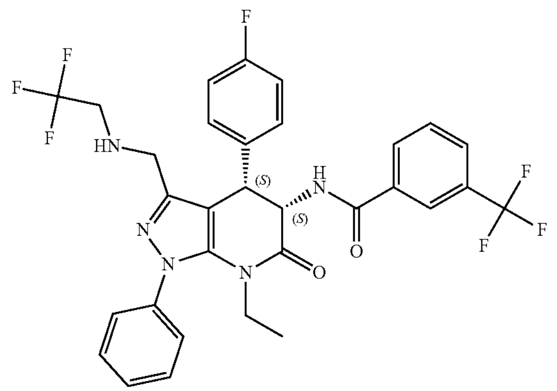 | 0.161 ± 0.0131 (n = 4) | N-[(4S,5S)-7-ethyl-4-(4-fluorophenyl)-6-oxo-1-phenyl-3-{[(2,2,2-trifluoroethyl)amino]methyl}-1H,4H,5H,6H,7H-pyrazolo[3,4-b]pyridin-5-yl]-3-(trifluoromethyl)benzamide |
| RG-0014146 | 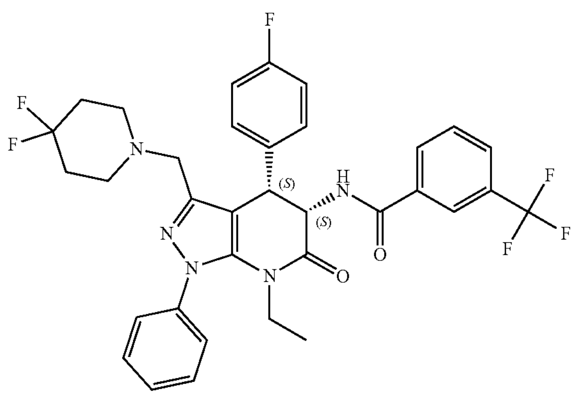 | 0.321 ± 0.0273 (n = 4) | N-[(4S,5S)-3-[(4,4-difluoropiperidin-1-yl)methyl]-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |
| RG-0014147 | 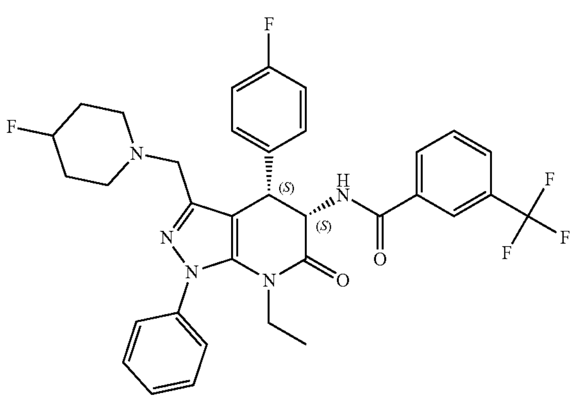 | 0.112 ± 0.016 (n = 4) | N-[(4S,5S)-7-ethyl-4-(4-fluorophenyl)-3-[(4-fluoropiperidin-1-yl)methyl]-6-oxo-1-phenyl-1H,4H,5H,6H,7H-pyrazolo[3,4-b]pyridin-5-yl]-3-(trifluoromethyl)benzamide |
| RG-0014148 | 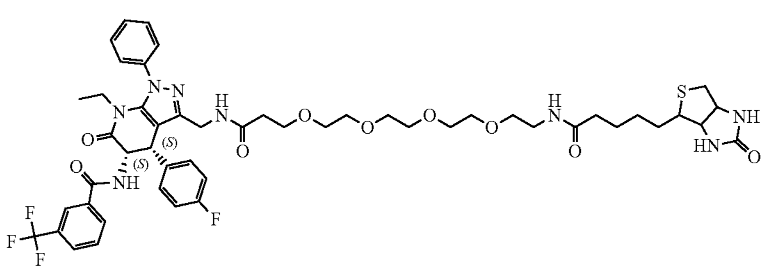 | 0.102 ± 0.0159 (n = 4) | N-{[(4S,5S)-7-ethyl-4-(4-fluorophenyl)-6-oxo-1-phenyl-5-[3-(trifluoromethyl)benzamido]-1H,4H,5H,6H,7H-pyrazolo[3,4-b]pyridin-3-yl]methyl}-1-(5-{2-oxo-hexahydro-1H-thieno[3,4-d]imidazol-4-yl}pentanamido)-3,6,9,12-tetraoxapentadecan-15-amide |

TABLE 1-continued

| Molecule Name | Structure | DCN1_TRFRET Mean EC50 (uM) | IUPAC Name |
|---|---|---|---|
| RG-0014149 | 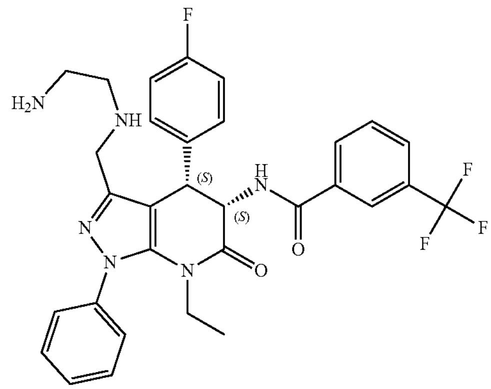 | 0.126 ± 0.0121 (n = 4) | N-[(4S,5S)-3-{[(2-aminoethyl)amino]methyl}-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |
| RG-0014150 | 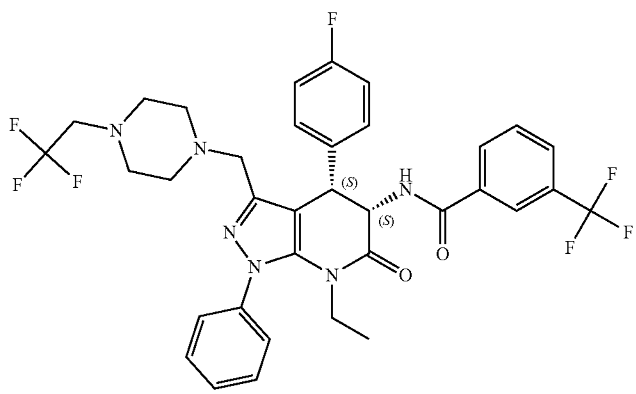 | 0.173 ± 0.0219 (n = 4) | N-[(4S,5S)-7-ethyl-4-(4-fluorophenyl)-6-oxo-1-phenyl-3-{[4-(2,2,2-trifluoroethyl)piperazin-1-yl]methyl}-1H,4H,5H,6H,7H-pyrazolo[3,4-b]pyridin-5-yl]-3-(trifluoromethyl)benzamide |
| RG-0014151 | 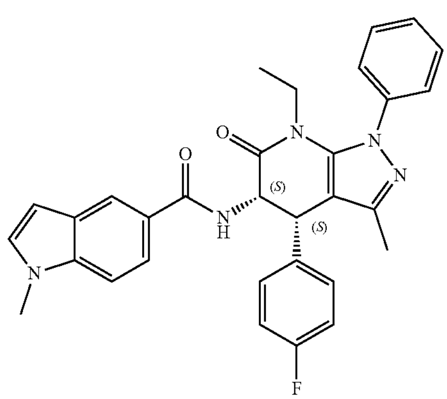 | 3.23 ± 0.806 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-1-methyl-1H-indole-5-carboxamide |

TABLE 1-continued

| Molecule Name | Structure | DCN1_TRFRET Mean EC50 (uM) | IUPAC Name |
|---|---|---|---|
| RG-0014152 | 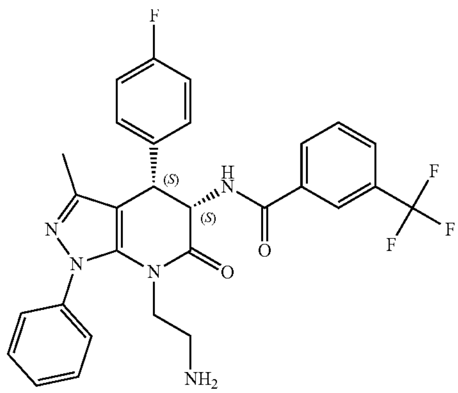 | 8.41 ± 2.49 (n = 4) | N-[(4S,5S)-7-(2-aminoethyl)-4-(4-fluorophenyl)-3-methyl-6-oxo-1-phenyl-1H,4H,5H,6H,7H-pyrazolo[3,4-b]pyridin-5-yl]-3-(trifluoromethyl)benzamide |
| RG-0014153 | 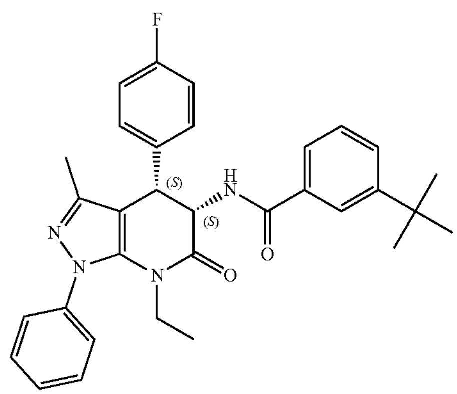 | 2.06 ± 0.163 (n = 4) | 3-tert-butyl-N-[(4S,5S)-7-ethyl-4-(4-fluorophenyl)-3-methyl-6-oxo-1-phenyl-1H,4H,5H,6H,7H-pyrazolo[3,4-b]pyridin-5-yl]benzamide |
| RG-0014154 | 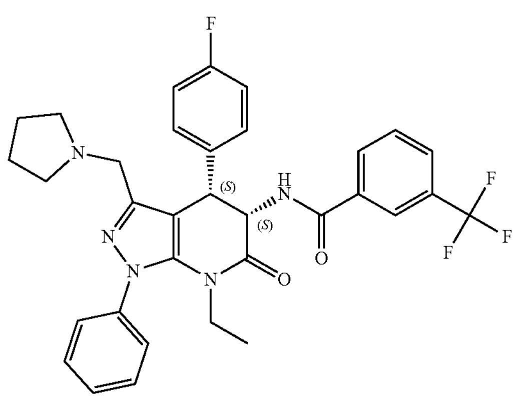 | 0.0835 ± 0.00939 (n = 4) | N-[(4S,5S)-7-ethyl-4-(4-fluorophenyl)-6-oxo-1-phenyl-3-[(pyrrolidin-1-yl)methyl]-1H,4H,5H,6H,7H-pyrazolo[3,4-b]pyridin-5-yl]-3-(trifluoromethyl)benzamide |

TABLE 1-continued

| Molecule Name | Structure | DCN1_TRFRET Mean EC50 (uM) | IUPAC Name |
|---|---|---|---|
| RG-0014155 | 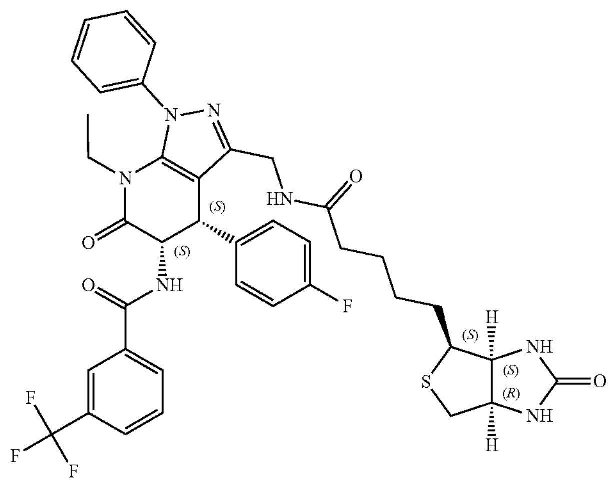 | 0.123 ± 0.0225 (n = 4) | N-[(4S,5S)-3-({5-[(3aS,4S,6aR)-2-oxo-hexahydro-1H-thieno[3,4-d]imidazol-4-yl]pentanamido}methyl)-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |
| RG-0014156 | 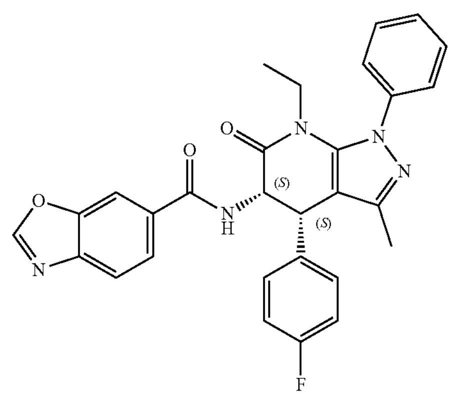 | >17.3 ± 13.7 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-1,3-benzoxazole-6-carboxamide |
| RG-0014157 | 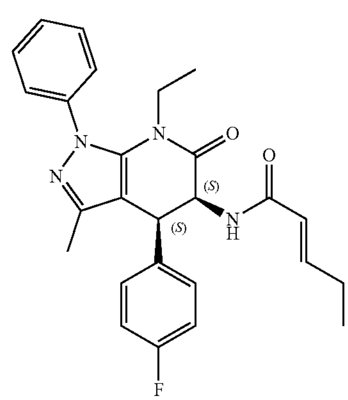 | >30.7 ± 11.5 (n = 4) | (2E)-N-[(4S,5S)-7-ethyl-4-(4-fluorophenyl)-3-methyl-6-oxo-1-phenyl-1H,4H,5H,6H,7H-pyrazolo[3,4-b]pyridin-5-yl]pent-2-enamide |

TABLE 1-continued

| Molecule Name | Structure | DCN1_TRFRET Mean EC50 (uM) | IUPAC Name |
|---|---|---|---|
| RG-0014158 | 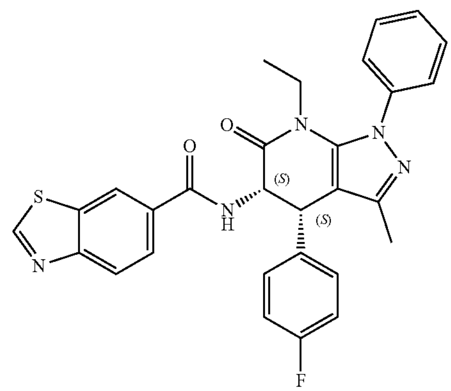 | 6.31 ± 0.465 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-1,3-benzothiazole-6-carboxamide |
| RG-0014159 | 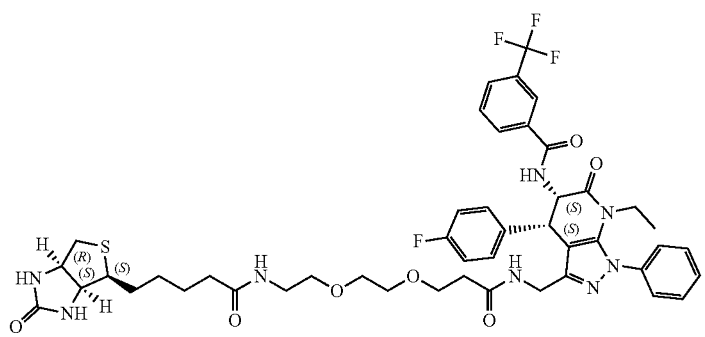 | 0.0896 ± 0.0109 (n = 4) | N-[(4S,5S)-3-({3-[2-(2-{5-[(3aS,4S,6aR)-2-oxo-hexahydro-1H-thieno[3,4-d]imidazol-4-yl]pentanamido}ethoxy)ethoxy]propanamido}methyl)-7-ethyl-4-(4-fluorophenyl)-6-oxo-1-phenyl-1H,4H,5H,6H,7H-pyrazolo[3,4-b]pyridin-5-yl]-3-(trifluoromethyl)benzamide |
| RG-0014160 | 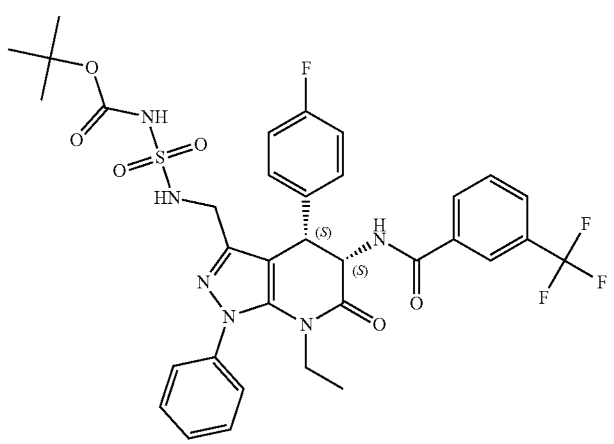 | 0.194 ± 0.0199 (n = 4) | tert-butyl N-({[(4S,5S)-7-ethyl-4-(4-fluorophenyl)-6-oxo-1-phenyl-5-[3-(trifluoromethyl)benzamido]-1H,4H,5H,6H,7H-pyrazolo[3,4-b]pyridin-3-yl]methyl}sulfamoyl)carbamate |

TABLE 1-continued

| Molecule Name | Structure | DCN1_TRFRET Mean EC50 (uM) | IUPAC Name |
|---|---|---|---|
| RG-0014161 | 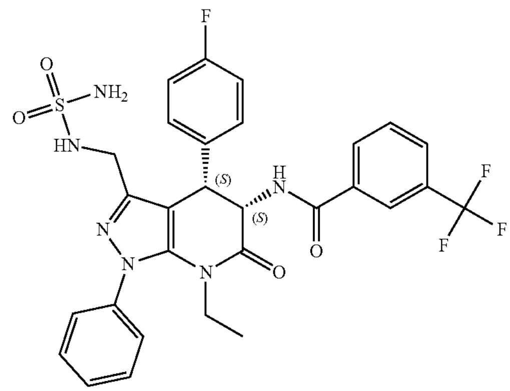 | 0.145 ± 0.0262 (n = 4) | N-[(4S,5S)-7-ethyl-4-(4-fluorophenyl)-6-oxo-1-phenyl-3-[(sulfamoylamino)methyl]-1H,4H,5H,6H,7H-pyrazolo[3,4-b]pyridin-5-yl]-3-(trifluoromethyl)benzamide |
| RG-0014162 | 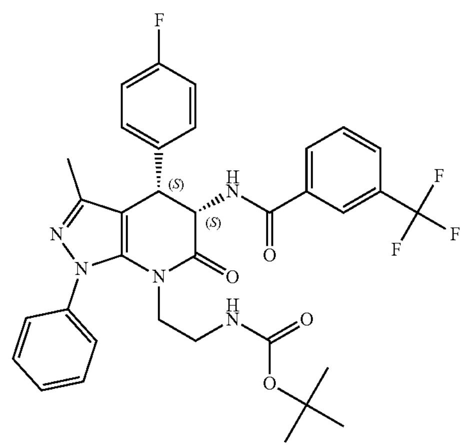 | >13.6 ± 15.6 (n = 4) | tert-butyl N-{2-[(4S,5S)-4-(4-fluorophenyl)-3-methyl-6-oxo-1-phenyl-5-[3-(trifluoromethyl)benzamido]-1H,4H,5H,6H,7H-pyrazolo[3,4-b]pyridin-7-yl]ethyl}carbamate |
| RG-0014163 | 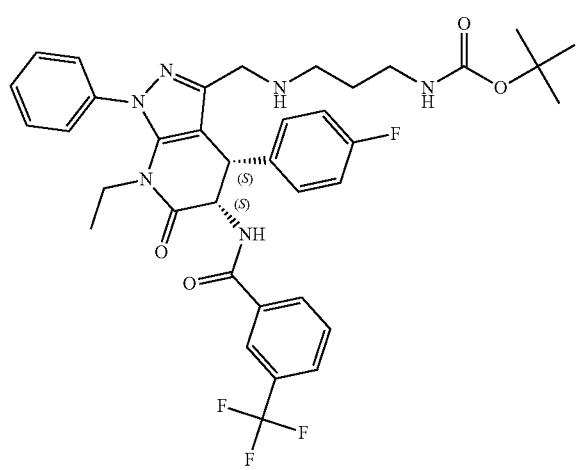 | 0.0956 ± 0.00721 (n = 4) | tert-butyl N-[3-({[(4S,5S)-7-ethyl-4-(4-fluorophenyl)-6-oxo-1-phenyl-5-[3-(trifluoromethyl)benzamido]-1H,4H,5H,6H,7H-pyrazolo[3,4-b]pyridin-3-yl]methyl}amino)propyl]carbamate |

TABLE 1-continued

| Molecule Name | Structure | DCN1_TRFRET Mean EC50 (uM) | IUPAC Name |
|---|---|---|---|
| RG-0014164 | 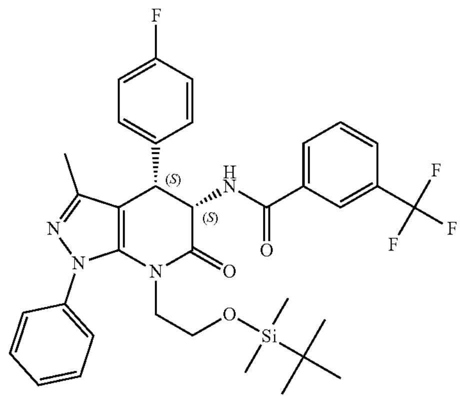 | >36.5 ± 0 (n = 4) | N-[(4S,5S)-7-{2-[(tert-butyldimethylsilyl)oxy]ethyl}-4-(4-fluorophenyl)-3-methyl-6-oxo-1-phenyl-1H,4H,5H,6H,7H-pyrazolo[3,4-b]pyridin-5-yl]-3-(trifluoromethyl)benzamide |
| RG-0014165 | 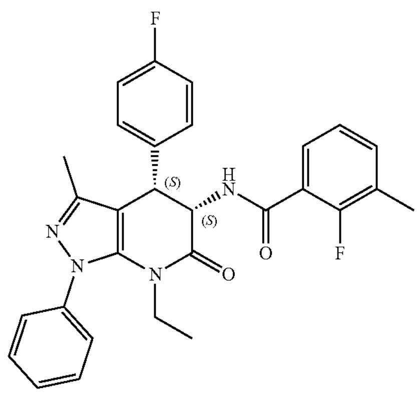 | 0.541 ± 0.0681 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-2-fluoro-3-methylbenzamide |
| RG-0014166 | 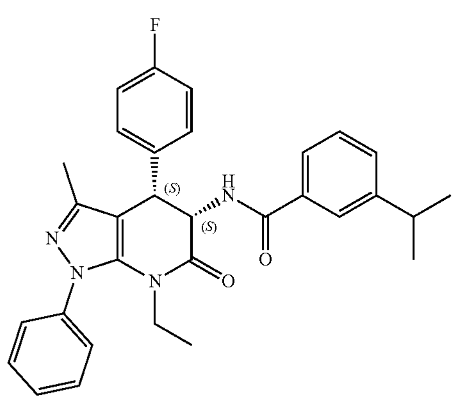 | 0.473 ± 0.0707 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-3-(propan-2-yl)benzamide |

TABLE 1-continued

| Molecule Name | Structure | DCN1_TRFRET Mean EC50 (uM) | IUPAC Name |
|---|---|---|---|
| RG-0014167 | 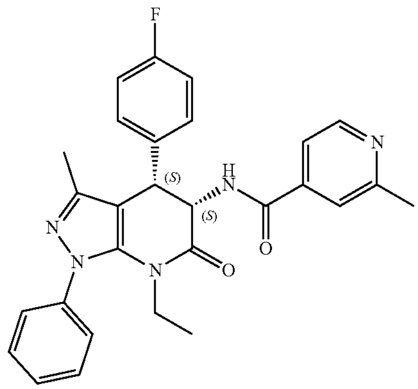 | >36.5 ± 0 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-2-methylpyridine-4-carboxamide |
| RG-0014168 | 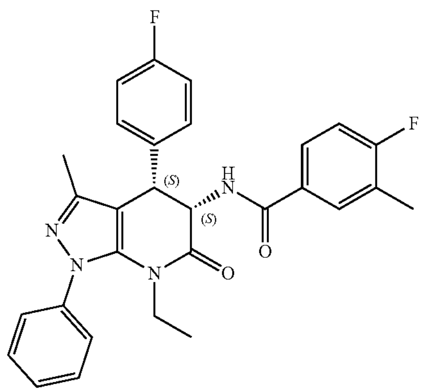 | 1.69 ± 0.115 (n = 4) | N-[(4S,5S)-7-ethyl-4-(4-fluorophenyl)-3-methyl-6-oxo-1-phenyl-1H,4H,5H,6H,7H-pyrazolo[3,4-b]pyridin-5-yl]-4-fluoro-3-methylbenzamide |
| RG-0014169 | 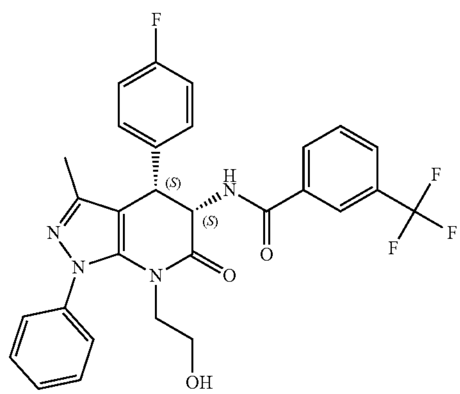 | 0.338 ± 0.0331 (n = 4) | N-[(4S,5S)-4-(4-fluorophenyl)-7-(2-hydroxyethyl)-3-methyl-6-oxo-1-phenyl-1H,4H,5H,6H,7H-pyrazolo[3,4-b]pyridin-5-yl]-3-(trifluoromethyl)benzamide |

In some embodiments, the compounds according to Formula I have increased potency as compared to existing compounds. For example, in one embodiment, the compounds according to Formula I include a cis-geometry across the pyridine ring of the general pyrazolo-pyridone structure (i.e., $R_3$ and $R_4$ are in S,S or R,R configuration). Although certain structures may be shown herein as either S,S or R,R, it should be understood by those skilled in the art that both S,S and R,R configurations are explicitly contemplated herein. That is, unless stated otherwise, an S,S or R,R configuration should be understood to represent both enantiomers as well as an enantiomer racemic mixture thereof. In contrast to existing compounds having a trans-geometry, the cis-geometry has been found to be substantially more potent. In another embodiment, the $R_2$ group of the compounds according to Formula I unexpectedly provides substantially improved potency as compared to existing compounds which contained a proton at this position (FIG. 2).

Additionally or alternatively, in some embodiments, the compounds according to Formula I have improved bioavailability, including improved oral bioavailability, as compared to existing compounds. For example, in one embodiment, the compounds according to Formula I include a polar substituent at the $R_5$ position (FIG. 2). In another embodiment, this polar substituent unexpectedly provides significantly improved oral bioavailability as compared to compounds lacking a polar substituent at this position. In a further embodiment, this polar substituent unexpectedly provides significantly improved potency as compared to compounds lacking a polar substituent at this position.

Figure 1:
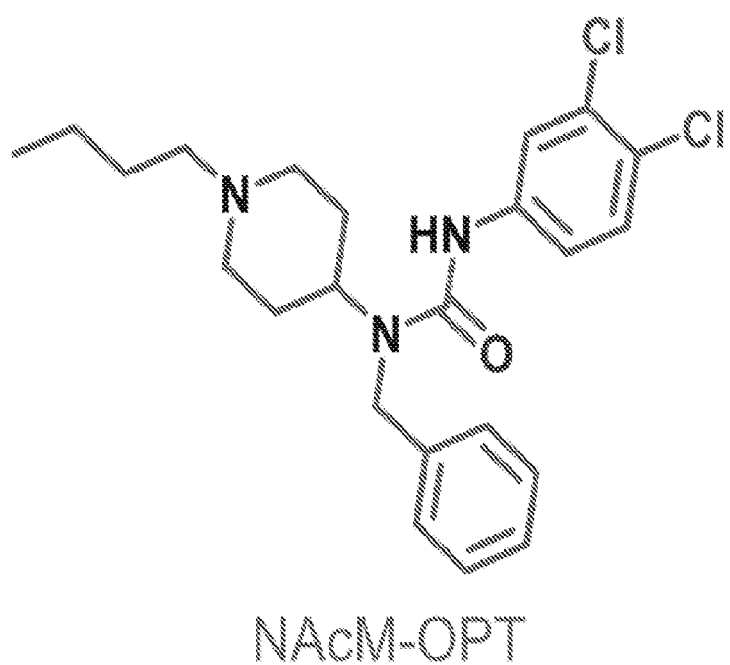
FIG. 1 shows an image illustrating the structure of NAcM-OPT.
Figure 2:
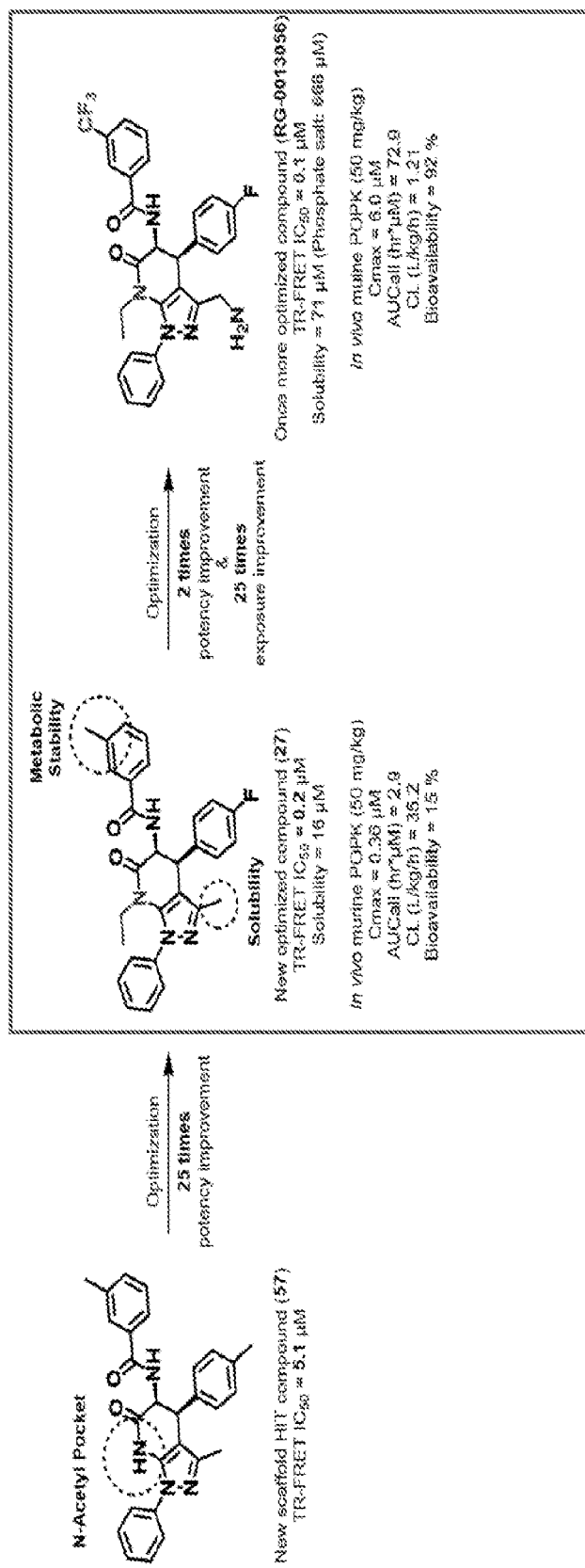
FIG. 2 shows a schematic illustrating various modifications to a pyrazolo-pyridone compound that improve potency and/or oral bioavailability.

In some embodiments, the compound according to Formula I includes one or more substitutions in the $R_6$ group (FIG. 2). For example, the $R_6$ group may include an aryl or heteroaryl with one or more substitutions. In one embodiment, such substitutions include, but are not limited to, one or more halogen, pseudohalide, alkyl, aryl, alkoxy, aryloxy, sulfo-oxo, —$CF_3$, —CN, —$NO_2$, $NH_2$, OH, —$S(O_2)CH_3$, or a combination thereof. In another embodiment, such substitutions unexpectedly provide improved oral bioavailability as compared to compounds lacking substitutions at this position.

The compounds according to one or more of the embodiments disclosed herein have two chiral centers that impart a greater degree of three-dimensional structure, which affords opportunities for increased binding potency, target selectivity, and improved solubility. The improved potency and/or in vivo metabolic stability of the compounds disclosed herein provides improved therapeutic index and/or reduces dosing schedule as compared to existing compounds. In some embodiments, the compounds disclosed herein engage DCN1 in cells and/or selectively reduce steady-state levels of Cul1 and Cul3 neddylation in cancer cells. Additionally or alternatively, the compounds disclosed herein provide an alternative chemical scaffold for target validation studies.

Also provided herein are methods of administering the compounds disclosed herein. In some embodiments, the compounds disclosed herein are inhibitors of DCN1-UBC12 interaction and/or inhibitors of DCN1-mediated cullin-RING ligase activity. In some embodiments, the compounds disclosed herein are anti-bacterial, anti-cancer, and/or anti-viral. Accordingly, in some embodiments, these compounds may be administered for treatment of disorders associated with dysfunctional DCN1 and/or UBC12, neurodegenerative diseases (e.g., Alzheimer's disease), bacterial infections, viral infections, and/or cancers. Additionally or alternatively, in some embodiments, the compounds disclosed herein may be administered for stem cell study, as chemical probes, and/or as chemical tools.

Further provided herein are methods of making the compounds disclosed herein. In some embodiments, the method includes a three-step procedure involving preparation of an oxazolone intermediate, pyrazolo-pyridone ring formation, and substitution using alkylation or acylation. In one embodiment, formation of the core pyrazolo-pyridone ring affords a separable mixture of cis and trans diastereomers. In another embodiment, the cis and trans isomers are distinguishable by $^1$H NMR and/or assigned based on application of the Karplus equation to the $^3J_{H-H}$ vicinal proton-proton coupling for the C4 or C5 protons of pyrazolo-pyridone ring (Cis=7-8 Hz, Trans=9-11 Hz). In a further embodiment, the inactive trans-isomer is converted to the active cis product by stirring with a catalytic amount of Lewis acid ($SnCl_2$) in refluxing chlorobenzene. In certain embodiments, converting the trans-isomer to a cis-isomer includes stirring with less than 10 equivalents of the Lewis acid, as use of 10+ equivalents may favor formation of dehydrated side products rather than pyrazolo-pyridone ring formation.

In some embodiments, the pyrazolo-pyridone ring formation, or annulation reaction, includes a non-polar or polar aprotic solvent such as chlorobenzene, DMF, or NMP. In one embodiment, these solvents provide improved yields and suppressed formation of side products as compared to nucleophilic polar protic solvents, such as ethylene glycol and acetic acid. Additionally or alternatively, in some embodiments, the method includes addition of a catalytic amount of tin (II) chloride followed by refluxing in chlorobenzene. In one embodiment, the addition of tin (II) chloride followed by refluxing favors formation of the cis-diastereomer. In another embodiment, the addition of tin (II) chloride followed by refluxing affords a 3:1 cis to trans ratio and/or isolated yields of pure cis product.

The presently-disclosed subject matter is further illustrated by the following specific but non-limiting examples. The following examples may include compilations of data that are representative of data gathered at various times during the course of development and experimentation related to the presently-disclosed subject matter. Those skilled in the art will recognize, or be able to ascertain, using no more than routine experimentation, numerous equivalents to the specific substances and procedures described herein.

EXAMPLES

Example 1

Chemical control of cullin neddylation is attracting increased attention based largely on the successes of the NEDD8-activating enzyme (E1) inhibitor Pevonedistat. Recently reported chemical probes enable selective and time-dependent inhibition of downstream members of the neddylation tri-enzymatic cascade including the co-E3, DCN1. It is a common feature of developing new classes of inhibitors that it can be difficult to tease out selectivity that is driven by the core structure of an inhibitor from that which is driven by the target itself. Having multiple classes of inhibitors blocking the DCN1-UBE2M interaction will permit interrogation of the function of sub-portions of the network, increasing the probability of unveiling fundamental principles of the regulation of protein homeostasis. In view thereof, the instant inventors sought a structurally unrelated class of small molecule inhibitors that might overcome the inherent liabilities of the piperidine class.

This Example describes the discovery and optimization of a novel class of small molecule inhibitors of the DCN1-UBE2M interaction. More specifically, this Example focuses on a second class of inhibitors that contain a pyrazolo-pyridone core. This class has two chiral centers thus imparting a greater degree of three-dimensional structure and affording opportunities for increased binding potency, target selectivity, and improved solubility. The overall strategy was to first identify the minimum pharmacophore for this class, next define the structural drivers of potency for binding to DCN1, and then use data gathered about optimal substituents from the first-generation inhibitors to optimize binding. During the course of the study, new compounds were designed based on hypotheses generated from combining empirically derived SAR and examination of X-ray co-structures. New analogs were tested for potency using the previously reported TR-FRET assay. Key compounds were evaluated for cellular target engagement and neddylation activity by immunoblotting for steady-state levels of cullin neddylation using a lung cancer cell line with amplified DCN1 expression (HCC95).

Utilizing rational design based on X-ray co-structures enabled optimization provided a 25-fold improvement in potency relative to the initial screening hit. The potency gains are largely attributed to additional hydrophobic interactions mimicking the N-terminal acetyl group that drives binding of UBE2M to DCN1. The compounds inhibit the protein-protein interaction, block NEDD8 transfer in biochemical assays, engage DCN1 in cells, and selectively reduce the steady-state neddylation of Cul1 and Cul3 in a squamous carcinoma cell line harboring DCN1 amplification.

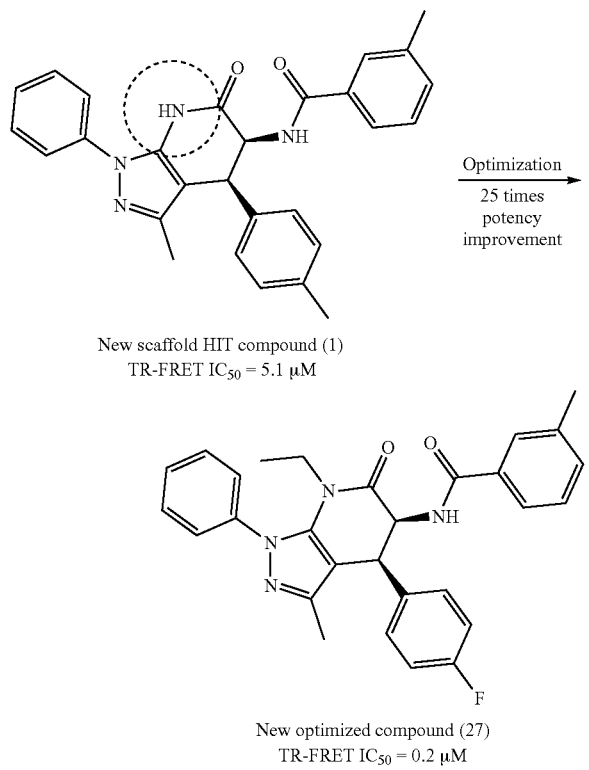

N-Acetyl Pocket

New scaffold HIT compound (1)
TR-FRET IC$_{50}$ = 5.1 µM

Optimization
25 times potency improvement

New optimized compound (27)
TR-FRET IC$_{50}$ = 0.2 µM

Results

The results of a high-throughput screen of roughly 600,000 compounds using a binding assay based on the TR-FRET signal between a biotinylated DCN1 protein, recognized by Terbium-linked streptavidin, and the helical stapled peptide derived from N-terminally acetylated UBE2M harboring a C-terminal AlexaFluor 488 have been reported. This work identified several structurally divergent inhibitors of the targeted binding event with potency (IC$_{50}$) ranging from 1 to 30 micromolar.

Figure 3:
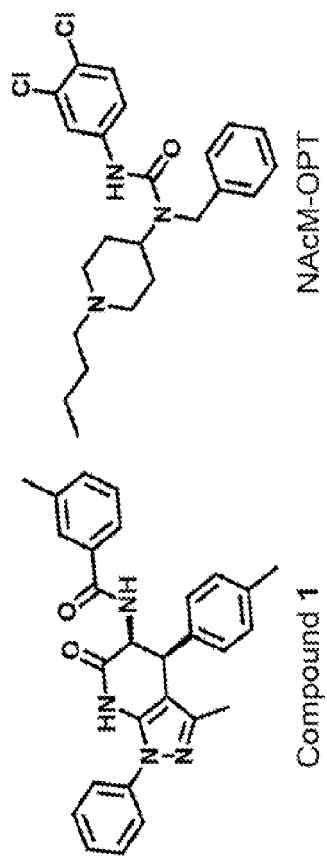
FIG. 3 shows images of chemical structures for compound 1 and NAcM-OPT, as well as an overlay of these structures with DCN1. Left: Overlay of 1(orange):DCN1 (gray) and NAcM-OPT(blue):DCN1 X-ray crystal co-structures (PDB XXX and 5V86), highlighting that 1 more efficiently occupies the N-acetyl pocket (yellow highlight). Hashed orange line represents a potential hydrogen-bonding interaction between the amide of 1 and backbone amide of Gln114. Right: 2D chemical structures of compound 1 and NAcM-OPT.
Figure 3:
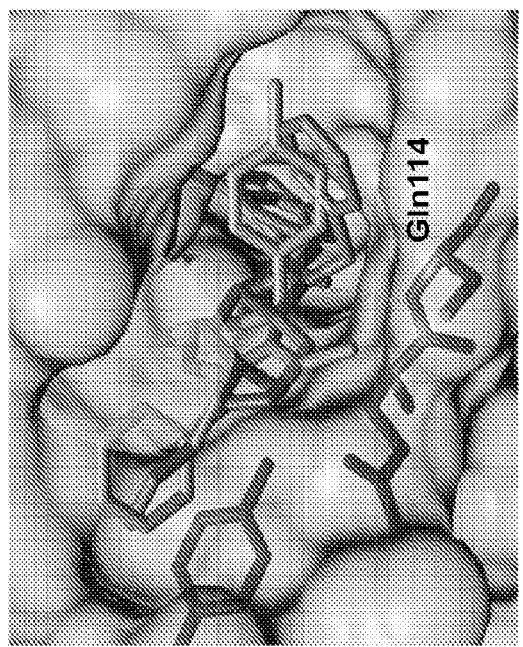
Figure 4:
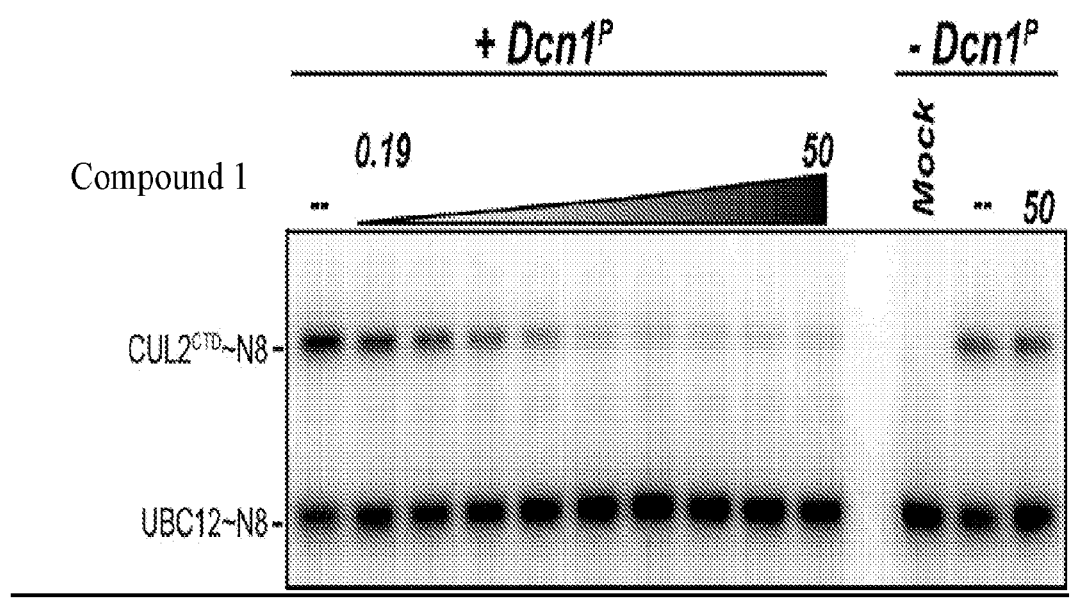
FIG. 4 shows an image illustrating pulse-chase data for compound 1.

Resynthesis of several analogs validated the potency of the pyrazolo-pyridone screening samples (FIG. 3, compound 1). Compound 1 also inhibited the transfer of NEDD8 from the activated E2 to its cullin substrate in a pulse-chase assay (FIG. 4). Finally, an X-ray co-structure of the compound 1 with DCN1 showed that it bound to the targeted UBE2M binding pocket (FIG. 3).

Design and Synthesis

Based on a validation of the screening hit, a hit-to-lead campaign aimed at delivering an early lead that overcame the challenges associated with our first-generation inhibitors embodied by NAcM-OPT was undertaken. The initial compound design was based on insights derived from overlaying the X-ray co-structures of 1:DCN1 (PDB 6P5W), UBE2M$^{NAc}$:DCN1 (PDB 3TDU), and NAcM-OPT:DCN1 (PDB 5V86) (FIG. 3) and is summarized in FIG. 5. Compound 1 aligns well with NAcM-OPT in addressing three binding sub-pockets: the Ile, Leu, and hinge pockets. Therefore, initial substitutions in these pockets were informed by the structure-activity relationships (SAR) derived during the optimization of first-generation lead NAcM-OPT. NAcM-OPT does not directly occupy the N-acetyl pocket (yellow highlight, FIG. 3). However, its piperidine ring is engaged in a hydrogen bonding network with a bound water molecule within the N-acetyl pocket that strongly suggests fulfilling this pocket could strengthen binding. This hypothesis is further supported by characterization of analogs of the native binding peptide, which demonstrated that occupancy by even a small hydrophobic group (acetyl vs. formyl) can enhance affinity 10-fold.

Figure 5:
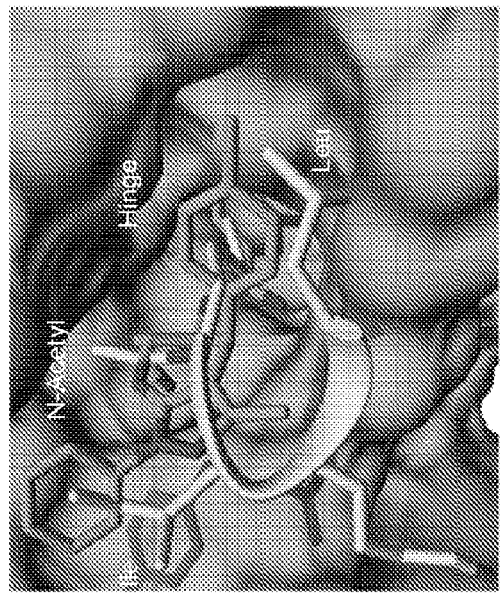
FIG. 5 shows images illustrating the interaction of compound 1 with DCN1. Left: Design strategy of compound 1. Right: X-ray co-structure overlay of compound 1:DCN1 (PDB XXX) and UBE2M:DCN1 (PDB 5V83), highlighting the key regions targeted for optimization.
Figure 5:
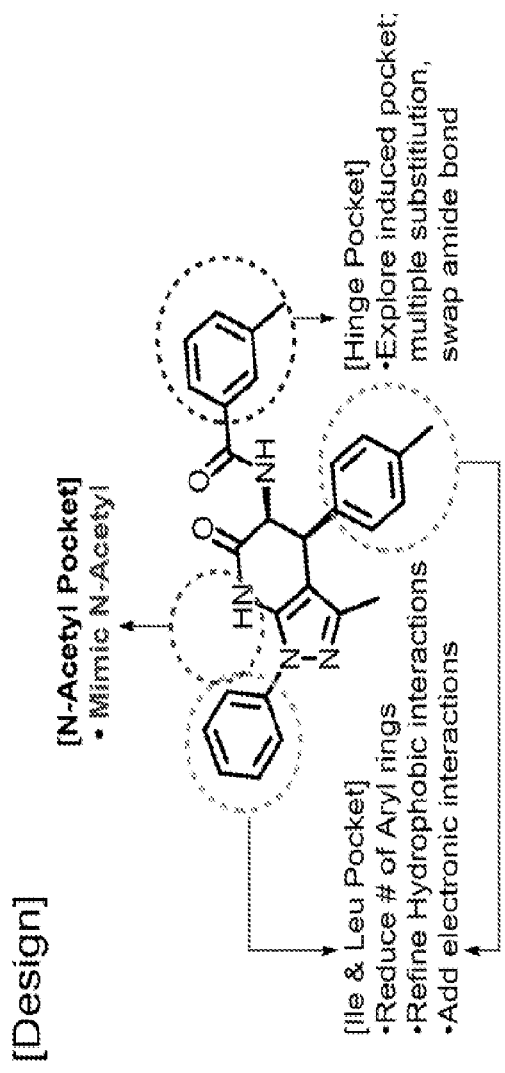

The X-ray co-structure of 1:DCN1 shows that compound 1 clearly positions the central pyrazolo-pyridone ring closer to the N-acetyl pocket (FIG. 3). Thus, analogs were designed to test whether substitution on the pyridone's nitrogen could induce tighter binding by direct hydrophobic packing rather than indirect water-mediated binding (FIG. 5). In addition, the base pharmacophore was explored for the pyrazolo-pyridone series by utilizing reversed amides in the hinge pocket to determine the significance of a predicted hydrogen bond between compound 1's amide and Gln114 of DCN1 (FIGS. 3 and 5). Compound 1 has four aromatic rings that could negatively affect its physiochemical properties and reduce its utility as a probe to study the cullin neddylation. To address this issue, tests were conducted to determine whether smaller, more flexible substituents could replace these aryl rings. A variety of substituent modifications were also tried on the aryl ring to introduce additional electronic or hydrophobic interactions (FIG. 5). The overall goal was to increase or maintain potency by targeted substitution of one ring while reducing total molecular weight by removing a less critical ring or substituent.

Figure 6:
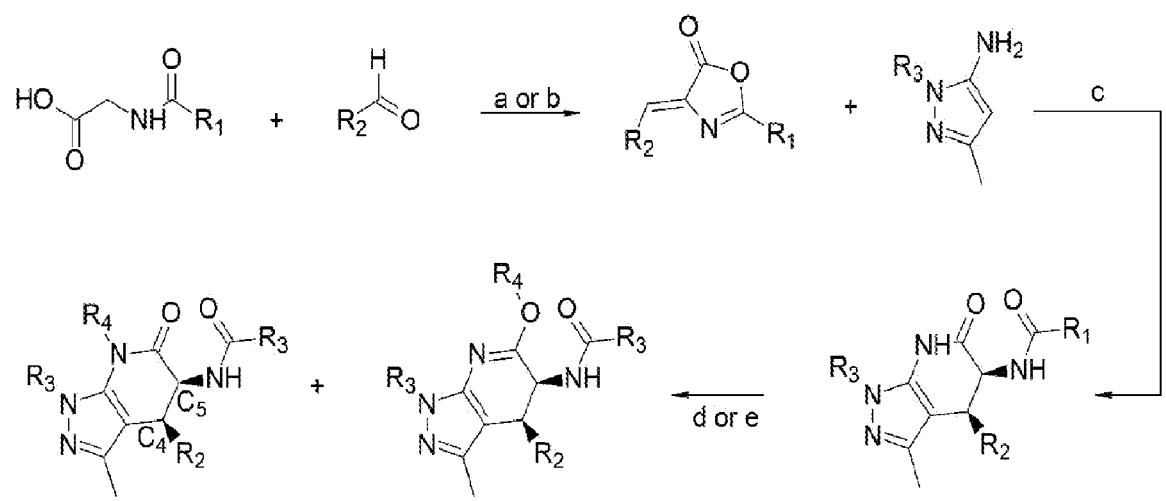
FIG. 6 shows a schematic illustrating the general synthesis of pyrazolo-pyridones. Reagents and conditions: (a) NaOAc, Ac$_2$O, 85-90° C., 1-2 h; (b) i) EDCI·HCl, DCM, r.t., 16 h; ii) Al$_2$O$_3$, 4 Å MS, DCM, r.t., 16 h; (c) SnCl$_2$, chlorobenzene, reflux, 16 h; (d) Cs$_2$CO$_3$, R—X (X=Br, I), DMF, r.t., 1-16 h; (e) AcCl, pyridine, DCM, r.t., 1 h.
Figure 7A:
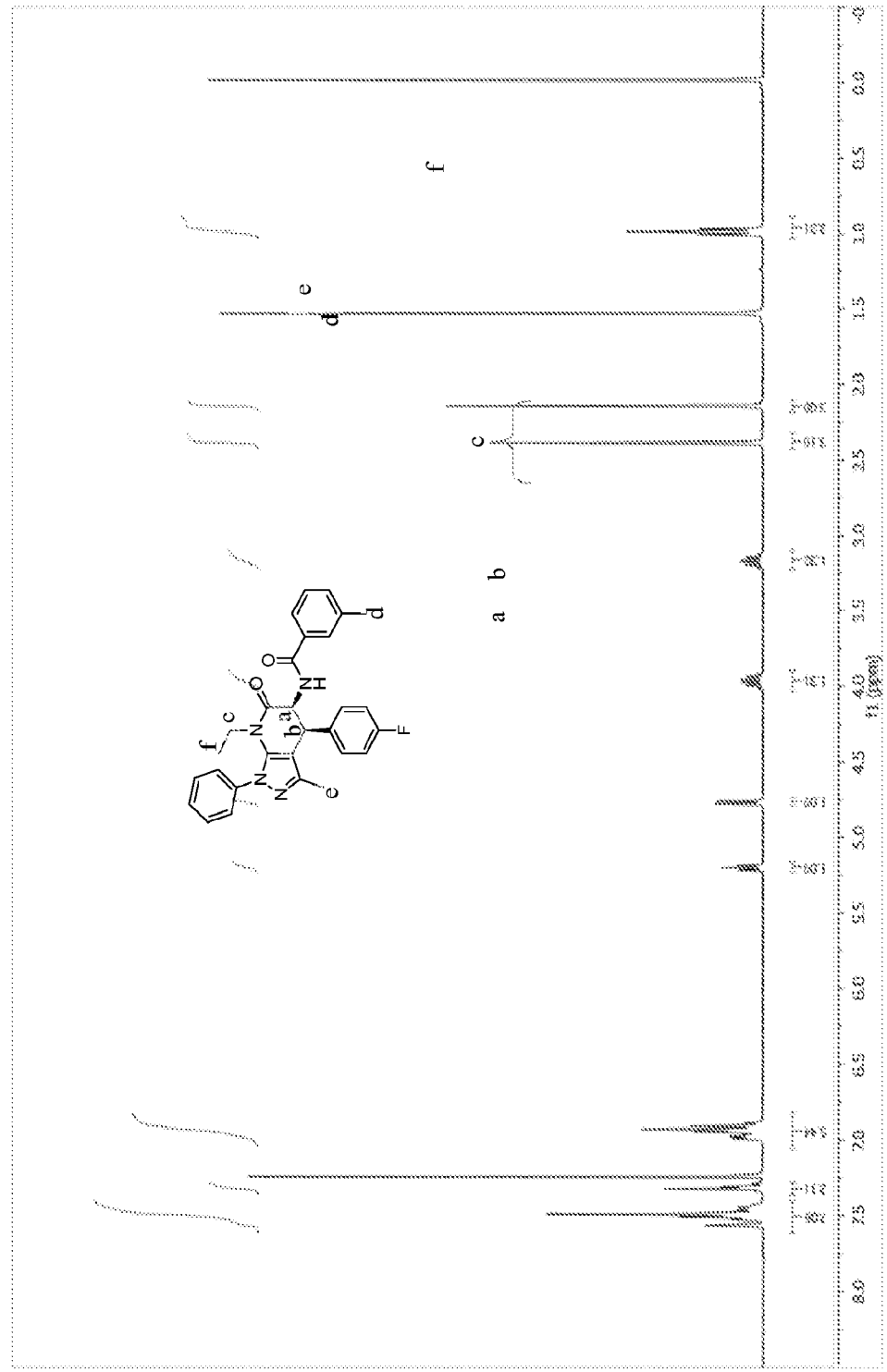
FIGS. 7A-F show images illustrating characterization of N/O alkylation of compounds 27 and 123. (A) $^1$H-NMR of compound 27. (B) $^{13}$C-NMR of compound 27. (C) HMBC of compound 27. (D) $^1$H-NMR of compound 123. (E) $^{13}$C-NMR of compound 123. (F) HMBC of compound 123.
Figure 7B:
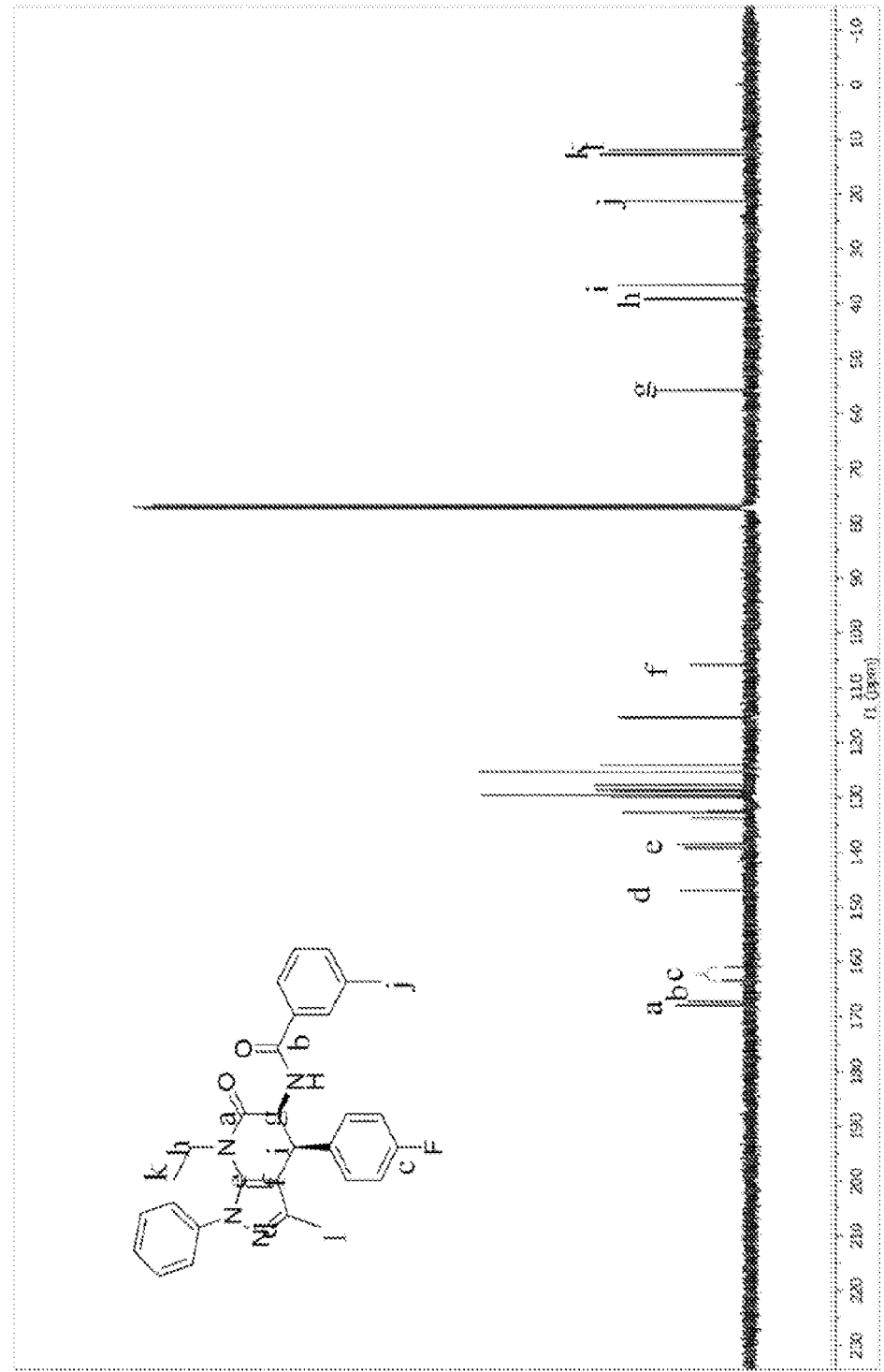
Figure 7C:
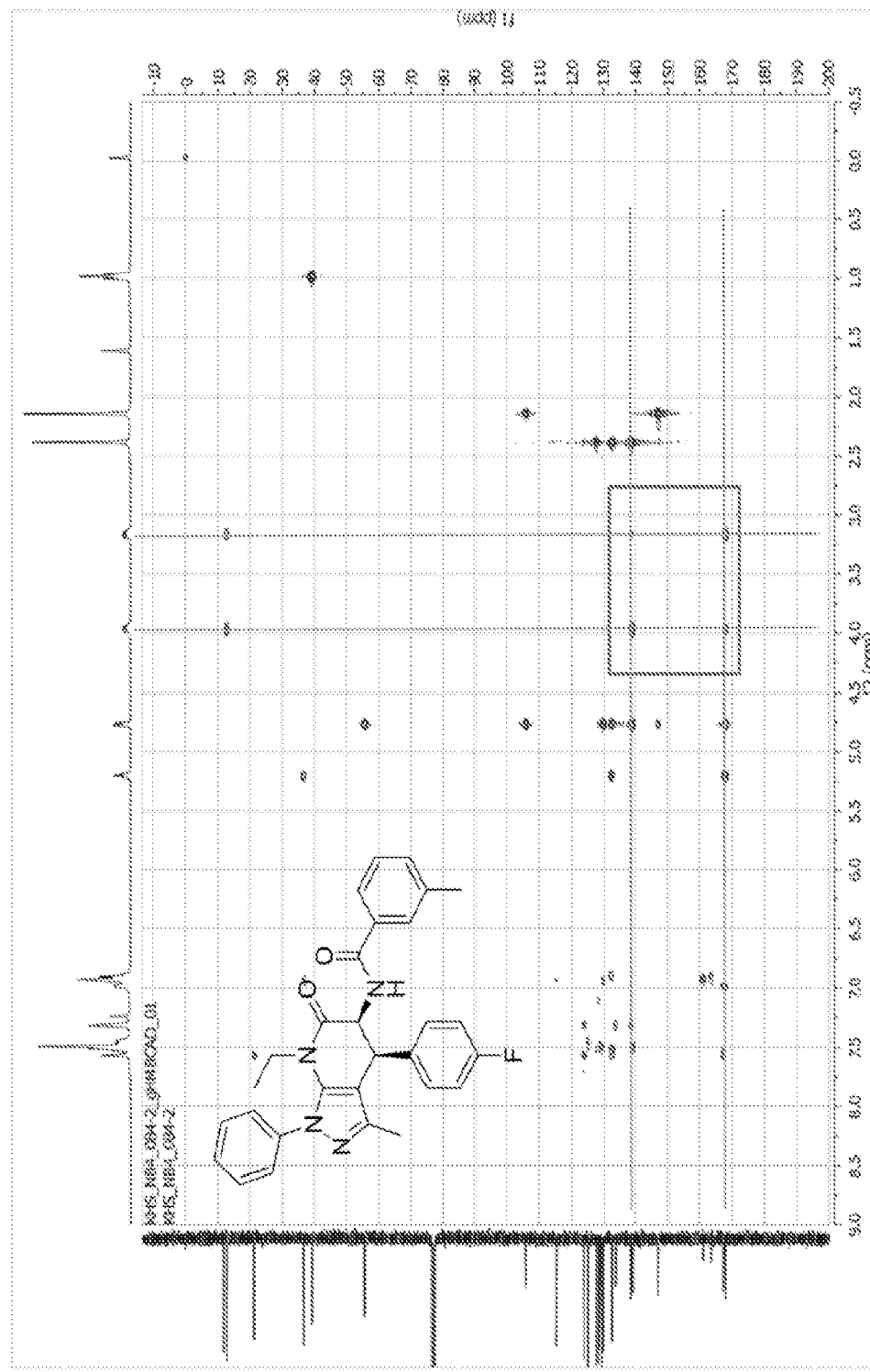
Figure 7D:
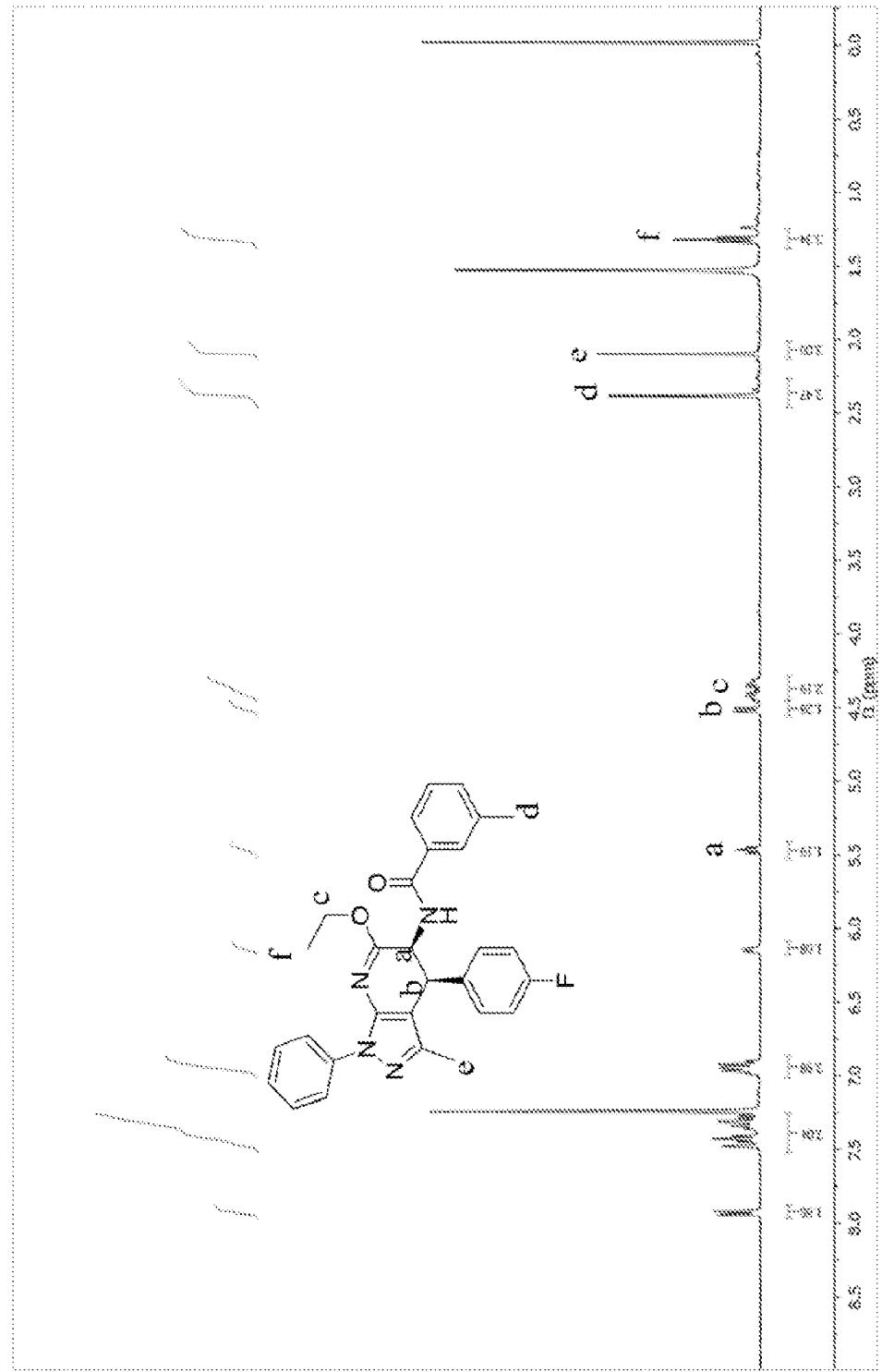
Figure 7E:
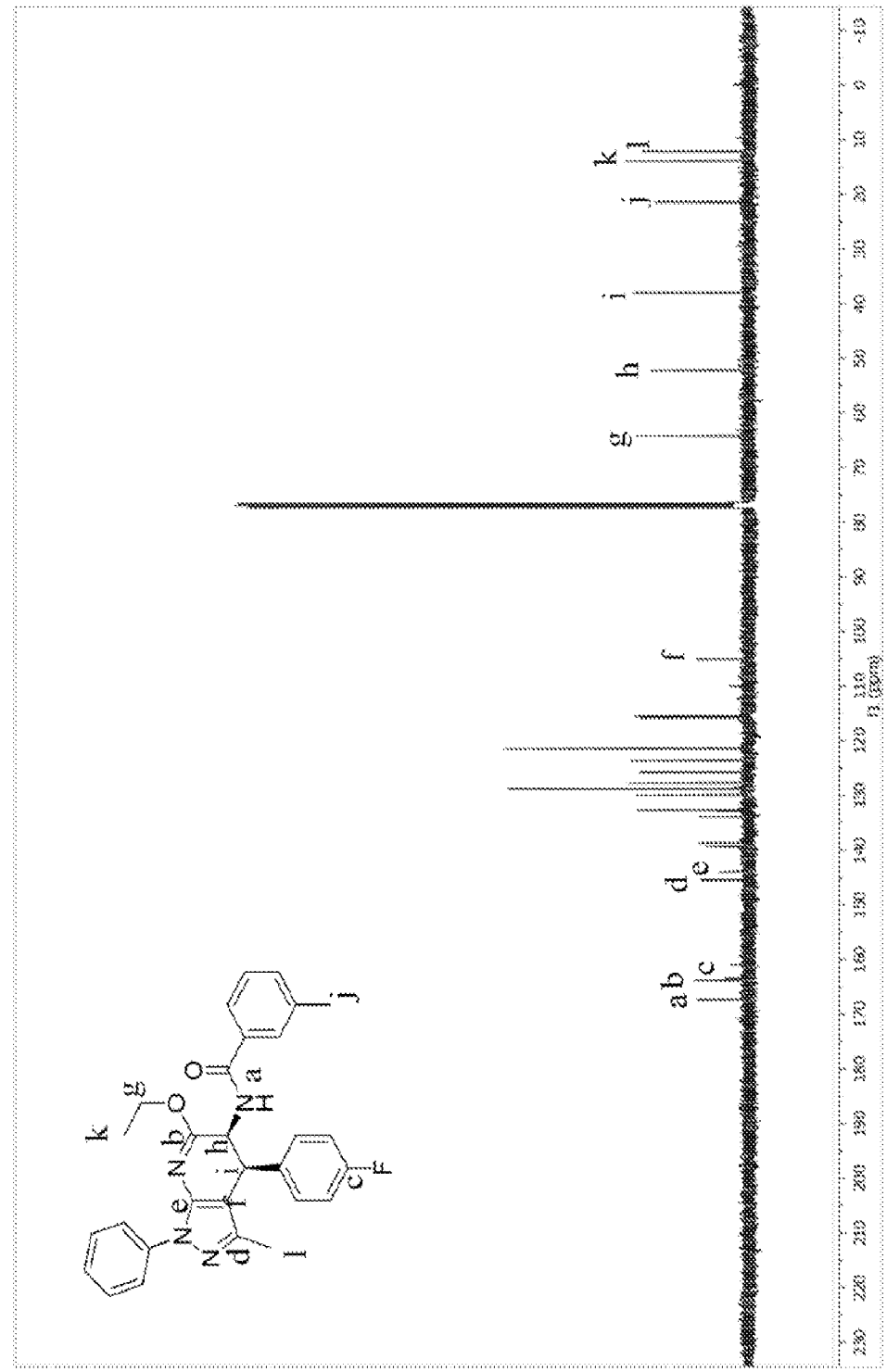
Figure 7F:
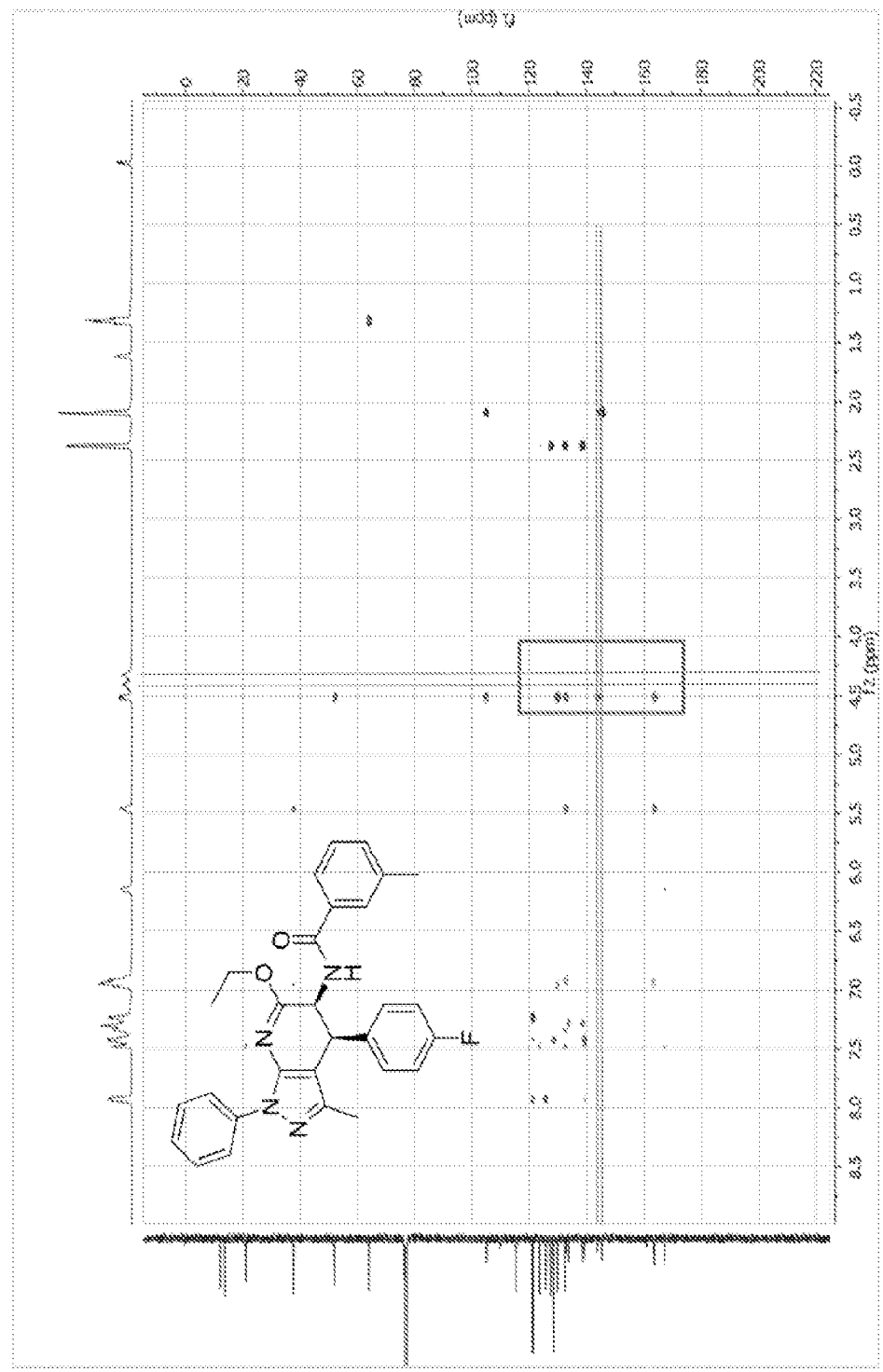

Compounds were synthesized by a short and efficient three-step procedure consisting of preparation of the oxazolone intermediate, pyrazolo-pyridone ring formation, and substitution using alkylation or acylation (FIG. 6). All compounds were purified to greater than 85% purity (as judged by HPLC/MS and proton NMR) prior to testing. Formation of the core pyrazolo-pyridone ring afforded a separable mixture of cis and trans diastereomers. Typically, the cis product appeared as the less polar spot by TLC (hexane/ethyl acetate). The cis and trans isomers were distinguished by $^1$H NMR and were assigned based on application of the Karplus equation to the $^3J_{H-H}$ vicinal proton-proton coupling for the C4 or C5 protons of pyrazolo-pyridone ring (Cis=7-8 Hz, Trans=9-11 Hz). The inactive trans-isomer could be converted to the active cis product by stirring with a catalytic amount of Lewis acid (SnCl$_2$) in refluxing chlorobenzene. However, use of a large excess of Lewis acid (10+ equivalents) favors formation of dehydrated side products rather than pyrazolo-pyridone ring formation.

Figure 8:
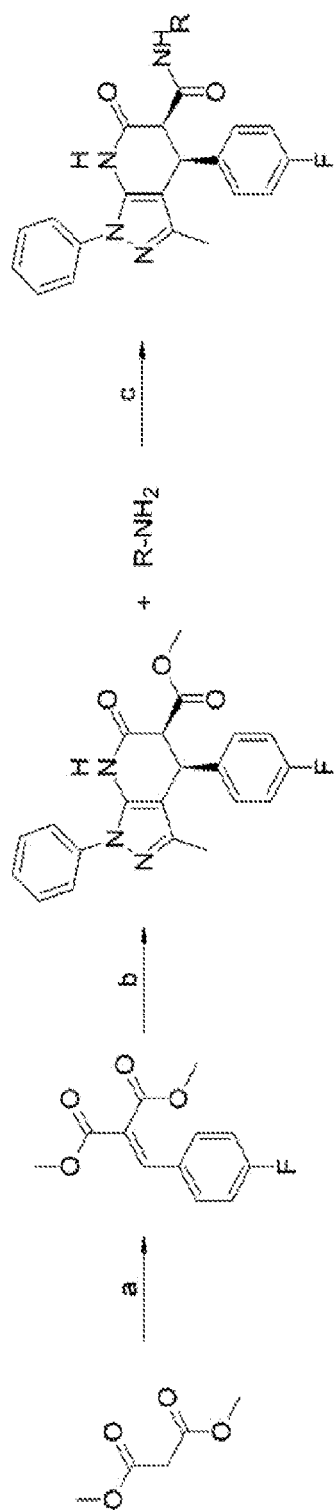
FIG. 8 shows a schematic of reverse amide synthesis. Reagents and conditions: (a) p-Fluorobenzaldehyde, piperidine, acetic acid, toluene, reflux, 16 h; (b) chlorobenzene, reflux, 16 h; (c) chlorobenzene, reflux, 16 h.
Figure 9A:
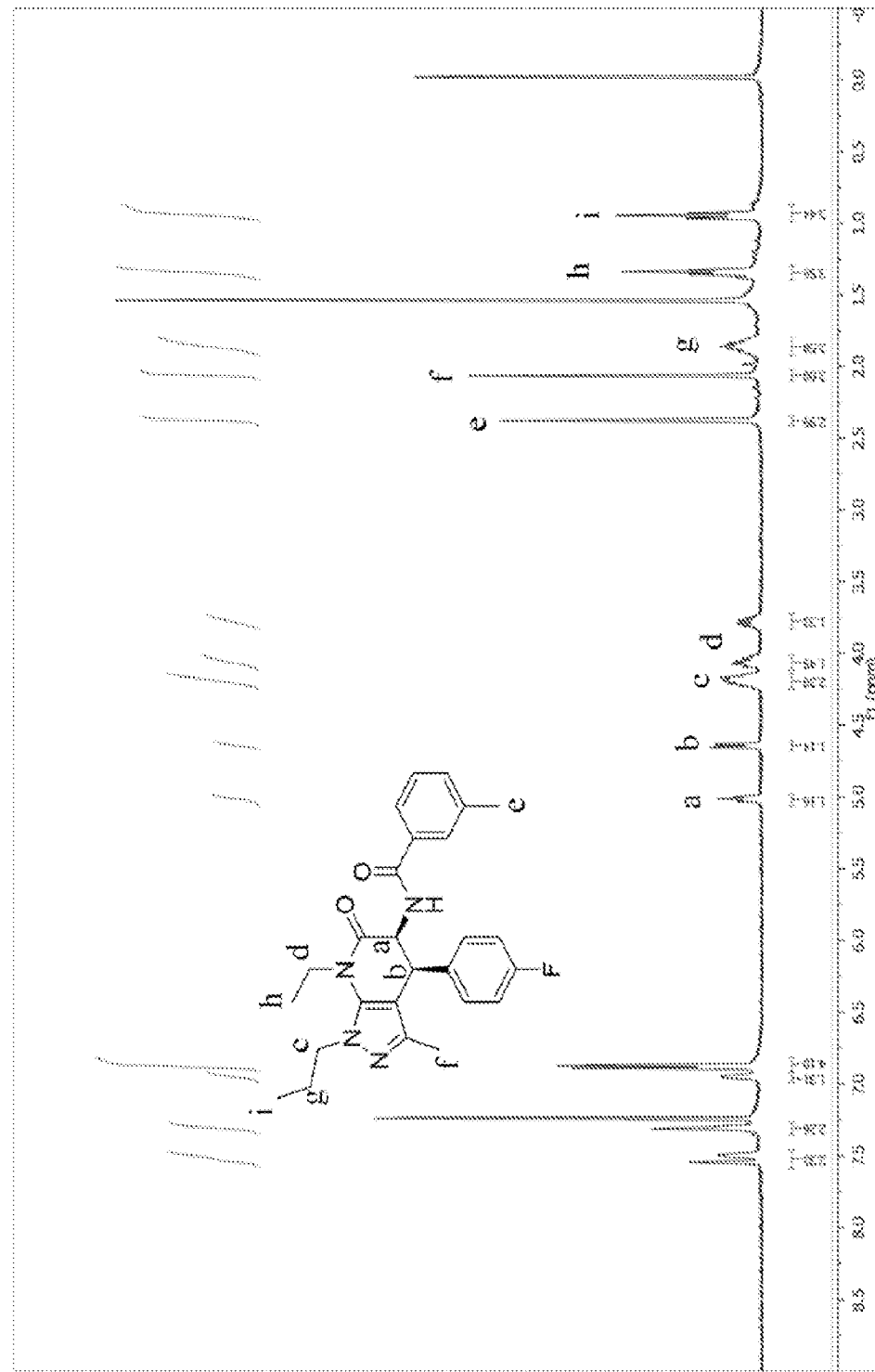
FIGS. 9A-F show images illustrating characterization of pyrazole isomers. (A) $^1$H-NMR of compound 31. (B) $^{13}$C-NMR of compound 31. (C) HMBC of compound 31. (D)
Figure 9B:
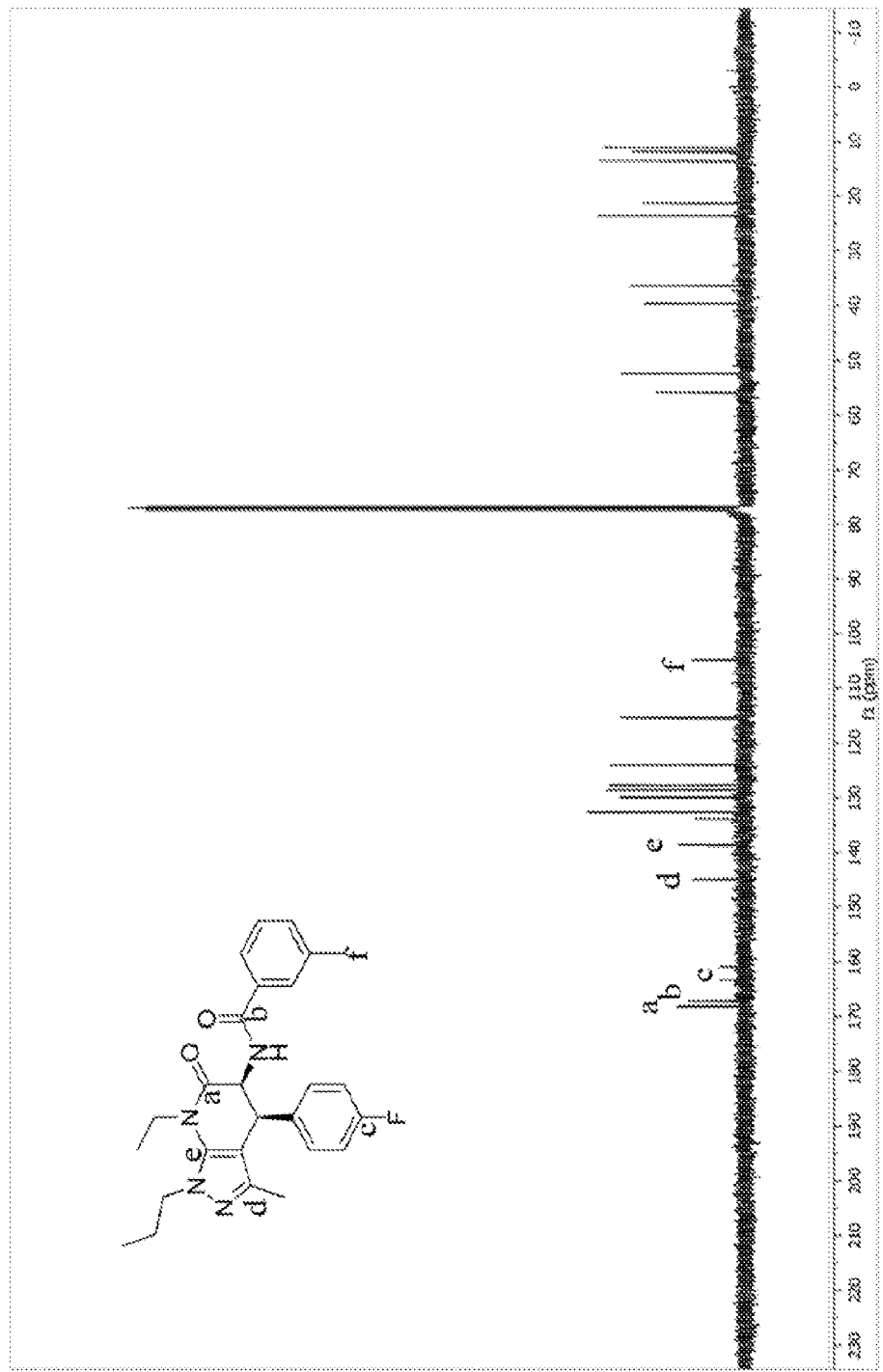
Figure 9C:
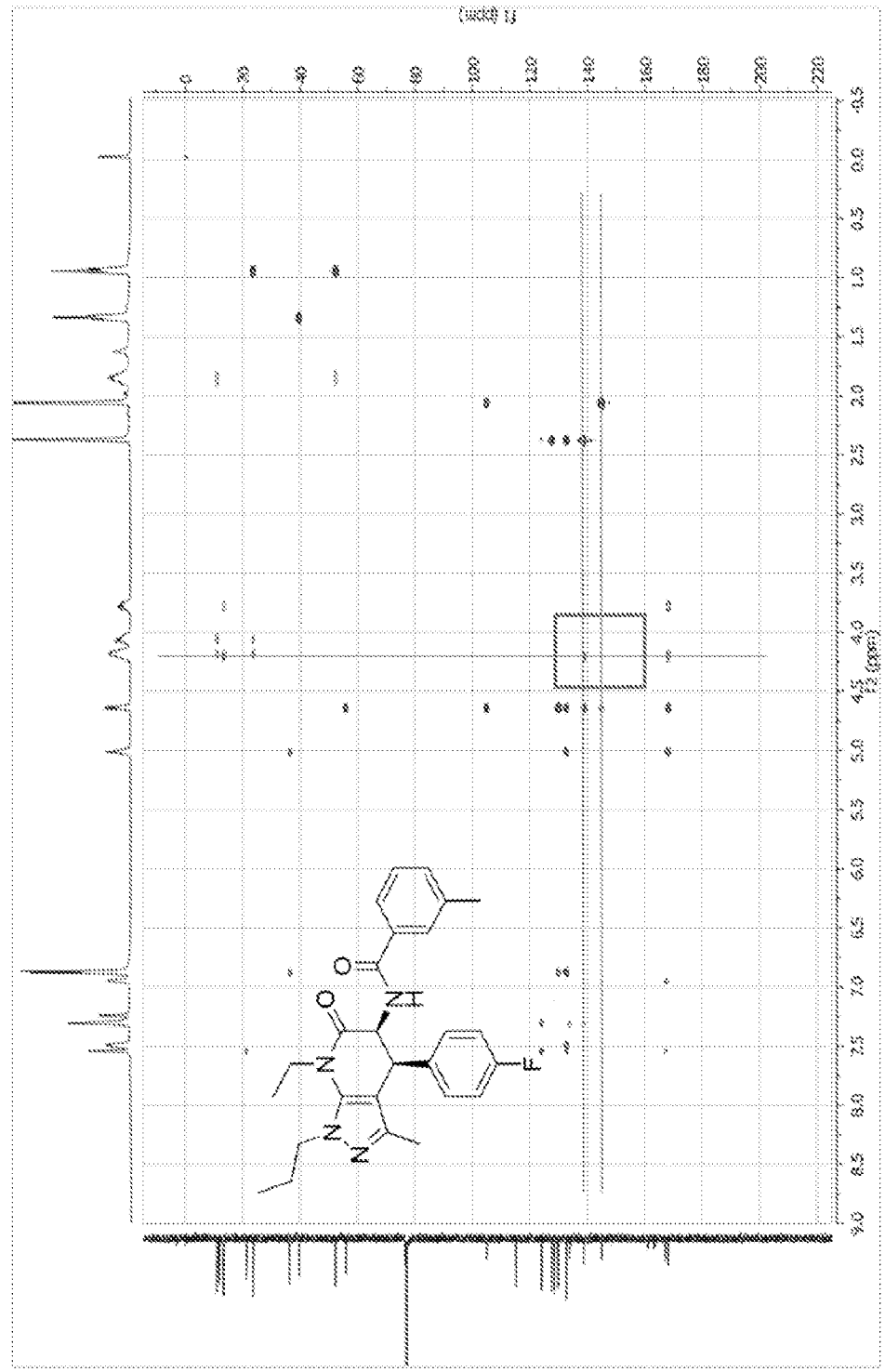
Figure 9D:
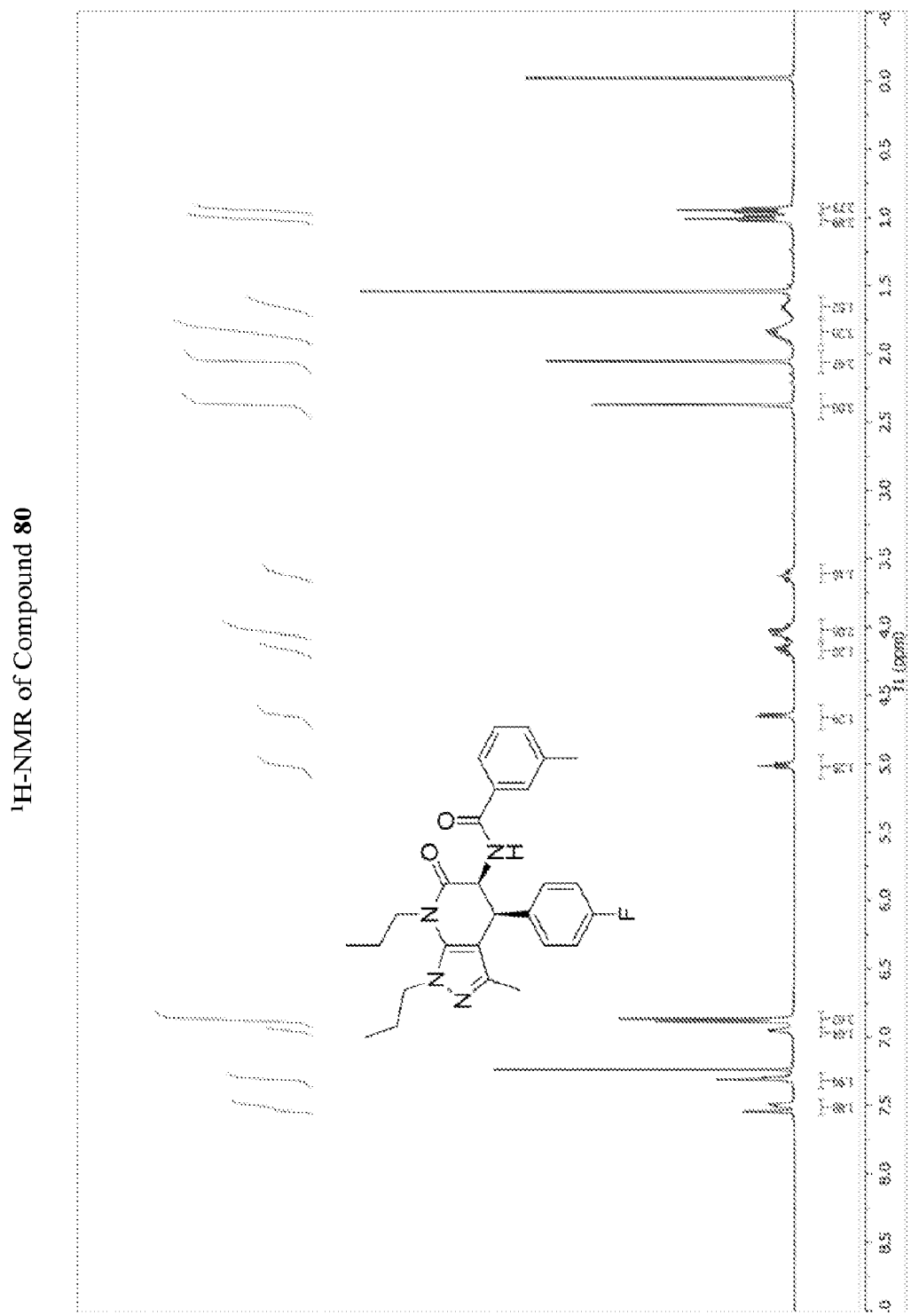
Figure 9E:
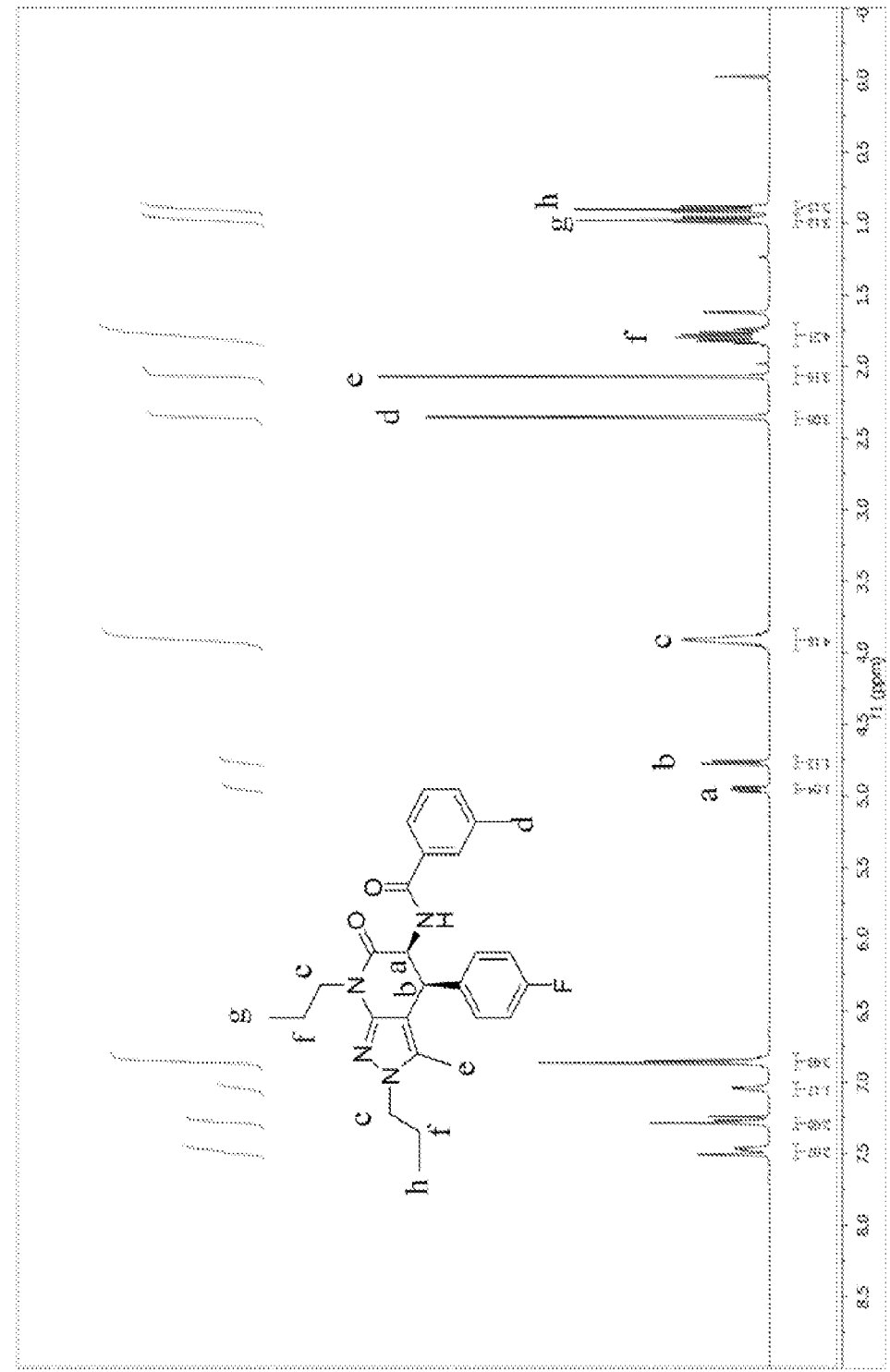
Figure 9F:
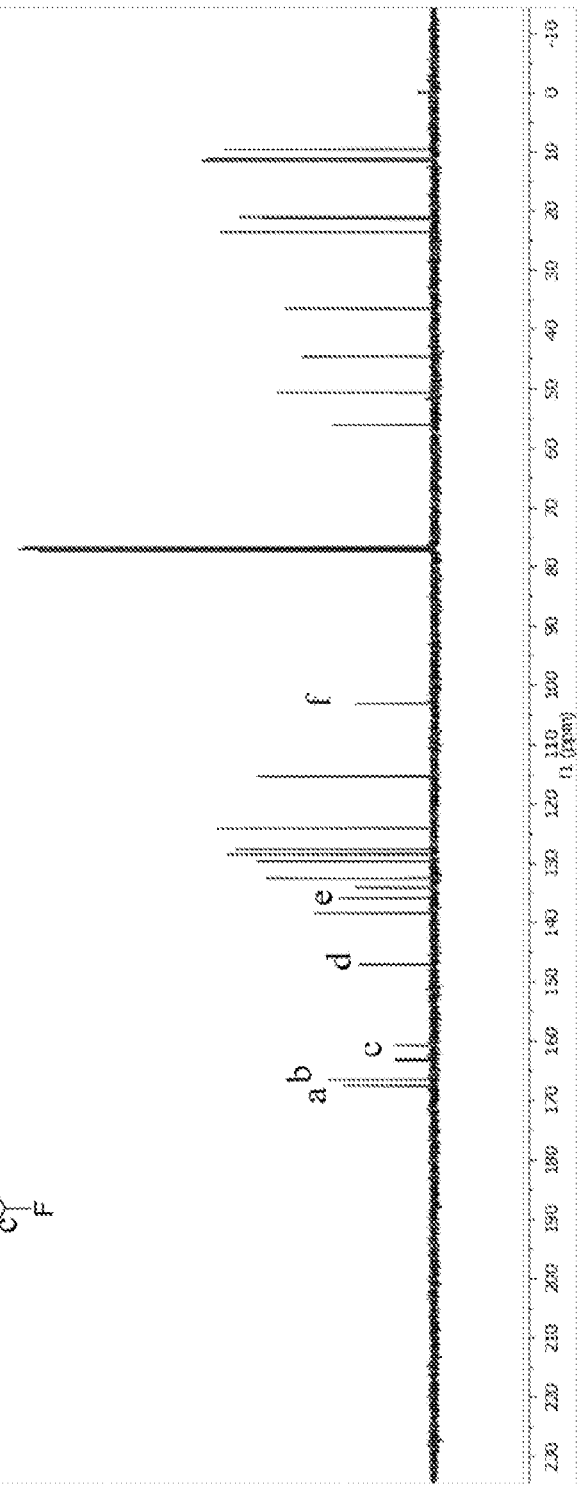
Figure 9G:
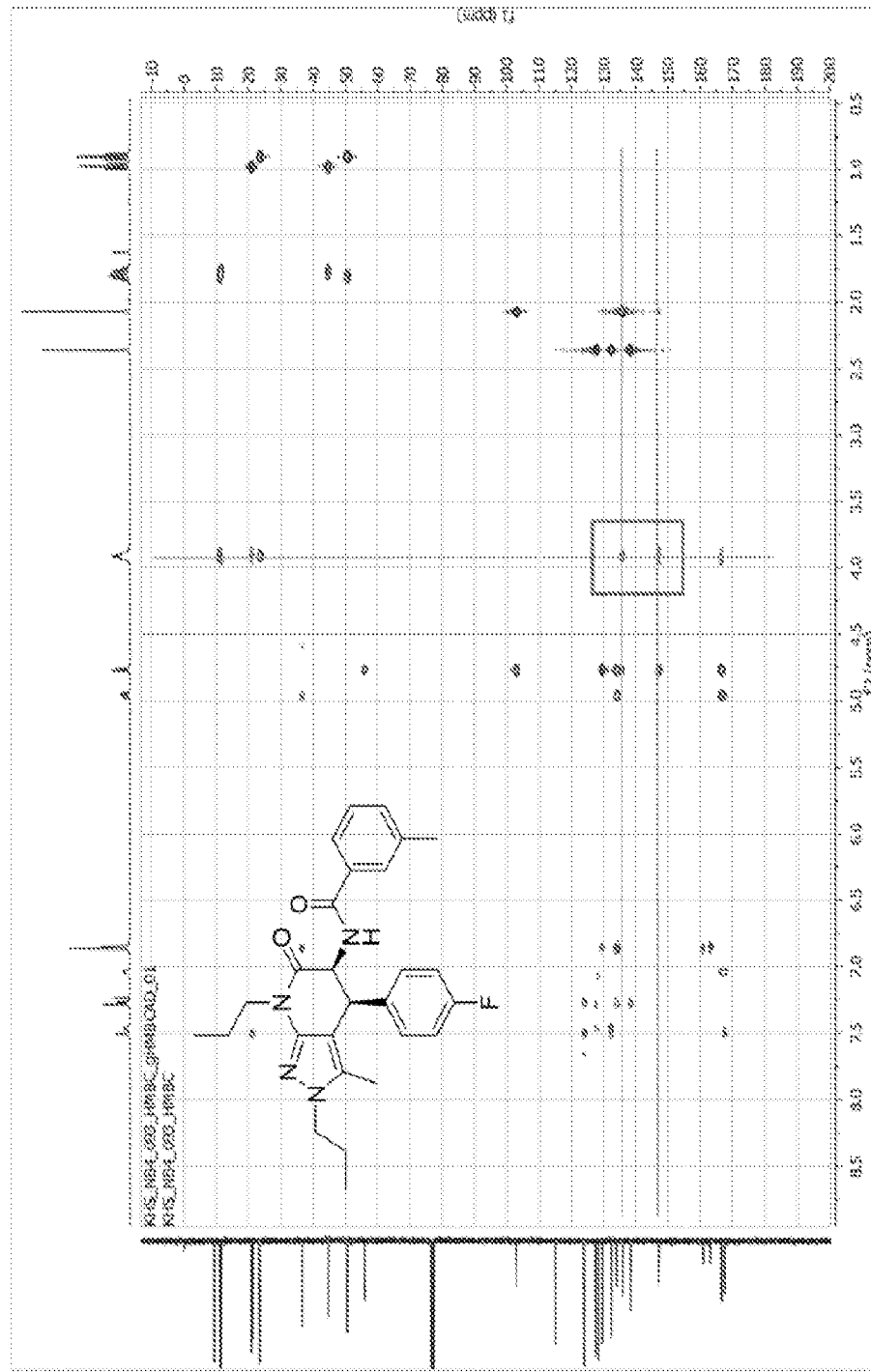

Alkyl substitution of the pyrazolo-pyridone amide proceeds under relatively mild conditions presumably due to the presence of adjacent electron-withdrawing groups that increase amide acidity. Most alkylations afforded a 5:1 mixture of N- vs. O-alkylation as determined by 2D HMBC NMR analysis (FIG. 7). Finally, a series of reverse amides were synthesized from dimethyl malonate through an alternate route: condensation, hydrolysis, and amide coupling (FIG. 8).

While the key annulation reaction (FIG. 6, step c) was previously reported using a mixture of ethylene glycol and acetic acid as the solvent, these conditions afforded low yields and complex mixtures, particularly formation of undesired ethylene glycol adducts. Switching from a nucleophilic polar protic solvent to a non-polar or polar aprotic solvent such as chlorobenzene, DMF, or NMP improved yields and suppressed formation of side products. As discussed below, the initial SAR showed that the cis-diastereomers were active and the trans-diastereomers inactive. Therefore, the reaction was optimized to favor formation of the cis-diastereomer. Addition of a catalytic amount of tin (II) chloride followed by refluxing in chlorobenzene overnight proved the most selective, affording a 3:1 cis to trans ratio, and moderate isolated yields of the pure cis product (30-40%).

Structure-Activity Relationships.

The main goal of the first phase of the work was to define and optimize the core pharmacophore by testing requirements for key rings and functional groups. The secondary goal was to define best range of pendant substituents occupying the key sub-pockets. The overall optimization strategy used a standard recursive process of sequential hypothesis-based design of analog sets and testing of those sets in models of increasing complexity to define possible structure-activity relationships (SAR) that drive further analog design. All novel analogs were prepared and tested as racemates. Potency was assessed using a TR-FRET binding assay. Four regions of the compounds were targeted, named according to the peptide ligand feature that they replace within the ligand-binding pocket, to systematically delineate the SAR: the Ile, N-acetyl, Leu, and hinge pockets (FIG. 5). During this study, over 140 analogs were prepared and tested. However, to improve clarity and readability, only key compounds, which clearly delineate SAR, are reported.

Initially, roughly 30 compounds were prepared to test the inhibitory effects of the cis- and trans-diastereomers about the core pyrazolo-pyridone ring. In general, only the cis diastereomers inhibited DCN1-UBE2M binding at or below the maximum tested concentration of 15 µM. All the trans isomers were inactive at the maximum tested concentration of 15 µM (TABLE 2). These results demonstrate the three-dimensional orientation of two aromatic rings is critical to activity. Therefore, subsequent work utilized only the purified cis-diastereomers and all data reported below represent that set of compounds.

TABLE 2

Trans-isomers

| No | R$_1$ | R$_2$ | R$_3$ | IC$_{50}$ (µM) (TR-FRET) |
|---|---|---|---|---|
| 87 | phenyl | 4-fluorophenyl | 3-methylphenyl | >15 |
| 88 | 2-fluorophenyl | 4-fluorophenyl | 3-methylphenyl | >15 |
| 89 | 4-fluorophenyl | 4-fluorophenyl | 3-methylphenyl | >15 |
| 90 | benzyl | 4-fluorophenyl | 3-methylphenyl | >15 |

TABLE 2-continued
Trans-isomers
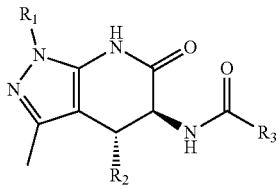
| No | R$_1$ | R$_2$ | R$_3$ | IC$_{50}$ (μM) (TR-FRET) |
|---|---|---|---|---|
| 91 | 2-pyridyl | 4-fluorophenyl | 3-methylphenyl | >15 |
| 92 | n-propyl | 4-fluorophenyl | 3-methylphenyl | >15 |
| 93 | n-butyl | 4-fluorophenyl | 3-methylphenyl | >15 |
| 94 | isopropyl | 4-fluorophenyl | 3-methylphenyl | >15 |
| 95 | tert-butyl | 4-fluorophenyl | 3-methylphenyl | >15 |
| 96 | sec-butyl | 4-fluorophenyl | 3-methylphenyl | >15 |

TABLE 2-continued

Trans-isomers

| No | R₁ | R₂ | R₃ | IC$_{50}$ (μM) (TR-FRET) |
|---|---|---|---|---|
| 97 | isobutyl | 4-fluorophenyl | 3-methylphenyl | >15 |
| 98 | NC-CH₂CH₂- | 4-fluorophenyl | 3-methylphenyl | >15 |
| 99 | cyclohexyl | 4-fluorophenyl | 3-methylphenyl | >15 |
| 100 | cyclopentyl | 4-fluorophenyl | 3-methylphenyl | >15 |
| 101 | cyclopropyl | 5-fluoropyridin-2-yl | 3-methylphenyl | >15 |
| 102 | H | 4-fluorophenyl | 3-methylphenyl | >15 |
| 103 | phenyl | phenyl | 3-methylphenyl | >15 |

TABLE 2-continued

Trans-isomers

| No | R₁ | R₂ | R₃ | IC₅₀ (μM) (TR-FRET) |
|---|---|---|---|---|
| 104 | phenyl | 3-fluorophenyl | 3-methylphenyl | >15 |
| 105 | phenyl | 3,4-difluorophenyl | 3-methylphenyl | >15 |
| 106 | phenyl | 4-chlorophenyl | 3-methylphenyl | >15 |
| 107 | phenyl | 4-bromophenyl | 3-methylphenyl | >15 |
| 108 | phenyl | 5-(trifluoromethyl)pyridin-2-yl | 3-methylphenyl | >15 |
| 109 | phenyl | 3-methylphenyl | 3-methylphenyl | >15 |
| 110 | phenyl | pyridin-4-yl | 3-methylphenyl | >15 |

TABLE 2-continued

Trans-isomers

| No | R₁ | R₂ | R₃ | IC₅₀ (μM) (TR-FRET) |
|---|---|---|---|---|
| 111 | phenyl | pyridin-3-yl | 3-methylphenyl | >15 |
| 112 | phenyl | 6-fluoropyridin-3-yl | 3-methylphenyl | >15 |
| 113 | phenyl | 4-fluorophenyl | 3-chlorophenyl | >15 |
| 114 | phenyl | 4-fluorophenyl | 3,4-dichlorophenyl | >15 |
| 115 | phenyl | 4-fluorophenyl | 3-(trifluoromethyl)phenyl | >15 |
| 116 | phenyl | 4-fluorophenyl | 4-(trifluoromethyl)phenyl | >15 |
| 117 | phenyl | 4-fluorophenyl | phenyl | >15 |

TABLE 2-continued

Trans-isomers

| No | R₁ | R₂ | R₃ | IC$_{50}$ (μM) (TR-FRET) |
|---|---|---|---|---|
| 118 | phenyl | 4-fluorophenyl | 2-methylphenyl | >15 |
| 119 | phenyl | 4-fluorophenyl | 4-methylphenyl | >15 |
| 120 | phenyl | 4-fluorophenyl | 1-naphthyl | >15 |
| 121 | tert-butyl | n-butyl | 3-methylphenyl | >15 |
| 122 | tert-butyl | cyclohexylmethyl | 3-methylphenyl | >15 |

Next, the steric and electronic requirements of the Leu pocket (TABLE 3) were examined. Introduction of a p-fluorine (3) increased potency relative to the unsubstituted benzene ring (2). A survey of other p-halogen substitutions (Cl or Br) or the p-methyl substitution (1) revealed that they were less potent than the p-fluorine (3) analog (TABLE 4). Introduction of either the p-cyano (42) or p-methoxy (43) group completely abolished activity (TABLE 4). Shifting the fluorine to the m-position of the phenyl ring (4) reduced potency by 5-fold. However, the m-, p-difluoro analog (38) retained the activity of 3. Together, these results suggest that the p-fluorine substitution is critical for binding and other small electron-withdrawing substituents, such as cyano, are not viable replacements. This trend was further reinforced by replacement with the isosteric pyridine (6), which was inactive at 15 μM, but whose activity could be partially rescued by addition of a p-fluoro substituent onto the pyridine (5). This represents a steep and narrow structure-activity relationship.

TABLE 3

SAR of Leu and hinge pocket.

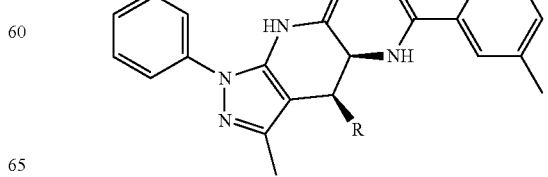

TABLE 3-continued

SAR of Leu and hinge pocket.

| No | R | IC$_{50}$ (μM) (TR-FRET) |
|---|---|---|
| 1 | 4-methylphenyl | 5.1 ± 0.6 |
| 2 | phenyl | 4.0 ± 0.5 |
| 3 | 4-fluorophenyl | 1.4 ± 0.2 |
| 4 | 3-fluorophenyl | 7.1 ± 2.6 |
| 5 | 6-fluoropyridin-3-yl | 3.5 ± 0.2 |
| 6 | pyridin-3-yl | >15 |
| 7 | benzyl | 3.0 ± 0.3 |
| 8 | propyl | 3.1 ± 0.2 |
| 9 | cyclohexyl | 1.3 ± 0.1 |

TABLE 3-continued

SAR of Leu and hinge pocket.

| No | R | IC$_{50}$ (μM) (TR-FRET) |
|---|---|---|
| 10 | phenyl | 13 ± 4 |
| 3 | 3-methylphenyl | 1.4 ± 0.2 |
| 11 | 3-CF$_3$-phenyl | 3.5 ± 0.5 |
| 12 | 3-iodophenyl | 7.1 ± 0.9 |
| 13 | 3,4-dichlorophenyl | >15 |
| 14 | 4,6-dimethylpyridazin-3-yl | >15 |
| 15 | 2-methylphenyl | >15 |
| 16 | 5-methylpyridin-3-yl | >15 |

TABLE 3-continued

SAR of Leu and hinge pocket.

| No | R | IC$_{50}$ (µM) (TR-FRET) |
|---|---|---|
| 17 | 3-tert-butylphenyl | >15 |

IC$_{50}$ values were generated using our TR-FRET binding assay and are represented as the mean of three replicates with errors reported as the standard deviation.

TABLE 4

Leu pocket

| No | R | IC$_{50}$ (µM) (TR-FRET) |
|---|---|---|
| 2 | phenyl | 4.0 ± 0.5 |
| 3 | 4-fluorophenyl | 1.4 ± 0.2 |
| 36 | 4-chlorophenyl | 3.7 ± 1.2 |
| 37 | 4-bromophenyl | 5.6 ± 2.4 |
| 38 | 3,4-difluorophenyl | 1.2 ± 0.3 |
| 4 | 3-fluorophenyl | 7.1 ± 2.6 |
| 39 | 3-methylphenyl | >15 |
| 7 | benzyl | 3.0 ± 0.3 |
| 5 | 6-fluoropyridin-3-yl | 3.5 ± 0.2 |
| 6 | pyridin-3-yl | >15 |
| 40 | pyridin-4-yl | >15 |
| 41 | 4-(trifluoromethyl)phenyl | >15 |

TABLE 4-continued

Leu pocket

[Structure: pyrazolopyridinone core with N-phenyl, methyl, R substituent, and m-tolyl benzamide]

| No | R | IC$_{50}$ (µM) (TR-FRET) |
|---|---|---|
| 1 | 4-methylphenyl | 5.1 ± 0.6 |
| 42 | 4-cyanophenyl | >15 |
| 43 | 4-methoxyphenyl | >15 |
| 44 | n-butyl | 3.1 ± 0.7 |
| 8 | n-propyl | 3.1 ± 0.2 |
| 9 | cyclohexyl | 1.3 ± 0.1 |
| 45 | cyclopentyl | 6.0 ± 0.6 |
| 46 | 4,4-difluorocyclohexylmethyl | 2.2 ± 0.2 |
| 47 | isopropyl | >15 |

The effects of more flexible substituents were also investigated. These findings were somewhat in constraint with those seen with the phenyl ring. Replacement of the phenyl ring with a benzyl group (7) retained the potency of the unsubstituted phenyl analog (2). Replacement of the aryl ring with a variety of linear (propyl or butyl) or cyclic (cyclohexyl and cyclopentyl) alkyl groups was well tolerated (8, 9, and 44-46, TABLE 4). However, introduction of the shorter, isopropyl substituent (47) removed activity. Overall, the data suggest that occupation of the hydrophobic Leu pocket is a critical driver of potency but that the pocket is relatively forgiving, within the constraints of a fixed steric bulk, with respect to precise substitutions and affords a site that could be manipulated to modulate the physiochemical properties of the inhibitors. Due to its superior potency and inert chemical nature, the remainder of our SAR study fixed the substituent targeting the Leu pocket as the p-F-phenyl.

Surveying possible phenyl ring substituents for the hinge pocket (TABLES 3 and 5) revealed that m-substitution of the phenyl ring was critical for potency. Removal of the m-methyl from the phenyl ring (10) reduced potency by 10-fold. In addition, changing the position of methyl to either the p- (14) or o- (15) position completely abrogated activity. The introduction of bulky m-substituents, such as tert-butyl (17), was not favorable. Replacement of m-CH$_3$ with the potentially less metabolically labile m-CF$_3$ group (11) resulted in a two-fold reduction in potency. Replacement with smaller halogens (F (53), Cl (54)) was not tolerated but larger, roughly isosteric, halogens (Br (55) and I (12)) retained some activity (TABLE 5). This sharp SAR about the hinge pocket is consistent with the SAR studies of NAcM-OPT. Similar to the binding of NAcM-OPT, the X-ray co-structure of 1:DCN1 revealed that the hinge pocket undergoes a structural rearrangement to produce a deep narrow hydrophobic cavity composed of alkyl and aromatic residues (Ile86, Phe89, Val102, Ile105, Ala106, Phe109, Ala111, Phe117, Phe122, Phe164) that tightly interacts with the phenyl ring.

TABLE 5

| No | R | IC$_{50}$ (μM) (TR-FRET) |
|---|---|---|
| 10 | phenyl | 13 ± 4.0 |
| 3 | 3-methylphenyl | 1.4 ± 0.2 |
| 11 | 3-CF$_3$-phenyl | 3.5 ± 0.5 |
| 53 | 3-F-phenyl | >15 |
| 54 | 3-Cl-phenyl | >15 |
| 55 | 3-Br-phenyl | 12 ± 7.6 |
| 12 | 3-I-phenyl | 7.1 ± 0.9 |
| 13 | 3,4-diCl-phenyl | >15 |
| 14 | 4-methylphenyl | >15 |

TABLE 5-continued

| No | R | IC$_{50}$ (μM) (TR-FRET) |
|---|---|---|
| 56 | 4-CF$_3$-phenyl | >15 |
| 15 | 2-methylphenyl | >15 |
| 57 | 3-F-5-methylphenyl | >15 |
| 16 | 5-methylpyridin-3-yl | >15 |
| 58 | naphthalen-2-yl | 12 ± 1.5 |
| 59 | isoquinolin-1-yl | >15 |
| 17 | 3-tert-butylphenyl | >15 |
| 60 | butyl | >15 |

Rather unexpectedly, the 3,4-dichloro phenyl analog (13), which mimics NAcM-OPT, was completely devoid of activity. This result suggests that the pyrazolo-pyridone analog does not present the aryl ring to the induced hinge pocket in the same way that NAcM-OPT does. A potential driver of this difference is the key hydrogen bond of both series with the amide backbone of Gln114 on DCN1, which locks the compound in a specific orientation. Examination of the X-ray co-structures revealed that both series have a H-bond with the same residue. However, while NAcM-OPT participates as an H-bond donor through its urea, compound 1 interacts as a H-bond acceptor through the oxygen of its amide. The highly restrictive steric and electronic requirements of this pocket are further illustrated by the complete loss of potency with either a m-F-phenyl (57) or a pyridine replacement (16). Converting the phenyl group to an aliphatic butyl chain (60) also results in loss of activity (TABLE 5). Taken together, the SAR reveals that the hinge pocket requires a phenyl ring with a small hydrophobic substituent, most efficiently met by a m-methyl substituted phenyl ring.

Finally, with respect to the Leu pocket, whether the reverse amide could maintain the key hydrogen bonding interaction with Gln114 or potentially switch the mode of interaction for compound 1 from an H-bond acceptor to an H-bond donor, as observed with NAcM-OPT, was tested. Investigating five analogs, including the m-methyl (128) and m-, p-dichloro phenyl (131) derivatives, it was found that the reverse amide was not tolerated (TABLE 6). Further optimization studies fixed the substituent targeting the Leu pocket as the p-F-phenyl and the substituent targeting the hinge pocket as m-tolyl.

TABLE 6

Reverse amide

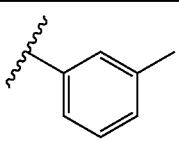

| No | R | IC$_{50}$ (µM) (TR-FRET) |
|---|---|---|
| 128 | 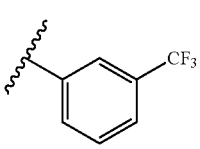 [SMILES: *c1cccc(C(F)(F)F)c1] | >15 |
| 129 | 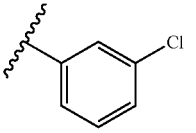 [SMILES: *c1cccc(Cl)c1] | >15 |

TABLE 6-continued

Reverse amide

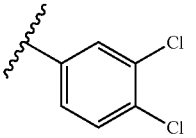 [SMILES: *c1ccc(Cl)c(Cl)c1]

| No | R | IC$_{50}$ (µM) (TR-FRET) |
|---|---|---|
| 130 | 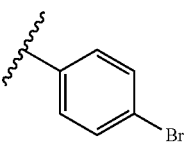 [SMILES: *c1ccc(Br)cc1] | >15 |
| 131 | | >15 |
| 132 | | >15 |

Next, the SAR of substituents reaching into the Ile pocket (TABLES 7-8) was explored. Introduction of a methylene between the phenyl and pyrazole rings (18) reduced activity by 10 times. Thus, there is a limitation on the size of the substituent targeting this pocket. Introduction of a fluoro substitution at either the o- (61) or p- (62) positions had little effect on potency (TABLE 8). Since one of the design goals was to reduce the aryl ring count, replacements of the phenyl ring were investigated. Replacements of aryl ring with aliphatic chain was successful in many cases (22-25). Linear alkyl chains three (21) or two (65) carbons in length proved roughly equipotent to the phenyl derivative (3), while a four-carbon chain (63) resulted in a three-fold reduction in potency. The unsubstituted (20) and methylated (66) pyrazoles were inactive (TABLE 8). Introduction of substituted alkyl chains (22, 23, and 24), designed to mimic the Ile residue displayed two-five times better potency than the phenyl derivative (3). Introduction of a methyl group alpha to the pyrazole afforded an additional chiral center and the resulting diastereomers were separable by silica gel chromatography. In the case of the 2-butyl derivative, the diastereomers proved roughly equally potent (22a, b). However, in the cases of the 1-cyclopropyl-2-propane (70a, b) and 1,1, 1-trifluoro-2-propane (71a, b) derivatives, one isomer was two to three times more potent. The cyclopropyl compound (25) was roughly equipotent to the phenyl (3). However, the cyclopentyl (24) and cyclohexyl (72) and two and three-fold more potent respectively. The replacement of the phenyl ring with a polar pyridine (19) or addition of a polar atom to the linear chain (26) significantly decreased potency, demonstrating a strong preference for hydrophobic substituents.

TABLE 7

SAR of Ile and N-acetyl pocket.

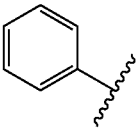 [SMILES: *c1ccccc1]

| No | R | IC$_{50}$ (μM) (TR-FRET) |
|---|---|---|
| 3 | 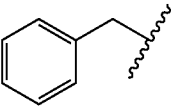 [SMILES: *Cc1ccccc1] | 1.4 ± 0.2 |
| 18 | 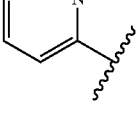 | >15 |
| 19 | 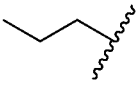 [SMILES: *CCC] | >15 |
| 20 | H | >15 |
| 21 | 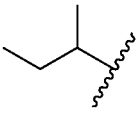 [SMILES: *C(C)CC] | 1.2 ± 0.2 |
| 22-a, b | 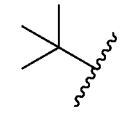 [SMILES: *C(C)(C)C] | 0.7 ± 0.1 (TLC-up) 0.6 ± 0.1 (TLC-down) |
| 23 | 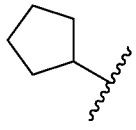 | 0.5 ± 0.1 |
| 24 | 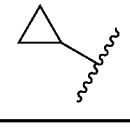 | 0.3 ± 0.1 |
| 25 | 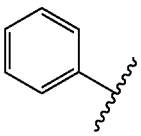 [SMILES: *c1ccccc1] | 2.0 ± 0.1 |

TABLE 7-continued

SAR of Ile and N-acetyl pocket.

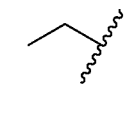

| No | R$_1$ | R$_2$ | IC$_{50}$ (μM) (TR-FRET) |
|---|---|---|---|
| 27 | 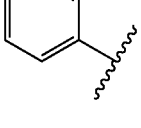 | 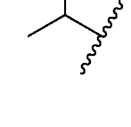 [SMILES: *CC] | 0.2 ± 0.1 |
| 28 | 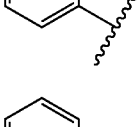 | 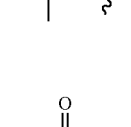 | 4.1 ± 0.8 |
| 29 | 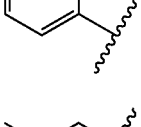 | 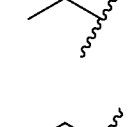 | 7.1 ± 1.7 |
| 30 | 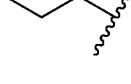 | 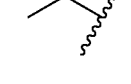 | 5.6 ± 0.8 |
| 31 | 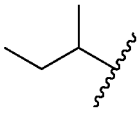 | 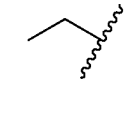 [SMILES: *CC] | 0.2 ± 0.1 |
| 32-a, b |  |  | 1.2 ± 0.1 (TLC-up) 0.5 ± 0.2 (TLC-down) |
| 33 | 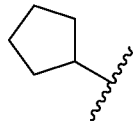 | | 2.3 ± 0.8 |
| 34 | 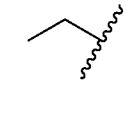 | 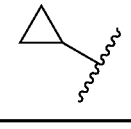 | 0.8 ± 0.1 |
| 35 | 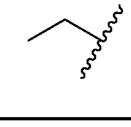 | | 0.2 ± 0.1 |

IC$_{50}$ values were generated using our TR-FRET binding assay and are represented as the mean of three replicates with errors reported as the standard deviation.

TABLE 8

Ile pocket

| No | R or Structure | IC$_{50}$ (μM) (TR-FRET) |
|---|---|---|
| 3 | phenyl | 1.4 ± 0.2 |
| 61 | 2-fluorophenyl | 1.0 ± 0.2 |
| 62 | 4-fluorophenyl | 2.3 ± 0.1 |
| 18 | benzyl | >15 |
| 19 | 2-pyridyl | >15 |
| 63 | n-pentyl | 4.7 ± 0.9 |
| 21 | n-butyl | 1.2 ± 0.2 |
| 64 | CF$_3$CH$_2$- | 4.1 ± 1.0 |
| 65 | n-propyl (branched) | 1.3 ± 0.1 |

TABLE 8-continued

Ile pocket

| No | R or Structure | IC$_{50}$ (μM) (TR-FRET) |
|---|---|---|
| 66 | methyl | >15 |
| 20 | H | >15 |
| 26 | HO-CH$_2$CH$_2$- | >15 |
| 67 | NC-CH$_2$CH$_2$- | 9.1 ± 1.6 |
| 22-a, b | sec-butyl | 0.7 ± 0.1 (TLC-up) 0.6 ± 0.1 (TLC-down) |
| 68 | isobutyl | 1.3 ± 0.2 |
| 69 | isopropyl | 0.3 ± 0.1 |
| 23 | tert-butyl | 0.5 ± 0.1 |
| 70-a, b | cyclopropyl-CH(CH$_3$)- | 0.7 ± 0.1 (TLC up) 0.3 ± 0.1 (TLC down) |
| 71-a, b | F$_3$C-CH(CH$_3$)- | 2.3 ± 0.1 (TLC-up) 0.9 ± 0.1 (TLC-down) |
| 72 | cyclohexyl | 0.5 ± 0.1 |

TABLE 8-continued

Ile pocket

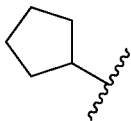

| No | R or Structure | IC$_{50}$ (µM) (TR-FRET) |
|---|---|---|
| 24 | 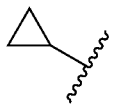 [SMILES: *C1CC1] | 0.3 ± 0.1 |
| 25 |  | 2.0 ± 0.1 |

The effects of substituting the other pyrazole nitrogen were also examined (TABLE 9; FIG. 9). All such analogs were inactive at the maximum tested concentration of 15 µM. Therefore, the alignment of pyrazolo-pyridone scaffold's amide bond and pyrazole's substituent are both crucial for binding.

TABLE 9

Pyrazole position isomer

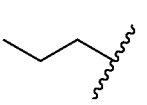

| No | R$_1$ | R$_2$ | IC$_{50}$ (µM) (TR-FRET) |
|---|---|---|---|
| 133 | H | 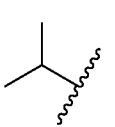 | >15 |
| 134 | H | 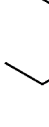 | >15 |
| 135 | H | 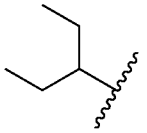 [SMILES: *C(CC)CC] | >15 |
| 136 | H | 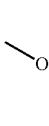 | >15 |
| 137 | H | 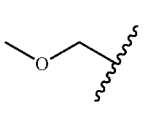 | 5.7 ± 0.9 |
| 138 | H |  | >15 |
| 139 | H | 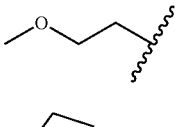 | >15 |
| 140 | H | 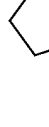 | 5.4 ± 0.5 |
| 141 | 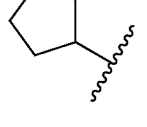 |  | >15 |
| 142 | 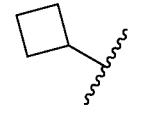 [SMILES: *C1CCC1] | 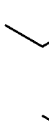 | >15 |
| 143 | 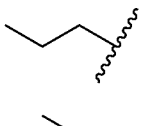 | 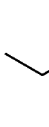 | >15 |

To understand requirements for binding to the N-acetyl pocket, whether substitution of the pyridone ring nitrogen (TABLES 7 and 10) could mimic the N-terminal acetyl of the native UBE2M substrate was investigated. Alkyl substitution significantly increased potency with a relative order of no-substituent<propyl<methyl<ethyl (TABLE 10). In addition to efficiently occupying the N-acetyl pocket, alkyl substitution of the pyridone improves hydrophobic interactions in the Leu pocket by pushing the p-F-phenyl substituent deeper into the Leu hydrophobic pocket (FIG. 10).

Interestingly, introduction of acyl groups (29, 30), directly mimicking UBE2M's N-terminal acetyl, gave compounds with poor potency. The magnitude of the observed potency improvement is consistent with previous binding studies of the native substrate, which demonstrated that capping of UBE2M's N-terminus with an acetyl enhances affinity 10-times relative to capping with a formyl group.

TABLE 10

Ile & N-acetyl pocket

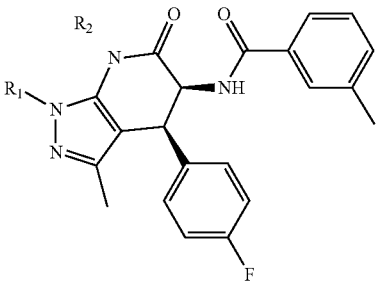

| No | R₁ | R₂ | IC$_{50}$ (μM) (TR-FRET) |
|---|---|---|---|
| 73 | phenyl | t-Bu-like | 0.5 ± 0.1 |
| 27 | phenyl | i-Pr | 0.2 ± 0.1 |
| 74 | phenyl | n-Pr | 1.0 ± 0.2 |
| 28 | phenyl | i-Bu | 4.1 ± 0.8 |
| 75 | phenyl | CH₂CF₃ | 7.0 ± 1.7 |
| 76 | phenyl | CH₂OCH₃ | 0.5 ± 0.1 |
| 29 | phenyl | CH₂C(O)CH₃ | 7.1 ± 1.7 |

TABLE 10-continued

Ile & N-acetyl pocket

| No | R₁ | R₂ | IC$_{50}$ (μM) (TR-FRET) |
|---|---|---|---|
| 30 | phenyl | C(O)CH₃ | 5.6 ± 0.8 |
| 77 | 2-F-phenyl | i-Pr | 0.2 ± 0.1 |
| 78 | 4-F-phenyl | i-Pr | 0.5 ± 0.1 |
| 79 | n-Bu | i-Pr | 0.6 ± 0.1 |
| 31 | n-Pr | i-Pr | 0.2 ± 0.1 |
| 80 | n-Pr | n-Pr | 1.2 ± 0.1 |
| 81 | Et | i-Pr | 0.4 ± 0.1 |
| 82 | CH₂CF₃ | i-Pr | 0.7 ± 0.1 |
| 32-a, b | sec-Bu | i-Pr | 1.2 ± 0.1 (TLC-up) 0.5 ± 0.1 (TLC-down) |
| 83 | sec-Bu | C(O)CH₃ | 5.3 ± 0.9 |

TABLE 10-continued

Ile & N-acetyl pocket

[Structure: pyrazolo-pyridinone scaffold with R1 on pyrazole N, R2 on amide N, 4-fluorophenyl at C4, and N-(3-methylbenzoyl)amide]

| No | R1 | R2 | IC$_{50}$ (μM) (TR-FRET) |
|---|---|---|---|
| 84 | isopropyl | sec-butyl | 0.5 ± 0.1 |
| 33 | tert-butyl | sec-butyl | 2.3 ± 0.8 |
| 85 | 1,1,1-trifluoro-isopropyl (F$_3$C-CH(CH$_3$)-) | sec-butyl | 7.3 ± 1.1 (TLC-up) |
| 86 | cyclohexylmethyl | sec-butyl | 0.8 ± 0.1 |
| 34 | cyclopentylmethyl | sec-butyl | 0.8 ± 0.1 |
| 35 | cyclopropylmethyl | sec-butyl | 0.2 ± 0.1 |

The compound reorientation, induced by substituting the pyridone, subtly effected the SAR about the Ile pocket. Linear alkyl and aryl Ile substituents remained roughly equally potent. However, sterically hindered alkyl Ile substituents (32-34) showed decreased potency relative to the unmodified pyridone. These results imply a steric interaction between the two adjacent substituents at the Ile and the N-acetyl pocket that induce an unfavorable change in their orientation. Interestingly, the cyclopropyl group (35) was an exception to this trend and increased potency about 10 times from its parent moiety. O-alkylated isomers were also prepared but proved inactive at the maximum tested concentration of 15 μM (TABLE 11).

TABLE 11

O-alkylated isomer

[Structure: O-alkylated pyrazolo-pyridine scaffold with R1 on pyrazole N, R2 on the O, 4-fluorophenyl at C4, and N-(3-methylbenzoyl)amide]

| No | R1 | R2 | IC$_{50}$ (μM) (TR-FRET) |
|---|---|---|---|
| 123 | benzyl | sec-butyl | >15 |
| 124 | benzyl | n-butyl | >15 |
| 125 | benzyl | isobutyl | >15 |
| 126 | 4-fluorobenzyl | sec-butyl | >15 |
| 127 | neopentyl | sec-butyl | 6.4 ± 0.6 |

Biochemical and Cellular Profiling of Compound 27

As discussed above, DCN1 is one of the five human paralogues (DCN1-5), which display high structural similarity. In biochemical assays, all five isoforms can stimulate cullin neddylation. In order to assess selectivity, a pulse-chase assay was used to test the effect of the most potent compound (27) on NEDD8 transfer stimulated by each of the five DCN isoforms. At the concentration employed for cellular studies (10 μM), compound 27 was highly selective, inhibiting DCN1 and DCN2, which are 100% identical in the N-Ac-Met binding pocket, but not DCN3, DCN4, or DCN5 stimulated cullin neddylation (FIG. 11). The observed selectivity can be explained by subtle differences between the binding pockets on DCN1/2 and DCNs 3-5. The high specificity of 27 amongst the highly homologous family of enzymes implies it is likely to be selective against other less-related binding pockets, as has been demonstrated for NAcM-OPT.

To confirm the cellular effects on cullin neddylation, the most potent compound (27) and an inactive trans-isomer

(87) were tested for inhibition of steady-state cullin neddylation using an immunoblot assay in HCC95 cells (FIG. 12). As previously observed for other DCN1/2 selective inhibitors, compound 27 and NAcM-OPT but not the negative control (87) or DMSO selectively inhibits steady-state Cul1 and Cul3 neddylation in HCC95 cells. As previously seen with NAcM-OPT, the maximal efficacy of inhibition of neddylation by DCN1 inhibition is less than that seen with inhibition of the E1 by MLN4924. It was previously demonstrated that the residual activity is due to DCN1-independent neddylation. The residual neddylation instead likely represents the basal activity of RBX1, the other co-E3 enzyme that works with DCN1.

Discussion and Conclusions

In conclusion, a series of pyrazolo-pyridone analogs were investigated as novel inhibitors of the DCN1-UBE2M interaction and cullin neddylation. The efficient synthetic routes outlined in FIG. 6 enabled rapid access to analogs to define the SAR and also allowed gram scale preparation of analog 27. Comparative analysis of multiple X-ray co-crystal structures enabled rational drug design to access the N-acetyl pocket and refine peripheral interactions, providing a 10-fold boost in potency. Empirical systematic investigations on the structure-activity relationships yielded compound (27) with 25-fold better potency than the hit compound (1). Together, the data also allowed defining the minimum pharmacophore. The SAR revealed three critical drivers for potency (FIG. 10): (1) stereochemistry of the pyrazolo-pyridones, with the cis isomer being much more active than its trans isomer; (2) filling the N-acetyl binding pocket, with the ethyl substitution on pyrazolo-pyridone ring increasing potency 5-10 fold; and (3) utilization of a small branched alkyl chain to fill the Ile pocket. Finally, a high-resolution X-ray co-crystal structure of compound 27 bound to DCN1 was acquired, confirming the binding mode and SAR hypotheses that the ethyl group on pyrazolo-pyridone ring efficiently fills the N-acetyl pocket and pushes the compound deeper into the Leu pocket (FIG. 10).

Compound 27 binds to the targeted pocket on DCN1 (FIG. 10), blocks DCN1-mediated cullin neddylation (FIG. 11), selectively reduces level of steady-state Cul1 and Cul3 neddylation in HCC95 cells (FIG. 12), and engages cellular DCN1 (FIG. 13). Compound 27 more potently inhibits cellular neddylation than the first-generation inhibitor NAcM-OPT, showing that the original design goal of filling the N-acetyl pocket successfully provided more potent inhibitors. The cellular activity of the compound suggests strong potential to deliver a potent and selective DCN1 inhibitor enabling pharmacological validation of DCN1 in animal models.

Experimental Section

TR-FRET Assay.

The TR-FRET assay was carried out in black 384-well microtiter plates at a final volume of 20 µM per well. To screen library compounds, the assay cocktail was prepared as a mixture of 50 nM biotin-DCN1, 20 nM Ac-UBE2M12-AlexaFluor488, 2.5 nM Tb streptavidin (ThermoFisher) in assay buffer (25 mM HEPES, 100 mM NaCl, 0.1% Triton X-100, 0.5 mM DTT, pH 7.5). The assay cocktail was then incubated for 1 h at room temperature and distributed using a WellMate instrument (Matrix). Compounds to be screened were added to assay plates from DMSO stock solutions by pin transfer using 50SS pins (V&P Scientific). The assay mixture was incubated for 1 h at room temperature prior to measuring the TR-FRET signal with a PHERAstar or Clariostar plate reader (BMG Labtech)) equipped with excitation modules at 337 nm and emissions at 490 and 520 nm. We set the integration start to 100 s and the integration time to 200 s. The number of flashes was set to 100. The ratio of 520:490 was used as TR-FRET signal in calculations. Assay end points were normalized from 0% (DMSO only) to 100% inhibition (unlabeled competitor peptide) for hit selection and curve fitting. All compounds were tested in triplicate or more.

Cellular Thermal Shift Assay.

The cellular thermal shift assay (CETSA) was performed according to the previously published procedure. Briefly, 500,000 HCC95 cells were aliquoted in 100 µL of PBS and DMSO or the indicated compound (10 µM) was added (0.1% final DMSO). Mixtures were incubated on ice for 1 h, and the cells were washed three times with PBS buffer. Cell pellets were resuspended in 50 µL of PBS and heated for 3 min at the indicated temperature in a thermocycler. Cells were lysed by three rounds of freezing in liquid nitrogen and thawing on ice. After pelleting at 20,000 rpm for 20 min at 4° C., equal amounts of supernatant were removed and blotted with the indicated antibodies.

Chemistry Experimental

General. All NMR data was collected at room temperature in $CDCl_3$ or $(CD_3)_2SO$ on a 400 or 500 MHz Bruker or Agilent instrument. Chemical shifts (δ) are reported in parts per million (ppm) with internal $CHCl_3$ (δ 7.26 ppm for $^1H$ and 77.00 ppm for $^{13}C$), internal DMSO (S 2.50 ppm for $^1H$ and 39.52 ppm for $^{13}C$), or internal TMS (S 0.0 ppm for $^1H$ and 0.0 ppm for $^{13}C$) as the reference. $^1H$ NMR data are reported as follows: chemical shift, multiplicity (s=singlet, bs=broad singlet, d=doublet, t=triplet, q=quartet, p=pentet, sext=sextet, sep=septet, m=multiplet, dd=doublet of doublets, dt=doublet of triplets, td=triplet of doublets, qd=quartet of doublets), coupling constant(s) (J) in Hertz (Hz), and integration. Flash column chromatography was performed using a Biotage Isolera One and Biotage KP-SIL SNAP cartridges. Purity was assessed by LC/MS/UV using a Waters Acquity UPLC-MS and by NMR spectroscopy. All compounds were confirmed to ≥85% purity prior to testing. Compounds that proved critical to our SAR analysis were further characterized using $^1H$ NMR and HRMS/LRMS.

General Procedure

A. Oxazolone Key Intermediate Cyclization

Under a nitrogen atmosphere, sodium acetate (1.0 mmol) and aldehyde (1.0 mmol) were added to a solution of carboxylic acid (1.0 mmol) in acetic anhydride (3.0 mmol). The resulting mixture was stirred at 85° C. for 2 h, cooled to room temperature, quenched with ice in ethanol, and stirred at room temperature overnight. The resulting solid was filtered, washed with water and diethyl ether, and dried under reduced pressure.

B. Oxazolone Key Intermediate with Aliphatic Chain

B.1. Glycine Coupling

Carbonyl chloride (1.0 mmol) was added to a stirred solution of glycine (1.0 mmol) in 1N aqueous sodium hydroxide (3.0 ml), dropwise. The reaction mixture was stirred at room temperature overnight. Then, the pH of the mixture was adjusted to 1-2 with 1N aqueous HCl. The resulting solution was extracted with $CH_2Cl_2$, dried over $MgSO_4$, filtered, concentrated under reduced pressure, and purified by flash chromatography.

B.2. EDC-Cyclization

Under a nitrogen atmosphere, the amine (1.0 mmol), EDCI·HCl (1.3 mmol) and DIPEA (1.3 mmol) were added to a solution of the carboxylic acid (1.0 mmol) in $CH_2Cl_2$ (3 ml). The reaction mixture was stirred at room temperature overnight. The resulting solution was extracted with CH$_2$Cl$_2$, dried over MgSO$_4$, filtered, concentrated under reduced pressure, and purified by flash chromatography.

B.3. Al$_2$O$_3$-Condensation

Under a nitrogen atmosphere, the aldehyde (0.5 mmol) was added dropwise to a suspension of oxazolone (0.1 mmol), activated molecular sieves 4 Å (1.0 g), and activated aluminum oxide (1.0 mmol) in anhydrous CH$_2$Cl$_2$ (3 ml). The reaction mixture was stirred at room temperature for 6 h. The resulting solid was filtered, filtered through a pad of Celite® to remove molecular sieves and Al$_2$O$_3$. The filtrate was dried under reduced pressure and then purified by flash chromatography.

C. Dihydropyridinone-Cyclization

Under a nitrogen atmosphere, the oxazolone (0.5 mmol) and tin (II) chloride (0.05 mmol) were added to a solution of the amine (0.5 mmol) in chlorobenzene (1.0 ml). The reaction mixture was refluxed overnight. After cooling to room temperature, the mixture was extracted with EtOAc, washed with brine, dried over MgSO$_4$, filtered, concentrated under reduced pressure, and purified by flash chromatography.

Note: Compound 20 (Ile-R1=H) is derived from compound 23 (Ile-R1=t-butyl) that was dissolved in chlorobenzene/TFA (1:1, 0.3 M) and refluxed for 2 h. When the starting material was consumed, the mixture was neutralized with saturated aqueous sodium bicarbonate, extracted with EtOAc, dried over MgSO$_4$, filtered, concentrated under reduced pressure, and purified by flash chromatography.

D. Dihydropyridinone-Amide Alkylation

Under a nitrogen atmosphere, cesium carbonate (1.1 mmol) and the alkyl halide (1.1 mmol) were added to a solution of the dihydropyridinone (0.1 mmol) in DMF (1 ml). The reaction mixture was stirred overnight at room temperature or heated at 100° C. for 3 h. Then the mixture was extracted with EtOAc, washed with brine, dried over MgSO$_4$, filtered, concentrated under reduced pressure, and purified by flash chromatography.

E. Dihydropyridinone-Amide Acylation

Under a nitrogen atmosphere, pyridine (0.075 mmol) and the acyl chloride (0.075 mmol) were added to a solution of the dihydropyiridinone (0.05 mmol) in CH$_2$Cl$_2$ (1.0 mL). The reaction mixture was stirred at room temperature overnight. Then the mixture was extracted with EtOAc, washed with brine, dried over MgSO$_4$, filtered, concentrated under reduced pressure, and purified by flash chromatography.

F. Malonate-Condensation

Under a nitrogen atmosphere, 4-fluorobenzaldehyde (1.0 mmol), acetic acid (0.1 mmol) and piperidine (0.1 mmol) were added to a solution of dimethyl malonate (1.0 mmol) in toluene (2.0 ml). The reaction mixture was refluxed overnight. The crude mixture was concentrated under reduced pressure to remove the toluene, diluted with EtOAc, washed with brine, dried over MgSO$_4$, filtered, concentrated under reduced pressure, and purified by flash chromatography.

G. Amide Coupling (Reverse Amide)

The amine (0.1 mmol) was added to a solution of the ester (0.1 mmol) in chlorobenzene (0.3 ml). The reaction mixture was refluxed overnight. Then the mixture was extracted with EtOAc, washed with brine, dried over MgSO4, filtered, concentrated under reduced pressure, and purified by flash chromatography.

Spectral Characterization of Key Compounds.

3-methyl-N-(rel-(4S,5S)-3-methyl-6-oxo-1-phenyl-4-(p-tolyl)-4,5,6,7-tetrahydro-1H-pyrazolo[3,4-b]pyridin-5-yl)benzamide (Compound 1)

Compound 1 was synthesized by general procedure A, C and D starting from 4-methylbenzaldehyde, (3-methylbenzoyl)glycine and 3-methyl-1-phenyl-1H-pyrazol-5-amine.
$^1$H NMR (400 MHz, Chloroform-d) δ 9.33 (s, 1H), 7.52-7.44 (m, 3H), 7.42-7.35 (m, 1H), 7.35-7.32 (m, 1H), 7.32-7.23 (m, 3H), 7.07-6.96 (m, 3H), 6.89 (d, J=7.9 Hz, 2H), 6.54 (d, J=6.1 Hz, 1H), 5.27 (dd, J=7.5, 6.1 Hz, 1H), 4.75 (d, J=7.5 Hz, 1H), 2.40 (s, 3H), 2.28 (s, 3H), 2.13 (s, 3H). $^{13}$C NMR (101 MHz, Chloroform-d) δ 169.3, 167.5, 147.2, 138.6, 137.5, 137.5, 136.0, 134.3, 133.9, 132.7, 129.6 (2C), 129.5 (2C), 128.6, 128.1 (2C), 127.9, 127.6, 124.2, 122.8 (2C), 104.1, 55.2, 38.0, 21.5, 21.1, 12.1. LRMS (ESI+) m/z calcd for C$_{28}$H$_{27}$N$_4$O$_2$$^+$ [M+H]$^+$ 451.2 found 451.5.

N-(rel-(4S,5S)-7-ethyl-4-(4-fluorophenyl)-3-methyl-6-oxo-1-phenyl-4,5,6,7-tetrahydro-1H-pyrazolo[3,4-b]pyridin-5-yl)-3-methylbenzamide (Compound 27)

Compound 27 was synthesized by general procedure A, C and D starting from 4-fluorobenzaldehyde, (3-methylbenzoyl)glycine and 3-methyl-1-phenyl-1H-pyrazol-5-amine.
$^1$H NMR (400 MHz, Chloroform-d) δ 7.57 (s, 1H), 7.55-7.42 (m, 6H), 7.35-7.28 (m, 2H), 7.01-6.87 (m, 5H), 5.20 (dd, J=7.1, 5.6 Hz, 1H), 4.77 (d, J=7.0 Hz, 1H), 4.05-3.82 (m, 1H), 3.17 (dq, J=14.0, 7.0 Hz, 1H), 2.39 (s, 3H), 2.14 (s, 3H), 0.99 (t, J=7.1 Hz, 3H). $^{13}$C NMR (101 MHz, Chloroform-d) δ 168.0, 167.3, 161.0 (d, J=246.8 Hz), 147.0, 139.1, 139.0, 138.6, 133.7, 132.7, 132.5, 132.4, 130.0, 129.9, 129.6 (2C), 128.8, 128.6, 127.7, 125.3, 124.0, 115.5, 115.3, 105.9, 55.7, 39.2, 36.7, 21.3, 12.7, 11.9. HRMS (ESI+) m/z calcd for C$_{29}$H$_{28}$FN$_4$O$_2$$^+$ [M+H]$^+$ 483.2191, found 483.2193.

4-(4-fluorobenzylidene)-2-(m-tolyl)oxazol-5(4H)-one (Compound 144)

Compound 144 was synthesized by general procedure A starting from 4-fluorobenzaldehyde and (3-methylbenzoyl)glycine.
$^1$H NMR (400 MHz, Chloroform-d) δ 8.21-8.12 (m, 2H), 7.98-7.88 (m, 2H), 7.40-7.32 (m, 2H), 7.16-7.06 (m, 3H), 2.40 (s, 3H). LRMS (ESI+) m/z calcd for C$_{17}$H$_{13}$FNO$_2$$^+$ [M+H]$^+$ 477.2, found 477.1.

Chemistry Experimental

General.

All NMR data was collected at room temperature in CDCl$_3$ or (CD$_3$)$_2$SO on a 400 or 500 MHz Bruker or Agilent instrument. Chemical shifts (δ) are reported in parts per million (ppm) with internal CHCl$_3$ (δ 7.26 ppm for $^1$H and 77.00 ppm for $^{13}$C), internal DMSO (δ 2.50 ppm for $^1$H and 39.52 ppm for $^{13}$C), or internal TMS (δ 0.0 ppm for $^1$H and 0.0 ppm for $^{13}$C) as the reference. $^1$H NMR data are reported as follows: chemical shift, multiplicity (s=singlet, bs=broad singlet, d=doublet, t=triplet, q=quartet, p=pentet, sext=sextet, sep=septet, m=multiplet, dd=doublet of doublets, dt=doublet of triplets, td=triplet of doublets, qd=quartet of doublets), coupling constant(s) (J) in Hertz (Hz), and integration. Flash column chromatography was performed using a Biotage Isolera One and Biotage KP-SIL SNAP cartridges. Purity was assessed by LC/MS/UV using a Waters Acquity UPLC-MS and by NMR spectroscopy. All compounds were confirmed to ≥85% purity prior to testing.

Compounds that proved critical to our SAR analysis were further characterized using $^1$H NMR and HRMS/LRMS.

General Procedure

A. Oxazolone Key Intermediate Cyclization

Under a nitrogen atmosphere, sodium acetate (1.0 mmol) and aldehyde (1.0 mmol) were added to a solution of carboxylic acid (1.0 mmol) in acetic anhydride (3.0 mmol). The resulting mixture was stirred at 85° C. for 2 h, cooled to room temperature, quenched with ice in ethanol, and stirred at room temperature overnight. The resulting solid was filtered, washed with water and diethyl ether, and dried under reduced pressure.

B. Oxazolone Key Intermediate with Aliphatic Chain

B.1. Glycine Coupling

Carbonyl chloride (1.0 mmol) was added to a stirred solution of glycine (1.0 mmol) in 1N aqueous sodium hydroxide (3.0 ml), dropwise. The reaction mixture was stirred at room temperature overnight. The following morning, the pH of the mixture was adjusted to 1-2 with 1N aqueous HCl. The resulting solution was extracted with $CH_2Cl_2$, dried over $MgSO_4$, filtered, concentrated under reduced pressure, and purified by flash chromatography.

B.2. EDC-Cyclization

Under a nitrogen atmosphere, the amine (1.0 mmol), EDCI·HCl (1.3 mmol) and DIPEA (1.3 mmol) were added to a solution of the carboxylic acid (1.0 mmol) in $CH_2Cl_2$ (3 ml). The reaction mixture was stirred at room temperature overnight. The resulting solution was extracted with $CH_2Cl_2$, dried over MgSO4, filtered, concentrated under reduced pressure, and purified by flash chromatography.

B.3. $Al_2O_3$-Condensation

Under a nitrogen atmosphere, the aldehyde (0.5 mmol) was added by drops to a suspension of oxazolone (0.1 mmol), activated molecular sieves 4 Å (1.0 g), and activated aluminum oxide (1.0 mmol) in anhydrous $CH_2Cl_2$ (3 ml). The reaction mixture was stirred at room temperature for 6 h. The resulting solid was filtered, washed through a pad of Celite® to remove molecular sieves and $Al_2O_3$. The filtrate was dried under reduced pressure and then purified by flash chromatography.

C. Dihydropyridinone-Cyclization

Under a nitrogen atmosphere, the oxazolone (0.5 mmol) and tin (II) chloride (0.05 mmol) was added to a solution of the amine (0.5 mmol) in chlorobenzene (1.0 ml). The reaction mixture was refluxed overnight. After cooling to room temperature, the mixture was extracted with EtOAc, washed with brine, dried over $MgSO_4$, filtered, concentrated under reduced pressure, and purified by flash chromatography.

Note: Compound 20 (Ile-R1=H) is derived from compound 23 (Ile-R1=t-butyl) that was dissolved in chlorobenzene/TFA (1:1, 0.3 M) and refluxed for 2 h. When the starting material was consumed, the mixture was neutralized with saturated aqueous sodium bicarbonate, extracted with EtOAc, dried over $MgSO_4$, filtered, concentrated under reduced pressure, and purified by flash chromatography.

D. Dihydropyridinone-Amide Alkylation

Under a nitrogen atmosphere, cesium carbonate (1.1 mmol) and the alkyl halide (1.1 mmol) was added to a solution of the dihydropyridinone (0.1 mmol) in DMF (1 ml). The reaction mixture was stirred overnight at room temperature or heated at 100° C. for 3 h. Then the mixture was extracted with EtOAc, washed with brine, dried over $MgSO_4$, filtered, concentrated under reduced pressure, and purified by flash chromatography.

E. Dihydropyridinone-Amide Acylation

Under a nitrogen atmosphere, pyridine (0.075 mmol) and the acyl chloride (0.075 mmol) was added to a solution of the dihydropyiridinone (0.05 mmol) in $CH_2Cl_2$ (1.0 mL). The reaction mixture was stirred at room temperature overnight. Then the mixture was extracted with EtOAc, washed with brine, dried over MgSO4, filtered, concentrated under reduced pressure, and purified by flash chromatography.

F. Malonate-Condensation

Under a nitrogen atmosphere, 4-fluorobenzaldehyde (1.0 mmol), acetic acid (0.1 mmol) and piperidine (0.1 mmol) were added to a solution of dimethyl malonate (1.0 mmol) in toluene (2.0 ml). The reaction mixture was refluxed overnight. After toluene was evaporated, the mixture was extracted with EtOAc, washed with brine, dried over MgSO4, filtered, concentrated under reduced pressure, and purified by flash chromatography. G. Amide coupling (Reverse amide)

The amine (0.1 mmol) was added to a solution of the ester (0.1 mmol) in chlorobenzene (0.3 ml). The reaction mixture was refluxed overnight. The mixture was concentrated under reduced pressure, and then purified by flash chromatography.

Example 2

This Example compares the compounds disclosed herein to the compound series previously disclosed by the instant inventors. In a 2017 Nature Chemical Biology (NCB) article (Nat. Chem. Biol. 2017, 13 (8), 850-857), the instant inventors reported a different scaffold of piperidinyl ureas, represented by NAcM-OPT. While the main text of the NCB paper did not mention the pyrazolo-pyridones, Supplementary Data Set 1 listed the SMILES code and TR-FRET $IC_{50}$ potency values for roughly 860 compounds, 7 of which were pyrazolo-pyridones. That said, all of these commercially available compounds (originally purchased from Enamine in 2008) contained the trans diastereomer about the central pyridone ring.

This piperidinyl urea scaffold was also discussed in WO 2017/049295, as well as J Med Chem 2018, 61 (7), 2694-2706; J Med Chem 2018, 61 (7), 2680-2693. The existing patent (WO 2017/049295) similarly focuses on the piperidinyl urea scaffold, represented by NAcM-OPT. It includes detailed composition of matter claims for this unrelated scaffold, as well as the 33 commercial pyrazol o-pyri done analogs shown in TABLE 12 below. In contrast to the compounds disclosed herein, the previously disclosed compounds of TABLE 12 all lack substitution of the pyridone amide of core scaffold, which afforded an unexpected boost in potency. Additionally, WO2017049295 also fails to appreciate or disclose that the cis, and not the trans, diastereomer is in fact the active diastereomer.

TABLE 12
| REGNO | Batch | Structure | IC50 AVG | IC50 STD | Pulse-Chase inh @ 30 uM | Avg. Sol (uM) | Avg. Perm (10^-6 cm/s) |
|---|---|---|---|---|---|---|---|
| SJ000398145 | 2 | 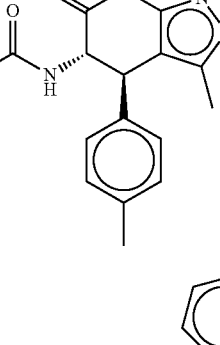 | 2.77 | 1.33 | | H | 325.1 |
| SJ000398145 | 1 | 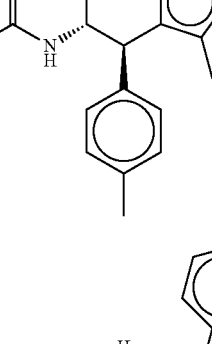 | 5.64 | 0.06 | | | 325.1 |
| SJ000400727 | 1 | 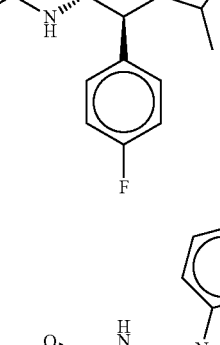 | 8.51 | 9.52 | | | 908.7 |
| SJ000400727 | 2 | 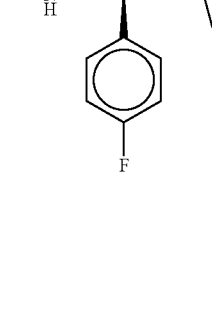 | 40.06 | | | H | 908.7 |

TABLE 12-continued

| REGNO | Batch | Structure | IC50 AVG | IC50 STD | Pulse-Chase inh @ 30 uM | Avg. Sol (uM) | Avg. Perm (10^-6 cm/s) |
|---|---|---|---|---|---|---|---|
| SJ000401413 | 1 | 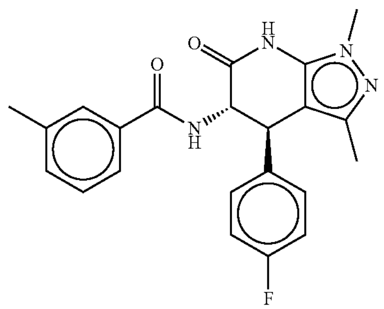 | 14.23 | 2.28 | | | 271.7 |
| SJ000398158 | 1 | 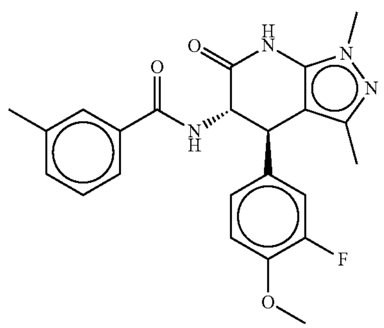 | 25.37 | 14.26 | M-L | 2.7 | 358.5 |
| SJ000399569 | 1 | 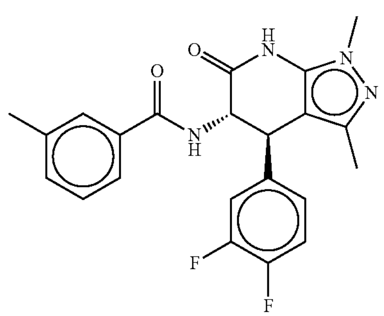 | 28.03 | 4.68 | | 14 | 79.9 |
| SJ000399627 | 2 | 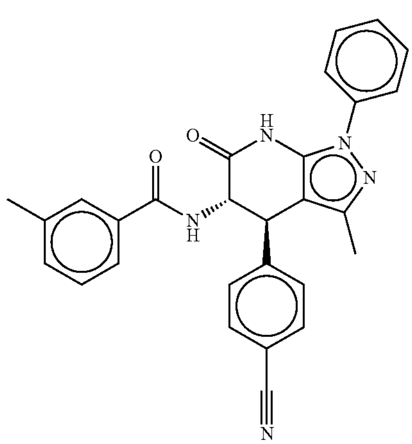 | 35.10 | | M | 19.3 | 603.5 |

TABLE 12-continued

| REGNO | Batch | Structure | IC50 AVG | IC50 STD | Pulse-Chase inh @ 30 uM | Avg. Sol (uM) | Avg. Perm (10^-6 cm/s) |
|---|---|---|---|---|---|---|---|
| SJ000398155 | 1 | 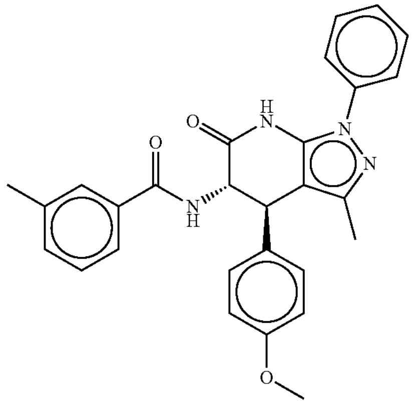 | 36.98 | 24.95 | | | |
| SJ000398159 | 1 | 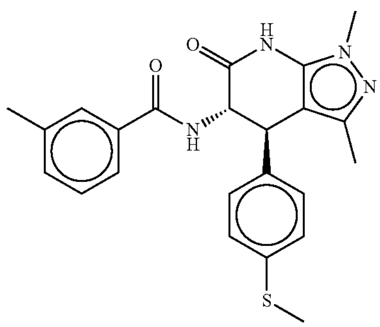 | 39.50 | | | | |
| SJ000398158 | 2 | 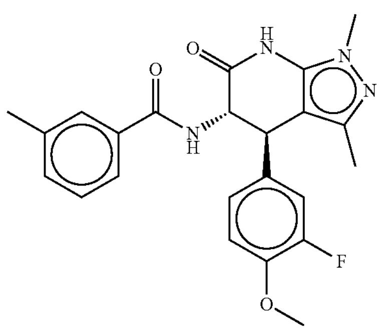 | 41.53 | | | 2.7 | 358.5 |
| SJ000399627 | 1 | 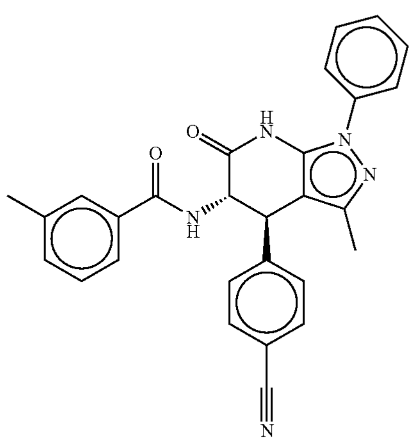 | 43.13 | | | 19.3 | 603.5 |

TABLE 12-continued

| REGNO | Batch | Structure | IC50 AVG | IC50 STD | Pulse-Chase inh @ 30 uM | Avg. Sol (uM) | Avg. Perm (10^-6 cm/s) |
|---|---|---|---|---|---|---|---|
| SJ000397970 | 1 | 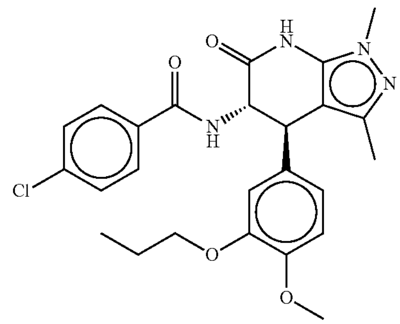 | | | >67.57 | | |
| SJ000397980 | 1 | 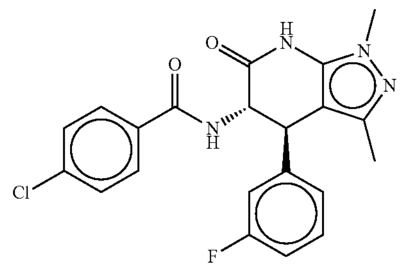 | | | >67.57 | | |
| SJ000397990 | 1 | 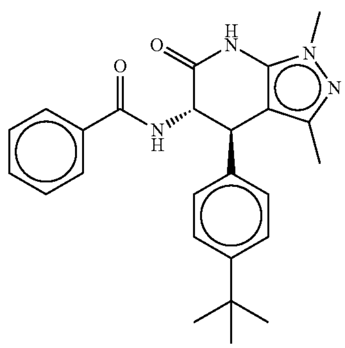 | | | >67.57 | | |
| SJ000398000 | 1 | 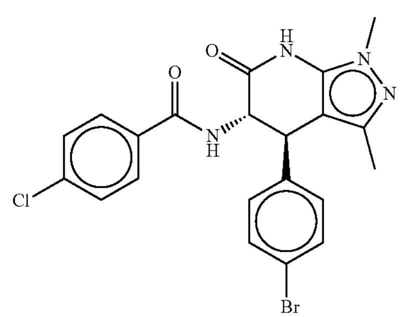 | | | >67.57 | | |

TABLE 12-continued

| REGNO | Batch | Structure | IC50 AVG | IC50 STD | Pulse-Chase inh @ 30 uM | Avg. Sol (uM) | Avg. Perm (10^-6 cm/s) |
| --- | --- | --- | --- | --- | --- | --- | --- |
| SJ000398039 | 1 | 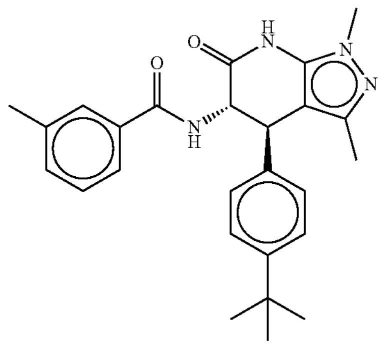 | | | >67.57 | | |
| SJ000398135 | 1 | 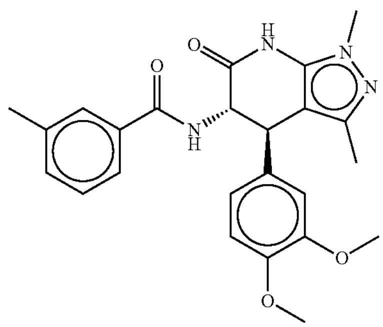 | | | >67.57 | | |
| SJ000398168 | 1 | 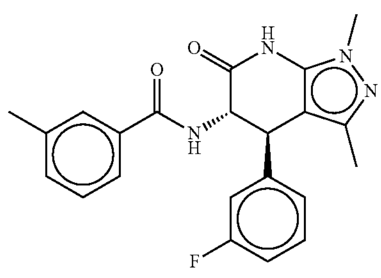 | | | >67.57 | | |
| SJ000398179 | 1 | 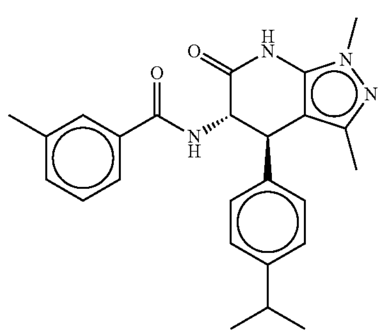 | | | >67.57 | | |

TABLE 12-continued

| REGNO | Batch | Structure | IC50 AVG | IC50 STD | Pulse-Chase inh @ 30 uM | Avg. Sol (uM) | Avg. Perm (10^-6 cm/s) |
|---|---|---|---|---|---|---|---|
| SJ000398188 | 1 | 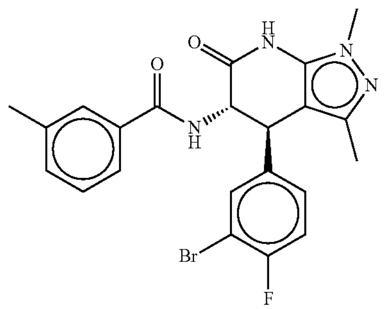 | >67.57 | | | | |
| SJ000399558 | 1 | 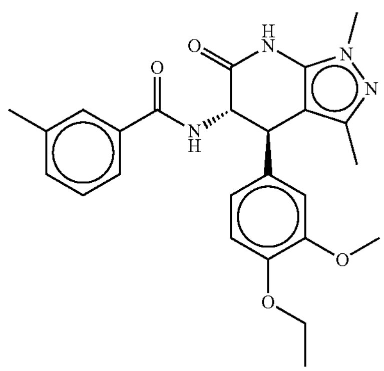 | >67.57 | | | | |
| SJ000399559 | 1 | 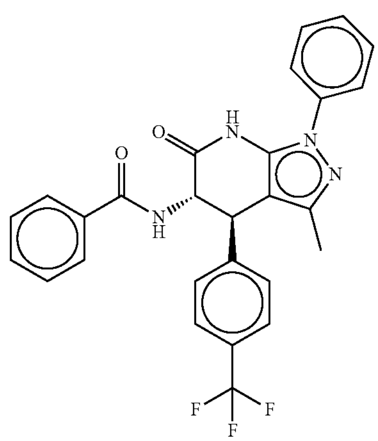 | >67.57 | | | | |
| SJ000399560 | 1 | 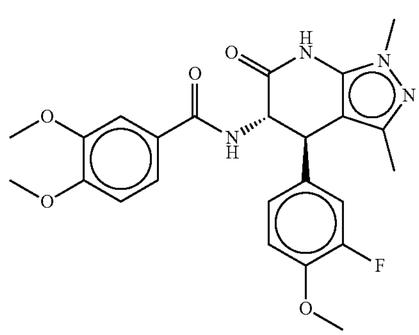 | >67.57 | | | | |

TABLE 12-continued

| REGNO | Batch | Structure | IC50 AVG | IC50 STD | Pulse-Chase inh @ 30 uM | Avg. Sol (uM) | Avg. Perm (10^-6 cm/s) |
| --- | --- | --- | --- | --- | --- | --- | --- |
| SJ000399568 | 1 | 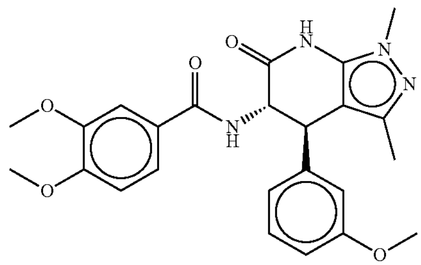 | >67.57 | | | | |
| SJ000399577 | 1 | 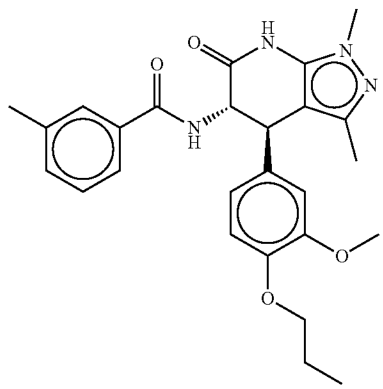 | >67.57 | | | | |
| SJ000399579 | 1 | 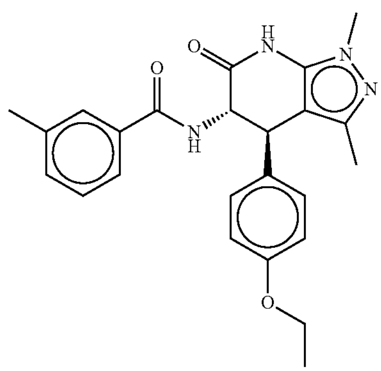 | >67.57 | | | | |
| SJ000399587 | 1 | 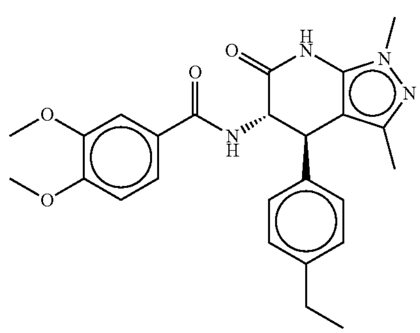 | >67.57 | | | | |

TABLE 12-continued

| REGNO | Batch | Structure | IC50 AVG | IC50 STD | Pulse-Chase inh @ 30 uM | Avg. Sol (uM) | Avg. Perm (10^-6 cm/s) |
|---|---|---|---|---|---|---|---|
| SJ000399588 | 1 | 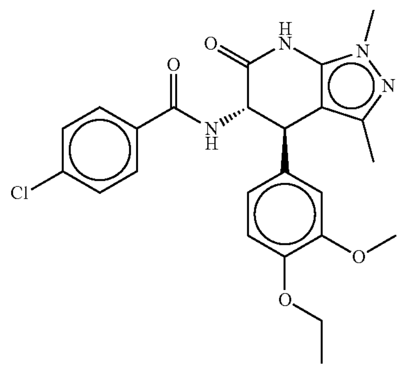 | >67.57 | | | | |
| SJ000399589 | 1 | 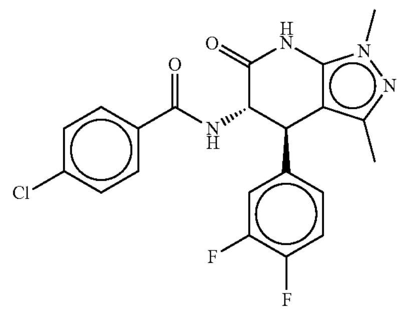 | >67.57 | | M-L | | |
| SJ000399597 | 1 | 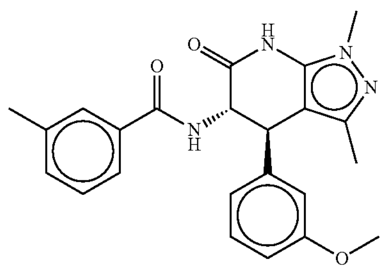 | >67.57 | | | | |
| SJ000399598 | 1 | 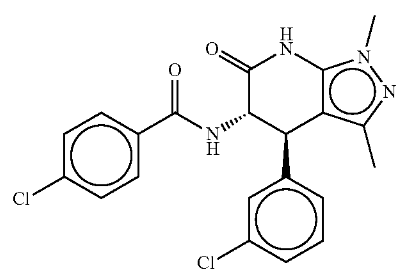 | >67.57 | | | | |
| SJ000399608 | 1 | 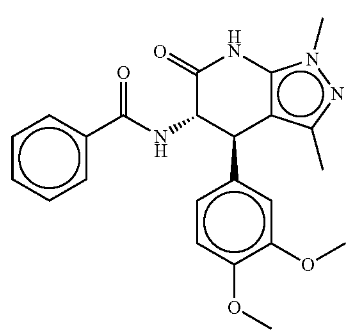 | >67.57 | | | | |

TABLE 12-continued

| REGNO | Batch | Structure | IC50 AVG | IC50 STD | Pulse-Chase inh @ 30 uM | Avg. Sol (uM) | Avg. Perm (10^-6 cm/s) |
|---|---|---|---|---|---|---|---|
| SJ000399617 | 1 | 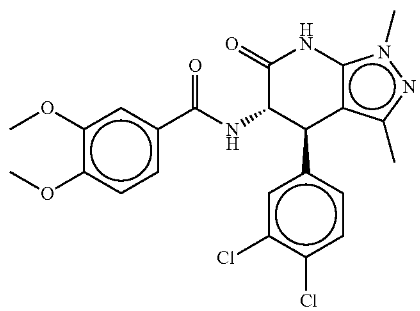 | >67.57 | | | | |
| SJ000401391 | 1 | 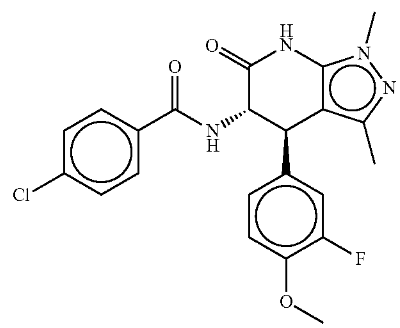 | >67.57 | | | | |
| SJ000401421 | 1 | 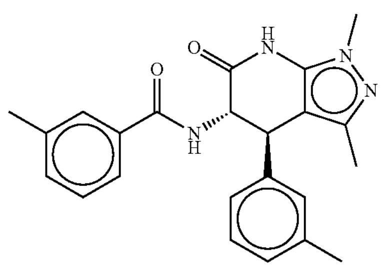 | >67.57 | | | | |
| SJ000401460 | 1 | 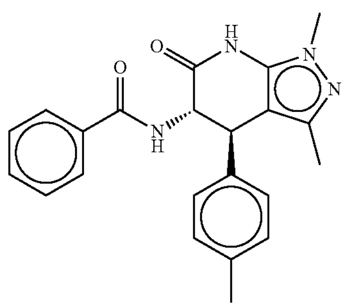 | >67.57 | | | 82.4 | 167.9 |

Therefore, as discussed in Example 1 above, the novel compounds demonstrate an unexpected increase in potency when containing previously undisclosed substitutions of the pyridone amide of core scaffold or substitutions of the methyl pyrazole. The novel compounds also demonstrate increased potency when possessing the cis-geometry, rather than the previously disclosed trans-geometry. This evidences a clear structural difference with other similar reported chemicals. The novel compounds also demonstrate an unanticipated improvement in oral bioavailability associated with specific substitutions that increases utility for use in vivo.

Example 3

Spectral Characterization

Compound 1

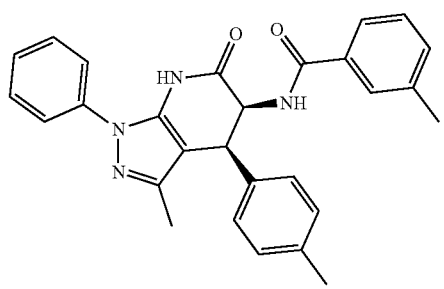

$^1$H NMR (400 MHz, Chloroform-d) δ 9.33 (s, 1H), 7.52-7.44 (m, 3H), 7.42-7.35 (m, 1H), 7.35-7.32 (m, 1H), 7.32-7.23 (m, 3H), 7.07-6.96 (m, 3H), 6.89 (d, J=7.9 Hz, 2H), 6.54 (d, J=6.1 Hz, 1H), 5.27 (dd, J=7.5, 6.1 Hz, 1H), 4.75 (d, J=7.5 Hz, 1H), 2.40 (s, 3H), 2.28 (s, 3H), 2.13 (s, 3H). $^{13}$C NMR (101 MHz, Chloroform-d) δ 169.3, 167.5, 147.1, 138.6, 137.5, 137.5, 136.0, 134.3, 133.9, 132.7, 129.6 (2C), 129.5 (2C), 128.6, 128.1 (2C), 127.9, 127.6, 124.2, 122.8 (2C), 104.1, 55.2, 38.0, 21.5, 21.1, 12.1. LRMS (ESI+) m/z calcd for $C_{28}H_{27}N_4O_2^+$ [M+H]$^+$ 451.2 found 451.5.

Compound 2

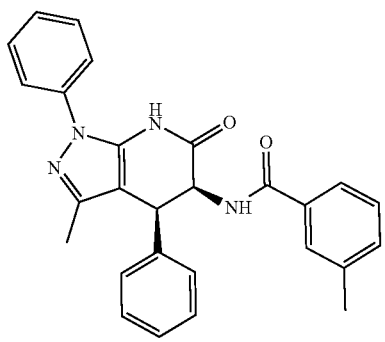

$^1$H NMR (400 MHz, Chloroform-d) δ 8.22 (s, 1H), 7.57-7.46 (m, 3H), 7.47-7.36 (m, 3H), 7.34-7.19 (m, 6H), 7.01 (dd, J=6.7, 2.9 Hz, 2H), 6.61 (d, J=6.1 Hz, 1H), 5.39-5.27 (t, J=7.6 Hz, 1H), 4.81 (d, J=7.6 Hz, 1H), 2.37 (s, 3H), 2.14 (s, 3H). HRMS (ESI+) m/z calcd for $C_{27}H_{25}N_4O_2^+$ [M+H]$^+$ 437.1972, found 437.1968.

Compound 3

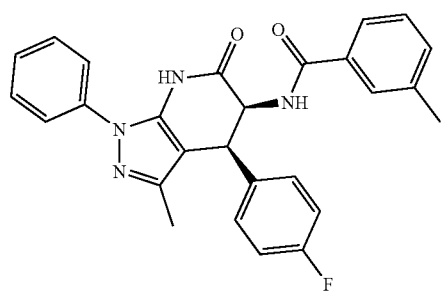

$^1$H NMR (500 MHz, Chloroform-d) δ 7.89 (s, 1H), 7.50-7.41 (m, 5H), 7.41-7.35 (m, 1H), 7.32-7.22 (m, 3H), 6.96-6.89 (m, 2H), 6.90-6.82 (m, 2H), 6.65 (d, J=5.7 Hz, 1H), 5.21 (dd, J=7.5, 5.7 Hz, 1H), 4.81 (d, J=7.5 Hz, 1H), 2.33 (s, 3H), 2.09 (s, 3H). HRMS (ESI+) m/z calcd for $C_{27}H_{24}FN_4O_2^+$ [M+H]$^+$ 455.1878, found 455.1860.

Compound 4

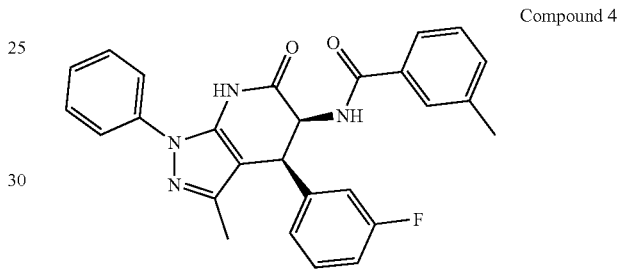

$^1$H NMR (500 MHz, Chloroform-d) δ 7.94 (s, 1H), 7.52-7.39 (m, 5H), 7.39 (dd, J=7.3, 1.7 Hz, 1H), 7.31-7.22 (m, 3H), 7.15 (td, J=8.0, 5.8 Hz, 1H), 6.87 (td, J=8.4, 2.6 Hz, 1H), 6.77 (dd, J=7.7, 1.5 Hz, 1H), 6.65 (dt, J=7.7, 2.1 Hz, 2H), 5.23 (dd, J=7.5, 5.8 Hz, 1H), 4.82 (d, J=7.6 Hz, 1H), 2.32 (s, 3H), 2.10 (s, 3H). HRMS (ESI+) m/z calcd for $C_{27}H_{24}FN_4O_2^+$ [M+H]$^+$ 455.1878, found 455.1871.

Compound 5

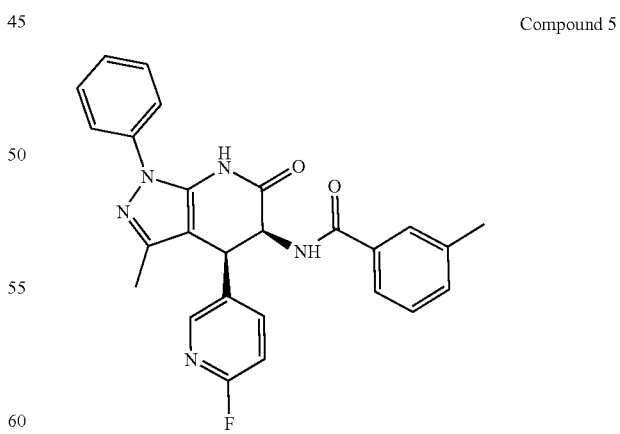

$^1$H NMR (400 MHz, Chloroform-d) δ 8.14 (s, 1H), 7.88 (s, 1H), 7.48 (ddt, J=13.8, 9.3, 4.6 Hz, 6H), 7.42-7.25 (m, 4H), 6.95-6.71 (m, 2H), 5.25-5.19 (m, 1H), 4.99 (d, J=7.5, 1H), 2.38 (s, 3H), 2.14 (s, 3H). HRMS (ESI+) m/z calcd for $C_{26}H_{23}FN_5O_2^+$ [M+H]$^+$ 456.1830, found 456.1823.

Compound 6

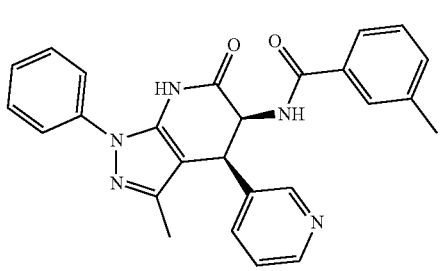

¹H NMR (500 MHz, Chloroform-d) δ 8.85 (s, 1H), 8.33-8.25 (m, 1H), 8.24-8.19 (m, 1H), 7.54-7.28 (m, 7H), 7.34-7.20 (m, 3H), 7.16 (dd, J=7.8, 4.9 Hz, 1H), 6.89 (d, J=5.2 Hz, 1H), 5.22 (dd, J=7.6, 5.1 Hz, 1H), 4.92 (d, J=7.6 Hz, 1H), 2.31 (s, 3H), 2.09 (s, 3H). HRMS (ESI+) m/z calcd for $C_{26}H_{24}N_5O_2^+$ [M+H]⁺ 438.1925, found 438.1960.

Compound 7

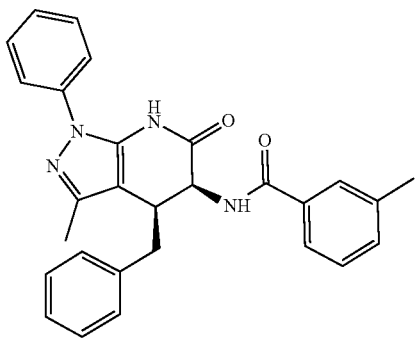

¹H NMR (400 MHz, Chloroform-d) δ 7.70 (s, 2H), 7.60-7.27 (m, 10H), 7.21-7.13 (m, 2H), 6.95 (d, J=6.3 Hz, 2H), 5.00 (t, J=5.2 Hz, 1H), 3.99-3.91 (m, 1H), 3.01-2.89 (m, 1H), 2.44 (s, 3H), 2.38 (d, J=12.9 Hz, 1H), 1.56 (s, 3H). HRMS (ESI+) m/z calcd for $C_{28}H_{27}N_4O_2^+$ [M+H]⁺ 451.2129, found 451.2134.

Compound 8

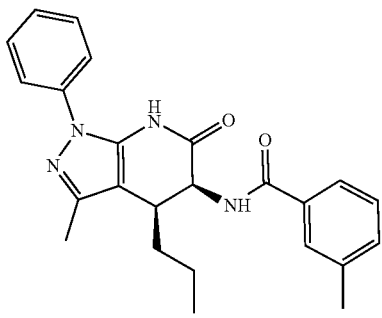

¹H NMR (400 MHz, Chloroform-d) δ 7.96 (s, 1H), 7.70-7.56 (m, 2H), 7.46 (m, 4H), 7.36 (m, 2H), 7.32-7.28 (m, 1H), 7.19 (d, J=5.0 Hz, 1H), 4.95 (t, J=5.6 Hz, 1H), 3.62 (m, 1H), 2.43 (s, 3H), 2.29 (s, 3H), 1.66-1.49 (m, 1H), 1.39-1.09 (m, 3H), 0.85 (t, J=7.6 Hz, 3H). HRMS (ESI+) m/z calcd for $C_{24}H_{27}N_4O_2^+$ [M+H]⁺ 403.2129, found 403.2112.

Compound 9

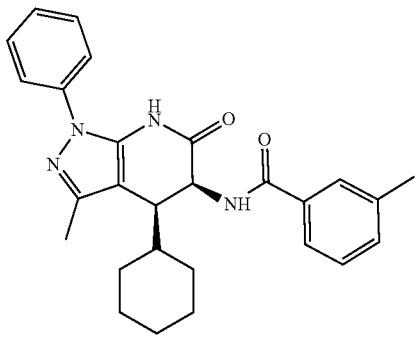

¹H NMR (400 MHz, Chloroform-d) δ 7.72-7.59 (m, 3H), 7.52-7.42 (m, 4H), 7.40-7.32 (m, 3H), 7.22-7.15 (m, 1H), 4.89 (dd, J=7.8, 4.1 Hz, 1H), 3.67 (m, 1H), 2.43 (s, 3H), 2.29 (s, 3H), 1.77-1.57 (m, 5H), 1.26-1.06 (m, 4H), 1.04-0.79 (m, 2H). HRMS (ESI+) m/z calcd for $C_{27}H_{31}N_4O_2^+$ [M+H]⁺ 443.2442, found 443.2444.

Compound 10

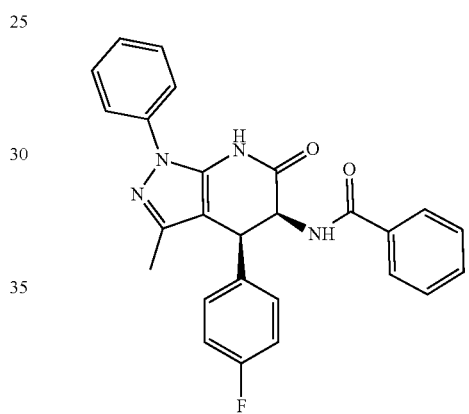

¹H NMR (400 MHz, Chloroform-d) δ 7.98 (s, 1H), 7.71-7.64 (m, 2H), 7.55-7.37 (m, 7H), 7.36-7.28 (m, 1H), 7.03-6.85 (m, 4H), 6.71 (s, 1H), 5.30-5.23 (m, 1H), 4.86 (d, J=7.6 Hz, 1H), 2.13 (s, 3H). HRMS (ESI+) m/z calcd for $C_{26}H_{22}FN_4O_2^+$ [M+H]⁺ 441.1721, found 441.1708.

Compound 11

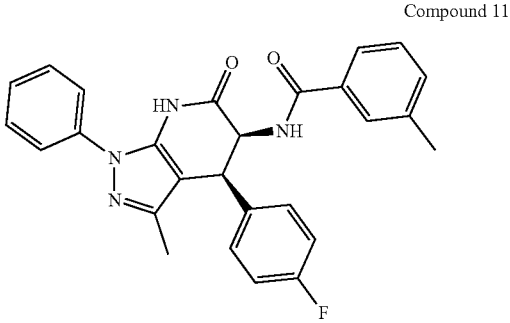 [SMILES: Cc1cccc(C(=O)N[C@@H]2C(=O)Nc3c(c(C)nn3-c3ccccc3)[C@@H]2c2ccc(F)cc2)c1]

¹H NMR (500 MHz, Chloroform-d) δ 7.91 (d, J=1.7 Hz, 1H), 7.81 (s, 1H), 7.77-7.69 (m, 2H), 7.54-7.41 (m, 5H), 7.33 (qt, J=5.6, 2.8 Hz, 1H), 6.96-6.84 (m, 4H), 6.71 (d, J=5.7 Hz, 1H), 5.22 (dd, J=7.6, 5.6 Hz, 1H), 4.81 (d, J=7.5 Hz, 1H), 2.10 (s, 3H). HRMS (ESI+) m/z calcd for $C_{27}H_{21}F_4N_4O_2^+$ [M+H]⁺ 509.1595, found 509.1602.

Compound 12

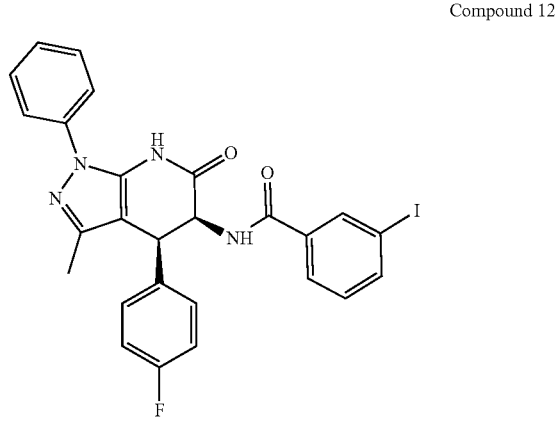 [SMILES: Cc1nn(-c2ccccc2)c2c1[C@H](c1ccc(F)cc1)[C@H](NC(=O)c1cccc(I)c1)C(=O)N2]

¹H NMR (400 MHz, Chloroform-d) δ 8.02 (s, 1H), 7.92 (s, 1H), 7.84 (d, J=7.8 Hz, 1H), 7.60-7.54 (m, 1H), 7.54-7.45 (m, 4H), 7.15 (t, J=7.9 Hz, 1H), 7.00-6.88 (m, 4H), 6.67 (d, J=5.6 Hz, 1H), 5.23 (dd, J=7.6, 5.5 Hz, 1H), 4.84 (d, J=7.5 Hz, 1H), 2.14 (s, 3H). HRMS (ESI+) m/z calcd for $C_{26}H_{21}FIN_4O_2^+$ [M+H]⁺ 567.0688, found 567.0695.

Compound 13

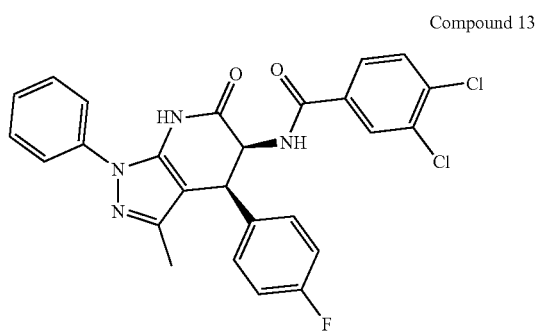 [SMILES: Cc1nn(-c2ccccc2)c2c1[C@H](c1ccc(F)cc1)[C@H](NC(=O)c1ccc(Cl)c(Cl)c1)C(=O)N2]

¹H NMR (500 MHz, Chloroform-d) δ 7.92 (s, 1H), 7.74 (d, J=2.0 Hz, 1H), 7.51-7.40 (m, 6H), 7.31 (tt, J=6.1, 2.3 Hz, 1H), 6.93-6.83 (m, 4H), 6.64 (d, J=5.6 Hz, 1H), 5.17 (dd, J=7.5, 5.6 Hz, 1H), 4.79 (d, J=7.5 Hz, 1H), 2.08 (s, 3H). HRMS (ESI+) m/z calcd for $C_{26}H_{20}Cl_2FN_4O_2^+$ [M+H]⁺ 509.0942, found 509.0934.

Compound 14

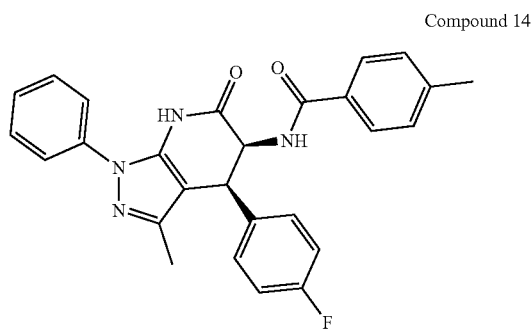 [SMILES: Cc1ccc(C(=O)N[C@@H]2C(=O)Nc3c(c(C)nn3-c3ccccc3)[C@@H]2c2ccc(F)cc2)cc1]

¹H NMR (500 MHz, DMSO-d₆) δ 11.08 (s, 1H), 7.70-7.59 (m, 5H), 7.57-7.17 (m, 5H), 7.10 (t, J=8.8 Hz, 2H), 6.99 (dd, J=8.6, 5.6 Hz, 2H), 5.25 (m, 1H), 4.60 (d, J=7.4 Hz, 1H), 2.35 (s, 3H), 2.03 (s, 3H). HRMS (ESI+) m/z calcd for $C_{27}H_{24}FN_4O_2^+$ [M+H]⁺ 455.1878, found 455.1835.

Compound 15

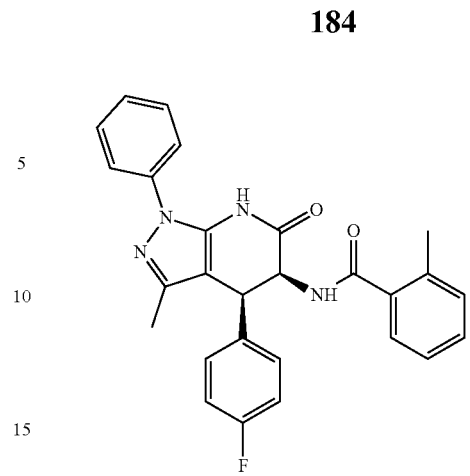

¹H NMR (400 MHz, Chloroform-d) δ 7.92 (s, 1H), 7.53-7.43 (m, 4H), 7.36-7.27 (m, 2H), 7.23-7.12 (m, 3H), 7.08-7.01 (m, 2H), 6.99-6.92 (m, 2H), 6.44 (d, J=5.5 Hz, 1H), 5.23 (dd, J=7.6, 5.6 Hz, 1H), 4.92 (d, J=7.6 Hz, 1H), 2.41 (s, 3H), 2.14 (s, 3H). HRMS (ESI+) m/z calcd for $C_{27}H_{24}FN_4O_2^+$ [M+H]⁺ 455.1878, found 455.1894.

Compound 16

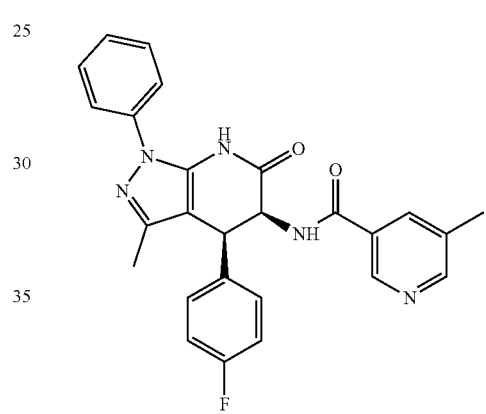

¹H NMR (400 MHz, Chloroform-d) δ 8.62 (s, 1H), 8.53 (s, 1H), 8.02 (s, 1H), 7.81 (s, 1H), 7.58-7.42 (m, 4H), 7.42-7.31 (m, 1H), 7.01-6.85 (m, 4H), 6.74 (d, J=5.7 Hz, 1H), 5.26 (dd, J=7.0, 6.3 Hz, 1H), 4.85 (d, J=7.6 Hz, 1H), 2.38 (s, 3H), 2.14 (s, 3H). HRMS (ESI+) m/z calcd for $C_{26}H_{23}FN_5O_2^+$ [M+H]⁺ 456.1830, found 456.1832.

Compound 17

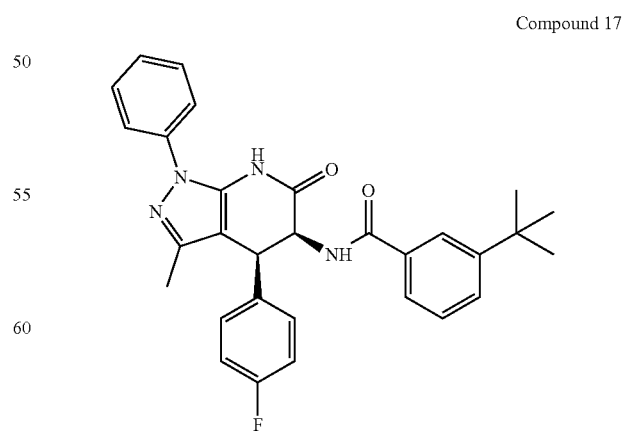

¹H NMR (400 MHz, Chloroform-d) δ 7.81 (s, 1H), 7.73 (s, 1H), 7.57-7.47 (m, 5H), 7.39-7.28 (m, 3H), 7.01-6.89 (m, 4H), 6.67 (s, 1H), 5.32-5.24 (m, 1H), 4.85 (d, J=7.9 Hz, 1H), 2.14 (s, 3H), 1.32 (s, 9H). HRMS (ESI+) m/z calcd for $C_{30}H_{30}FN_4O_2^+$ [M+H]$^+$ 497.2347, found 497.2345.

Compound 18

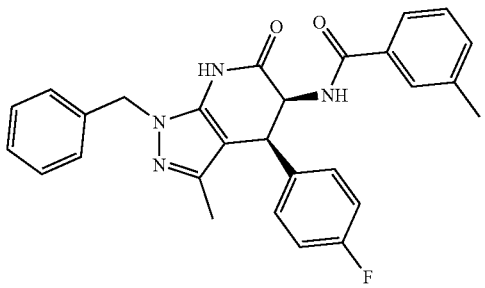

$^1$H NMR (500 MHz, Chloroform-d) δ 8.04 (s, 1H), 7.42 (d, J=1.8 Hz, 1H), 7.37-7.20 (m, 6H), 7.16-7.09 (m, 2H), 6.84 (d, J=6.9 Hz, 4H), 6.57 (d, J=5.8 Hz, 1H), 5.27 (d, J=16.1 Hz, 1H), 5.14 (d, J=16.0 Hz, 1H), 5.08 (dd, J=7.4, 5.8 Hz, 1H), 4.70 (d, J=7.5 Hz, 1H), 2.30 (s, 3H), 2.03 (s, 3H). HRMS (ESI+) m/z calcd for $C_{28}H_{26}FN_4O_2^+$ [M+H]$^+$ 469.2034, found 469.2077.

Compound 19

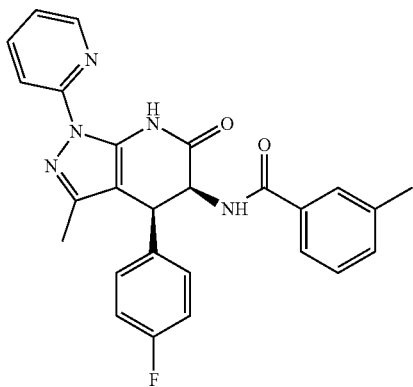

$^1$H NMR (400 MHz, Chloroform-d) δ 10.48 (s, 1H), 8.36 (d, J=4.8 Hz, 1H), 7.96-7.88 (m, 1H), 7.89-7.78 (m, 1H), 7.49 (s, 1H), 7.47-7.40 (m, 1H), 7.33-7.25 (m, 2H), 7.17 (t, J=7.4 Hz, 1H), 7.02 (dd, J=7.8, 5.1 Hz, 2H), 6.90 (t, J=8.7 Hz, 2H), 6.79 (d, J=5.3 Hz, 1H), 5.21-5.13 (m, 1H), 4.87 (d, J=7.6 Hz, 1H), 2.37 (s, 3H), 2.13 (s, 3H). HRMS (ESI+) m/z calcd for $C_{26}H_{23}FN_5O_2^+$ [M+H]$^+$ 456.1830, found 456.1835.

Compound 20

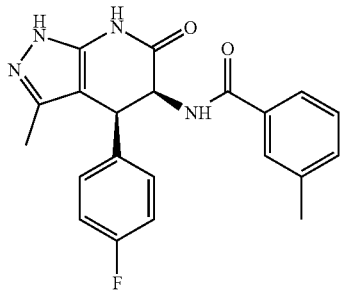

$^1$H NMR (400 MHz, Chloroform-d) δ 10.72 (s, 1H), 10.04 (s, 1H), 7.52 (s, 1H), 7.46 (d, J=6.8 Hz, 1H), 7.30 (d, J=6.8 Hz, 2H), 6.98 (dd, J=8.2, 5.2 Hz, 2H), 6.95-6.83 (m, 3H), 5.12 (t, J=7.2 Hz, 1H), 4.88 (d, J=7.2 Hz, 1H), 2.38 (s, 3H), 2.16 (s, 3H). HRMS (ESI+) m/z calcd for $C_{21}H_{20}FN_4O_2^+$ [M+H]$^+$ 379.1565, found 379.1567.

Compound 21

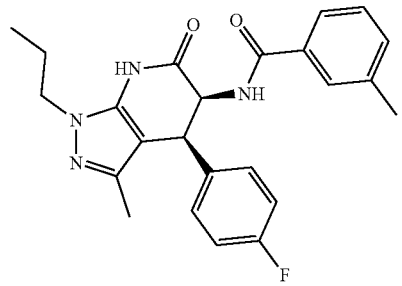

$^1$H NMR (500 MHz, Chloroform-d) δ 8.64 (s, 1H), 7.45 (d, J=1.7 Hz, 1H), 7.38 (dt, J=7.2, 1.8 Hz, 1H), 7.30-7.19 (m, 2H), 6.92-6.82 (m, 4H), 6.60 (d, J=6.0 Hz, 1H), 5.14 (dd, J=7.5, 6.0 Hz, 1H), 4.69 (d, J=7.5 Hz, 1H), 3.86 (td, J=7.0, 1.8 Hz, 2H), 2.32 (s, 3H), 1.99 (s, 3H), 1.78 (h, J=7.3 Hz, 2H), 0.83 (t, J=7.4 Hz, 3H). HRMS (ESI+) m/z calcd for $C_{24}H_{26}FN_4O_2^+$ [M+H]$^+$ 421.2034, found 421.2029.

Compound 22-a

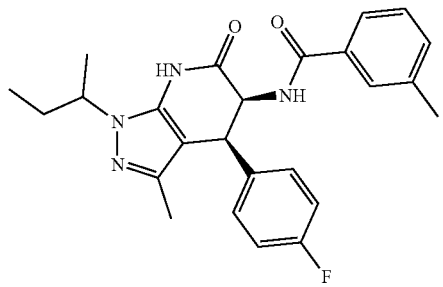

Pure cis-diastereomer on dihydropyirine core ring, one diastereomer on branched alkyl group. (TLC-up)

$^1$H NMR (500 MHz, Chloroform-d) δ 8.49 (s, 1H), 7.46 (s, 1H), 7.39 (dt, J=7.3, 1.7 Hz, 1H), 7.29-7.22 (m, 2H), 6.90-6.83 (m, 4H), 6.64 (d, J=5.9 Hz, 1H), 5.14 (dd, J=7.4, 6.0 Hz, 1H), 4.68 (d, J=7.5 Hz, 1H), 3.95-3.86 (m, 1H), 2.33 (s, 3H), 2.00 (s, 3H), 1.89 (m, 1H), 1.76-1.64 (m, 1H), 1.46 (d, J=6.7 Hz, 3H), 0.74 (t, J=7.4 Hz, 3H). HRMS (ESI+) m/z calcd for $C_{25}H_{28}FN_4O_2^+$ [M+H]$^+$ 435.2191, found 435.2184.

Compound 22-b

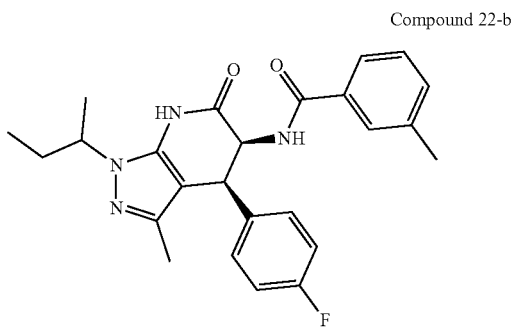 [SMILES: CCC(C)n1nc(C)c2c1NC(=O)[C@@H](NC(=O)c1cccc(C)c1)[C@H]2c1ccc(F)cc1]

Pure cis-diastereomer on dihydropyirine core ring, one diastereomer on branched alkyl group. (TLC-down)
¹H NMR (500 MHz, Chloroform-d) δ 8.63 (d, J=3.1 Hz, 1H), 7.46 (s, 1H), 7.42-7.35 (m, 1H), 7.26 (m, 2H), 6.86 (m, 4H), 6.62 (dd, J=6.1, 2.9 Hz, 1H), 5.13 (td, J=7.0, 2.9 Hz, 1H), 4.67 (dd, J=7.7, 2.9 Hz, 1H), 3.91 (m, 1H), 2.32 (s, 3H), 2.00 (s, 3H), 1.95-1.83 (m, 1H), 1.77-1.64 (m, 1H), 1.48-1.42 (m, 3H), 0.81-0.75 (m, 3H). HRMS (ESI+) m/z calcd for $C_{25}H_{28}FN_4O_2^+$ [M+H]⁺ 435.2191, found 435.2184.

Compound 23

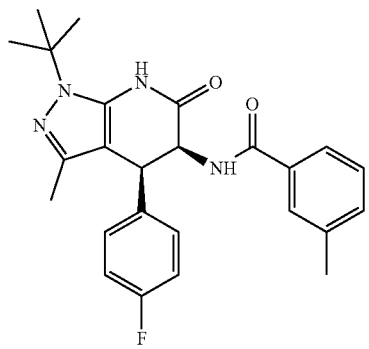

¹H NMR (400 MHz, Chloroform-d) δ 7.76 (s, 1H), 7.52 (s, 1H), 7.45 (d, J=6.9 Hz, 1H), 7.30 (m, 2H), 7.06-6.85 (m, 4H), 6.72 (d, J=5.8 Hz, 1H), 5.15 (t, J=7.4 Hz, 1H), 4.71 (d, J=7.4 Hz, 1H), 2.38 (s, 3H), 2.04 (s, 3H), 1.65 (s, 9H). HRMS (ESI+) m/z calcd for $C_{25}H_{28}FN_4O_2^+$ [M+H]⁺ 435.2191, found 435.2210.

Compound 24

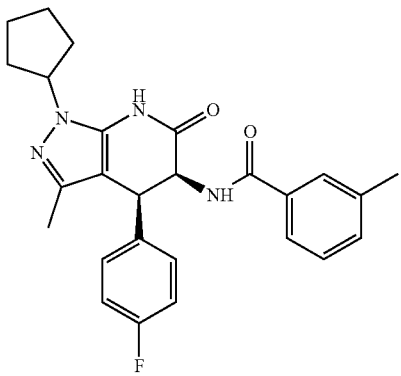

¹H NMR (400 MHz, Chloroform-d) δ 8.32 (s, 1H), 7.51 (s, 1H), 7.45-7.39 (m, 1H), 7.35-7.25 (m, 2H), 6.98-6.85 (m, 4H), 6.67 (d, J=6.0 Hz, 1H), 5.18 (dd, J=6.5, 5.7 Hz, 1H), 4.73 (d, J=7.5 Hz, 1H), 4.36 (p, J=7.8 Hz, 1H), 2.37 (s, 3H), 2.13-2.05 (m, 4H), 2.04 (s, 3H), 1.98-1.81 (m, 2H), 1.69-1.56 (m, 2H). HRMS (ESI+) m/z calcd for $C_{26}H_{28}FN_4O_2^+$ [M+H]⁺ 447.2191, found 447.2206.

Compound 25

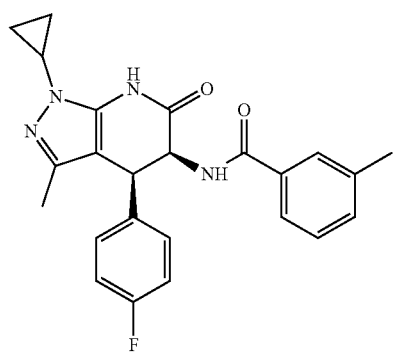

¹H NMR (400 MHz, Chloroform-d) δ 7.92 (s, 1H), 7.49 (s, 1H), 7.42 (d, 1H), 7.35-7.25 (m, 2H), 6.98-6.84 (m, 4H), 6.68 (d, J=5.8 Hz, 1H), 5.23-5.06 (m, 1H), 4.74 (d, J=7.5 Hz, 1H), 3.35-3.20 (m, 1H), 2.37 (s, 3H), 2.02 (s, 3H), 1.28-1.06 (m, 4H). HRMS (ESI+) m/z calcd for $C_{24}H_{24}FN_4O_2^+$ [M+H]⁺ 419.1878, found 419.1898.

Compound 26

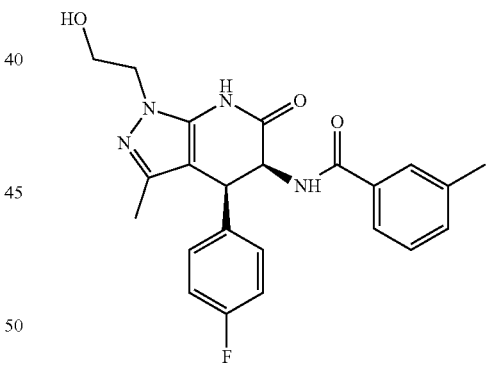

¹H NMR (400 MHz, Chloroform-d) δ 8.72 (s, 1H), 7.50 (s, 1H), 7.43 (d, J=6.9 Hz, 1H), 7.33-7.25 (m, 2H), 7.00-6.84 (m, 4H), 6.77 (d, J=5.6 Hz, 1H), 5.09 (dd, J=7.4, 5.6 Hz, 1H), 4.77 (d, J=7.4 Hz, 1H), 4.35-4.23 (m, 1H), 4.22-3.99 (m, 3H), 2.41-2.38 (m, 1H), 2.37 (s, 3H), 2.05 (s, 3H). HRMS (ESI+) m/z calcd for $C_{23}H_{24}FN_4O_3^+$ [M+H]⁺ 423.1827, found 423.1832.

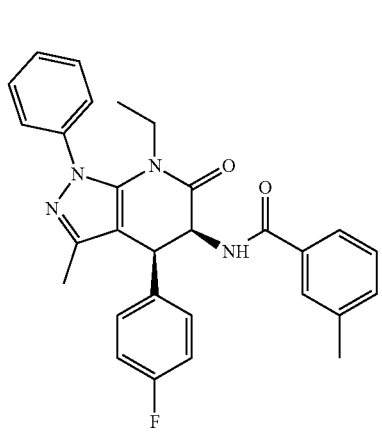

Compound 27

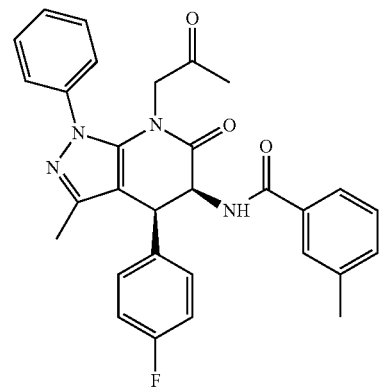

Compound 29

Compound 27 was synthesized by general procedure A, C and D starting from 4-fluorobenzaldehyde, (3-methylbenzoyl)glycine and 3-methyl-1-phenyl-1H-pyrazol-5-amine.

$^1$H NMR (400 MHz, Chloroform-d) δ 7.57 (s, 1H), 7.55-7.42 (m, 6H), 7.35-7.28 (m, 2H), 7.01-6.87 (m, 5H), 5.20 (dd, J=7.1, 5.6 Hz, 1H), 4.77 (d, J=7.0 Hz, 1H), 4.05-3.82 (m, 1H), 3.17 (dq, J=14.0, 7.0 Hz, 1H), 2.39 (s, 3H), 2.14 (s, 3H), 0.99 (t, J=7.1 Hz, 3H). $^{13}$C NMR (101 MHz, Chloroform-d) δ 168.0, 167.3, 161.0 (d, J=246.8 Hz), 147.0, 139.1, 139.0, 138.6, 133.7, 132.7, 132.5, 132.4, 130.0, 129.9, 129.6 (2C), 128.8, 128.6, 127.7, 125.3, 124.1, 115.5, 115.3, 105.9, 55.7, 39.2, 36.7, 21.3, 12.7, 11.9. HRMS (ESI+) m/z calcd for $C_{29}H_{28}FN_4O_2^+$ [M+H]$^+$ 483.2191, found 483.2193.

The PK data for compound 27 is shown in FIG. 14.

$^1$H NMR (400 MHz, Chloroform-d) δ 7.60-7.26 (m, 9H), 7.23-7.15 (m, 2H), 7.02-6.87 (m, 2H), 6.77 (s, 1H), 5.41-5.31 (m, 1H), 4.78 (d, J=7.4 Hz, 1H), 4.60 (d, J=18.2 Hz, 1H), 4.06 (d, J=18.4 Hz, 1H), 2.36 (s, 3H), 2.12 (s, 3H), 1.74 (s, 3H). HRMS (ESI+) m/z calcd for $C_{30}H_{28}FN_4O_3^+$ [M+H]$^+$ 511.2140, found 511.2144.

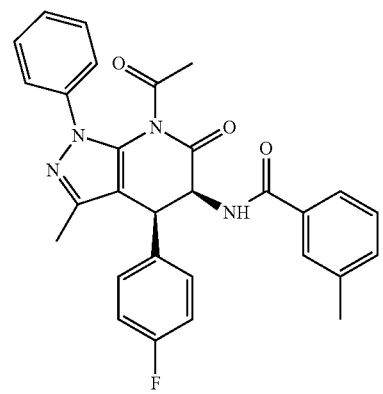

Compound 30

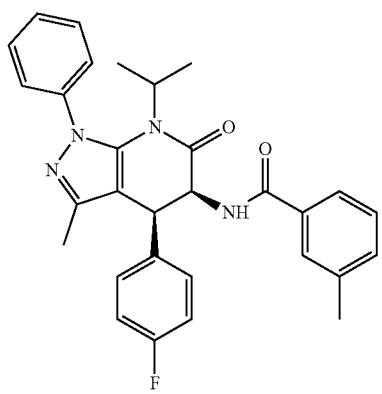

Compound 28

$^1$H NMR (400 MHz, Chloroform-d) δ 7.59 (s, 1H), 7.56-7.49 (m, 1H), 7.49-7.38 (m, 4H), 7.38-7.31 (m, 4H), 7.01-6.86 (m, 4H), 6.74 (d, J=6.5 Hz, 1H), 5.36 (t, J=6.5, 1H), 4.71 (d, J=6.6, 1H), 2.44 (s, 3H), 2.40 (s, 3H), 2.23 (s, 3H). HRMS (ESI+) m/z calcd for $C_{29}H_{26}FN_4O_3^+$ [M+H]$^+$ 497.1983, found 497.1994.

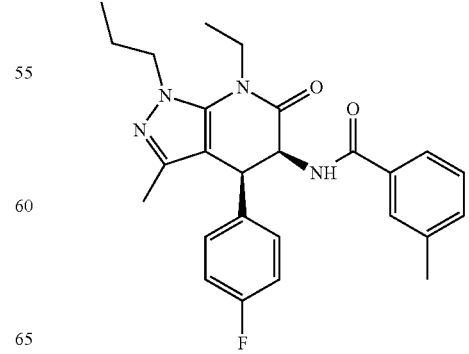

Compound 31

$^1$H NMR (400 MHz, Chloroform-d) δ 7.59 (s, 1H), 7.55-7.38 (m, 7H), 7.31 (d, J=6.5 Hz, 2H), 7.02 (t, J=6.2 Hz, 3H), 6.95-6.84 (m, 2H), 5.11 (t, J=5.4 Hz, 1H), 4.72 (d, J=7.2 Hz, 1H), 3.76-3.61 (m, 1H), 2.39 (s, 3H), 2.15 (s, 3H), 1.32 (t, J=6.5 Hz, 1H), 1.29 (t, J=6.8 Hz, 3H). HRMS (ESI+) m/z calcd for $C_{30}H_{30}FN_4O_2^+$ [M+H]$^+$ 497.2347, found 497.2336.

¹H NMR (400 MHz, Chloroform-d) δ 7.55 (s, 1H), 7.49 (m, 1H), 7.34-7.29 (m, 2H), 6.95 (s, 1H), 6.88 (d, J=7.0 Hz, 4H), 5.01 (dd, J=7.0, 5.5 Hz, 1H), 4.64 (dd, J=7.1 Hz, 1H), 4.29-4.10 (m, 2H), 4.12-3.99 (m, 1H), 3.85-3.70 (m, 1H), 2.38 (s, 3H), 2.06 (s, 3H), 1.86 (qt, J=15.8, 8.2 Hz, 2H), 1.34 (t, J=7.1 Hz, 3H), 1.01-0.81 (t, J=7.5 Hz, 3H). HRMS (ESI+) m/z calcd for $C_{26}H_{30}FN_4O_2^+$ [M+H]$^+$ 449.2347, found 449.2353.

Compound 32-a

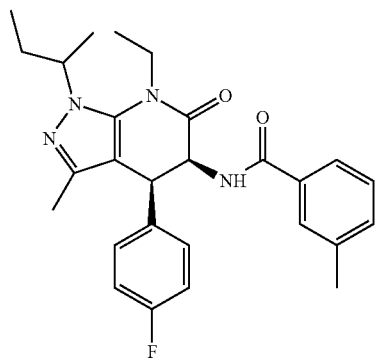

Pure cis-diastereomer on dihydropyirine core ring, one diastereomer on branched alkyl group. (TLC-up)

¹H NMR (400 MHz, Chloroform-d) δ 7.54 (s, 1H), 7.52-7.46 (m, 1H), 7.37-7.29 (m, 2H), 6.98 (d, J=5.5 Hz, 1H), 6.89-6.85 (m, 4H), 5.02-4.93 (m, 1H), 4.63 (d, J=7.1 Hz, 1H), 4.22-4.06 (m, 1H), 4.03-3.84 (m, 2H), 2.38 (s, 3H), 2.08 (s, 3H), 2.01-1.88 (m, 1H), 1.78-1.68 (m, 1H), 1.66 (d, J=6.5 Hz, 3H), 1.38 (t, J=7.3 Hz, 3H), 0.66 (t, J=7.4 Hz, 3H). HRMS (ESI+) m/z calcd for $C_{27}H_{32}FN_4O_2^+$ [M+H]$^+$ 463.2504, found 463.2494.

Compound 32-b

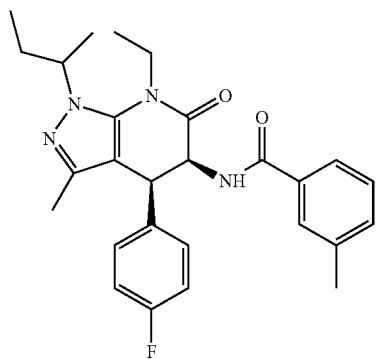

Pure cis-diastereomer on dihydropyirine core ring, one diastereomer on branched alkyl group. (TLC-down)

¹H NMR (400 MHz, Chloroform-d) δ 7.55 (s, 1H), 7.51 (d, J=6.3 Hz, 1H), 7.31 (d, J=6.2 Hz, 2H), 7.00-6.93 (m, 1H), 6.88 (d, J=7.3 Hz, 4H), 5.03-4.98 (m, 1H), 4.61 (d, J=7.2 Hz, 1H), 4.22-4.14 (m, 1H), 4.03-3.88 (m, 2H), 2.38 (s, 3H), 2.29-2.19 (m, 1H), 2.08 (s, 3H), 2.01-1.90 (m, 1H), 1.44-1.31 (m, 6H), 1.06 (t, J=7.3 Hz, 3H). HRMS (ESI+) m/z calcd for $C_{27}H_{32}FN_4O_2^+$ [M+H]$^+$ 463.2504, found 463.2509.

Compound 33

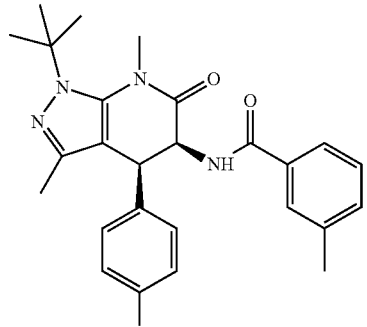

¹H NMR (400 MHz, Chloroform-d) δ 7.57 (s, 1H), 7.52 (m, 1H), 7.35-7.28 (m, 2H), 6.98 (d, J=5.9 Hz, 1H), 6.94-6.80 (m, 4H), 5.00 (t, J=6.3 Hz, 1H), 4.56 (d, J=6.6 Hz, 1H), 3.45 (s, 3H), 2.39 (s, 3H), 2.08 (s, 3H), 1.69 (s, 9H). HRMS (ESI+) m/z calcd for $C_{26}H_{30}FN_4O_2^+$ [M+H]$^+$ 449.2347, found 449.2342.

Compound 34

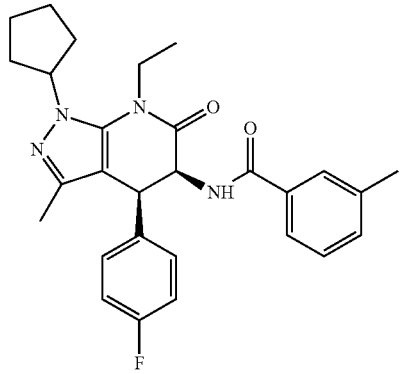

¹H NMR (400 MHz, Chloroform-d) δ 7.55 (s, 1H), 7.51 (d, J=6.4 Hz, 1H), 7.36-7.25 (m, 2H), 6.96 (d, J=5.8 Hz, 1H), 6.92-6.83 (m, 4H), 5.00 (dd, J=6.9, 5.3 Hz, 1H), 4.66-4.51 (m, 2H), 4.10-3.86 (m, 2H), 2.37 (s, 3H), 2.37-2.30 (m, 1H), 2.22-2.08 (m, 1H), 2.06 (s, 3H), 2.04-1.84 (m, 4H), 1.74-7.59 (m, 2H), 1.36 (t, J=7.2 Hz, 3H). HRMS (ESI+) m/z calcd for $C_{28}H_{32}FN_4O_2^+$ [M+H]$^+$ 475.2504, found 475.2508.

Compound 35

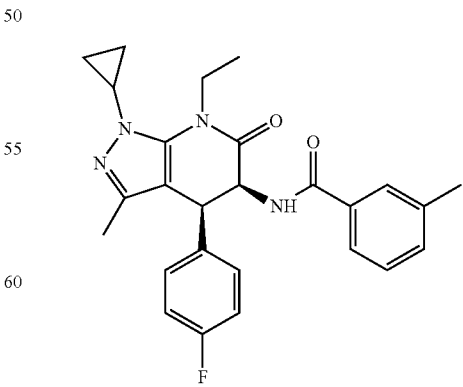

¹H NMR (400 MHz, Chloroform-d) δ 7.54 (s, 1H), 7.50 (d, J=6.3 Hz, 1H), 7.34-7.27 (m, 2H), 6.95 (d, J=5.8 Hz, 1H), 6.89 (d, J=7.8 Hz, 4H), 5.00 (dd, J=7.0, 5.3 Hz, 1H), 4.62 (d, J=7.2 Hz, 1H), 4.41 (dq, J=14.4, 7.2 Hz, 1H), 4.22 (dq, J=14.2, 7.1 Hz, 1H), 3.55-3.42 (m, 1H), 2.37 (s, 3H), 2.04 (s, 3H), 1.42-1.36 (m, 1H), 1.33 (t, J=7.1 Hz, 3H), 1.27-1.16 (m, 2H), 1.06 (d, J=7.9 Hz, 1H). HRMS (ESI+) m/z calcd for $C_{26}H_{28}FN_4O_2^+$ [M+H]$^+$ 447.2191, found 447.2215.

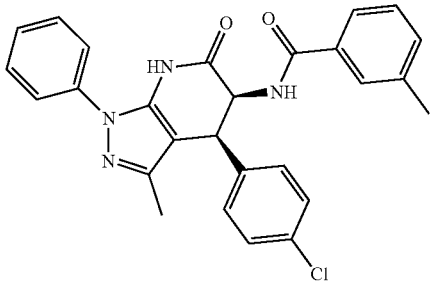

Compound 36

$^1$H NMR (500 MHz, Chloroform-d) δ 7.96 (s, 1H), 7.48-7.45 (m, 3H), 7.42 (d, J=8.4 Hz, 2H), 7.39 (dt, J=7.2, 1.9 Hz, 1H), 7.31-7.22 (m, 3H), 7.16-7.12 (m, 2H), 6.91-6.86 (m, 2H), 6.66 (d, J=5.6 Hz, 1H), 5.21 (dd, J=7.6, 5.6 Hz, 1H), 4.81 (d, J=7.6 Hz, 1H), 2.33 (s, 3H), 2.09 (s, 3H). HRMS (ESI+) m/z calcd for $C_{27}H_{24}ClN_4O_2^+$ [M+H]$^+$ 471.1582, found 471.1589.

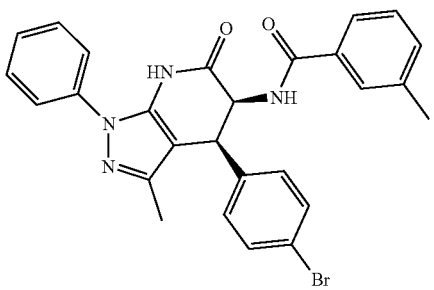

Compound 37

$^1$H NMR (500 MHz, Chloroform-d) δ 7.88 (s, 1H), 7.46 (m, 3H), 7.51-7.40 (m, 2H), 7.42-7.36 (m, 1H), 7.33-7.20 (m, 6H), 6.86-6.79 (m, 2H), 6.68 (d, J=5.6 Hz, 1H), 5.21 (dd, J=7.5, 5.6 Hz, 1H), 4.80 (d, J=7.5 Hz, 1H), 2.33 (s, 3H), 2.08 (s, 3H). HRMS (ESI+) m/z calcd for $C_{27}H_{24}BrN_4O_2^+$ [M+H]$^+$ 515.1077, found 515.1077.

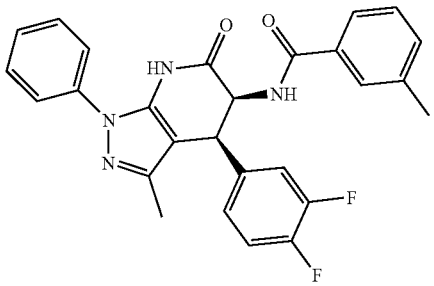

Compound 38

$^1$H NMR (500 MHz, Chloroform-d) δ 7.89 (s, 1H), 7.49-7.35 (m, 7H), 7.36-7.20 (m, 3H), 6.96 (dt, J=10.0, 8.2 Hz, 1H), 6.79-6.67 (m, 2H), 5.17 (dd, J=7.5, 5.3 Hz, 1H), 4.83 (d, J=7.6 Hz, 1H), 2.34 (s, 3H), 2.09 (s, 3H). HRMS (ESI+) m/z calcd for $C_{27}H_{23}F_2N_4O_2^+$ [M+H]$^+$ 473.1784, found 473.1768.

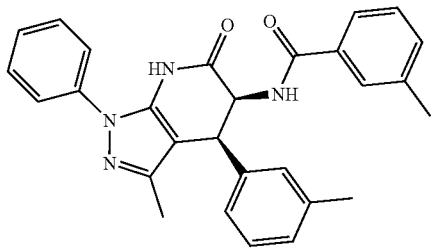

Compound 39

$^1$H NMR (500 MHz, Chloroform-d) δ 8.08 (s, 1H), 7.47 (dd, J=8.3, 1.3 Hz, 2H), 7.45-7.34 (m, 4H), 7.31-7.20 (m, 3H), 7.07 (t, J=7.5 Hz, 1H), 6.98 (d, J=7.6 Hz, 1H), 6.78-6.72 (m, 2H), 6.53 (d, J=6.4 Hz, 1H), 5.27 (t, J=7.0 Hz, 1H), 4.70 (d, J=7.5 Hz, 1H), 2.31 (s, 3H), 2.16 (s, 3H), 2.10 (s, 3H). HRMS (ESI+) m/z calcd for $C_{28}H_{27}N_4O_2^+$ [M+H]$^+$ 451.2129, found 451.2124.

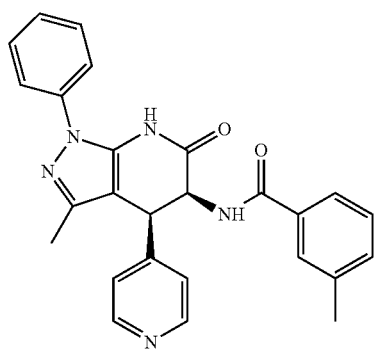

Compound 40

$^1$H NMR (400 MHz, Chloroform-d) δ 8.44 (s, 2H), 8.27 (s, 1H), 7.59-7.39 (m, 6H), 7.31 (m, 3H), 6.93 (m, 2H), 6.79 (m, 1H), 5.27 (t, J=7.8 Hz, 1H), 4.93 (d, J=7.8, 1H), 2.38 (s, 3H), 2.15 (s, 3H). HRMS (ESI+) m/z calcd for $C_{26}H_{24}N_5O_2^+$ [M+H]$^+$ 438.1925, found 438.1914.

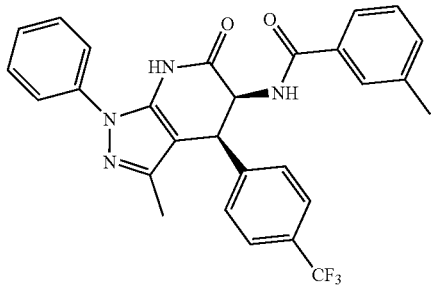

Compound 41

$^1$H NMR (500 MHz, Chloroform-d) δ 7.91 (s, 1H), 7.49-7.41 (m, 7H), 7.41-7.34 (m, 1H), 7.33-7.22 (m, 3H), 7.08 (d, J=8.1 Hz, 2H), 6.69 (d, J=5.4 Hz, 1H), 5.24 (dd, J=7.6, 5.3 Hz, 1H), 4.93 (d, J=7.6 Hz, 1H), 2.32 (s, 3H), 2.09 (s, 3H). HRMS (ESI+) m/z calcd for $C_{28}H_{24}F_3N_4O_2^+$ [M+H]$^+$ 505.1846, found 505.1825.

Compound 42

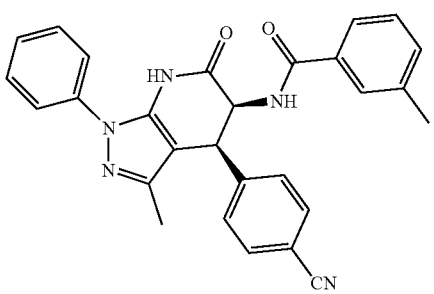

Purchased from Commercial Source

Compound 43

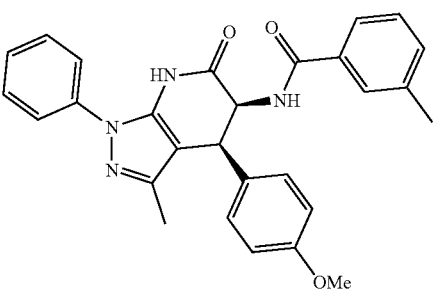

Purchased from Commercial Source

Compound 44

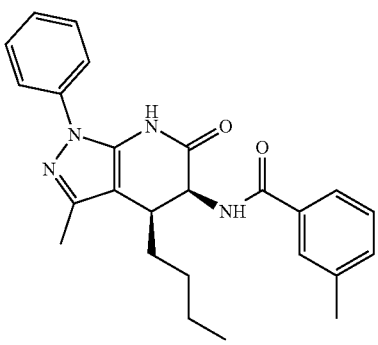

¹H NMR (400 MHz, Chloroform-d) δ 7.85 (s, 1H), 7.70-7.59 (m, 2H), 7.47 (m, 4H), 7.41-7.29 (m, 3H), 7.20 (m, 1H), 4.96 (t, J=5.7 Hz, 1H), 3.61 (m, 1H), 2.42 (s, 3H), 2.29 (s, 3H), 1.41-1.01 (m, 6H), 0.82 (t, J=7.6 Hz, 3H). HRMS (ESI+) m/z calcd for $C_{25}H_{29}N_4O_2^+$ [M+H]$^+$ 417.2285, found 417.2301.

Compound 45

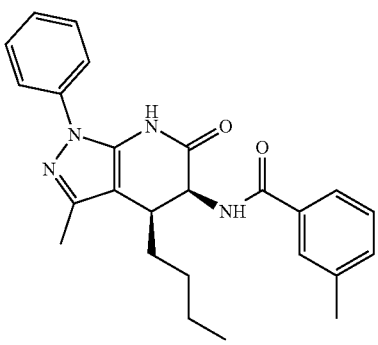

¹H NMR (400 MHz, Chloroform-d) δ 7.67 (s, 3H), 7.46 (m, 5H), 7.34 (m, 3H), 4.95 (dd, J=7.0, 4.5 Hz, 1H), 3.81 (m, 1H), 2.42 (s, 3H), 2.30 (s, 3H), 2.05-1.91 (m, 1H), 1.84-1.70 (m, 1H), 1.48-1.35 (m, 3H), 1.33-1.16 (m, 2H), 1.07-0.89 (m, 2H). HRMS (ESI+) m/z calcd for $C_{26}H_{29}N_4O_2^+$ [M+H]$^+$ 429.2285, found 429.2286.

Compound 46

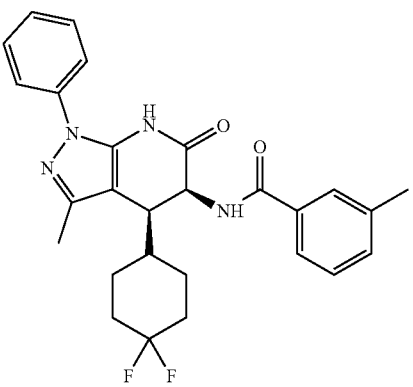

¹H NMR (400 MHz, Chloroform-d) δ 7.71-7.64 (m, 2H), 7.58-7.33 (m, 8H), 7.30 (s, 1H), 4.91-4.84 (m, 1H), 3.85 (d, J=7.1 Hz, 1H), 2.44 (s, 3H), 2.30 (s, 3H), 2.16-1.90 (m, 3H), 1.82-1.57 (m, 4H), 1.53-1.37 (m, 1H), 1.30-1.15 (m, 1H). HRMS (ESI+) m/z calcd for $C_{27}H_{29}F_2N_4O_2^+$ [M+H]$^+$ 479.2253, found 479.2259.

Compound 47

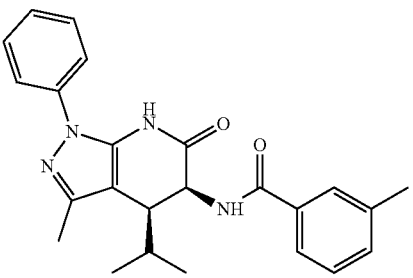

¹H NMR (400 MHz, Chloroform-d) δ 7.71-7.58 (m, 3H), 7.52-7.40 (m, 5H), 7.35 (d, J=5.5 Hz, 3H), 4.92 (dd, J=7.1, 5.1 Hz, 1H), 3.73 (dd, J=7.4, 3.5 Hz, 1H), 2.42 (s, 3H), 2.30

(s, 3H), 0.96 (d, J=7.0 Hz, 3H), 0.73 (d, J=6.7 Hz, 3H). HRMS (ESI+) m/z calcd for $C_{24}H_{27}N_4O_2^+$ [M+H]$^+$ 403.2129, found 403.2134.

Compound 48

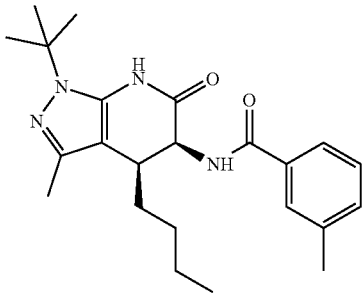

$^1$H NMR (400 MHz, Chloroform-d) δ 7.73-7.57 (m, 3H), 7.34 (m, 2H), 7.21 (d, J=5.4 Hz, 1H), 4.85 (t, J=5.7 Hz, 1H), 3.43 (m, 1H), 2.41 (s, 3H), 2.18 (s, 3H), 1.69-1.59 (m, 2H), 1.60 (s, 9H), 1.34-1.04 (m, 4H), 0.79 (t, J=6.0 Hz, 3H). HRMS (ESI+) m/z calcd for $C_{23}H_{33}N_4O_2^+$ [M+H]$^+$ 397.2598, found 397.2597.

Compound 49

$^1$H NMR (400 MHz, Chloroform-d) δ 7.68 (s, 1H), 7.68-7.64 (m, 1H), 7.60 (s, 1H), 7.40-7.31 (m, 2H), 7.21 (d, J=5.2 Hz, 1H), 4.80 (dd, J=7.3, 5.1 Hz, 1H), 3.50 (d, J=7.3, 1H), 2.42 (s, 3H), 2.18 (s, 3H), 1.72-1.40 (m, 7H), 1.60 (s, 9H), 1.28-1.01 (m, 2H), 1.01-0.73 (m, 2H). HRMS (ESI+) m/z calcd for $C_{25}H_{35}N_4O_2^+$ [M+H]$^+$ 423.2755, found 423.2757.

Compound 50

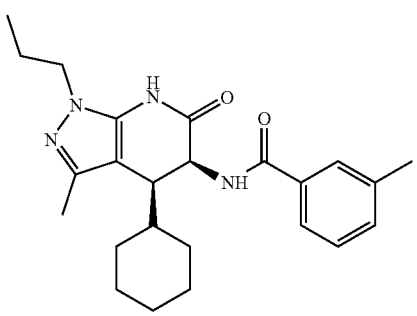

$^1$H NMR (400 MHz, Chloroform-d) δ 8.20 (s, 1H), 7.68 (s, 1H), 7.67-7.62 (m, 1H), 7.39-7.30 (m, 2H), 7.17 (d, J=5.1 Hz, 1H), 4.82 (dd, J=7.4, 6.5 Hz, 1H), 3.89 (m, 2H), 3.56 (d, J=7.4 Hz, 1H), 2.42 (s, 3H), 2.20 (s, 3H), 1.89-1.76 (m, 2H), 1.72-1.60 (m, 3H), 1.46 (d, J=12.6 Hz, 1H), 1.27-0.93 (m, 6H), 0.89 (t, J=7.4 Hz, 3H), 0.84-0.74 (m, 1H). HRMS (ESI+) m/z calcd for $C_{24}H_{33}N_4O_2^+$ [M+H]$^+$ 409.2598, found 409.2602.

Compound 51

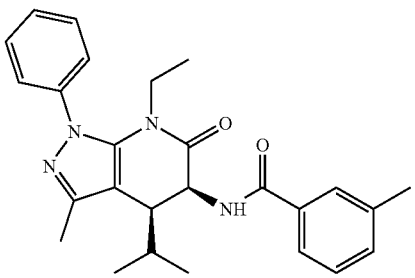

$^1$H NMR (400 MHz, Chloroform-d) δ 7.72-7.65 (m, 1H), 7.49-7.31 (m, 8H), 3.99-3.85 (m, 1H), 3.60-3.53 (m, 1H), 3.07 (qd, J=14.3, 7.1 Hz, 1H), 2.42 (s, 3H), 2.00-1.89 (m, 1H), 0.98 (d, J=7.1 Hz, 3H), 0.89 (t, J=7.1 Hz, 3H), 0.69 (d, J=6.8 Hz, 3H). HRMS (ESI+) m/z calcd for $C_{26}H_{31}N_4O_2^+$ [M+H]$^+$ 431.2442, found 431.2444.

Compound 52

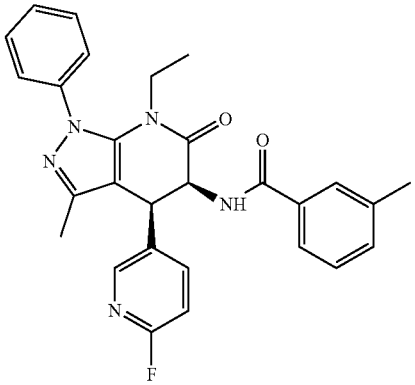

$^1$H NMR (400 MHz, Chloroform-d) δ 7.85 (s, 1H), 7.61-7.43 (m, 7H), 7.42-7.30 (m, 3H), 7.12 (d, J=5.0 Hz, 1H), 6.87-6.76 (m, 1H), 5.19 (dd, J=7.0, 5.0 Hz, 1H), 4.89 (d, J=7.1 Hz, 1H), 3.97 (dq, J=14.0, 7.1 Hz, 1H), 3.23-3.12 (m, 1H), 2.40 (s, 3H), 2.16 (s, 3H), 0.98 (t, J=7.1 Hz, 3H). HRMS (ESI+) m/z calcd for $C_{28}H_{27}FN_5O_2^+$ [M+H]$^+$ 484.2143, found 484.2157.

Compound 53

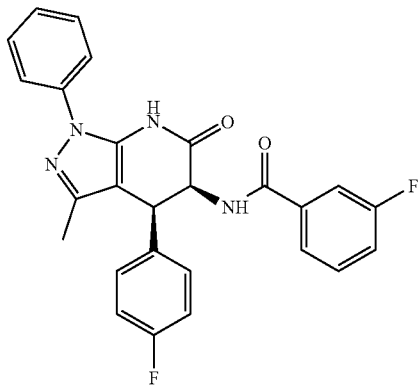

¹H NMR (400 MHz, Chloroform-d) δ 8.07 (s, 1H), 7.56-7.29 (m, 8H), 7.23-7.17 (m, 1H), 7.00-6.89 (m, 4H), 6.77-6.67 (m, 1H), 5.24 (dd, J=8.3, 5.7 Hz, 1H), 4.85 (d, J=7.5 Hz, 1H), 2.13 (s, 3H). HRMS (ESI+) m/z calcd for C₂₆H₂₁F₂N₄O₂⁺ [M+H]⁺ 459.1627, found 459.1626.

Compound 54

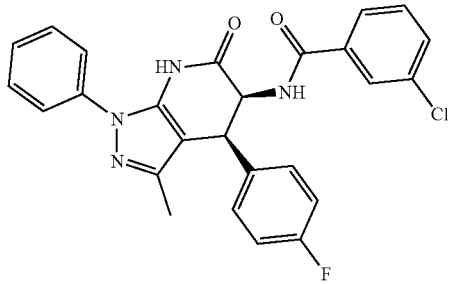

¹H NMR (500 MHz, Chloroform-d) δ 8.03 (s, 1H), 7.62 (t, J=1.9 Hz, 1H), 7.49-7.39 (m, 6H), 7.35-7.22 (m, 2H), 6.95-6.83 (m, 4H), 6.64 (d, J=5.6 Hz, 1H), 5.18 (dd, J=7.6, 5.6 Hz, 1H), 4.80 (d, J=7.5 Hz, 1H), 2.09 (s, 3H). HRMS (ESI+) m/z calcd for C₂₆H₂₁ClFN₄O₂⁺ [M+H]⁺ 475.1332, found 475.1279.

Compound 55

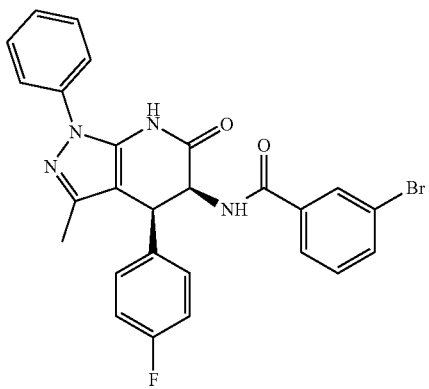

¹H NMR (400 MHz, Chloroform-d) δ 7.98 (s, 1H), 7.83 (s, 1H), 7.64 (d, J=8.1 Hz, 1H), 7.56-7.46 (m, 5H), 7.42-7.26 (m, 2H), 6.99-6.88 (m, 4H), 6.73-6.65 (m, 1H), 5.23 (dd, J=7.5, 5.6 Hz, 1H), 4.85 (d, J=7.5 Hz, 1H), 2.14 (s, 3H). HRMS (ESI+) m/z calcd for C₂₆H₂₁BrFN₄O₂⁺ [M+H]⁺ 519.0826, found 519.0832.

Compound 56

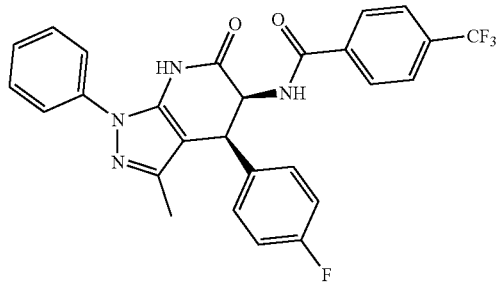

¹H NMR (500 MHz, Chloroform-d) δ 7.78-7.69 (m, 3H), 7.63 (d, J=8.2 Hz, 2H), 7.50-7.41 (m, 4H), 7.38-7.29 (m, 1H), 6.96-6.82 (m, 4H), 6.73 (d, J=5.6 Hz, 1H), 5.20 (dd, J=7.5, 5.6 Hz, 1H), 4.82 (d, J=7.5 Hz, 1H), 2.09 (s, 3H). HRMS (ESI+) m/z calcd for C₂₇H₂₁F₄N₄O₂⁺ [M+H]⁺ 509.1595, found 509.1580.

Compound 57

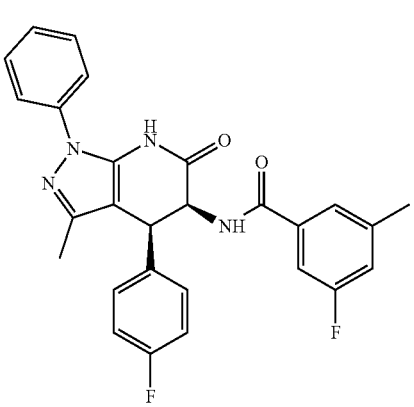

¹H NMR (400 MHz, Chloroform-d) δ 8.04 (s, 1H), 7.59-7.39 (m, 4H), 7.38-7.30 (m, 1H), 7.22-7.13 (m, 2H), 7.02 (d, J=9.6 Hz, 1H), 6.99-6.88 (m, 4H), 6.67 (s, 1H), 5.25-5.19 (m, 1H), 4.85 (d, J=7.7 Hz, 1H), 2.37 (s, 3H), 2.13 (s, 3H). HRMS (ESI+) m/z calcd for C₂₇H₂₃F₂N₄O₂⁺ [M+H]⁺ 473.1784, found 473.1781.

Compound 58

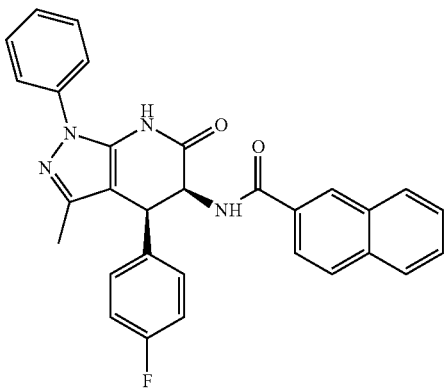

¹H NMR (400 MHz, Chloroform-d) δ 8.18 (s, 1H), 7.93 (s, 1H), 7.91-7.84 (m, 3H), 7.75 (d, J=9.2 Hz, 1H), 7.53 (m, 6H), 7.38-7.30 (m, 1H), 7.05-6.97 (m, 2H), 6.95-6.87 (m, 3H), 5.33 (dd, J=7.7, 5.5 1H), 4.92 (d, J=7.7 Hz, 1H), 2.15 (s, 3H). HRMS (ESI+) m/z calcd for $C_{30}H_{24}FN_4O_2^+$ [M+H]$^+$ 491.1878, found 491.1884.

Compound 59

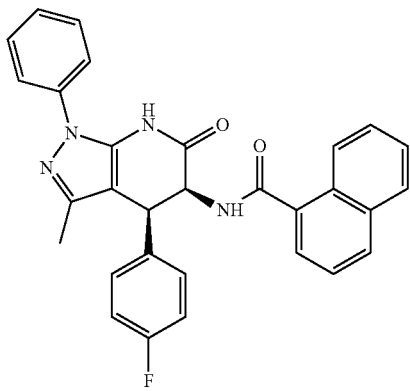

$^1$H NMR (400 MHz, Chloroform-d) δ 8.21 (s, 1H), 7.96-7.76 (m, 3H), 7.57-7.36 (m, 8H), 7.34-7.27 (m, 1H), 7.14-7.03 (m, 2H), 6.99-6.90 (m, 2H), 6.65 (s, 1H), 5.36 (m, 1H), 5.01 (d, J=7.7, 1H), 2.17 (s, 3H). HRMS (ESI+) m/z calcd for $C_{30}H_{24}FN_4O_2^+$ [M+H]$^+$ 491.1878, found 491.1883.

Compound 60

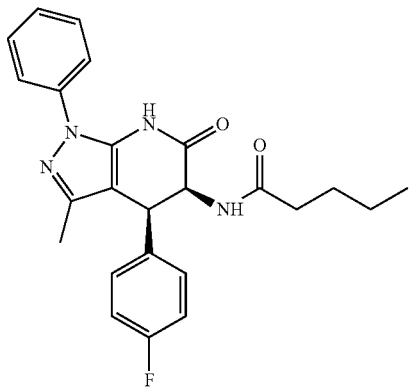

$^1$H NMR (400 MHz, Chloroform-d) δ 7.69 (s, 1H), 7.56-7.46 (m, 4H), 7.39 (d, J=7.0 Hz, 1H), 7.01-6.85 (m, 4H), 6.02 (d, J=5.7 Hz, 1H), 5.08 (dd, J=7.4, 6.8 Hz, 1H), 4.71 (d, J=7.4 Hz, 1H), 2.25-2.12 (m, 2H), 2.10 (s, 3H), 1.61-1.55 (m, 2H), 1.30 (q, J=7.7 Hz, 2H), 0.89 (t, J=7.7 Hz, 3H). HRMS (ESI+) m/z calcd for $C_{24}H_{26}FN_4O_2^+$ [M+H]$^+$ 421.2034, found 421.2041.

Compound 61

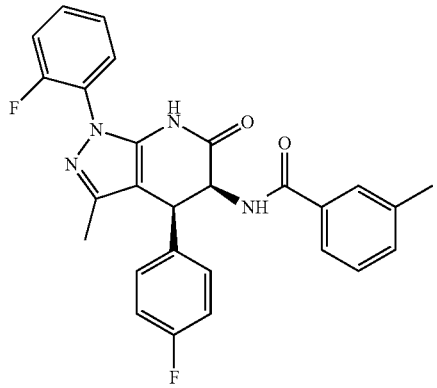

$^1$H NMR (400 MHz, Chloroform-d) δ 7.86 (s, 1H), 7.65 (t, J=7.8 Hz, 1H), 7.50 (s, 1H), 7.43 (d, J=7.0 Hz, 1H), 7.41-7.34 (m, 1H), 7.34-7.26 (m, 4H), 7.05-6.97 (m, 2H), 6.97-6.90 (m, 2H), 6.70 (d, J=5.6 Hz, 1H), 5.24-5.17 (m, 1H), 4.85 (d, J=7.5 Hz, 1H), 2.38 (s, 3H), 2.15 (s, 3H). HRMS (ESI+) m/z calcd for $C_{27}H_{23}F_2N_4O_2^+$ [M+H]$^+$ 473.1784, found 473.1768.

Compound 62

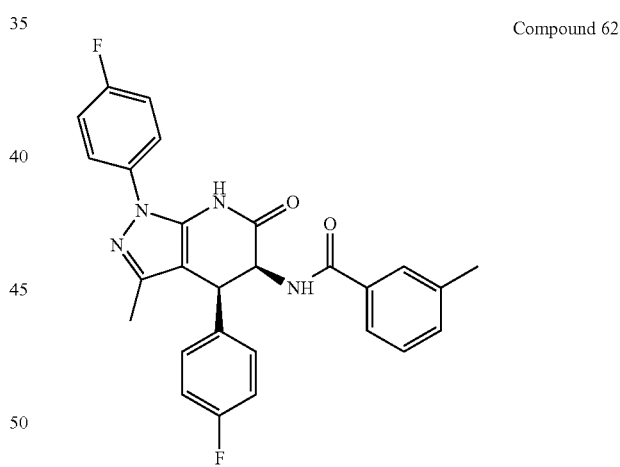

$^1$H NMR (400 MHz, Chloroform-d) δ 7.76 (s, 1H), 7.57-7.44 (m, 3H), 7.43 (d, J=7.0 Hz, 1H), 7.35-7.26 (m, 2H), 7.23-7.16 (m, 2H), 7.00-6.88 (m, 4H), 6.70 (d, J=5.8 Hz, 1H), 5.26 (dd, J=7.5, 5.7 Hz, 1H), 4.85 (d, J=7.5 Hz, 1H), 2.37 (s, 3H), 2.13 (s, 3H). HRMS (ESI+) m/z calcd for $C_{27}H_{23}F_2N_4O_2^+$ [M+H]$^+$ 473.1784, found 473.1767.

Compound 63

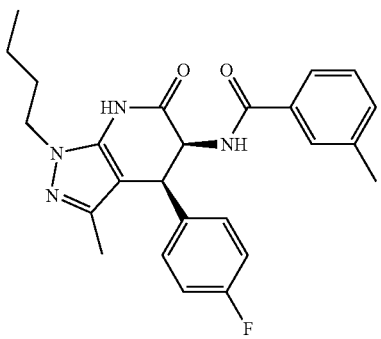

¹H NMR (500 MHz, Chloroform-d) δ 8.65 (s, 1H), 7.45 (s, 1H), 7.40-7.34 (m, 1H), 7.29-7.22 (m, 2H), 6.92-6.82 (m, 4H), 6.59 (d, J=6.0 Hz, 1H), 5.14 (dd, J=7.4, 6.0 Hz, 1H), 4.68 (d, J=7.5 Hz, 1H), 3.89 (t, J=7.3 Hz, 2H), 2.33 (s, 3H), 1.99 (s, 3H), 1.73 (pt, J=8.1, 4.2 Hz, 2H), 1.24 (dqd, J=14.5, 7.3, 1.9 Hz, 2H), 0.82 (t, J=7.4 Hz, 3H). HRMS (ESI+) m/z calcd for $C_{25}H_{28}FN_4O_2^+$ [M+H]$^+$ 435.2191, found 435.2185.

Compound 64

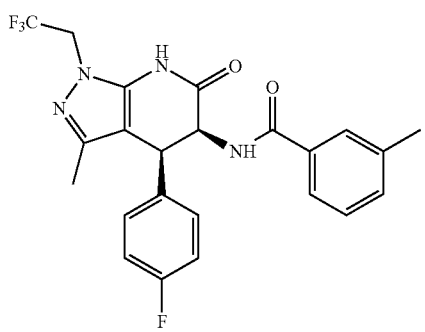

¹H NMR (400 MHz, Chloroform-d) δ 8.97 (s, 1H), 7.49 (s, 1H), 7.42 (d, J=7.5 Hz, 1H), 7.35-7.25 (m, 2H), 6.93 (d, J=6.7 Hz, 4H), 6.63 (d, 1H), 5.25-5.13 (m, 1H), 4.76 (d, J=7.5 Hz, 1H), 4.73-4.62 (m, 1H), 4.59-4.43 (m, 1H), 2.37 (s, 3H), 2.06 (s, 3H). HRMS (ESI+) m/z calcd for $C_{23}H_{21}F_4N_4O_2^+$ [M+H]$^+$ 461.1595, found 461.1604.

Compound 65

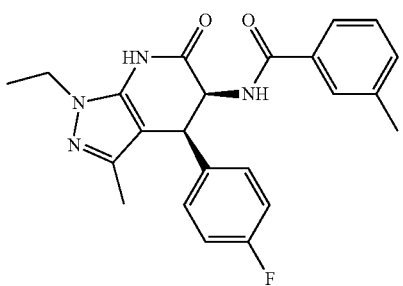

¹H NMR (500 MHz, Chloroform-d) δ 8.75 (s, 1H), 7.45 (s, 1H), 7.38 (dd, J=7.3, 1.8 Hz, 1H), 7.30-7.22 (m, 2H), 6.92-6.82 (m, 4H), 6.61 (d, J=6.0 Hz, 1H), 5.14 (dd, J=7.4, 6.1 Hz, 1H), 4.69 (d, J=7.5 Hz, 1H), 3.96 (q, J=7.3 Hz, 2H), 2.32 (s, 3H), 2.00 (s, 3H), 1.37 (t, J=7.2 Hz, 3H). HRMS (ESI+) m/z calcd for $C_{23}H_{24}FN_4O_2^+$ [M+H]$^+$ 407.1878, found 407.1878.

Compound 66

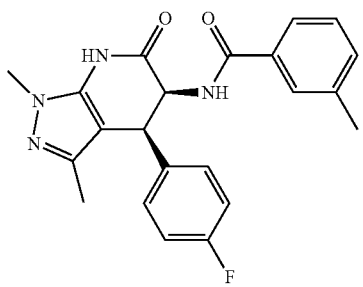

Purchased from Commercial Source

Compound 67

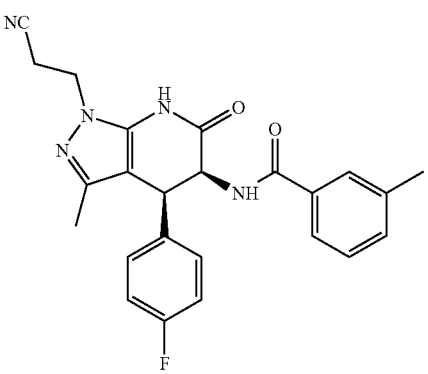

¹H NMR (400 MHz, Chloroform-d) δ 8.79 (s, 1H), 7.51 (s, 1H), 7.43 (d, J=7.1 Hz, 1H), 7.30 (d, J=7.5 Hz, 2H), 7.01-6.84 (m, 4H), 6.69 (d, J=6.1 Hz, 1H), 5.20 (dd, J=7.4, 6.8 Hz, 1H), 4.73 (d, J=7.4 Hz, 1H), 4.36-4.14 (m, 2H), 3.06-2.91 (m, 1H), 2.81 (dt, J=16.9, 5.2 Hz, 1H), 2.37 (s, 3H), 2.05 (s, 3H). HRMS (ESI+) m/z calcd for $C_{24}H_{23}FN_5O_2^+$ [M+H]$^+$ 432.1840, found 432.1843.

Compound 68

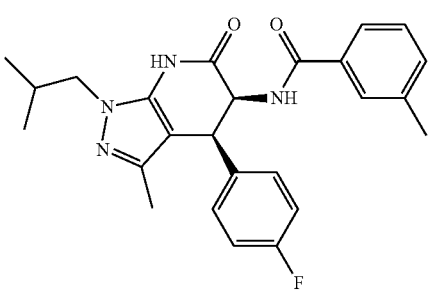

¹H NMR (500 MHz, Chloroform-d) δ 8.93 (s, 1H), 7.45 (d, J=1.9 Hz, 1H), 7.41-7.35 (m, 1H), 7.28-7.22 (m, 2H), 6.92-6.83 (m, 4H), 6.60 (d, J=6.0 Hz, 1H), 5.14 (dd, J=7.4, 6.0 Hz, 1H), 4.68 (d, J=7.5 Hz, 1H), 3.69 (m, 2H), 2.32 (s, 3H), 2.14 (hept, J=7.1 Hz, 1H), 1.99 (s, 3H), 0.83 (d, 6.7 Hz, 3H), 0.81 (d, 6.7 Hz, 3H). HRMS (ESI+) m/z calcd for $C_{25}H_{28}FN_4O_2^+$ [M+H]$^+$ 435.2191, found 435.2195.

Compound 69

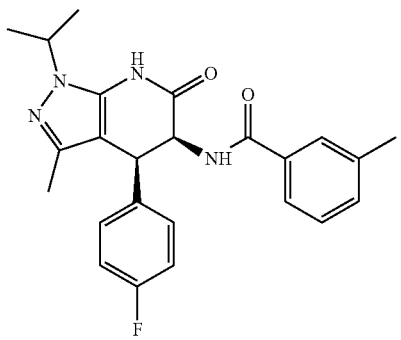

¹H NMR (400 MHz, Chloroform-d) δ 8.52 (s, 1H), 7.51 (s, 1H), 7.46-7.38 (m, 1H), 7.36-7.26 (m, 2H), 6.99-6.84 (m, 4H), 6.73-6.62 (m, 1H), 5.19 (m, 1H), 4.72 (d, J=7.3 Hz, 1H), 4.27 (m, 1H), 2.37 (s, 3H), 2.05 (s, 3H), 1.48 (t, J=5.3 Hz, 6H). HRMS (ESI+) m/z calcd for $C_{24}H_{26}FN_4O_2^+$ [M+H]⁺ 421.2034, found 421.2053.

Compound 70-a

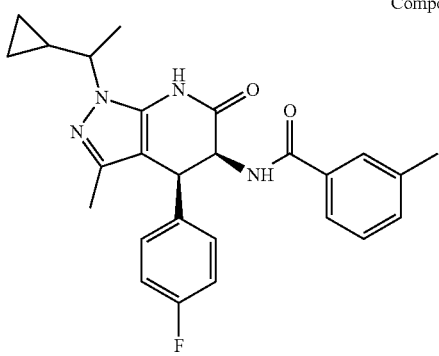

Pure cis-diastereomer on dihydropyirine core ring, one diastereomer on branched alkyl group. (TLC-up)
¹H NMR (400 MHz, Chloroform-d) δ 8.24-8.07 (m, 1H), 7.51 (s, 1H), 7.46-7.40 (m, 1H), 7.30 (d, J=8.1 Hz, 2H), 6.91 (d, J=7.2 Hz, 4H), 6.67 (d, J=6.2 Hz, 1H), 5.19 (t, J=7.1 Hz, 1H), 4.73 (d, J=7.4 Hz, 1H), 3.57-3.42 (m, 1H), 2.37 (s, 3H), 2.05 (s, 3H), 1.57 (m, 3H), 1.42-1.25 (m, 1H), 0.75-0.64 (m, 1H), 0.64-0.52 (m, 1H), 0.40-0.22 (m, 2H). HRMS (ESI+) m/z calcd for $C_{26}H_{28}FN_4O_2^+$ [M+H]⁺ 447.2191, found 447.2202.

Compound 70-b

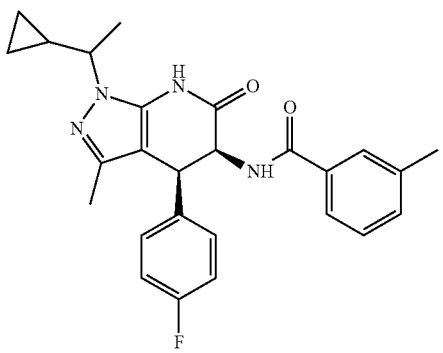

Pure cis-diastereomer on dihydropyirine core ring, one diastereomer on branched alkyl group. (TLC-down)
¹H NMR (400 MHz, Chloroform-d) δ 8.55 (s, 1H), 7.52 (s, 1H), 7.45 (d, J=7.2 Hz, 1H), 7.36-7.25 (m, 2H), 6.93 (d, J=6.8 Hz, 4H), 6.65 (d, J=6.0 Hz, 1H), 5.19 (t, J=6.9 Hz, 1H), 4.72 (dd, J=7.5 Hz, 1H), 3.53-3.36 (m, 1H), 2.38 (s, 3H), 2.06 (s, 3H), 1.59 (s, 3H), 1.40-1.27 (m, 1H), 0.66-0.58 (m, 1H), 0.56-0.47 (m, 1H), 0.38-0.26 (m, 1H), 0.24-0.13 (m, 1H). HRMS (ESI+) m/z calcd for $C_{26}H_{28}FN_4O_2^+$ [M+H]⁺ 447.2191, found 447.2207.

Compound 71-a

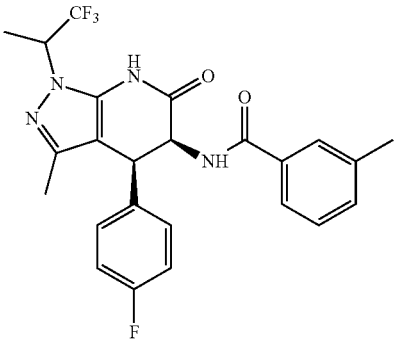

¹H NMR (400 MHz, Chloroform-d) δ 8.68 (s, 1H), 7.50 (s, 1H), 7.43 (d, J=7.2 Hz, 1H), 7.35-7.26 (m, 2H), 6.96-6.89 (m, 4H), 6.63 (d, J=6.1 Hz, 1H), 5.22 (dd, J=7.5, 6.8 Hz, 1H), 4.79 (p, J=7.3 Hz, 1H), 4.72 (d, J=7.5 Hz, 1H), 2.37 (s, 3H), 2.05 (s, 3H), 1.75 (d, J=7.2 Hz, 3H). HRMS (ESI+) m/z calcd for $C_{24}H_{23}F_4N_4O_2^+$ [M+H]⁺ 475.1752, found 475.1753.

Compound 71-b

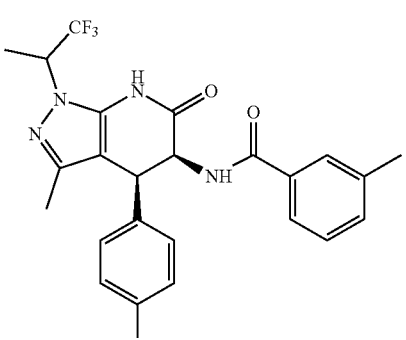

¹H NMR (400 MHz, Chloroform-d) δ 8.72 (s, 1H), 7.50 (s, 1H), 7.44 (d, J=6.9 Hz, 1H), 7.31 (d, J=7.4 Hz, 2H), 7.01-6.85 (m, 4H), 6.67 (d, J=5.9 Hz, 1H), 5.28-5.09 (m, 1H), 4.75 (d, J=7.4 Hz, 1H), 4.57 (p, J=6.8 Hz, 1H), 2.38 (s, 3H), 2.07 (s, 3H), 1.83 (d, J=7.0 Hz, 3H). HRMS (ESI+) m/z calcd for $C_{24}H_{23}F_4N_4O_2^+$ [M+H]⁺ 475.1752, found 475.1755.

Compound 72

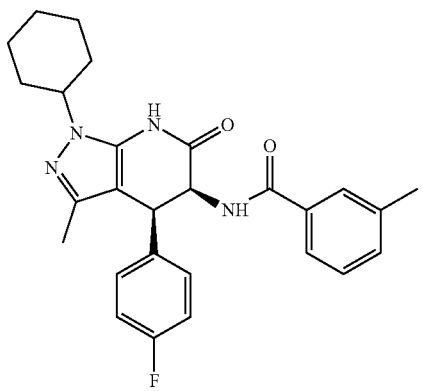

¹H NMR (400 MHz, Chloroform-d) δ 8.75 (s, 1H), 7.51 (s, 1H), 7.42 (d, J=7.3 Hz, 1H), 7.34-7.25 (m, 2H), 6.96-6.83 (m, 3H), 6.64 (d, J=6.0 Hz, 1H), 5.21 (t, J=7.1 Hz, 1H), 4.71 (d, J=7.3 Hz, 1H), 3.87-3.63 (m, 1H), 2.37 (s, 3H), 2.04 (s, 3H), 2.00-1.73 (m, 6H), 1.32-1.14 (m, 4H). HRMS (ESI+) m/z calcd for $C_{27}H_{30}FN_4O_2^+$ [M+H]⁺ 461.2347, found 461.2353.

Compound 73

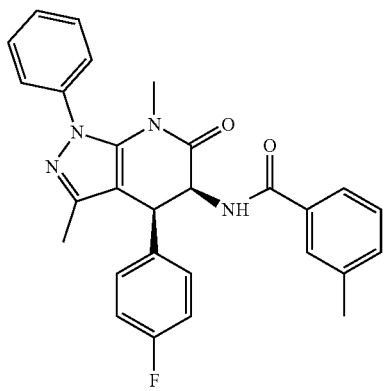

¹H NMR (400 MHz, Chloroform-d) δ 7.55 (s, 1H), 7.50 (m, 4H), 7.43 (m, 1H), 7.31 (m, 2H), 6.97-6.85 (m, 6H), 5.22 (t, J=7.1 Hz, 1H), 4.77 (d, J=7.1, 1H), 3.03 (s, 3H), 2.38 (s, 3H), 2.16 (s, 3H). HRMS (ESI+) m/z calcd for $C_{28}H_{26}FN_4O_2^+$ [M+H]⁺ 469.2034, found 469.2053.

Compound 74

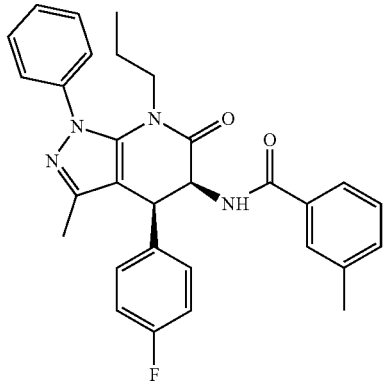

¹H NMR (400 MHz, Chloroform-d) δ 7.56 (s, 1H), 7.54-7.44 (m, 6H), 7.34-7.26 (m, 2H), 7.00-6.85 (m, 5H), 5.20 (dd, J=7.3, 5.6 Hz, 1H), 4.77 (d, J=7.3 Hz, 1H), 3.83 (m, 1H), 3.04-2.87 (m, 1H), 2.38 (s, 3H), 2.14 (s, 3H), 1.50-1.27 (m, 2H), 0.57 (t, J=7.4 Hz, 3H). HRMS (ESI+) m/z calcd for $C_{30}H_{30}FN_4O_2^+$ [M+H]⁺ 497.2347, found 497.2359.

Compound 75

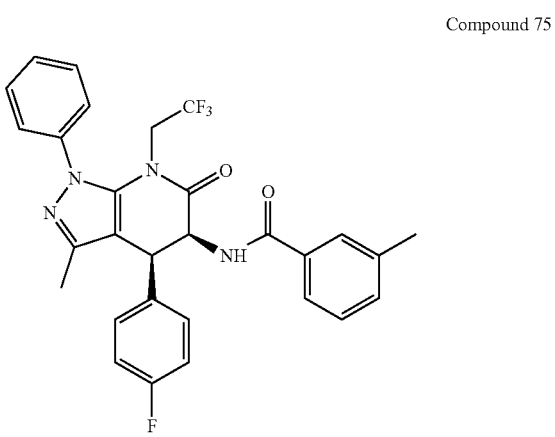 [SMILES: Cc1cccc(C(=O)N[C@@H]2C(=O)N(CC(F)(F)F)c3c(c(C)nn3-c3ccccc3)[C@@H]2c2ccc(F)cc2)c1]

¹H NMR (400 MHz, Chloroform-d) δ 7.66-7.40 (m, 7H), 7.38-7.29 (m, 2H), 7.02-6.89 (m, 4H), 6.84 (s, 1H), 5.37-5.31 (m, 1H), 4.77 (d, J=7.5 Hz, 1H), 4.75-4.63 (m, 1H), 3.60-3.46 (m, 1H), 2.40 (s, 3H), 2.15 (s, 3H). HRMS (ESI+) m/z calcd for $C_{29}H_{25}F_4N_4O_2^+$ [M+H]⁺ 537.1908, found 537.1901.

Compound 76

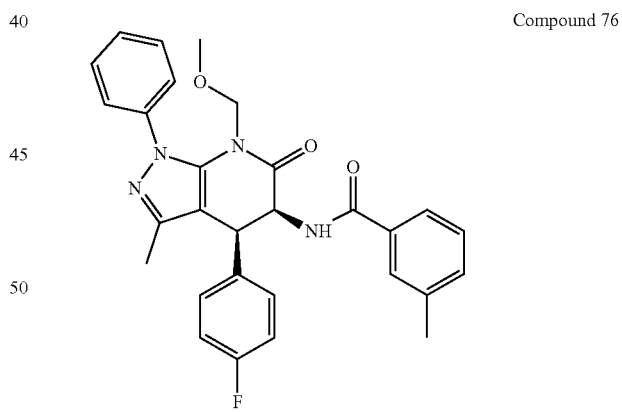

¹H NMR (400 MHz, Chloroform-d) δ 7.55 (s, 1H), 7.54-7.39 (m, 6H), 7.36-7.27 (m, 2H), 7.11-7.01 (m, 2H), 6.98-6.85 (m, 3H), 5.32-5.18 (m, 2H), 4.76 (d, J=6.9 Hz, 1H), 4.38 (d, J=9.9 Hz, 1H), 3.13 (s, 3H), 2.38 (s, 3H), 2.14 (s, 3H). HRMS (ESI+) m/z calcd for $C_{29}H_{28}FN_4O_3^+$ [M+H]⁺ 499.2140, found 499.2142.

Compound 77

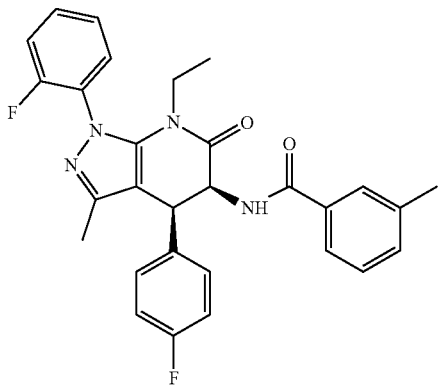

¹H NMR (400 MHz, Chloroform-d) δ 7.74 (s, 1H), 7.55 (s, 1H), 7.52-7.42 (m, 2H), 7.39-7.23 (m, 4H), 7.03-6.84 (m, 5H), 5.25-5.12 (m, 1H), 4.77 (d, 7.3 Hz, 1H), 4.06-3.83 (m, 1H), 3.21-3.07 (m, 1H), 2.38 (s, 3H), 2.14 (s, 3H), 0.99 (t, J=7.1 Hz, 3H). HRMS (ESI+) m/z calcd for $C_{29}H_{27}F_2N_4O_2^+$ [M+H]$^+$ 501.2097, found 501.2133.

Compound 78

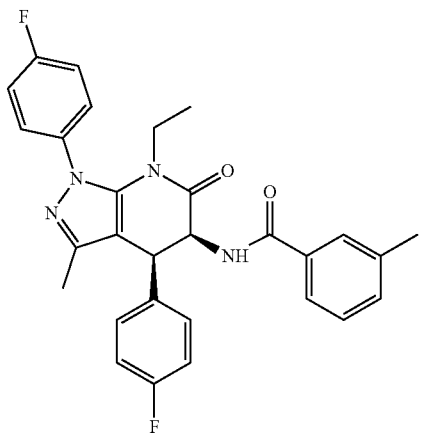

¹H NMR (400 MHz, Chloroform-d) δ 7.56 (s, 1H), 7.54-7.42 (m, 3H), 7.35-7.27 (m, 2H), 7.23-7.15 (m, 2H), 7.02-6.84 (m, 5H), 5.24-5.13 (m, 1H), 4.75 (d, J=7.4 Hz, 1H), 4.05-3.88 (m, 1H), 3.21-3.05 (m, 1H), 2.38 (s, 3H), 2.13 (s, 3H), 0.99 (t, J=7.3 Hz, 3H). HRMS (ESI+) m/z calcd for $C_{29}H_{27}F_2N_4O_2^+$ [M+H]$^+$ 501.2097, found 501.2086.

Compound 79

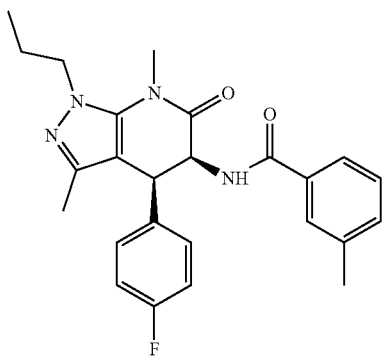

¹H NMR (400 MHz, Chloroform-d) δ 7.53 (s, 1H), 7.51-7.45 (m, 1H), 7.35-7.28 (m, 2H), 6.96-6.77 (m, 5H), 5.05-4.99 (m, 1H), 4.65 (d, J=6.9 Hz, 1H), 4.24-4.06 (m, 2H), 3.50 (s, 3H), 2.38 (s, 3H), 2.07 (s, 3H), 1.95-1.76 (m, 2H), 0.94 (d, J=7.2 Hz, 3H). HRMS (ESI+) m/z calcd for $C_{25}H_{28}FN_4O_2^+$ [M+H]$^+$ 435.2191, found 435.2202.

Compound 80

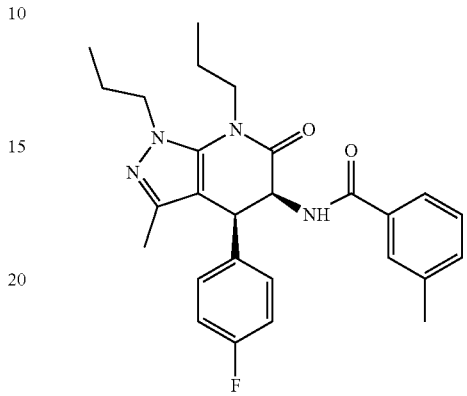

¹H NMR (400 MHz, Chloroform-d) δ 7.54 (s, 1H), 7.53-7.47 (m, 1H), 7.35-7.26 (m, 2H), 6.95 (d, J=5.6 Hz, 1H), 6.88 (d, J=7.1 Hz, 4H), 5.02 (dd, J=7.2, 5.6 Hz, 1H), 4.65 (d, J=7.2 Hz, 1H), 4.22-4.12 (m, 1H), 4.11-3.97 (m, 2H), 3.68-3.55 (m, 1H), 2.38 (s, 3H), 2.06 (s, 3H), 1.86 (qt, J=20.5, 7.2 Hz, 3H), 1.73-1.57 (m, 1H), 1.01 (t, J=7.4 Hz, 3H), 0.95 (t, J=7.4 Hz, 3H). HRMS (ESI+) m/z calcd for $C_{27}H_{32}FN_4O_2^+$ [M+H]$^+$ 463.2504, found 463.2509.

Compound 81

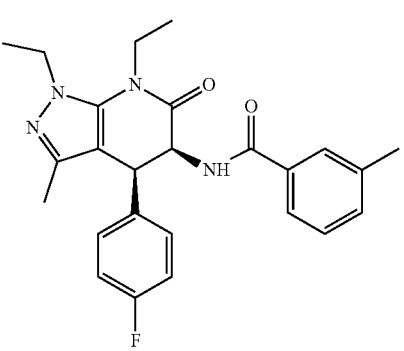

¹H NMR (400 MHz, Chloroform-d) δ 7.55 (s, 1H), 7.52-7.46 (m, 1H), 7.35-7.26 (m, 2H), 6.94 (d, J=5.6 Hz, 1H), 6.88 (d, J=7.0 Hz, 4H), 5.02 (dd, J=7.0, 5.7 Hz, 1H), 4.64 (d, J=7.2 Hz, 1H), 4.37-4.07 (m, 3H), 3.82 (dq, J=14.2, 7.0 Hz, 1H), 2.38 (s, 3H), 2.07 (s, 3H), 1.47 (t, J=7.2 Hz, 3H), 1.35 (t, J=7.2 Hz, 3H). HRMS (ESI+) m/z calcd for $C_{25}H_{28}FN_4O_2^+$ [M+H]$^+$ 435.2191, found 435.2213.

Compound 82

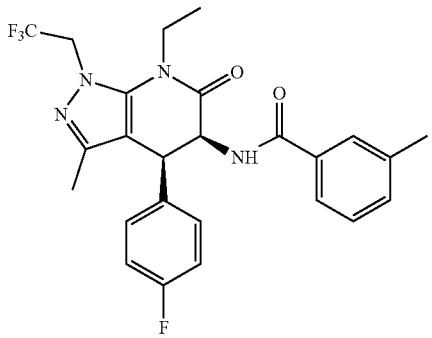

¹H NMR (400 MHz, Chloroform-d) δ 7.54 (s, 1H), 7.49 (d, J=6.7 Hz, 1H), 7.35-7.27 (m, 2H), 6.98-6.81 (m, 5H), 5.04 (dd, J=7.2, 5.5 Hz, 1H), 4.85 (dq, J=16.4, 8.1 Hz, 1H), 4.68 (d, J=7.2 Hz, 1H), 4.69-4.56 (m, 1H), 4.25 (dq, J=14.8, 7.3 Hz, 1H), 3.76 (dq, J=14.4, 7.1 Hz, 1H), 2.38 (s, 3H), 2.09 (s, 3H), 1.33 (t, J=5.9 Hz, 3H). HRMS (ESI+) m/z calcd for $C_{25}H_{25}F_4N_4O_2^+$ [M+H]⁺ 489.1908, found 489.1943.

Compound 83

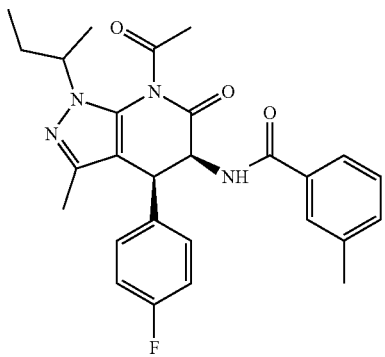

Pure trans-diastereomer on dihydropyirine core ring but diastereomeric mixture on branched alkyl group.

¹H NMR (400 MHz, Chloroform-d) δ 7.57 (s, 1H), 7.52 (m, 1H), 7.34 (m, 2H), 6.95-6.84 (m, 4H), 6.75 (s, 1H), 5.11-4.99 (m, 1H), 4.62 (d, J=5.3 Hz, 1H), 3.54 (m, 1H), 2.68 (s, 3H), 2.40 (s, 3H), 2.17 (s, 3H), 1.93-1.77 (m, 1H), 1.70-1.60 (m, 1H), 1.59 (dt, J=6.4, 2.7 Hz, 3H), 0.64-0.53 (t, J=6.4, 3H). LRMS (ESI+) m/z calcd for $C_{27}H_{30}FN_4O_3^+$ [M+H]⁺ 477.2 found 477.0.

Compound 84

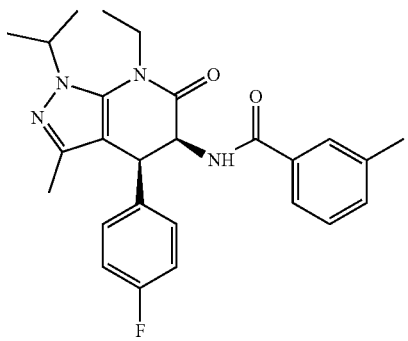

¹H NMR (400 MHz, Chloroform-d) δ 7.55 (s, 1H), 7.52-7.48 (m, 1H), 7.34-7.28 (m, 2H), 6.96 (d, J=5.7 Hz, 1H), 6.88 (d, J=7.0 Hz, 4H), 5.01 (dd, J=7.0, 5.8 Hz, 1H), 4.61 (d, J=7.0 Hz, 1H), 4.45 (p, J=6.4 Hz, 1H), 4.05-3.89 (m, 2H), 2.38 (s, 3H), 2.08 (s, 3H), 1.68 (d, J=6.6 Hz, 3H), 1.41 (d, J=6.5 Hz, 3H), 1.37 (t, J=7.1 Hz, 3H). HRMS (ESI+) m/z calcd for $C_{26}H_{30}FN_4O_2^+$ [M+H]⁺ 449.2347, found 449.2335.

Compound 85

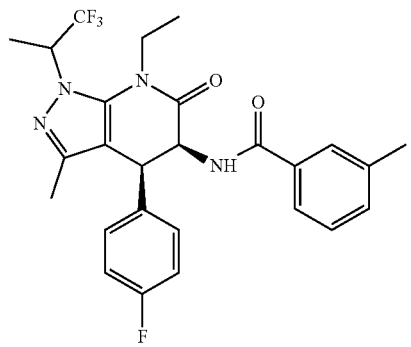

¹H NMR (400 MHz, Chloroform-d) δ 7.54 (s, 1H), 7.51-7.43 (m, 1H), 7.35-7.26 (m, 2H), 6.96-6.82 (m, 5H), 5.02 (d, J=7.1, 6.1 Hz, 1H), 4.76-4.61 (m, 2H), 3.93 (qd, J=14.4, 8.0 Hz, 2H), 2.38 (s, 3H), 2.09 (s, 3H), 1.94 (d, J=6.9 Hz, 3H), 1.37 (t, J=7.3 Hz, 3H). HRMS (ESI+) m/z calcd for $C_{26}H_{27}F_4N_4O_2^+$ [M+H]⁺ 503.2065, found 503.2058.

Compound 86

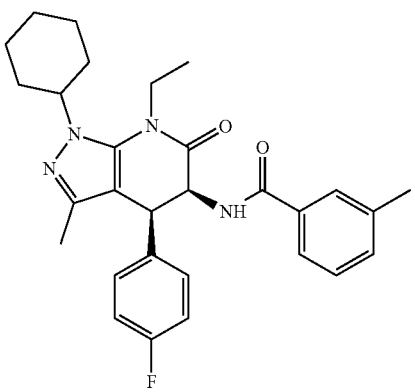

¹H NMR (400 MHz, Chloroform-d) δ 7.55 (s, 1H), 7.50 (d, J=6.3 Hz, 1H), 7.30 (d, J=5.8 Hz, 2H), 7.03-6.78 (m, 5H), 5.00 (dd, J=6.9, 6.4 Hz, 1H), 4.60 (d, J=7.1 Hz, 1H), 4.05-3.87 (m, 3H), 2.37 (s, 3H), 2.18-2.20 (m, 2H), 2.06 (s, 3H), 2.04-1.65 (m, 6H), 1.41-1.34 (m, 3H), 1.35-1.21 (m, 2H). HRMS (ESI+) m/z calcd for $C_{29}H_{34}FN_4O_2^+$ [M+H]⁺ 489.2660, found 489.2668.

Compound 87

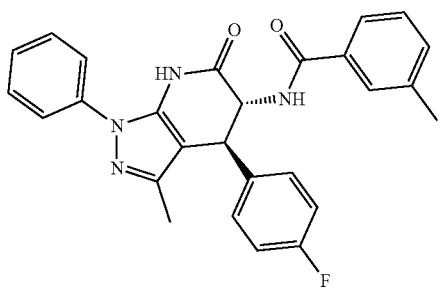

¹H NMR (500 MHz, Chloroform-d) δ 7.75 (s, 1H), 7.47-7.38 (m, 5H), 7.39-7.33 (m, 1H), 7.30 (m, 3H), 7.25-7.16 (m, 2H), 6.98 (t, J=8.6 Hz, 2H), 6.33 (d, J=8.7 Hz, 1H), 5.08 (dd, J=12.2, 8.7 Hz, 1H), 4.25 (d, J=12.2 Hz, 1H), 2.29 (s, 3H), 1.58 (s, 3H). HRMS (ESI+) m/z calcd for $C_{27}H_{24}FN_4O_2^+$ [M+H]$^+$ 455.1878, found 455.1883.

Compound 88

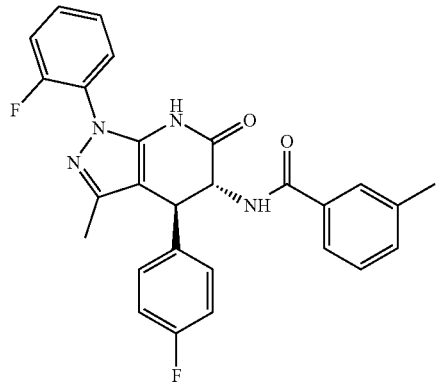

¹H NMR (400 MHz, Chloroform-d) δ 7.74 (s, 1H), 7.61-7.51 (m, 1H), 7.46 (s, 1H), 7.43-7.25 (m, 8H), 7.10-6.91 (m, 2H), 6.34 (d, J=8.8 Hz, 1H), 5.22-5.02 (m, 1H), 4.33 (d, J=12.8 Hz, 1H), 2.34 (s, 3H), 1.63 (s, 3H). HRMS (ESI+) m/z calcd for $C_{27}H_{23}F_2N_4O_2^+$ [M+H]$^+$ 473.1784, found 473.1766.

Compound 89

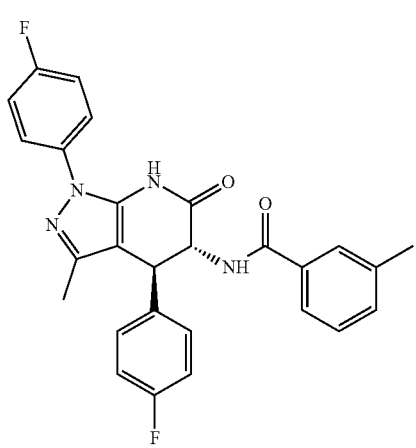

¹H NMR (400 MHz, Chloroform-d) δ 7.75 (s, 1H), 7.51-7.37 (m, 4H), 7.37-7.31 (m, 2H), 7.32-7.24 (m, 2H), 7.20-7.12 (m, 2H), 7.04 (t, J=8.7 Hz, 2H), 6.37 (d, J=8.4 Hz, 1H), 5.22-5.01 (m, 1H), 4.30 (d, J=12.2 Hz, 1H), 2.34 (s, 3H), 1.61 (s, 3H). HRMS (ESI+) m/z calcd for $C_{27}H_{23}F_2N_4O_2^+$ [M+H]$^+$ 473.1784, found 473.1767.

Compound 90

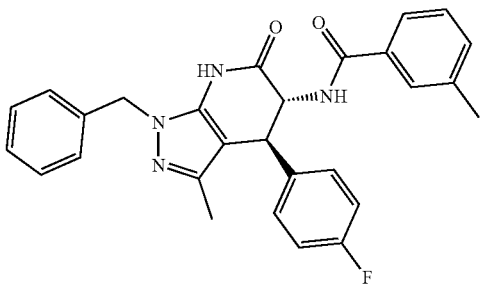

¹H NMR (500 MHz, Chloroform-d) δ 8.72 (br-s, 1H), 7.37 (s, 1H), 7.31 (d, J=7.5 Hz, 1H), 7.28-7.05 (m, 9H), 6.94 (t, J=8.4 Hz, 2H), 6.35 (s, 1H), 5.17 (d, J=16.0 Hz, 1H), 5.06 (d, J=15.9 Hz, 1H), 4.92 (dd, J=12.0, 8.6 Hz, 1H), 4.20 (d, J=12.1 Hz, 1H), 2.25 (s, 3H), 1.51 (s, 3H). HRMS (ESI+) m/z calcd for $C_{28}H_{26}FN_4O_2^+$ [M+H]$^+$ 469.2034, found 469.2076.

Compound 91

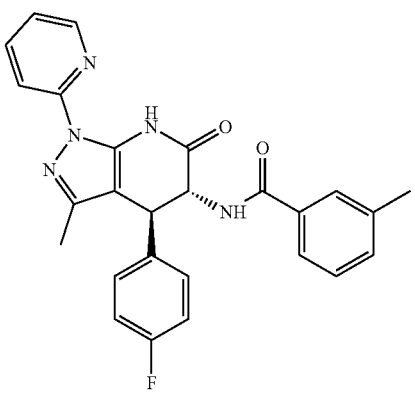

¹H NMR (400 MHz, Chloroform-d) δ 10.58 (s, 1H), 8.39-8.28 (m, 1H), 7.89 (d, J=8.4 Hz, 1H), 7.84-7.77 (m, 1H), 7.50 (s, 1H), 7.44 (d, J=6.5 Hz, 1H), 7.37-7.29 (m, 2H), 7.30-7.24 (m, 2H), 7.15 (dd, J=7.3, 5.0 Hz, 1H), 7.02 (t, J=8.6 Hz, 2H), 6.41 (d, J=8.6 Hz, 1H), 5.07 (dd, J=11.7, 8.6 Hz, 1H), 4.33 (d, J=11.7 Hz, 1H), 2.35 (s, 3H), 1.66 (s, 3H). HRMS (ESI+) m/z calcd for $C_{26}H_{23}FN_5O_2^+$ [M+H]$^+$ 456.1830, found 456.1835.

Compound 92

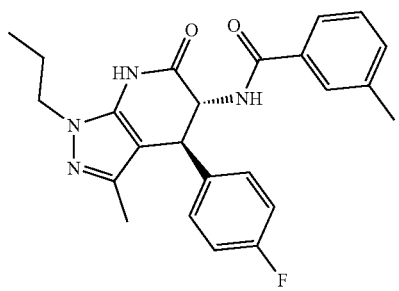

¹H NMR (500 MHz, Chloroform-d) δ 9.30 (s, 1H), 7.41 (d, J=1.9 Hz, 1H), 7.35 (dt, J=7.2, 1.8 Hz, 1H), 7.26-7.18 (m, 4H), 6.95 (t, J=8.6 Hz, 2H), 6.30 (d, J=8.7 Hz, 1H), 4.96 (dd, J=11.9, 8.7 Hz, 1H), 4.21 (d, J=11.9 Hz, 1H), 3.78 (td, J=7.1, 1.9 Hz, 2H), 2.29 (s, 3H), 1.68 (q, J=7.3 Hz, 2H), 1.49 (s, 3H), 0.75 (t, J=7.4 Hz, 3H). HRMS (ESI+) m/z calcd for $C_{24}H_{26}FN_4O_2^+$ [M+H]⁺ 421.2034, found 421.2033.

Compound 93

¹H NMR (500 MHz, Chloroform-d) δ 9.41 (s, 1H), 7.41 (d, J=1.7 Hz, 1H), 7.35 (dt, J=7.2, 1.8 Hz, 1H), 7.23 (ddd, J=7.2, 5.3, 2.6 Hz, 4H), 6.99-6.91 (m, 2H), 6.32 (d, J=8.7 Hz, 1H), 4.96 (dd, J=12.0, 8.7 Hz, 1H), 4.20 (d, J=12.0 Hz, 1H), 3.81 (td, J=7.1, 2.7 Hz, 2H), 2.29 (s, 3H), 1.63 (dt, J=8.5, 6.9 Hz, 2H), 1.49 (s, 3H), 1.15 (dtt, J=15.5, 7.7, 3.6 Hz, 2H), 0.75 (t, J=7.4 Hz, 3H). HRMS (ESI+) m/z calcd for $C_{25}H_{28}FN_4O_2^+$ [M+H]⁺ 435.2191, found 435.2192.

Compound 94

¹H NMR (400 MHz, Chloroform-d) δ 9.06 (s, 1H), 7.46 (s, 1H), 7.43-7.35 (m, 1H), 7.32-7.25 (m, 4H), 7.05-6.95 (m, 2H), 6.30 (d, J=8.7 Hz, 1H), 5.04 (t, J=10.8 Hz, 1H), 4.23 (m, 2H), 2.34 (s, 3H), 1.56 (s, 3H), 1.41 (d, J=6.3 Hz, 3H), 1.36 (d, J=6.6 Hz, 3H). HRMS (ESI+) m/z calcd for $C_{24}H_{26}FN_4O_2^+$ [M+H]⁺ 421.2034, found 421.2036.

Compound 95

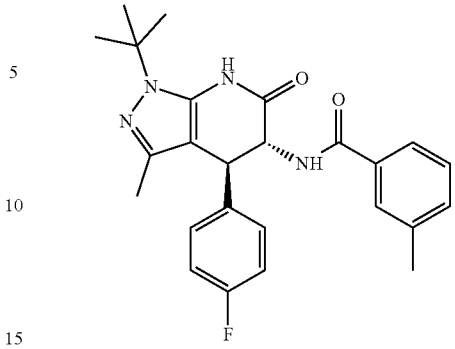

¹H NMR (400 MHz, Chloroform-d) δ 7.88 (s, 1H), 7.44 (s, 1H), 7.41-7.35 (m, 1H), 7.32-7.25 (m, 4H), 7.00 (m, 2H), 6.29 (d, J=8.9 Hz, 1H), 5.16 (dd, J=12.5, 8.9 Hz, 1H), 4.16 (d, J=12.5 Hz, 1H), 2.34 (s, 3H), 1.61 (s, 9H), 1.50 (s, 3H). HRMS (ESI+) m/z calcd for $C_{25}H_{28}FN_4O_2^+$ [M+H]⁺ 435.2191, found 435.2185.

Compound 96

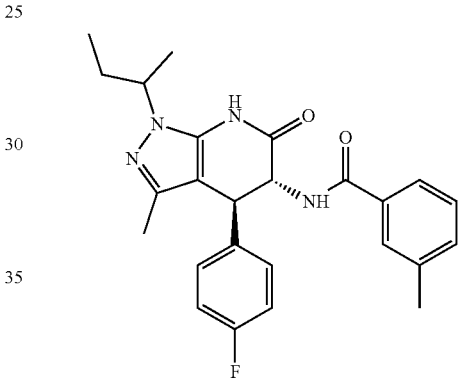

Pure trans-diastereomer on dihydropyirine core ring but diastereomeric mixture on branched alkyl group.

¹H NMR (400 MHz, Chloroform-d) δ 9.56-9.47 (m, 1H), 7.46 (s, 1H), 7.41 (m, 1H), 7.35-7.25 (m, 4H), 7.01 (t, J=8.6 Hz, 2H), 6.31 (t, J=9.0 Hz, 1H), 5.06 (ddd, J=12.4, 8.8, 3.6 Hz, 1H), 4.31-4.17 (m, 1H), 3.96 (h, J=7.0 Hz, 1H), 2.35 (s, 3H), 1.94-1.60 (m, 2H), 1.55 (d, J=4.9 Hz, 3H), 1.36 (dd, J=22.7, 6.6 Hz, 3H), 0.72 (dt, J=23.6, 7.4 Hz, 3H). HRMS (ESI+) m/z calcd for $C_{25}H_{28}FN_4O_2^+$ [M+H]⁺ 435.2191, found 435.2184.

Compound 97

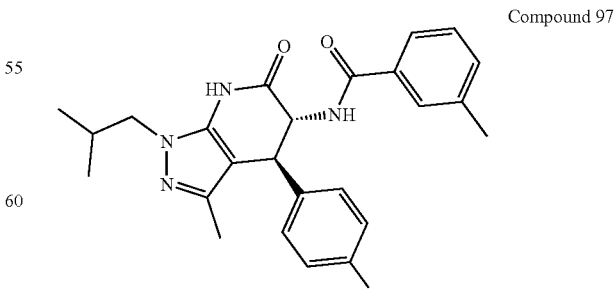

¹H NMR (500 MHz, Chloroform-d) δ 9.59 (s, 1H), 7.41 (s, 1H), 7.36 (dd, J=7.2, 1.8 Hz, 1H), 7.26-7.16 (m, 4H), 6.95

(t, J=8.5 Hz, 2H), 6.36 (d, J=8.7 Hz, 1H), 4.97 (dd, J=11.9, 8.7 Hz, 1H), 4.21 (d, J=11.9 Hz, 1H), 3.68-3.55 (m, 2H), 2.29 (s, 3H), 2.04 (hept, J=6.8 Hz, 1H), 1.49 (s, 3H), 0.73 (d, J=6.7 Hz, 3H), 0.71 (d, J=6.7 Hz, 3H). HRMS (ESI+) m/z calcd for $C_{25}H_{28}FN_4O_2^+$ [M+H]$^+$ 435.2191, found 435.2184.

Compound 98

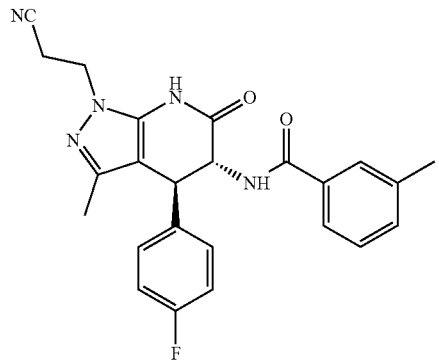

$^1$H NMR (400 MHz, Chloroform-d) δ 10.37 (s, 1H), 7.51 (s, 1H), 7.46 (d, J=7.2 Hz, 1H), 7.33-7.25 (m, 4H), 6.99 (t, J=8.4 Hz, 2H), 6.67 (d, J=8.7 Hz, 1H), 5.15-4.92 (m, 1H), 4.29 (d, J=11.4 Hz, 1H), 4.17 (m, 2H), 2.92-2.75 (m, 1H), 2.66 (dt, J=16.8, 5.6 Hz, 1H), 2.34 (s, 3H), 1.56 (s, 3H). HRMS (ESI+) m/z calcd for $C_{24}H_{23}FN_5O_2^+$ [M+H]$^+$ 432.1840, found 432.1836.

Compound 99

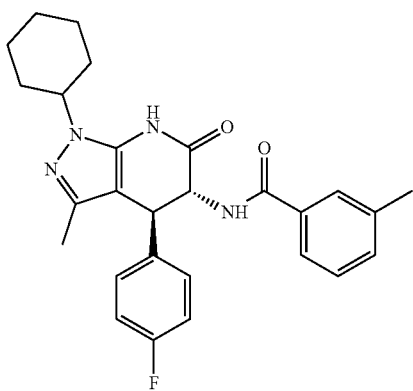

$^1$H NMR (400 MHz, Chloroform-d) δ 9.56 (s, 1H), 7.47 (s, 1H), 7.43-7.37 (m, 1H), 7.32-7.26 (m, 4H), 7.03-6.95 (m, 2H), 6.38-6.24 (m, 1H), 5.08 (t, J=11.0 Hz, 1H), 4.24 (d, J=12.5 Hz, 1H), 3.85 (m, 1H), 2.34 (s, 3H), 1.97-1.68 (m, 5H), 1.60 (m, 1H), 1.56 (s, 3H), 1.28 (m, 3H), 1.12 (m, 3H). HRMS (ESI+) m/z calcd for $C_{27}H_{30}FN_4O_2^+$ [M+H]$^+$ 461.2347, found 461.2354.

Compound 100

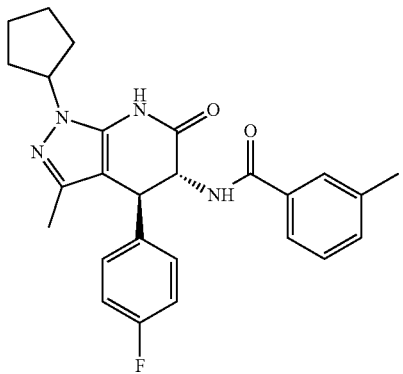

$^1$H NMR (400 MHz, Chloroform-d) δ 9.08 (s, 1H), 7.46 (s, 1H), 7.40 (d, J=7.1 Hz, 1H), 7.34-7.26 (m, 4H), 7.00 (t, J=8.4 Hz, 2H), 6.29 (d, J=8.8 Hz, 1H), 5.05 (dd, J=12.2, 8.7 Hz, 1H), 4.35 (p, J=7.7 Hz, 1H), 4.23 (d, J=12.3 Hz, 1H), 2.34 (s, 3H), 2.14-1.90 (m, 4H), 1.88-1.68 (m, 2H), 1.56 (s, 3H), 1.52-1.35 (m, 2H). HRMS (ESI+) m/z calcd for $C_{26}H_{28}FN_4O_2^+$ [M+H]$^+$ 447.2191, found 447.2205.

Compound 101

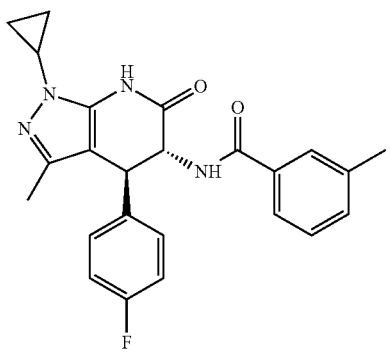

$^1$H NMR (400 MHz, Chloroform-d) δ 8.17 (s, 1H), 7.46 (s, 1H), 7.44-7.37 (m, 1H), 7.31-7.25 (m, 4H), 7.00 (t, J=8.6 Hz, 2H), 6.34 (d, J=8.6 Hz, 1H), 5.05-4.94 (m, 1H), 4.24 (d, J=12.2 Hz, 1H), 3.22-3.15 (m, 1H), 2.34 (s, 3H), 1.52 (s, 3H), 1.20-0.98 (m, 4H). HRMS (ESI+) m/z calcd for $C_{24}H_{24}FN_4O_2^+$ [M+H]$^+$ 419.1878, found 419.1895.

Compound 102

$^1$H NMR (400 MHz, Methanol-d$_4$) δ 7.47 (d, J=1.7 Hz, 1H), 7.46-7.41 (m, 1H), 7.39-7.32 (m, 2H), 7.27 (dd, J=14.0, 7.6 Hz, 2H), 7.05 (t, J=8.6 Hz, 2H), 4.97 (d, J=12.5 Hz, 1H), 4.34 (d, J=12.5 Hz, 1H), 2.33 (s, 3H), 1.60-1.50 (m, 3H). HRMS (ESI+) m/z calcd for $C_{21}H_{20}FN_4O_2^+$ [M+H]$^+$ 379.1565, found 379.1567.

Compound 103

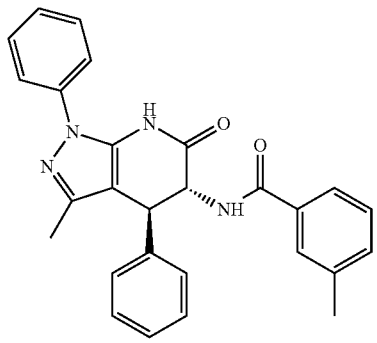

$^1$H NMR (400 MHz, Chloroform-d) δ 7.94 (m, 1H), 7.55-7.18 (m, 14H), 6.45-6.34 (m, 1H), 5.13 (d, J=12.2, 1H), 4.32 (d, J=12.4 Hz, 1H), 2.33 (s, 3H), 1.60 (s, 3H). HRMS (ESI+) m/z calcd for $C_{27}H_{25}N_4O_2^+$ [M+H]$^+$ 437.1972, found 437.1973.

Compound 104

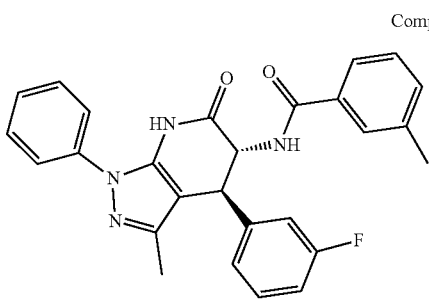

$^1$H NMR (500 MHz, Chloroform-d) δ 7.80-7.76 (m, 1H), 7.50-7.14 (m, 10H), 7.12 (d, J=7.6 Hz, 1H), 7.03 (dd, J=9.7, 2.1 Hz, 1H), 6.94 (td, J=8.4, 2.6 Hz, 1H), 6.36 (d, J=8.6 Hz, 1H), 5.04 (dd, J=12.0, 8.6 Hz, 1H), 4.29 (d, J=12.0 Hz, 1H), 2.29 (s, 3H), 1.61 (s, 3H). HRMS (ESI+) m/z calcd for $C_{27}H_{24}FN_4O_2^+$ [M+H]$^+$ 455.1878, found 455.1875.

Compound 105

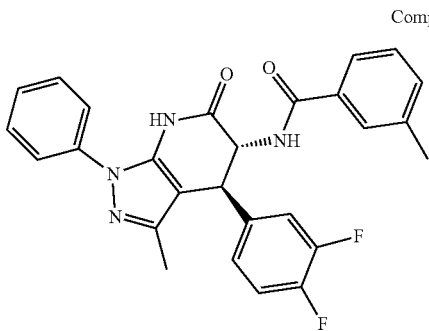

$^1$H NMR (500 MHz, Chloroform-d) δ 7.79 (s, 1H), 7.49-7.34 (m, 6H), 7.33-7.21 (m, 3H), 7.16-7.03 (m, 3H), 6.39 (d, J=8.5 Hz, 1H), 5.03 (dd, J=12.0, 8.6 Hz, 1H), 4.24 (d, J=12.0 Hz, 1H), 2.30 (s, 3H), 1.63 (s, 3H). HRMS (ESI+) m/z calcd for $C_{27}H_{23}F_2N_4O_2^+$ [M+H]$^+$ 473.1784, found 473.1742.

Compound 106

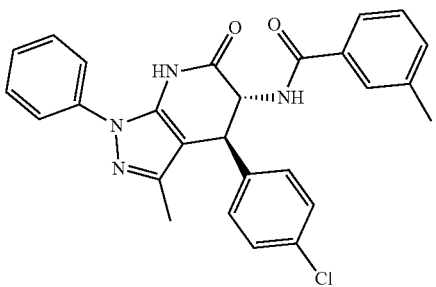

$^1$H NMR (500 MHz, Chloroform-d) δ 7.75 (s, 1H), 7.46-7.41 (m, 5H), 7.37 (dd, J=7.1, 1.8 Hz, 1H), 7.27 (s, 5H), 7.25-7.20 (m, 2H), 6.35 (d, J=8.7 Hz, 1H), 5.05 (dd, J=12.2, 8.6 Hz, 1H), 4.27 (d, J=12.2 Hz, 1H), 2.30 (s, 3H), 1.60 (s, 3H). HRMS (ESI+) m/z calcd for $C_{27}H_{24}ClN_4O_2^+$ [M+H]$^+$ 471.1582, found 471.1583.

Compound 107

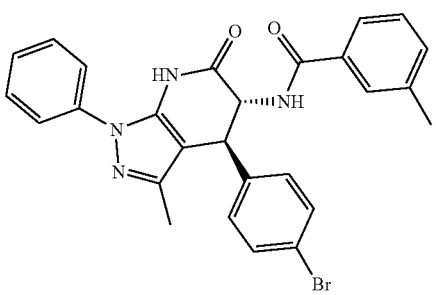

$^1$H NMR (500 MHz, Chloroform-d) δ 7.75 (s, 1H), 7.48-7.28 (m, 10H), 7.22 (h, J=1.9 Hz, 3H), 6.34 (d, J=8.7 Hz, 1H), 5.05 (dd, J=12.1, 8.6 Hz, 1H), 4.25 (d, J=12.1 Hz, 1H), 2.30 (s, 3H), 1.59 (s, 3H). HRMS (ESI+) m/z calcd for $C_{27}H_{24}BrN_4O_2^+$ [M+H]$^+$ 515.1077, found 515.1069.

Compound 108

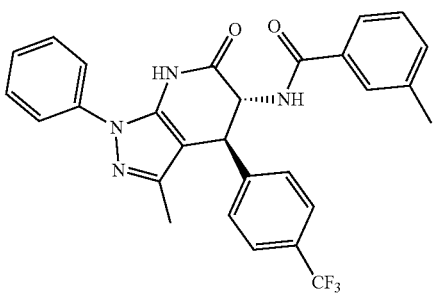

$^1$H NMR (500 MHz, Chloroform-d) δ 7.84 (s, 1H), 7.56 (d, J=8.1 Hz, 2H), 7.49-7.28 (m, 9H), 7.25-7.20 (m, 2H), 6.38 (d, J=8.6 Hz, 1H), 5.08 (dd, J=12.1, 8.6 Hz, 1H), 4.37 (d, J=12.1 Hz, 1H), 2.29 (s, 3H), 1.55 (s, 3H). HRMS (ESI+) m/z calcd for $C_{28}H_{24}F_3N_4O_2^+$ [M+H]$^+$ 505.1846, found 505.1826.

Compound 109

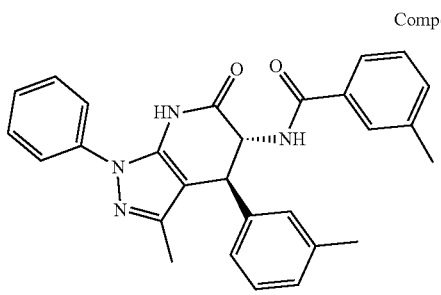

¹H NMR (500 MHz, Chloroform-d) δ 7.79 (s, 1H), 7.42 (d, J=4.4 Hz, 5H), 7.40-7.31 (m, 1H), 7.28 (m, 1H), 7.26-7.12 (m, 3H), 7.13-7.01 (m, 3H), 6.29 (d, J=8.6 Hz, 1H), 5.00 (dd, J=12.0, 8.5 Hz, 1H), 4.25 (d, J=12.0 Hz, 1H), 2.28 (s, 3H), 2.26 (s, 3H), 1.58 (s, 3H). HRMS (ESI+) m/z calcd for $C_{28}H_{27}N_4O_2^+$ [M+H]⁺ 451.2129, found 451.2128.

Compound 110

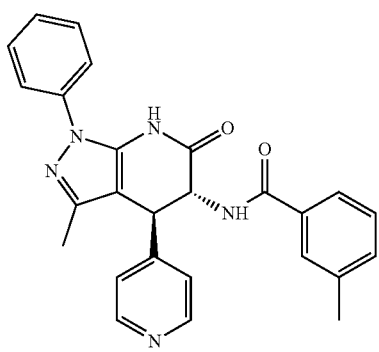

¹H NMR (400 MHz, Methanol-d₄) δ 8.53-8.49 (m, 2H), 7.61-7.39 (m, 9H), 7.36-7.22 (m, 2H), 5.18 (d, J=12.3 Hz, 1H), 4.47 (d, J=12.3 Hz, 1H), 2.34 (s, 3H), 1.61 (s, 3H). HRMS (ESI+) m/z calcd for $C_{26}H_{24}N_5O_2^+$ [M+H]⁺ 438.1925, found 438.1917.

Compound 111

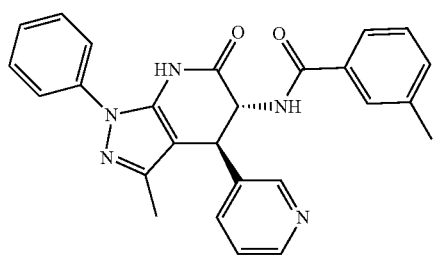

¹H NMR (500 MHz, Chloroform-d) δ 8.55 (s, 1H), 8.48 (s, 1H), 7.96 (m, 1H), 7.84 (m, 1H), 7.50-7.24 (m, 8H), 7.19 (m, 5H), 6.62 (m, 1H), 5.16 (dd, J=12.3, 8.6 Hz, 1H), 4.32 (d, J=12.4 Hz, 1H), 2.27 (s, 3H), 1.57 (s, 3H). HRMS (ESI+) m/z calcd for $C_{26}H_{24}N_5O_2^+$ [M+H]⁺ 438.1925, found 438.1965.

Compound 112

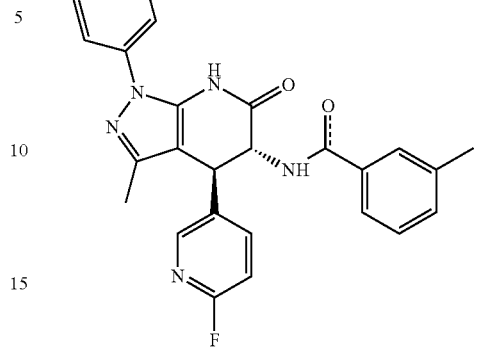

¹H NMR (400 MHz, Chloroform-d) δ 8.14 (d, J=2.7 Hz, 1H), 7.94 (td, J=8.0, 2.5 Hz, 1H), 7.86 (s, 1H), 7.55-7.30 (m, 7H), 7.31-7.25 (m, 2H), 6.97 (dd, J=8.6, 2.9 Hz, 1H), 6.52 (d, J=8.6 Hz, 1H), 5.20 (dd, J=12.4, 8.6 Hz, 1H), 4.31 (d, J=12.4 Hz, 1H), 2.34 (s, 3H), 1.67 (s, 3H). HRMS (ESI+) m/z calcd for $C_{26}H_{23}FN_5O_2^+$ [M+H]⁺ 456.1830, found 456.1827.

Compound 113

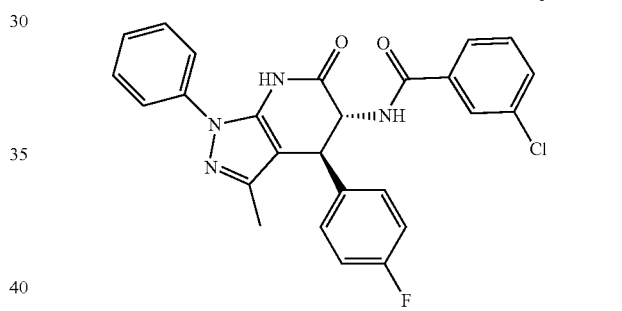

¹H NMR (500 MHz, Chloroform-d) δ 7.89 (s, 1H), 7.56 (t, J=1.9 Hz, 1H), 7.50-7.33 (m, 6H), 7.33-7.21 (m, 4H), 6.98 (t, J=8.6 Hz, 2H), 6.44 (d, J=8.7 Hz, 1H), 5.07 (dd, J=12.4, 8.7 Hz, 1H), 4.22 (d, J=12.4 Hz, 1H), 1.57 (s, 3H). HRMS (ESI+) m/z calcd for $C_{26}H_{21}ClFN_4O_2^+$ [M+H]⁺ 475.1332, found 475.1280.

Compound 114

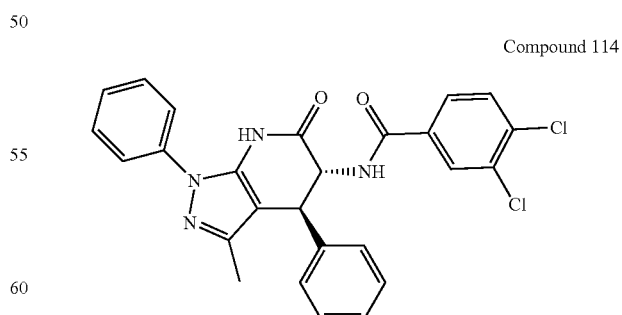

¹H NMR (500 MHz, Chloroform-d) δ 7.78 (s, 1H), 7.67 (s, 1H), 7.48-7.37 (m, 6H), 7.36-7.29 (m, 1H), 7.32-7.24 (m, 2H), 6.99 (t, J=8.6 Hz, 2H), 6.42 (d, J=8.7 Hz, 1H), 5.08 (dd, J=12.5, 8.7 Hz, 1H), 4.22 (d, J=12.4 Hz, 1H), 1.57 (s, 3H). HRMS (ESI+) m/z calcd for $C_{26}H_{20}Cl_2FN_4O_2^+$ [M+H]$^+$ 509.0942, found 509.0938.

7.09-7.00 (m, 2H), 6.39 (d, J=8.7 Hz, 1H), 5.20-5.08 (m, 1H), 4.31 (d, J=12.1 Hz, 1H), 1.63 (s, 3H). HRMS (ESI+) m/z calcd for $C_{26}H_{22}FN_4O_2^+$ [M+H]$^+$ 441.1721, found 441.1727.

Compound 115

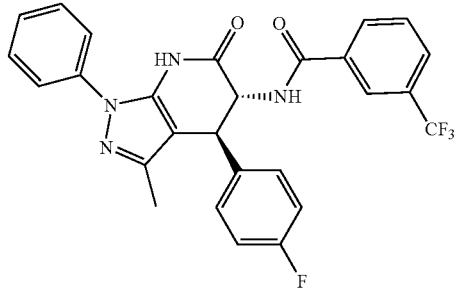

$^1$H NMR (500 MHz, Chloroform-d) δ 7.84 (d, J=2.1 Hz, 1H), 7.80-7.73 (m, 2H), 7.67 (d, J=7.7 Hz, 1H), 7.50-7.39 (m, 5H), 7.35-7.26 (m, 3H), 6.99 (t, J=8.6 Hz, 2H), 6.45 (d, J=8.7 Hz, 1H), 5.12 (dd, J=12.4, 8.7 Hz, 1H), 4.25 (d, J=12.4 Hz, 1H), 1.58 (s, 3H). HRMS (ESI+) m/z calcd for $C_{27}H_{21}F_4N_4O_2^+$ [M+H]$^+$ 509.1595, found 509.1595.

Compound 118

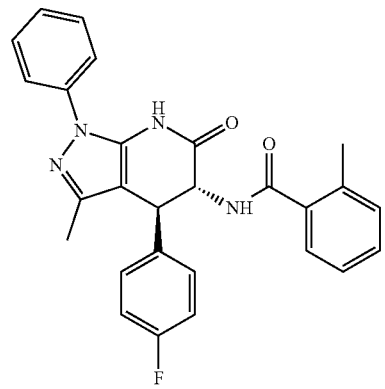

$^1$H NMR (400 MHz, Chloroform-d) δ 7.67 (s, 1H), 7.56-7.44 (m, 4H), 7.41-7.30 (m, 4H), 7.30-7.19 (m, 1H), 7.17-7.03 (m, 4H), 6.00 (d, J=9.2 Hz, 1H), 5.22 (dd, J=12.5, 9.2 Hz, 1H), 4.24 (d, J=12.6 Hz, 1H), 2.17 (s, 3H), 1.63 (s, 3H). HRMS (ESI+) m/z calcd for $C_{27}H_{24}FN_4O_2^+$ [M+H]$^+$ 455.1878, found 455.1887.

Compound 116

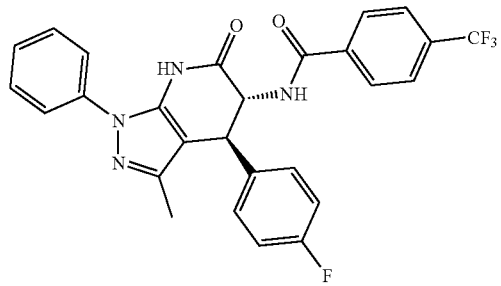

$^1$H NMR (500 MHz, Chloroform-d) δ 7.73 (s, 1H), 7.68 (d, J=8.1 Hz, 2H), 7.58 (d, J=8.1 Hz, 2H), 7.49-7.36 (m, 4H), 7.38-7.26 (m, 3H), 6.99 (t, J=8.6 Hz, 2H), 6.47 (d, J=8.7 Hz, 1H), 5.12 (dd, J=12.3, 8.7 Hz, 1H), 4.25 (d, J=12.4 Hz, 1H), 1.59 (s, 3H). HRMS (ESI+) m/z calcd for $C_{27}H_{21}F_4N_4O_2^+$ [M+H]$^+$ 509.1595, found 509.1581.

Compound 119

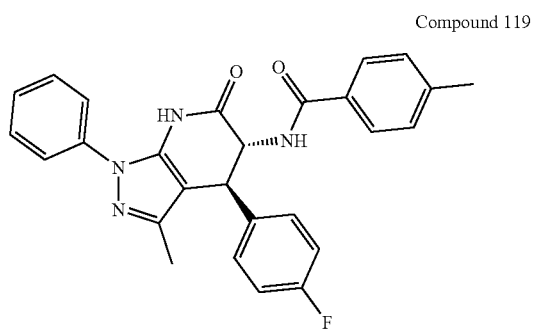 [SMILES: Cc1ccc(C(=O)N[C@H]2C(=O)Nc3c(c(C)nn3-c3ccccc3)[C@@H]2c2ccc(F)cc2)cc1]

$^1$H NMR (500 MHz, DMSO-d$_6$) δ 10.79 (s, 1H), 8.59 (d, J=8.9 Hz, 1H), 7.68-7.46 (m, 6H), 7.45-7.32 (m, 3H), 7.29-7.07 (m, 4H), 5.00 (dd, J=12.1, 8.9 Hz, 1H), 4.40 (d, J=12.2 Hz, 1H), 2.33 (s, 3H), 1.48 (s, 3H). HRMS (ESI+) m/z calcd for $C_{27}H_{24}FN_4O_2^+$ [M+H]$^+$ 455.1878, found 455.1843.

Compound 117

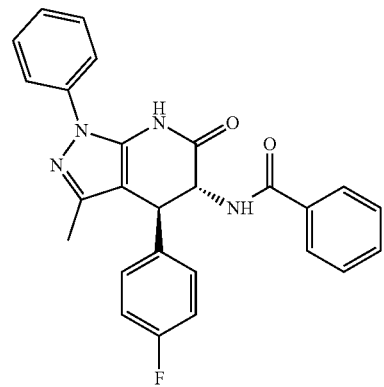

$^1$H NMR (400 MHz, Chloroform-d) δ 7.78 (s, 1H), 7.68-7.61 (m, 2H), 7.53-7.42 (m, 5H), 7.42-7.31 (m, 5H), Compound 120

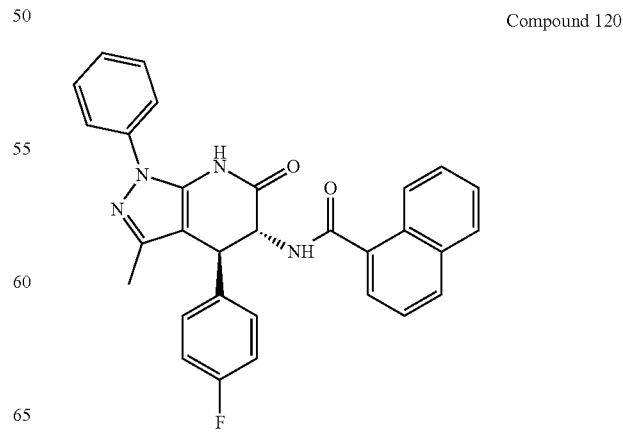

¹H NMR (400 MHz, Chloroform-d) δ 7.83 (d, J=8.3 Hz, 1H), 7.78 (d, J=8.5 Hz, 1H), 7.73 (d, J=8.3, 1.5 Hz, 1H), 7.60 (s, 1H), 7.56-7.34 (m, 11H), 7.12 (t, J=8.5 Hz, 2H), 6.27 (d, J=9.2 Hz, 1H), 5.35 (dd, J=12.7, 9.2 Hz, 1H), 4.22 (d, J=12.7 Hz, 1H), 1.65 (s, 3H). HRMS (ESI+) m/z calcd for $C_{30}H_{24}FN_4O_2^+$ [M+H]⁺ 491.1878, found 491.1883.

¹H NMR (400 MHz, Chloroform-d) δ 7.93 (d, J=7.6, 2H), 7.48 (s, 1H), 7.46-7.39 (m, 2H), 7.38-7.25 (m, 4H), 7.03-6.82 (m, 4H), 6.15 (d, J=7.7 Hz, 1H), 5.47 (td, J=8.0, 7.3 Hz, 1H), 4.51 (d, J=8.4 Hz, 1H), 4.47-4.28 (m, 2H), 2.38 (s, 3H), 2.10 (s, 3H), 1.32 (t, J=7.1 Hz, 3H). HRMS (ESI+) m/z calcd for $C_{29}H_{28}FN_4O_2^+$ [M+H]⁺ 483.2191, found 483.2213.

Compound 121

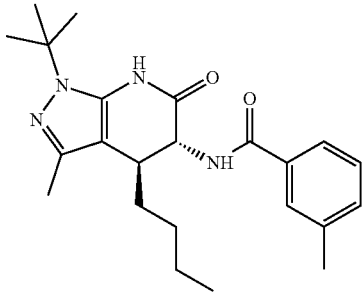

¹H NMR (400 MHz, Chloroform-d) δ 7.63 (s, 1H), 7.56 (s, 1H), 7.51-7.44 (m, 1H), 7.33-7.27 (m, 2H), 6.24 (d, J=9.1 Hz, 1H), 4.96 (t, J=8.7 Hz, 1H), 2.95 (m, 1H), 2.37 (s, 3H), 2.18 (s, 3H), 1.69-1.59 (m, 2H), 1.58 (s, 9H), 1.39-1.21 (m, 4H), 0.87 (t, J=6.7 Hz, 3H). HRMS (ESI+) m/z calcd for $C_{23}H_{33}N_4O_2^+$ [M+H]⁺ 397.2598, found 397.2595.

Compound 124

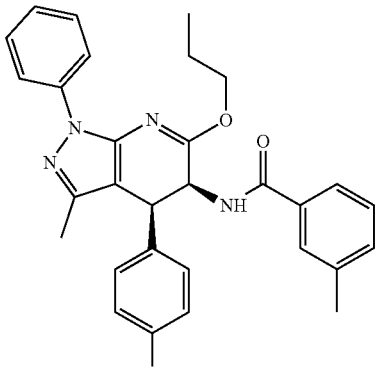

Compound 122

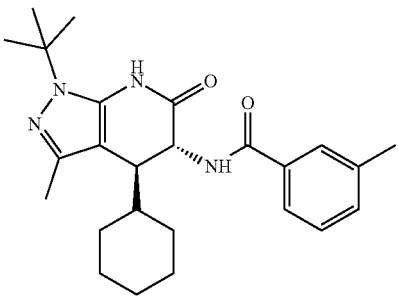

¹H NMR (400 MHz, Chloroform-d) δ 8.00-7.88 (m, 2H), 7.47 (s, 1H), 7.43 (t, J=8.0 Hz, 2H), 7.37-7.27 (m, 4H), 7.00-6.87 (m, 4H), 6.13 (d, J=7.7 Hz, 1H), 5.47 (t, J=8.1 Hz, 1H), 4.51 (d, J=8.4 Hz, 1H), 4.36-4.20 (m, 2H), 2.38 (s, 3H), 2.10 (s, 3H), 1.72 (h, J=7.2 Hz, 2H), 0.90 (t, J=7.4 Hz, 3H). HRMS (ESI+) m/z calcd for $C_{30}H_{30}FN_4O_2^+$ [M+H]⁺ 497.2347, found 497.2369.

Compound 125

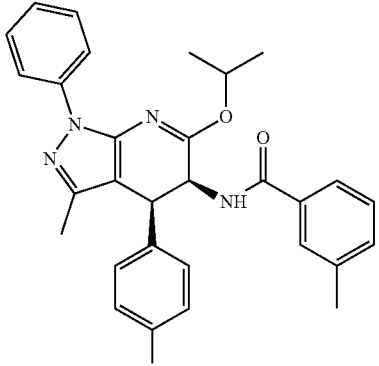

¹H NMR (400 MHz, Chloroform-d) δ 7.58 (s, 1H), 7.44 (s, 1H), 7.33 (d, J=7.1 Hz, 1H), 7.30-7.16 (m, 2H), 6.13 (d, J=8.9 Hz, 1H), 5.08 (d, J=8.8 Hz, 1H), 2.63 (dd, J=8.8, 5.0 Hz, 1H), 2.34 (s, 3H), 2.15 (s, 3H), 1.87 (d, J=12.3 Hz, 1H), 1.72 (t, J=13.3 Hz, 2H), 1.60 (s, 9H), 1.63-1.35 (m, 3H), 1.22-0.98 m, 5H). HRMS (ESI+) m/z calcd for $C_{25}H_{35}N_4O_2^+$ [M+H]⁺ 423.2755, found 423.2773.

Compound 123

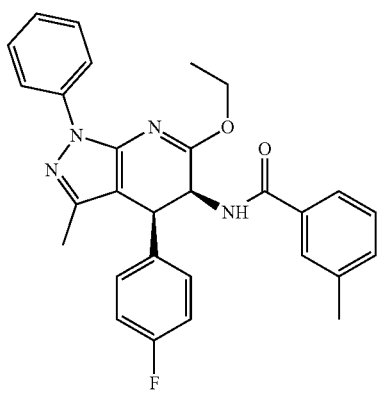

¹H NMR (400 MHz, Chloroform-d) δ 7.92 (d, J=7.9 Hz, 2H), 7.48 (s, 1H), 7.45-7.40 (m, 2H), 7.31 (m, 4H), 7.02-6.86 (m, 4H), 6.12 (d, J=7.4 Hz, 1H), 5.40 (t, J=8.3 Hz, 1H), 5.36-5.25 (m, 1H), 4.52 (d, J=8.1 Hz, 1H), 2.38 (s, 3H), 2.11 (s, 3H), 1.33 (t, J=5.2 Hz, 3H), 1.26 (d, J=6.0 Hz, 3H). HRMS (ESI+) m/z calcd for $C_{30}H_{30}FN_4O_2^+$ [M+H]⁺ 497.2347, found 497.2339.

Compound 126

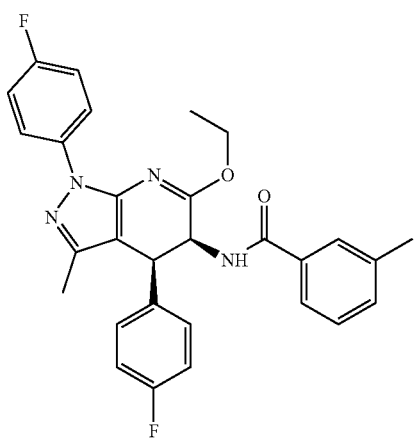

¹H NMR (400 MHz, Chloroform-d) δ 7.94-7.85 (m, 2H), 7.47 (s, 1H), 7.39-7.25 (m, 3H), 7.12 (t, J=8.6 Hz, 2H), 7.00-6.87 (m, 4H), 6.14 (d, J=7.7 Hz, 1H), 5.51-5.40 (m, 1H), 4.51 (d, J=8.5 Hz, 1H), 4.45-4.24 (m, 2H), 2.38 (s, 3H), 2.09 (s, 3H), 1.32 (t, J=6.8 Hz, 3H). HRMS (ESI+) m/z calcd for $C_{30}H_{30}FN_4O_2^+$ [M+H]$^+$ 497.2347, found 497.2339. HRMS (ESI+) m/z calcd for $C_{29}H_{27}F_2N_4O_2^+$ [M+H]$^+$ 501.2097, found 501.2080.

Compound 127

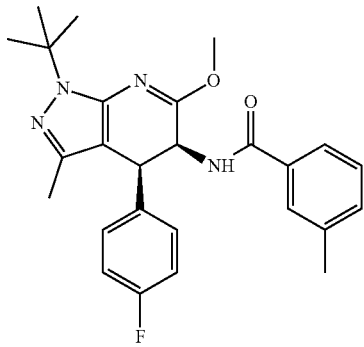

¹H NMR (400 MHz, Chloroform-d) δ 7.46 (s, 1H), 7.37-7.26 (m, 3H), 6.94-6.84 (m, 4H), 6.09 (d, J=8.0 Hz, 1H), 5.41 (t, J=8.2 Hz, 1H), 4.36 (d, J=8.4 Hz, 1H), 3.85 (s, 3H), 2.35 (s, 3H), 1.99 (s, 3H), 1.70 (s, 9H). HRMS (ESI+) m/z calcd for $C_{26}H_{30}FN_4O_2^+$ [M+H]$^+$ 449.2347, found 449.2347.

Compound 128

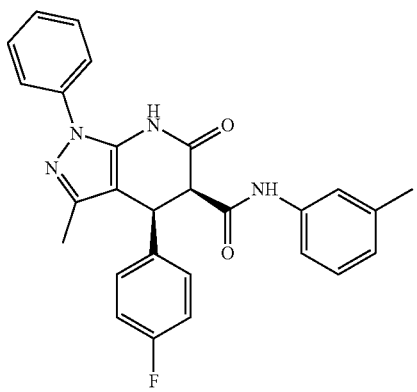

¹H NMR (400 MHz, Chloroform-d) δ 8.05 (s, 1H), 7.82 (s, 1H), 7.54-7.30 (m, 7H), 7.23-7.12 (m, 3H), 7.05-6.95 (m, 2H), 6.92 (d, J=7.3 Hz, 1H), 5.02 (d, J=3.7 Hz, 1H), 3.73 (d, J=3.7 Hz, 1H), 2.31 (s, 3H), 2.03 (s, 3H). HRMS (ESI+) m/z calcd for $C_{27}H_{24}FN_4O_2^+$ [M+H]$^+$ 455.1878, found 455.1889.

Compound 129

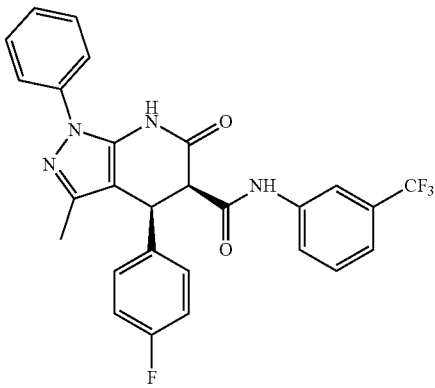

¹H NMR (400 MHz, Chloroform-d) δ 8.32 (s, 1H), 7.88 (s, 1H), 7.83 (s. 1H), 7.62 (d, J=8.0 Hz, 1H), 7.55-7.47 (m, 2H), 7.47-7.34 (m, 5H), 7.19 (dd, J=8.2, 5.1 Hz, 2H), 7.02 (t, J=8.5 Hz, 2H), 5.03 (d, J=3.9 Hz, 1H), 3.76 (d, J=3.6 Hz, 1H), 2.02 (s, 3H). HRMS (ESI+) m/z calcd for $C_{27}H_{21}F_4N_4O_2^+$ [M+H]$^+$ 509.1595, found 509.1608.

Compound 130

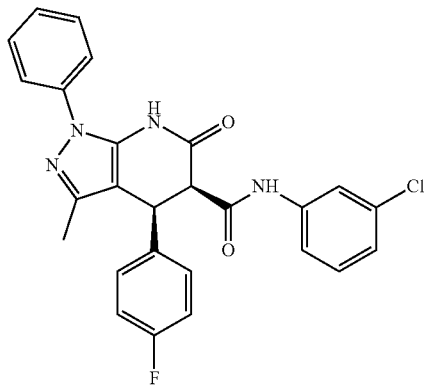

¹H NMR (400 MHz, Chloroform-d) δ 8.18 (s, 1H), 7.85 (s, 1H), 7.64 (s, 1H), 7.55-7.47 (m, 2H), 7.46-7.41 (m, 2H), 7.38 (dd, J=8.4, 7.0 Hz, 1H), 7.31-7.25 (m, 1H), 7.19 (dd, J=9.1, 4.5 Hz, 3H), 7.11-7.04 (m, 1H), 7.05-6.98 (m, 2H), 5.01 (d, J=4.0 Hz, 1H), 3.73 (d, J=4.1 Hz, 1H), 2.02 (s, 3H). HRMS (ESI+) m/z calcd for $C_{26}H_{21}ClFN_4O_2^+$ [M+H]$^+$ 475.1332, found 475.1336.

Compound 131

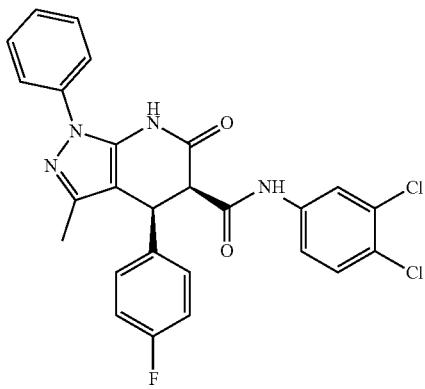

¹H NMR (400 MHz, Chloroform-d) δ 8.22 (s, 1H), 7.86 (s, 1H), 7.76 (s, 1H), 7.63-7.25 (m, 7H), 7.18 (m, 2H), 7.01 (t, J=8.5 Hz, 2H), 5.00 (d, J=3.8 Hz, 1H), 3.77-3.68 (m, 1H), 2.01 (s, 3H). HRMS (ESI+) m/z calcd for $C_{26}H_{20}Cl_2FN_4O_2^+$ [M+H]$^+$ 509.0942, found 509.0944.

Compound 132

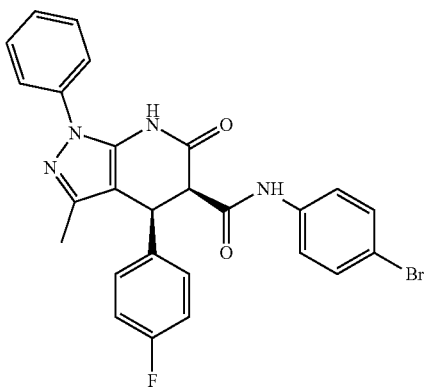

¹H NMR (400 MHz, Chloroform-d) δ 8.15 (s, 1H), 7.85 (s, 1H), 7.55-7.46 (m, 2H), 7.47-7.31 (m, 7H), 7.21-7.12 (m, 2H), 7.07-6.95 (m, 2H), 5.00 (d, J=4.0 Hz, 1H), 3.72 (d, J=4.0 Hz, 1H), 2.01 (s, 3H). HRMS (ESI+) m/z calcd for $C_{26}H_{21}BrFN_4O_2^+$ [M+H]$^+$ 519.0826, found 519.0832.

Compound 133

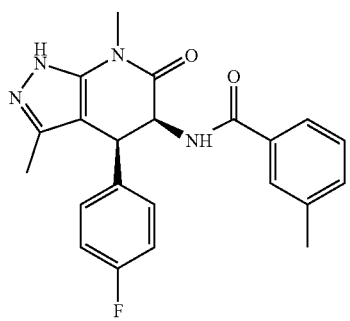

¹H NMR (400 MHz, Chloroform-d) δ 9.22 (s, 1H), 7.53-7.46 (m, 1H), 7.43 (s, 1H), 7.32-7.26 (m, 2H), 6.99 (s, 1H), 6.91-6.74 (m, 4H), 4.97 (m, 1H), 4.82 (d, J=7.1 Hz, 1H), 3.44 (s, 3H), 2.35 (s, 3H), 2.15 (s, 3H). HRMS (ESI+) m/z calcd for $C_{22}H_{22}FN_4O_2^+$ [M+H]$^+$ 393.1721, found 393.1726.

Compound 134

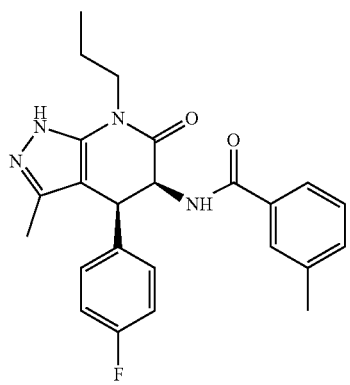

¹H NMR (400 MHz, Chloroform-d) δ 9.57 (s, 1H), 7.51 (s, 1H), 7.47 (m, 1H), 7.35-7.18 (m, 2H), 7.04 (m, 1H), 6.94-6.75 (m, 4H), 4.98 (dd, J=7.1, 5.0 Hz, 1H), 4.81 (d, J=7.2 Hz, 1H), 4.04-3.77 (m, 2H), 2.36 (s, 3H), 2.14 (s, 3H), 1.78 (p, J=7.6 Hz, 2H), 0.98 (t, J=7.5 Hz, 3H). HRMS (ESI+) m/z calcd for $C_{24}H_{26}FN_4O_2^+$ [M+H]$^+$ 421.2034, found 421.2050.

Compound 135

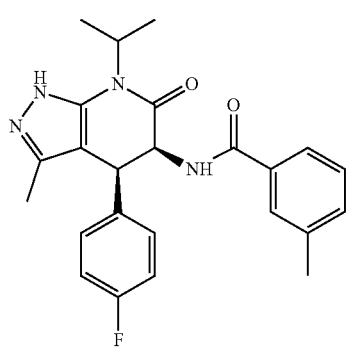

¹H NMR (400 MHz, Chloroform-d) δ 9.22 (s, 1H), 7.52 (s, 1H), 7.48 (d, J=6.1 Hz, 1H), 7.29 (d, J=6.0 Hz, 2H), 7.08 (d, J=4.9 Hz, 1H), 6.93-6.82 (m, 4H), 5.01 (hept, J=6.9 Hz, 1H), 4.92 (dd, J=7.0, 5.0 Hz, 1H), 4.78 (d, J=7.0 Hz, 1H), 2.37 (s, 3H), 2.15 (s, 3H), 1.62-1.44 (m, 6H). HRMS (ESI+) m/z calcd for $C_{24}H_{26}FN_4O_2^+$ [M+H]$^+$ 421.2034, found 421.2034.

Compound 136

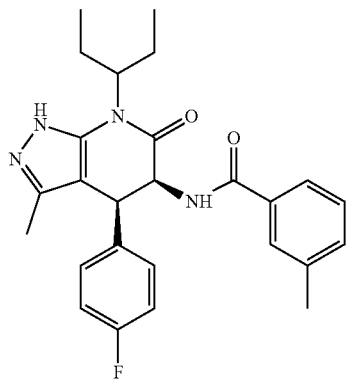

¹H NMR (400 MHz, Chloroform-d) δ 9.16 (s, 1H), 7.63-7.40 (m, 2H), 7.29 (m, 2H), 7.15-7.10 (m, 1H), 6.98-6.90 (m, 2H), 6.90-6.82 (m, 2H), 4.99 (dd, J=6.3, 4.8, 1H), 4.83 (d, J=6.6 Hz, 1H), 4.65-4.42 (m, 1H), 2.36 (s, 3H), 2.28-2.17 (m, 1H), 2.15 (s, 3H), 2.13-2.00 (m, 1H), 1.81 (dq, J=14.1, 7.1 Hz, 2H), 0.96-0.76 (m, 6H). HRMS (ESI+) m/z calcd for $C_{26}H_{30}FN_4O_2^+$ [M+H]$^+$ 449.2347, found 449.2360.

Compound 137

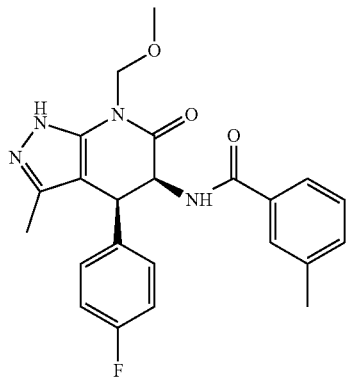

¹H NMR (400 MHz, Chloroform-d) δ 8.53 (s, 1H), 7.49 (s, 1H), 7.46-7.40 (m, 1H), 7.32-7.25 (m, 2H), 6.99-6.79 (m, 5H), 5.37-5.22 (m, 2H), 5.10-4.97 (m, 1H), 4.85 (d, J=7.2 Hz, 1H), 3.38-3.24 (s, 3H), 2.36 (s, 3H), 2.15 (s, 3H). HRMS (ESI+) m/z calcd for $C_{23}H_{24}FN_4O_3^+$ [M+H]$^+$ 423.1827, found 423.1826.

Compound 138

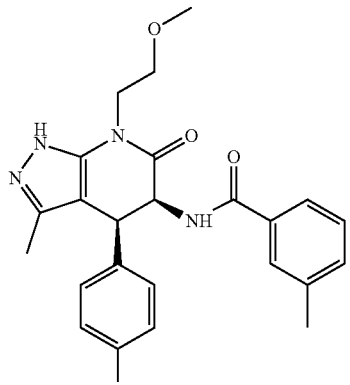

¹H NMR (400 MHz, Chloroform-d) δ 9.18 (s, 1H), 7.49 (s, 1H), 7.47-7.42 (m, 1H), 7.32-7.25 (m, 2H), 7.03-6.92 (m, 3H), 6.85 (t, J=8.6, 2H), 4.99 (dd, J=6.9, 4.8 Hz, 1H), 4.81 (d, J=7.3 Hz, 1H), 4.19 (m, 2H), 3.73 (m, 2H), 3.37 (s, 3H), 2.35 (s, 3H), 2.14 (s, 3H). HRMS (ESI+) m/z calcd for $C_{24}H_{26}FN_4O_3^+$ [M+H]$^+$ 437.1983, found 437.1961.

Compound 139

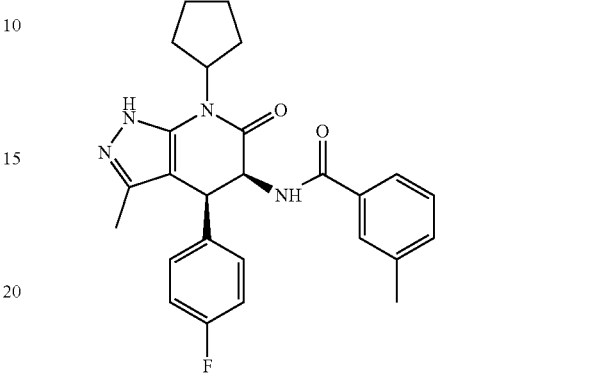

¹H NMR (400 MHz, Chloroform-d) δ 9.22 (s, 1H), 7.52 (s, 1H), 7.50-7.44 (m, 1H), 7.33-7.26 (m, 2H), 7.08 (d, J=5.0 Hz, 1H), 6.87 (d J=7.0 Hz, 4H), 5.09 (q, J=9.2, 8.7 Hz, 1H), 4.93 (dd, J=6.8, 4.9 Hz, 1H), 4.77 (d, J=6.9 Hz, 1H), 2.37 (s, 3H), 2.16 (s, 3H), 2.02-1.85 (m, 4H), 1.60 (m, 4H). HRMS (ESI+) m/z calcd for $C_{26}H_{28}FN_4O_2^+$ [M+H]$^+$ 447.2191, found 447.2210.

Compound 140

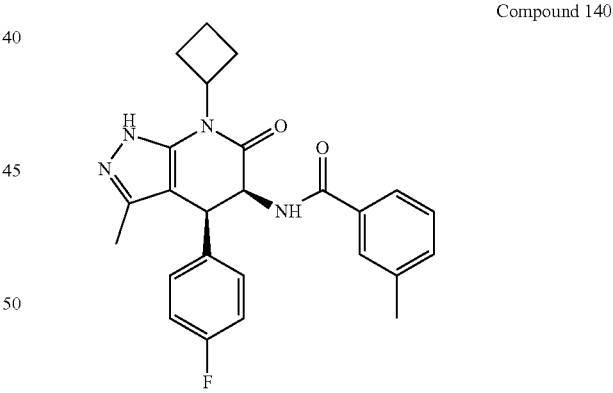

¹H NMR (400 MHz, Chloroform-d) δ 9.23 (s, 1H), 7.51 (s, 1H), 7.49-7.44 (m, 1H), 7.32-7.25 (m, 2H), 7.05 (d, J=5.0 Hz, 1H), 6.89-6.80 (m, 4H), 5.16 (p, J=8.8 Hz, 1H), 4.91 (dd, J=6.9, 5.0 Hz, 1H), 4.76 (d, J=6.9 Hz, 1H), 3.09 (td, J=10.7, 10.1 Hz, 1H), 3.02-2.88 (td, J=10.7, 10.1 Hz, 1H), 2.36 (s, 3H), 2.28 (m, 2H), 2.16 (s, 3H), 1.88-1.85 (m, 1H), 1.83-1.69 (m, 1H). HRMS (ESI+) m/z calcd for $C_{25}H_{26}FN_4O_2^+$ [M+H]$^+$ 433.2034, found 433.2036.

Compound 141

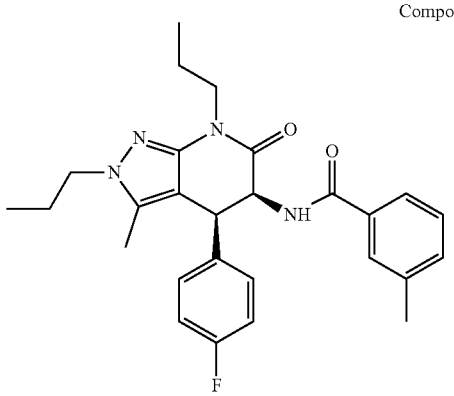

¹H NMR (400 MHz, Chloroform-d) δ 7.51 (s, 1H), 7.48-7.44 (m, 1H), 7.32-7.25 (m, 2H), 7.04 (d, J=5.0 Hz, 1H), 6.92-6.80 (m, 4H), 4.96 (t, J=7.2, 5.8 Hz, 1H), 4.77 (d, J=7.1 Hz, 1H), 4.02-3.82 (m, 4H), 2.36 (s, 3H), 2.07 (s, 3H), 1.79 (p, J=7.4 Hz, 4H), 0.98 (t, J=7.4 Hz, 3H), 0.90 (t, J=7.4 Hz, 3H). HRMS (ESI+) m/z calcd for $C_{27}H_{32}FN_4O_2^+$ [M+H]⁺ 463.2504, found 463.2512.

Compound 142

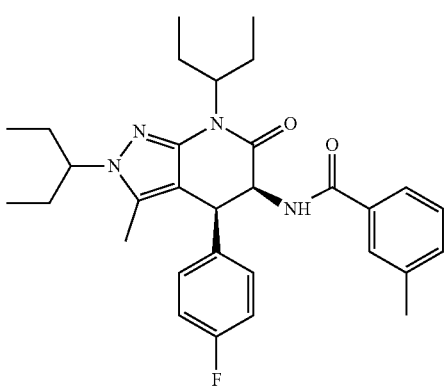

¹H NMR (400 MHz, Chloroform-d) δ 7.55-7.48 (m, 2H), 7.32-7.26 (m, 2H), 7.14 (m, 1H), 6.92 (dd, J=8.6, 5.5 Hz, 2H), 6.85 (m, 2H), 5.01 (dd, J=7.3, 5.0 Hz, 1H), 4.77 (d, J=7.3 Hz, 1H), 4.58 (m, 1H), 3.73 (tt, J=9.5, 4.5 Hz, 1H), 2.36 (s, 3H), 2.31-2.20 (m, 1H), 2.18-2.07 (m, 1H), 2.04 (s, 3H), 1.93-1.78 (m, 3H), 1.77-1.67 (m, 3H), 0.90 (tt, J=12.6, 7.4 Hz, 6H), 0.77 (t, J=7.4 Hz, 3H), 0.69 (t, J=7.3 Hz, 3H). HRMS (ESI+) m/z calcd for $C_{31}H_{40}FN_4O_2^+$ [M+H]⁺ 519.3130, found 519.3159.

Compound 143

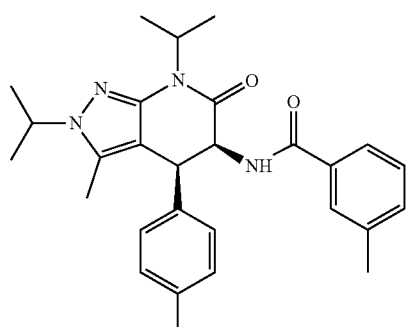

¹H NMR (400 MHz, Chloroform-d) δ 7.51 (s, 1H), 7.50-7.45 (m, 1H), 7.31-7.26 (m, 2H), 7.09 (d, J=5.0 Hz, 1H), 6.94-6.77 (m, 4H), 5.03 (hept, J=6.9 Hz, 1H), 4.91 (dd, J=6.5, 5.0 Hz, 1H), 4.71 (d, J=6.6 Hz, 1H), 4.32 (hept, J=6.5 Hz, 1H), 2.36 (s, 3H), 2.08 (s, 3H), 1.57 (d, J=6.9 Hz, 3H), 1.49 (d, J=6.9 Hz, 3H), 1.45 (d, J=6.5 Hz, 3H) 1.43 (d, J=6.5 Hz, 3H). HRMS (ESI+) m/z calcd for $C_{27}H_{32}FN_4O_2^+$ [M+H]⁺ 463.2504, found 463.2512.

Intermediate NMR

Compound 144

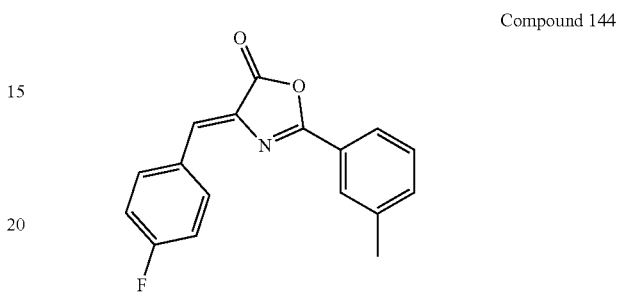

¹H NMR (400 MHz, Chloroform-d) δ 8.21-8.12 (m, 2H), 7.98-7.88 (m, 2H), 7.40-7.32 (m, 2H), 7.16-7.06 (m, 3H), 2.40 (s, 3H). LRMS (ESI+) m/z calcd for $C_{17}H_{13}FNO_2^+$ [M+H]⁺ 477.2, found 477.1.

Compound 145

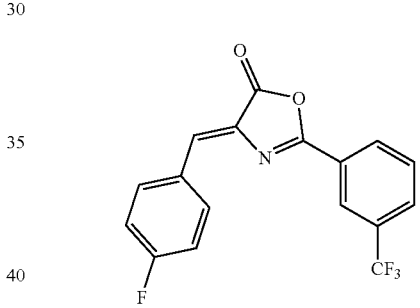

¹H NMR (500 MHz, Chloroform-d) δ 8.43 (s, 1H), 8.36 (d, J=7.9 Hz, 1H), 8.26-8.14 (m, 2H), 7.81 (d, J=7.8 Hz, 1H), 7.63 (t, J=7.8 Hz, 1H), 7.29 (s, 1H), 7.23-7.18 (m, 2H). LRMS (ESI+) m/z calcd for $C_{17}H_{10}F_4NO_2^+$ [M+H]⁺ 366.1, found 366.2.

Compound 146

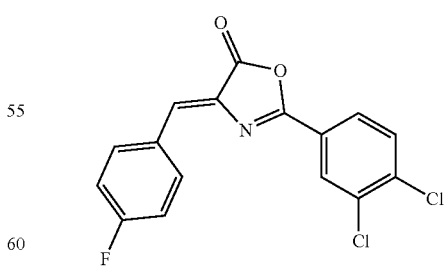

¹H NMR (400 MHz, Chloroform-d) δ 8.19 (d, J=2.0 Hz, 1H), 8.18-8.11 (m, 2H), 7.92 (dd, J=8.4, 2.0 Hz, 1H), 7.56 (d, J=8.4 Hz, 1H), 7.19 (s, 1H), 7.16-7.09 (m, 2H). LRMS (ESI+) m/z calcd for $C_{16}H_9Cl_2FNO_2^+$ [M+H]⁺ 336.0, found 336.0.

Compound 147

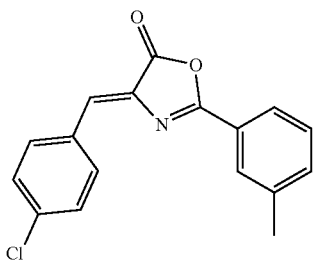

¹H NMR (400 MHz, Chloroform-d) δ 8.09 (d, J=8.5 Hz, 2H), 7.96-7.87 (m, 2H), 7.43-7.32 (m, 4H), 7.11 (s, 1H), 2.40 (s, 3H). LRMS (ESI+) m/z calcd for $C_{17}H_{13}ClNO_2^+$ [M+H]⁺ 298.1, found 298.1.

Compound 148

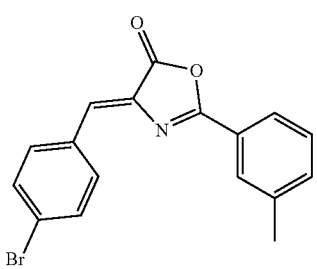

¹H NMR (400 MHz, Chloroform-d) δ 8.05-7.97 (m, 2H), 7.95-7.88 (m, 2H), 7.58-7.52 (m, 2H), 7.41-7.34 (m, 2H), 7.09 (s, 1H), 2.40 (s, 3H). LRMS (ESI+) m/z calcd for $C_{16}H_{10}BrFNO_2^+$ [M+H]⁺ 346.0, found 346.1.

Compound 149

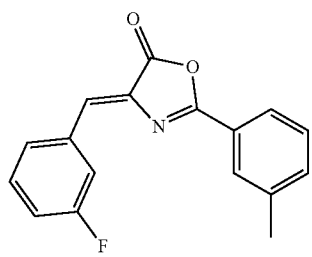

¹H NMR (400 MHz, Chloroform-d) δ 8.08 (ddd, J=10.2, 2.6, 1.5 Hz, 1H), 7.98-7.89 (m, 2H), 7.72 (dt, J=7.7, 1.2 Hz, 1H), 7.43-7.32 (m, 3H), 7.12 (s, 1H), 7.11-7.06 (m, 1H), 2.40 (s, 3H). LRMS (ESI+) m/z calcd for $C_{17}H_{13}FNO_2^+$ [M+H]⁺ 282.1, found 282.0.

Compound 150

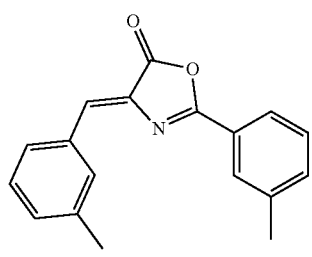

¹H NMR (400 MHz, Chloroform-d) δ 8.02 (d, J=7.7 Hz, 1H), 7.96-7.90 (m, 2H), 7.88 (d, J=2.0 Hz, 1H), 7.39-7.34 (m, 2H), 7.34-7.29 (m, 1H), 7.24-7.19 (m, 1H), 7.15 (s, 1H), 2.39 (s, 3H), 2.37 (s, 3H). LRMS (ESI+) m/z calcd for $C_{18}H_{16}NO_2^+$ [M+H]⁺ 278.1, found 278.2.

Compound 151

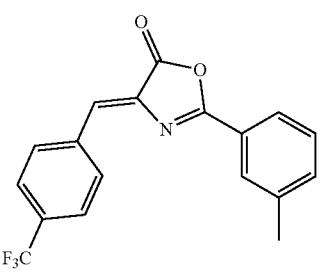

¹H NMR (500 MHz, Chloroform-d) δ 8.24 (d, J=8.1 Hz, 2H), 7.94-7.90 (m, 2H), 7.66 (d, J=8.2 Hz, 2H), 7.41-7.33 (m, 2H), 7.15 (s, 1H), 2.40 (s, 3H). LRMS (ESI+) m/z calcd for $C_{18}H_{13}F_3NO_2^+$ [M+H]⁺ 332.1, found 332.3.

Compound 152

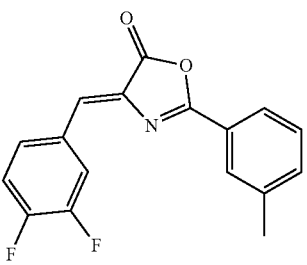

¹H NMR (500 MHz, Chloroform-d) δ 8.26 (ddd, J=11.6, 7.9, 2.1 Hz, 1H), 7.95-7.89 (m, 2H), 7.72-7.66 (m, 1H), 7.42-7.34 (m, 2H), 7.23-7.14 (m, 1H), 7.06 (s, 1H), 2.41 (s, 3H). LRMS (ESI+) m/z calcd for $C_{17}H_{12}F_2NO_2^+$ [M+H]⁺ 300.1, found 300.3.

Compound 153

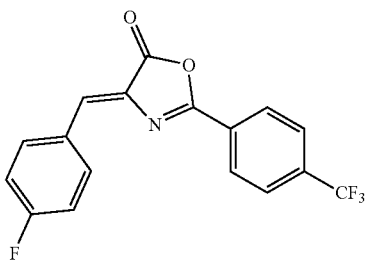

¹H NMR (400 MHz, Chloroform-d) δ 8.23 (d, J=7.7, 2H), 8.20-8.13 (m, 2H), 7.74 (d, J=8.3 Hz, 2H), 7.23 (s, 1H), 7.16-7.10 (m, 2H). LRMS (ESI+) m/z calcd for $C_{17}H_{10}F_4NO_2^+$ [M+H]⁺ 336.1, found 336.4.

Compound 154

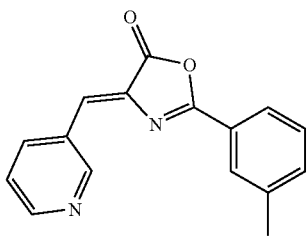

¹H NMR (400 MHz, Chloroform-d) δ 9.15 (d, J=2.2 Hz, 1H), 8.63 (dt, J=8.0, 2.0 Hz, 1H), 8.58 (dd, J=4.8, 1.7 Hz, 1H), 7.95 (s, 1H), 7.94-7.89 (m, 1H), 7.44-7.32 (m, 3H), 7.14 (s, 1H), 2.40 (s, 3H). LRMS (ESI+) m/z calcd for $C_{16}H_{13}N_2O_2^+$ [M+H]⁺ 265.1, found 265.1.

Compound 155

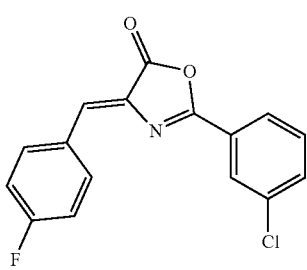

¹H NMR (400 MHz, Chloroform-d) δ 8.20-8.12 (m, 2H), 8.12-8.08 (m, 1H), 7.98 (d, J=7.8 Hz, 1H), 7.56-7.48 (m, 1H), 7.45-7.38 (m, 1H), 7.18 (s, 1H), 7.16-7.08 (m, 2H). LRMS (ESI+) m/z calcd for $C_{16}H_{10}ClFNO_2^+$ [M+H]⁺ 302.0, found 302.1.

Compound 156

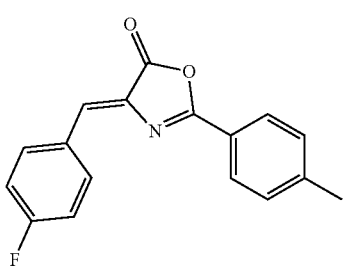

¹H NMR (400 MHz, Chloroform-d) δ 8.23-8.12 (m, 2H), 8.00 (d, J=8.0 Hz, 2H), 7.31-7.26 (m, 2H), 7.13-7.07 (m, 3H), 2.40 (s, 3H). LRMS (ESI+) m/z calcd for $C_{17}H_{13}FNO_2^+$ [M+H]⁺ 282.1, found 282.1.

Compound 157

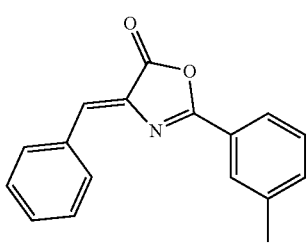

¹H NMR (400 MHz, Chloroform-d) δ 8.28-8.14 (m, 2H), 7.98 (d, J=8.1 Hz, 2H), 7.55-7.36 (m, 5H), 7.23 (s, 1H), 2.45 (s, 3H). LRMS (ESI+) m/z calcd for $C_{17}H_{14}NO_2^+$ [M+H]⁺ 264.3, found 264.1.

Compound 158

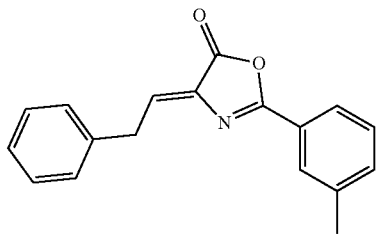

¹H NMR (400 MHz, Chloroform-d) δ 7.96-7.83 (m, 1H), 7.56-6.99 (m, 8H), 6.81-6.69 (m, 1H), 4.00 (s, 2H), 2.50-2.33 (s, 3H). LRMS (ESI+) m/z calcd for $C_{18}H_{16}NO_2^+$ [M+H]⁺ 278.3, found 278.1.

Compound 159

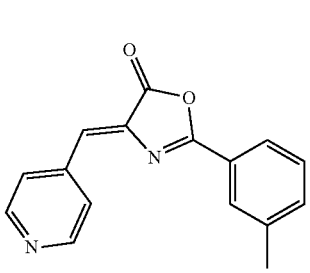

¹H NMR (400 MHz, Chloroform-d) δ 8.78-8.69 (m, 2H), 8.04-7.97 (m, 4H), 7.45 (d, J=8.3 Hz, 2H), 7.10 (s, 1H), 2.47 (s, 3H). LRMS (ESI+) m/z calcd for $C_{16}H_{13}N_2O_2^+$ [M+H]⁺ 265.3, found 265.1.

Compound 160

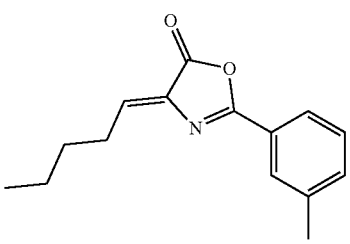

¹H NMR (400 MHz, Chloroform-d) δ 7.90 (s, 1H), 7.87-7.82 (m, 1H), 7.42-7.32 (m, 2H), 6.72-6.62 (m, 1H), 2.73-2.63 (m, 2H), 2.41 (s, 3H), 1.59-1.49 (m, 2H), 1.47-1.36 (m, 2H), 0.94 (t, J=7.3 Hz, 3H). LRMS (ESI+) m/z calcd for $C_{15}H_{18}NO_2^+$ [M+H]⁺ 244.3, found 244.2.

Compound 161

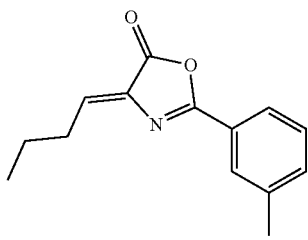

¹H NMR (400 MHz, Chloroform-d) δ 7.90 (s, 1H), 7.87 (d, J=5.0 Hz, 1H), 7.43-7.31 (m, 2H), 6.67 (t, J=8.0 Hz, 1H), 2.65 (q, J=7.9 Hz, 2H), 2.41 (s, 3H), 1.60 (qd, J=7.4, 2.1 Hz, 2H), 1.01 (t, J=7.2 Hz, 3H). LRMS (ESI+) m/z calcd for $C_{14}H_{16}NO_2^+$ [M+H]⁺ 230.3, found 230.0.

Compound 162

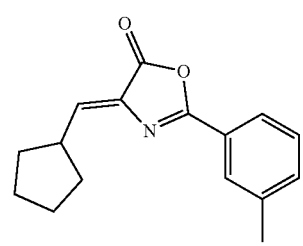

¹H NMR (400 MHz, Chloroform-d) δ 7.89 (s, 1H), 7.87-7.82 (m, 1H), 7.40-7.33 (m, 2H), 6.60 (d, J=10.4 Hz, 1H), 3.49-3.33 (m, 1H), 2.41 (s, 3H), 2.04-1.91 (m, 2H), 1.84-1.64 (m, 4H), 1.51-1.35 (m, 2H). LRMS (ESI+) m/z calcd for $C_{16}H_{16}NO_2^+$ [M+H]⁺ 256.3, found 256.1.

Compound 163

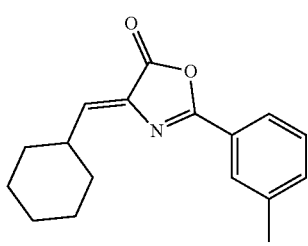

¹H NMR (400 MHz, Chloroform-d) δ 7.90 (s, 1H), 7.88-7.83 (m, 1H), 7.41-7.34 (m, 2H), 6.52 (d, J=10.1 Hz, 1H), 3.01 (p, J=11.1 Hz, 1H), 2.41 (s, 3H), 1.89-1.67 (m, 4H), 1.48-1.33 (m, 2H), 1.33-1.16 (m, 4H). LRMS (ESI+) m/z calcd for $C_{17}H_{20}NO_2^+$ [M+H]⁺ 270.2, found 270.1.

Compound 164

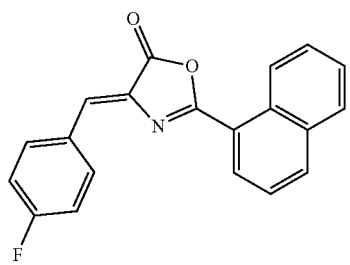

¹H NMR (400 MHz, Chloroform-d) δ 9.45 (d, J=8.7 Hz, 1H), 8.37 (dt, J=7.4, 1.3 Hz, 1H), 8.30-8.21 (m, 2H), 8.09 (d, J=8.4 Hz, 1H), 7.94 (d, J=8.2 Hz, 1H), 7.78-7.69 (m, 1H), 7.67-7.53 (m, 2H), 7.28 (s, 1H), 7.24-7.16 (m, 2H). LRMS (ESI+) m/z calcd for $C_{20}H_{13}FNO_2^+$ [M+H]⁺ 318.1, found 318.1.

Compound 165

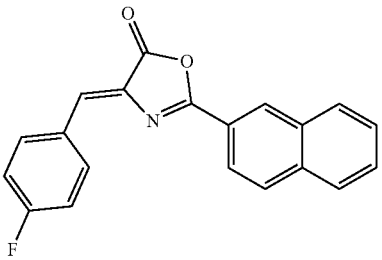

¹H NMR (400 MHz, Chloroform-d) δ 8.65 (s, 1H), 8.31-8.17 (m, 4H), 7.97 (t, J=9.1 Hz, 2H), 7.90 (d, J=8.1 Hz, 1H), 7.67-7.51 (m, 2H), 7.22-7.12 (m, 2H). LRMS (ESI+) m/z calcd for $C_{20}H_{13}FNO_2^+$ [M+H]⁺ 318.1, found 318.2.

Compound 166

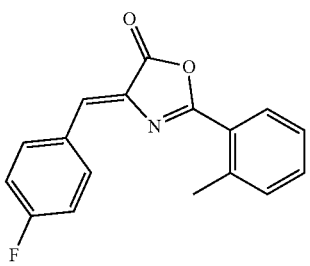

¹H NMR (400 MHz, Chloroform-d) δ 8.19 (dd, J=8.3, 5.5 Hz, 2H), 8.07 (d, J=7.9 Hz, 1H), 7.52-7.43 (m, 1H), 7.34 (dt, J=9.7, 4.9 Hz, 2H), 7.20 (s, 1H), 7.15 (t, J=8.8 Hz, 2H), 2.82 (s, 3H). LRMS (ESI+) m/z calcd for $C_{17}H_{13}FNO_2^+$ [M+H]⁺ 282.1, found 282.3.

Compound 167

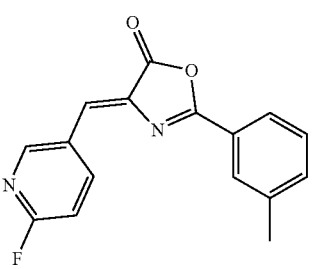

¹H NMR (400 MHz, Chloroform-d) δ 8.91-8.76 (m, 2H), 8.00-7.90 (m, 2H), 7.46-7.36 (m, 2H), 7.17 (s, 1H), 7.09-7.03 (m, 1H), 2.45 (s, 3H). LRMS (ESI+) m/z calcd for $C_{16}H_{12}FN_2O_2^+$ [M+H]⁺ 283.1, found 283.1.

Compound 168

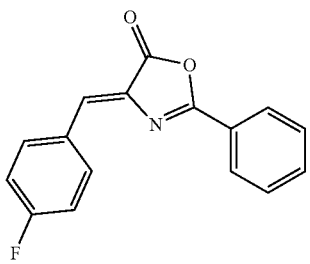

¹H NMR (400 MHz, Chloroform-d) δ 8.26-8.09 (m, 4H), 7.65-7.57 (m, 1H), 7.57-7.47 (m, 2H), 7.21-7.10 (m, 3H). LRMS (ESI+) m/z calcd for C₁₆H₁₁FNO₂⁺ [M+H]⁺ 268.1, found 268.1.

Compound 169

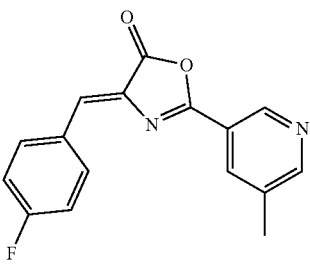

¹H NMR (400 MHz, Chloroform-d) δ 9.16 (s, 1H), 8.64 (s, 1H), 8.28-8.12 (m, 2H), 7.25 (s, 1H), 7.21-7.13 (m, 3H), 2.46 (s, 3H). LRMS (ESI+) m/z calcd for C₁₆H₁₂FN₂O₂⁺ [M+H]⁺ 283.1, found 283.3.

Compound 170

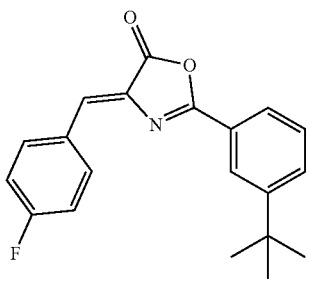

¹H NMR (400 MHz, Chloroform-d) δ 8.22 (dd, J=8.1, 5.5 Hz, 2H), 8.13 (s, 1H), 8.05-7.99 (m, 1H), 7.69-7.59 (m, 1H), 7.49-7.41 (m, 1H), 7.21-7.11 (m, 3H), 1.38 (s, 9H). LRMS (ESI+) m/z calcd for C₂₀H₁₉FNO₂⁺ [M+H]⁺ 324.1, found 324.3.

Compound 171

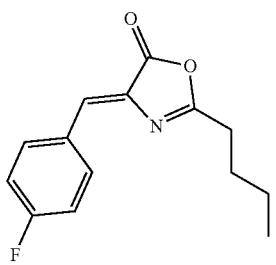

¹H NMR (400 MHz, Chloroform-d) δ 8.18-7.90 (m, 2H), 7.17-6.98 (m, 3H), 2.64 (t, J=7.6 Hz, 2H), 1.77 (p, J=7.5 Hz, 2H), 1.47-1.33 (m, 2H), 1.08-0.90 (m, 3H). LRMS (ESI+) m/z calcd for C₁₄H₁₅FNO₂⁺ [M+H]⁺ 248.1, found 248.1.

Compound 172

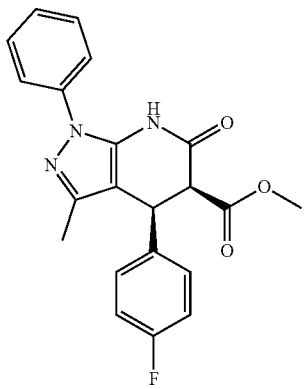

¹H NMR (400 MHz, Chloroform-d) δ 7.73 (s, 1H), 7.54-7.35 (m, 5H), 7.23-7.17 (m, 2H), 7.08-6.94 (m, 2H), 4.62 (d, J=7.7 Hz, 1H), 3.85-3.77 (m, 1H), 3.70 (s, 3H), 1.86 (s, 3H). LRMS (ESI+) m/z calcd for C₂₁H₁₉FN₃O₃⁺ [M+H]⁺ 380.1, found 380.1.

Compound 173

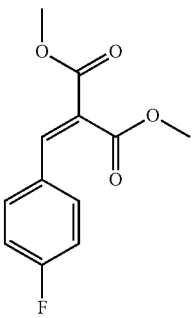

¹H NMR (400 MHz, Chloroform-d) δ 7.70 (s, 1H), 7.43-7.37 (m, 2H), 7.08-7.01 (m, 2H), 3.82 (s, 6H). LRMS (ESI+) m/z calcd for C₁₂H₁₂FO₄⁺ [M+H]⁺ 239.1, found 239.2.

Compound 174

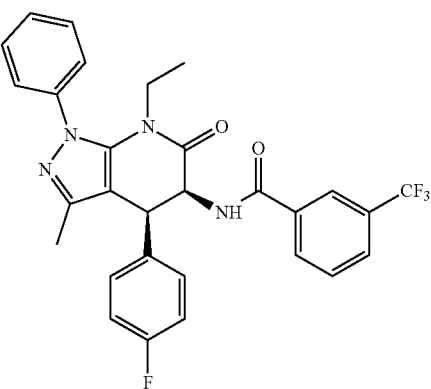

¹H NMR (400 MHz, Chloroform-d) δ 8.03 (s, 1H), 7.91-7.83 (m, 1H), 7.78 (d, J=7.8 Hz, 1H), 7.57 (t, J=7.8 Hz, 1H), 7.54-7.41 (m, 4H), 7.03 (d, J=5.6 Hz, 1H), 6.96-6.88 (m, 4H), 5.20 (dd, J=7.3, 5.7 Hz, 1H), 4.76 (d, J=7.3 Hz, 1H), 3.97 (dq, J=14.3, 7.2 Hz, 1H), 3.18 (dq, J=14.0, 7.0 Hz, 1H), 2.15 (s, 3H), 1.00 (t, J=7.0 Hz, 3H). ¹³C NMR (126 MHz, Chloroform-d) δ 170.3, 168.4, 166.0, 164.0, 149.7, 141.8, 141.5, 137.3, 135.0 (2C), 134.0 (d, J=33.2 Hz), 132.7, 132.5, 132.4, 132.3, 132.0, 131.6, 131.2 (q, J=3.4 Hz), 128.01, 127.0 (q, J=3.9 Hz), 126.3 (q, J=272.4 Hz), 118.3, 118.1, 108.4, 58.5, 42.0, 39.4, 15.4, 14.6. HRMS (ESI+) m/z calcd for $C_{29}H_{25}F_4N_4O_2^+$ $[M+H]^+$ 537.1908, found 537.1917.

The PK data for compound 174 is shown in FIG. 15.

Compound 175

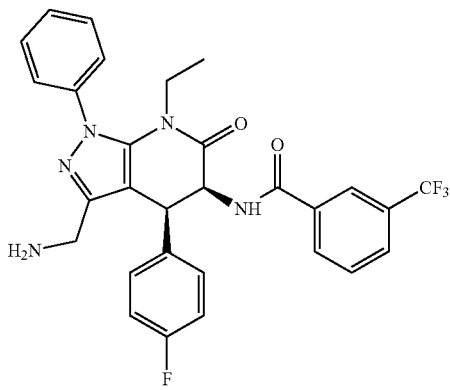

(RG-0008867 (KHS_NB5_069))

¹H NMR (400 MHz, Chloroform-d) δ 8.03 (s, 1H), 7.86 (d, J=7.8 Hz, 1H), 7.80-7.76 (m, 1H), 7.61-7.43 (m, 6H), 7.02 (d, J=5.6 Hz, 1H), 6.99-6.88 (m, 4H), 5.23 (dd, J=7.3, 5.6 Hz, 1H), 4.88 (d, J=7.3 Hz, 1H), 3.97 (dq, J=14.4, 7.2 Hz, 1H), 3.85-3.70 (m, 2H), 3.19 (dq, J=13.9, 6.9 Hz, 1H), 1.00 (t, J=7.1 Hz, 3H).

¹³C NMR (101 MHz, Chloroform-d) δ 167.7, 165.7, 163.6, 161.1, 151.4, 139.2, 139.1, 134.5, 132.4 (2C), 131.4 (q, J=32.9 Hz), 130.1, 129.8, 129.7, 129.6, 129.3, 129.1, 128.6 (q, J=3.7 Hz), 125.4, 124.3 (q, J=3.9 Hz), 122.2 (q, J=275.4 Hz), 115.8, 115.6, 104.7, 55.8, 39.3, 38.7, 36.6, 12.7. HRMS (ESI+) m/z calcd for $C_{29}H_{26}F_4N_5O_2^+$ $[M+H]^+$ 552.2017, found 552.2028.

The PK data for compound 175 is shown in FIG. 16.

Compound 176

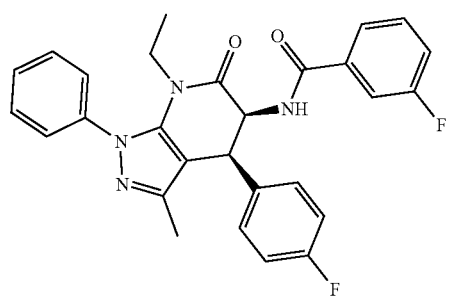

(RG-0008867 (KHS_NB5_069))

¹H NMR (400 MHz, Chloroform-d) δ 7.74 (d, J=8.2 Hz, 2H), 7.58-7.34 (m, 8H), 7.08-6.81 (m, 5H), 5.21 (dd, J=7.3, 5.7 Hz, 1H), 4.77 (d, J=7.3 Hz, 1H), 3.97 (dq, J=14.3, 7.2 Hz, 1H), 3.17 (dq, J=13.8, 6.8 Hz, 1H), 2.14 (s, 3H), 0.99 (t, J=7.0 Hz, 3H). HRMS (ESI+) m/z calcd for $C_{28}H_{26}FN_4O_2^+$ $[M+H]^+$ 469.2034, found 469.2008.

Compound 177

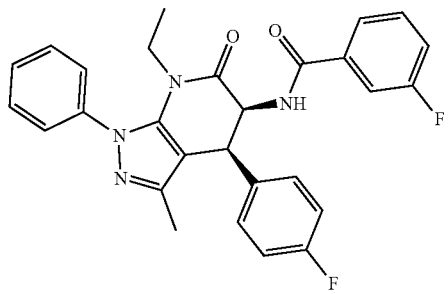

(RG-0013062 (KHS_NB7_011))

¹H NMR (400 MHz, Chloroform-d) δ 7.62-7.33 (m, 8H), 7.23-7.16 (m, 1H), 7.07-6.84 (m, 5H), 5.18 (dd, J=7.3, 5.5 Hz, 1H), 4.76 (d, J=7.2 Hz, 1H), 3.96 (dq, J=13.7, 6.7 Hz, 1H), 3.18 (dq, J=14.2, 7.2 Hz, 1H), 2.14 (s, 3H), 0.99 (t, J=6.9 Hz, 3H). HRMS (ESI+) m/z calcd for $C_{28}H_{25}F_2N_4O_2^+$ $[M+H]^+$ 487.1940, found 487.1940.

Compound 178

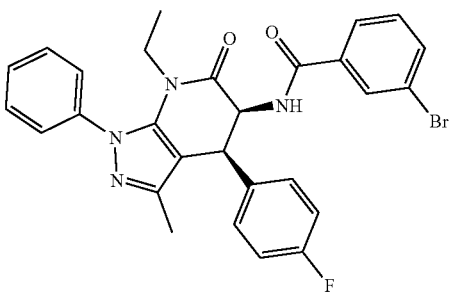

(RG-0013061 (KHS_NB7_007))

¹H NMR (400 MHz, Chloroform-d) δ 7.94-7.87 (m, 1H), 7.67-7.60 (m, 2H), 7.55-7.41 (m, 5H), 7.34-7.27 (m, 1H), 7.04-6.88 (m, 5H), 5.18 (dd, J=7.1, 5.5 Hz, 1H), 4.75 (d, J=7.3 Hz, 1H), 4.02-3.89 (m, 1H), 3.18 (dq, J=14.3, 7.2 Hz, 1H), 2.14 (s, 3H), 0.99 (t, J=7.1 Hz, 3H). HRMS (ESI+) m/z calcd for $C_{28}H_{25}BrFN_4O_2^+$ $[M+H]^+$ 547.1139, found 547.1145.

Compound 179

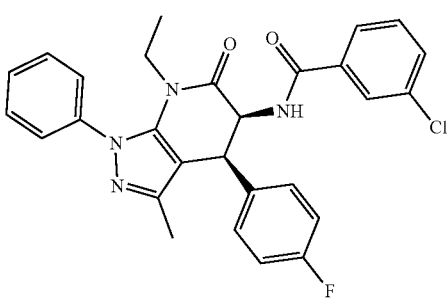

(RG-0013047 (KHS_NB6_067))

¹H NMR (400 MHz, Chloroform-d) δ 7.80-7.71 (m, 1H), 7.61-7.55 (m, 1H), 7.54-7.41 (m, 6H), 7.41-7.33 (m, 1H), 7.02-6.95 (m, 1H), 6.95-6.88 (m, 4H), 5.18 (dd, J=7.5, 5.5 Hz, 1H), 4.76 (d, J=7.2 Hz, 1H), 4.04-3.86 (m, 1H), 3.17 (dq, J=13.4, 6.9 Hz, 1H), 2.14 (s, 3H), 0.99 (t, J=7.1 Hz, 3H). HRMS (ESI+) m/z calcd for $C_{28}H_{25}ClFN_4O_2^+$ [M+H]⁺ 503.1645, found 503.1637.

Compound 180

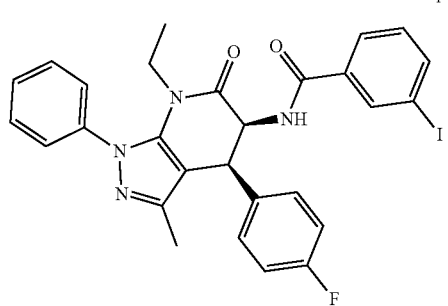

(RG-0013060 (KHS_NB7_006))

¹H NMR (400 MHz, Chloroform-d) δ 8.13-8.06 (m, 1H), 7.89-7.79 (m, 1H), 7.69-7.61 (m, 1H), 7.55-7.41 (m, 5H), 7.21-7.12 (m, 1H), 7.00-6.87 (m, 5H), 5.17 (dd, J=7.1, 5.6 Hz, 1H), 4.75 (d, J=7.4 Hz, 1H), 3.96 (dq, J=14.1, 7.1 Hz, 1H), 3.17 (dq, J=14.0, 7.0 Hz, 1H), 2.14 (s, 3H), 0.99 (t, J=7.1 Hz, 3H). HRMS (ESI+) m/z calcd for $C_{28}H_{25}FIN_4O_2^+$ [M+H]⁺ 595.1001, found 595.0987.

Compound 181

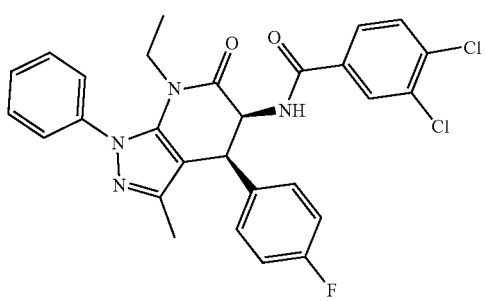

(RG-0009515 (KHS_NB6_064))

¹H NMR (400 MHz, Chloroform-d) δ 7.89-7.82 (m, 1H), 7.54-7.43 (m, 7H), 6.99-6.89 (m, 5H), 5.16 (dd, J=7.6, 5.4 Hz, 1H), 4.74 (d, J=7.3, 2.2 Hz, 1H), 4.01-3.91 (m, 1H), 3.23-3.13 (m, 1H), 2.14 (s, 3H), 0.99 (t, J=7.1 Hz, 3H). HRMS (ESI+) m/z calcd for $C_{28}H_{24}Cl_2FN_4O_2^+$ [M+H]⁺ 537.1255, found 537.1269.

Compound 182

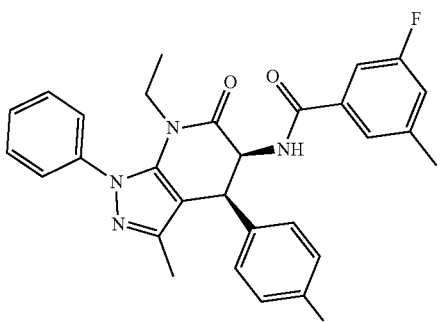

(RG-0013053 (KHS_NB6_087))

¹H NMR (400 MHz, Chloroform-d) δ 7.55-7.42 (m, 5H), 7.34-7.26 (m, 2H), 7.07-6.99 (m, 1H), 6.99-6.85 (m, 5H), 5.17 (dd, J=7.1, 5.6 Hz, 1H), 4.76 (d, J=7.3 Hz, 1H), 4.01-3.91 (m, 1H), 3.23-3.11 (m, 1H), 2.38 (s, 3H), 2.14 (s, 3H), 0.99 (t, J=7.1 Hz, 3H). HRMS (ESI+) m/z calcd for $C_{29}H_{27}F_2N_4O_2^+$ [M+H]⁺ 501.2097, found 501.2099.

Compound 183

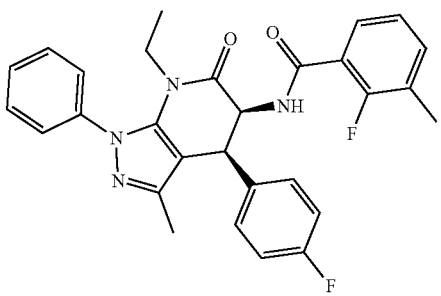

(RG-0014165 (KHS_NB10_033))

¹H NMR (400 MHz, Chloroform-d) δ 7.93-7.83 (m, 1H), 7.64-7.54 (m, 1H), 7.54-7.40 (m, 5H), 7.36-7.30 (m, 1H), 7.19-7.11 (m, 1H), 7.01-6.85 (m, 4H), 5.25 (dd, J=7.4, 5.7 Hz, 1H), 4.78 (d, J=7.2 Hz, 1H), 3.97 (dq, J=14.4, 7.2 Hz, 1H), 3.17 (dq, J=14.0, 7.0 Hz, 1H), 2.28 (s, 3H), 0.98 (t, J=7.1 Hz, 3H). HRMS (ESI+) m/z calcd for $C_{29}H_{27}F_2N_4O_2^+$ [M+H]⁺ 501.2097, found 501.2106.

Compound 184

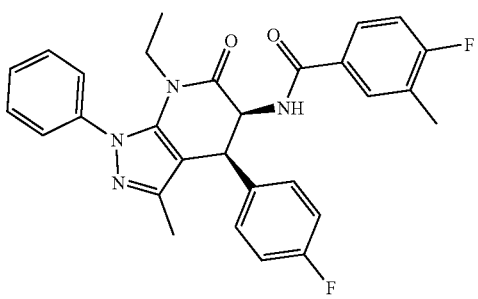

(RG-0014168 (KHS_NB10_037))

¹H NMR (400 MHz, Chloroform-d) δ 7.61 (d, J=7.3 Hz, 1H), 7.57-7.41 (m, 6H), 7.04 (t, 1H), 6.98-6.86 (m, 5H), 5.18 (dd, J=7.3, 5.6 Hz, 1H), 4.75 (d, J=7.3 Hz, 1H), 3.96 (dq, J=14.3, 7.2 Hz, 1H), 3.17 (dq, J=13.9, 6.9 Hz, 1H), 2.30 (d, J=1.9 Hz, 3H), 2.14 (s, 3H), 0.99 (t, J=7.0 Hz, 3H). HRMS (ESI+) m/z calcd for $C_{29}H_{27}F_2N_4O_2^+$ [M+H]$^+$ 501.2097, found 501.2111.

Compound 185

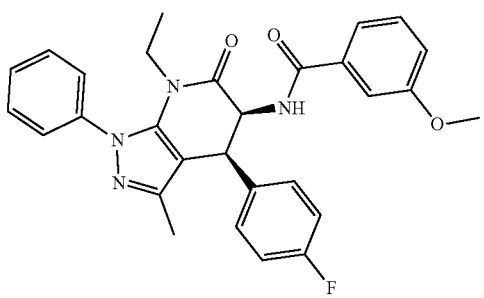

(RG-0013979 (KHS_NB8_069))

¹H NMR (400 MHz, Chloroform-d) δ 7.56-7.40 (m, 5H), 7.34-7.26 (m, 2H), 7.09-6.82 (m, 7H), 5.28-5.11 (m, 1H), 4.75 (d, J=7.2 Hz, 1H), 3.95 (dq, J=14.3, 7.1 Hz, 1H), 3.83 (s, 3H), 3.16 (dq, J=14.1, 7.0 Hz, 1H), 2.13 (s, 3H), 0.98 (t, J=7.0 Hz, 3H). HRMS (ESI+) m/z calcd for $C_{29}H_{28}FN_4O_3^+$ [M+H]$^+$ 499.2140, found 499.2135.

Compound 186

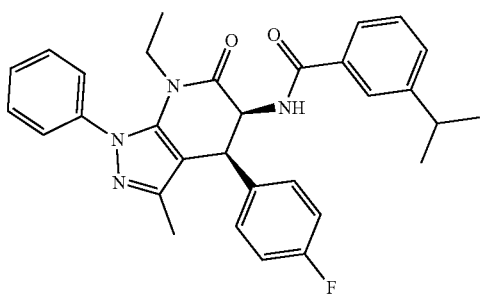

(RG-0014166 (KHS_NB10_034))

¹H NMR (400 MHz, Chloroform-d) δ 7.65-7.59 (m, 1H), 7.56-7.41 (m, 6H), 7.41-7.31 (m, 2H), 7.02-6.86 (m, 5H), 5.21 (dd, J=7.3, 5.7 Hz, 1H), 4.77 (d, J=7.3 Hz, 1H), 3.97 (dq, J=14.4, 7.2 Hz, 1H), 3.17 (dq, J=14.0, 7.0 Hz, 1H), 2.95 (hept, J=6.9 Hz, 1H), 2.14 (s, 3H), 1.27 (s, 3H), 1.25 (s, 3H), 0.99 (t, J=7.1 Hz, 3H). HRMS (ESI+) m/z calcd for $C_{31}H_{32}FN_4O_2^+$ [M+H]$^+$ 511.2504, found 511.2506.

Compound 187

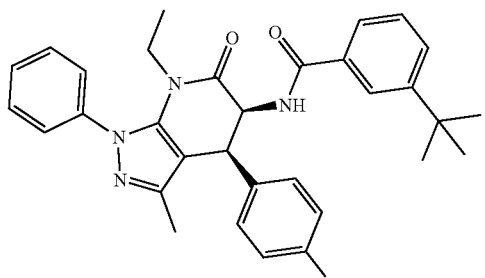

(RG-0014153 (KHS_NB10_024))

¹H NMR (400 MHz, Chloroform-d) δ 7.83-7.78 (m, 1H), 7.61-7.39 (m, 7H), 7.39-7.31 (m, 1H), 7.03-6.86 (m, 5H), 5.22 (dd, J=7.3, 5.7 Hz, 1H), 4.77 (d, J=7.3 Hz, 1H), 3.97 (dq, J=14.2, 7.1 Hz, 1H), 3.17 (dq, J=13.9, 6.9 Hz, 1H), 2.15 (s, 3H), 1.33 (s, 9H), 0.99 (t, J=7.1 Hz, 3H). HRMS (ESI+) m/z calcd for $C_{32}H_{34}FN_4O_2^+$ [M+H]$^+$ 525.2660, found 525.2673.

Compound 188

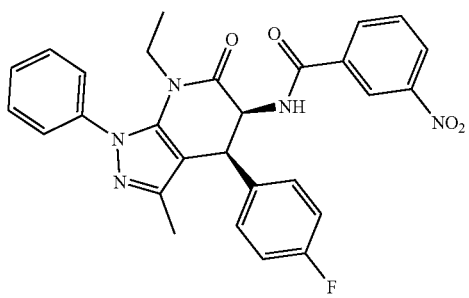

(RG-0013844 (KHS_NB8_058))

¹H NMR (400 MHz, Chloroform-d) δ 8.63-8.56 (m, 1H), 8.43-8.33 (m, 1H), 8.05-7.99 (m, 1H), 7.68-7.60 (m, 1H), 7.54-7.42 (m, 5H), 7.12-7.05 (m, 1H), 6.98-6.88 (m, 4H), 5.24-5.16 (m, 1H), 4.77 (d, J=7.3 Hz, 1H), 4.03-3.91 (m, 1H), 3.27-3.11 (m, 1H), 2.18-2.10 (m, 3H), 1.00 (t, J=7.3 Hz, 3H). HRMS (ESI+) m/z calcd for $C_{28}H_{25}FN_5O_4^+$ [M+H]$^+$ 514.1885, found 514.1880.

Compound 189

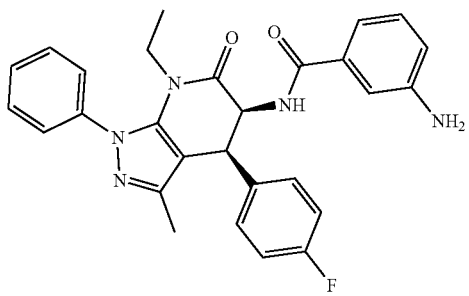

(RG-0013980 (KHS_NB8_074))

¹H NMR (400 MHz, Chloroform-d) δ 7.54-7.41 (m, 5H), 7.19 (t, J=7.8 Hz, 1H), 7.09 (t, J=2.1 Hz, 1H), 7.06-7.02 (m, 1H), 6.99-6.86 (m, 5H), 6.81 (dd, J=8.0, 2.4 Hz, 1H), 5.18 (dd, J=7.2, 5.7 Hz, 1H), 4.75 (d, J=7.2 Hz, 1H), 3.96 (dq, J=14.3, 7.2 Hz, 1H), 3.78 (s, 2H), 3.16 (dq, J=13.9, 6.9 Hz, 1H), 2.14 (s, 3H), 0.98 (t, J=7.1 Hz, 3H). HRMS (ESI+) m/z calcd for $C_{28}H_{27}FN_5O_2^+$ [M+H]$^+$ 484.2143, found 484.2137.

Compound 190

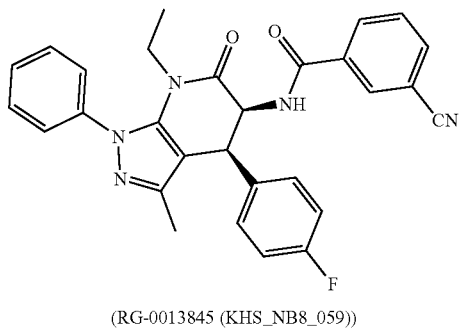

(RG-0013845 (KHS_NB8_059))

$^1$H NMR (400 MHz, Chloroform-d) δ 8.08-8.03 (m, 1H), 7.93-7.87 (m, 1H), 7.83-7.77 (m, 1H), 7.60-7.41 (m, 6H), 7.06-7.00 (m, 1H), 6.97-6.85 (m, 4H), 5.17 (dd, J=7.4, 5.4 Hz, 1H), 4.76 (d, J=7.4 Hz, 1H), 4.02-3.87 (m, 1H), 3.34-3.09 (m, 1H), 2.14 (s, 3H), 1.00 (t, J=7.1 Hz, 3H). HRMS (ESI+) m/z calcd for $C_{29}H_{25}FN_5O_2^+$ [M+H]$^+$ 494.1987, found 494.1987.

Compound 191

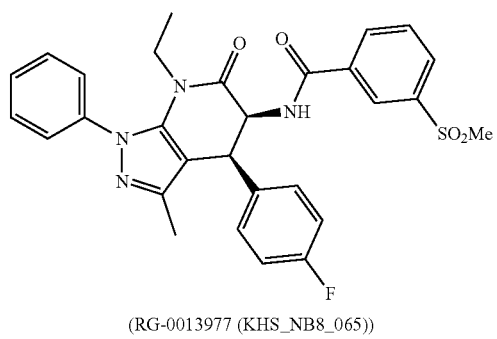

(RG-0013977 (KHS_NB8_065))

$^1$H NMR (400 MHz, Chloroform-d) δ 8.30 (s, 1H), 8.08 (d, J=7.9 Hz, 1H), 7.94 (d, J=7.7 Hz, 1H), 7.67-7.60 (m, 1H), 7.55-7.38 (m, 5H), 7.06-7.01 (m, 1H), 6.98-6.85 (m, 4H), 5.23-5.13 (m, 1H), 4.74 (d, J=7.5 Hz, 1H), 4.04-3.87 (m, 1H), 3.23-3.11 (m, 1H), 3.06 (s, 3H), 2.12 (s, 3H), 0.98 (t, J=7.1 Hz, 3H). HRMS (ESI+) m/z calcd for $C_{29}H_{28}FN_4O_4S^+$ [M+H]$^+$ 547.1810, found 547.1802.

Compound 192

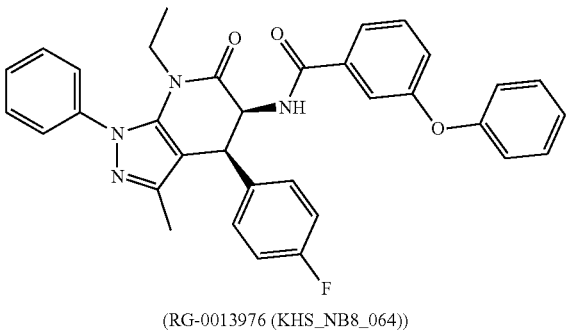

(RG-0013976 (KHS_NB8_064))

$^1$H NMR (400 MHz, Chloroform-d) δ 7.53-7.30 (m, 10H), 7.17-7.08 (m, 2H), 7.05-6.95 (m, 2H), 6.95-6.80 (m, 5H), 5.22-5.08 (m, 1H), 4.72 (d, J=7.4 Hz, 1H), 4.04-3.88 (m, 1H), 3.23-3.03 (m, 1H), 2.12 (s, 3H), 0.96 (t, J=7.0 Hz, 3H). HRMS (ESI+) m/z calcd for $C_{34}H_{30}FN_4O_3^+$ [M+H]$^+$ 561.2296, found 561.2286.

Compound 193

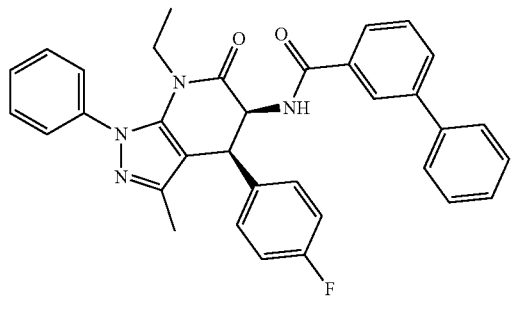

(RG-0013978 (KHS_NB8_068))

$^1$H NMR (400 MHz, Chloroform-d) δ 7.96 (s, 1H), 7.74 (d, J=7.8 Hz, 1H), 7.67 (d, J=7.9 Hz, 1H), 7.58 (d, J=8.1 Hz, 2H), 7.47 (d, J=18.3 Hz, 8H), 7.40-7.32 (m, 1H), 7.04 (d, J=5.6 Hz, 1H), 7.00-6.88 (m, 4H), 5.30-5.17 (m, 1H), 4.79 (d, J=7.0 Hz, 1H), 4.01-3.91 (m, 1H), 3.22-3.11 (m, 1H), 2.14 (s, 3H), 0.99 (t, J=6.9 Hz, 3H). HRMS (ESI+) m/z calcd for $C_{34}H_{30}FN_4O_2^+$ [M+H]$^+$ 545.2347, found 545.2339.

Compound 194

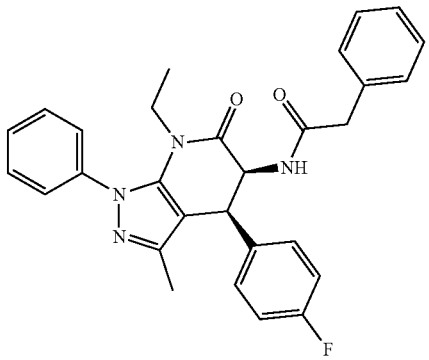

(RG-0013848 (KHS_NB8_062))

¹H NMR (400 MHz, Chloroform-d) δ 7.53-7.38 (m, 5H), 7.37-7.25 (m, 3H), 7.23-7.18 (m, 2H), 6.83-6.74 (m, 2H), 6.75-6.66 (m, 2H), 6.28-6.20 (m, 1H), 5.04-4.96 (m, 1H), 4.51 (d, J=7.2 Hz, 1H), 3.94-3.83 (m, 1H), 3.64-3.52 (m, 2H), 3.15-3.03 (m, 1H), 0.91 (t, J=7.2 Hz, 3H). HRMS (ESI+) m/z calcd for $C_{29}H_{28}FN_4O_2^+$ [M+H]⁺ 483.2191, found 483.2194.

Compound 195

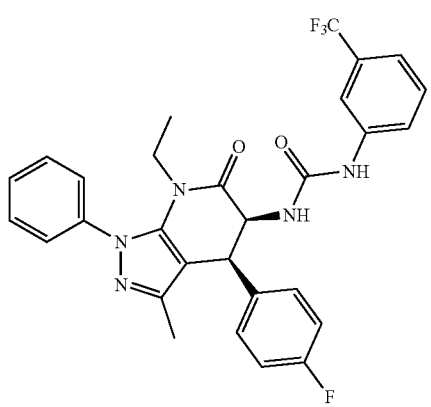

(RG-0014061 (KHS_NB9_077))

¹H NMR (400 MHz, Chloroform-d) δ 8.49 (d, J=7.3 Hz, 1H), 8.41 (d, J=7.8 Hz, 1H), 8.13-8.02 (m, 1H), 7.89-7.77 (m, 1H), 7.55-7.39 (m, 5H), 7.01-6.87 (m, 4H), 5.30 (t, J=7.2 Hz, 1H), 4.61 (d, J=7.1 Hz, 1H), 3.99 (dq, J=14.4, 7.2 Hz, 1H), 3.16 (dq, J=14.0, 6.9 Hz, 1H), 2.15 (s, 3H), 0.98 (t, J=7.1 Hz, 3H). HRMS (ESI+) m/z calcd for $C_{28}H_{24}F_4N_5O_2^+$ [M+H]⁺ 538.1861, found 538.1852.

Compound 196

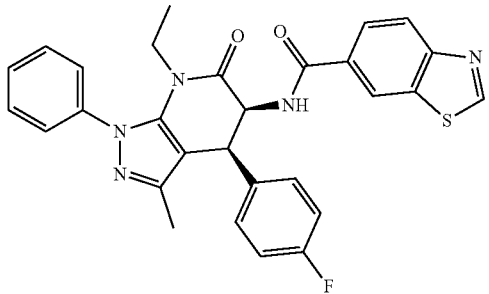

(RG-0014158 (KHS_NB10_039))

¹H NMR (400 MHz, Chloroform-d) δ 9.12 (s, 1H), 8.44 (s, 1H), 8.17 (d, J=8.5 Hz, 1H), 7.96-7.75 (m, 1H), 7.61-7.36 (m, 5H), 7.11 (d, J=5.6 Hz, 1H), 7.04-6.78 (m, 4H), 5.32-5.15 (m, 1H), 4.80 (d, J=7.5 Hz, 1H), 3.98 (dq, J=14.3, 7.1 Hz, 1H), 3.19 (dq, J=13.9, 6.9 Hz, 1H), 2.16 (s, 3H), 1.00 (t, J=7.1 Hz, 3H). HRMS (ESI+) m/z calcd for $C_{29}H_{25}FN_5O_2S^+$ [M+H]⁺ 526.1708, found 526.1711.

Compound 197

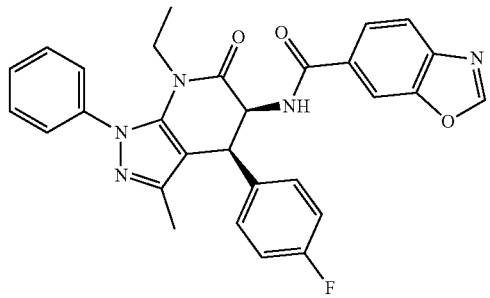

(RG-0014156 (KHS_NB10_030))

¹H NMR (400 MHz, Chloroform-d) δ 8.20 (s, 1H), 8.08-8.02 (m, 1H), 7.83 (d, J=8.3 Hz, 1H), 7.76-7.70 (m, 1H), 7.58-7.37 (m, 5H), 7.07 (d, J=5.5 Hz, 1H), 7.00-6.85 (m, 4H), 5.23 (dd, J=7.3, 5.6 Hz, 1H), 4.79 (d, J=7.2 Hz, 1H), 3.98 (dq, J=14.4, 7.3 Hz, 1H), 3.19 (dq, J=14.0, 6.9 Hz, 1H), 2.15 (s, 3H), 1.00 (t, J=7.1 Hz, 3H). HRMS (ESI+) m/z calcd for $C_{29}H_{25}FN_5O_3^+$ [M+H]⁺ 510.1936, found 510.1941.

Compound 198

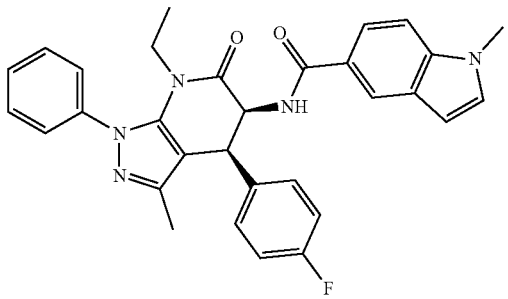

(RG-0014151 (KHS_NB10_020))

¹H NMR (400 MHz, Chloroform-d) δ 8.08 (s, 1H), 7.70-7.65 (m, 1H), 7.54-7.48 (m, 5H), 7.47-7.42 (m, 1H), 7.36-7.31 (m, 1H), 7.11 (d, J=3.2 Hz, 1H), 7.08-7.03 (m, 1H), 7.00-6.94 (m, 2H), 6.93-6.85 (m, 2H), 6.57-6.54 (m, 1H), 5.27 (dd, J=7.2, 5.6 Hz, 1H), 4.81 (d, J=7.2 Hz, 1H), 3.98 (dq, J=14.3, 7.2 Hz, 1H), 3.82 (s, 3H), 3.17 (dq, J=13.8, 6.8 Hz, 1H), 2.15 (s, 3H), 0.99 (t, J=7.1 Hz, 3H). HRMS (ESI+) m/z calcd for $C_{31}H_{29}FN_5O_2^+$ [M+H]⁺ 522.2300, found 522.2311.

Compound 199

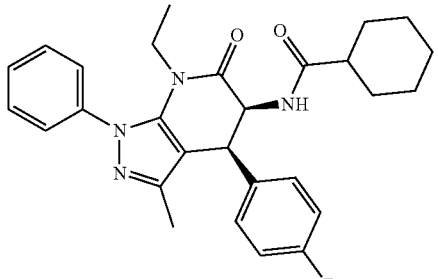

(RG-0013986 (KHS_NB8_092))

¹H NMR (400 MHz, Chloroform-d) δ 7.54-7.37 (m, 5H), 7.01-6.83 (m, 4H), 6.30 (d, J=5.7 Hz, 1H), 4.99 (dd, J=7.3, 5.7 Hz, 1H), 4.62 (d, J=7.4 Hz, 1H), 3.92 (dq, J=14.3, 7.2 Hz, 1H), 3.14 (dq, J=14.0, 6.9 Hz, 1H), 2.18-2.11 (m, 1H), 2.10 (s, 3H) 1.89-1.74 (m, 4H), 1.69-1.60 (m, 1H), 1.48-1.36 (m, 2H), 1.31-1.17 (m, 3H), 0.96 (t, J=7.1 Hz, 3H). HRMS (ESI+) m/z calcd for $C_{28}H_{32}FN_4O_2^+$ [M+H]⁺ 475.2504, found 475.2508.

Compound 200

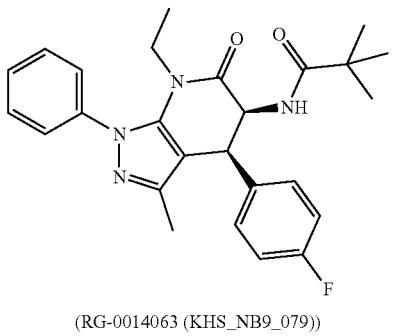

(RG-0014063 (KHS_NB9_079))

¹H NMR (400 MHz, Chloroform-d) δ 7.52-7.40 (m, 5H), 6.96-6.86 (m, 4H), 6.52 (d, J=5.5 Hz, 1H), 5.02-4.83 (m, 2H), 4.65 (d, J=7.3 Hz, 1H), 3.92 (dq, J=14.2, 7.1 Hz, 2H), 3.15 (dq, J=14.0, 7.0 Hz, 2H), 2.11 (s, 3H), 1.18 (s, 9H), 0.97 (d, J=7.1 Hz, 3H). HRMS (ESI+) m/z calcd for $C_{26}H_{30}FN_4O_2^+$ [M+H]⁺ 449.2347, found 449.2334.

Compound 201

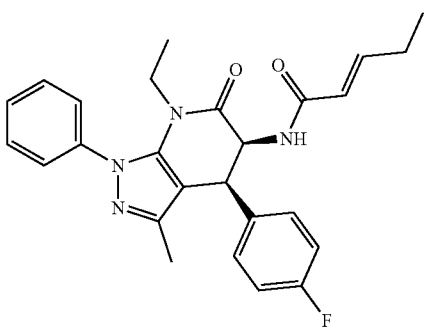

(RG-0014157 (KHS_NB10_038))

¹H NMR (400 MHz, Chloroform-d) δ 7.56-7.37 (m, 5H), 7.01-6.82 (m, 5H), 6.28 (d, J=5.9 Hz, 1H), 5.81 (d, J=15.4 Hz, 1H), 5.13-5.04 (m, 1H), 4.64 (d, J=7.3 Hz, 1H), 3.94 (dq, J=14.3, 7.2 Hz, 1H), 3.14 (dq, J=14.1, 7.0 Hz, 1H), 2.22 (qd, J=7.9, 7.4, 4.1 Hz, 2H), 2.11 (s, 3H), 1.07 (t, J=7.3 Hz, 3H), 0.96 (t, J=7.1 Hz, 3H). HRMS (ESI+) m/z calcd for $C_{26}H_{28}FN_4O_2^+$ [M+H]⁺ 447.2191, found 447.2188.

Compound 202

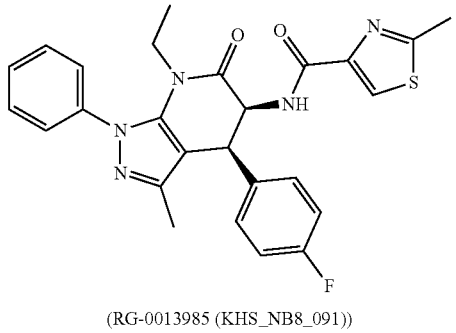

(RG-0013985 (KHS_NB8_091))

¹H NMR (400 MHz, Chloroform-d) δ 8.03 (d, J=6.6 Hz, 1H), 7.99 (s, 1H), 7.54-7.37 (m, 5H), 7.01-6.82 (m, 4H), 5.30-5.16 (m, 1H), 4.68 (d, J=7.2 Hz, 1H), 3.97 (dq, J=14.4, 7.3 Hz, 1H), 3.15 (dq, J=13.9, 6.9 Hz, 1H), 2.66 (s, 3H), 2.14 (s, 3H), 0.97 (t, J=7.1 Hz, 3H). HRMS (ESI+) m/z calcd for $C_{26}H_{25}FN_5O_2S^+$ [M+H]⁺ 490.1708, found 490.1705.

Compound 203

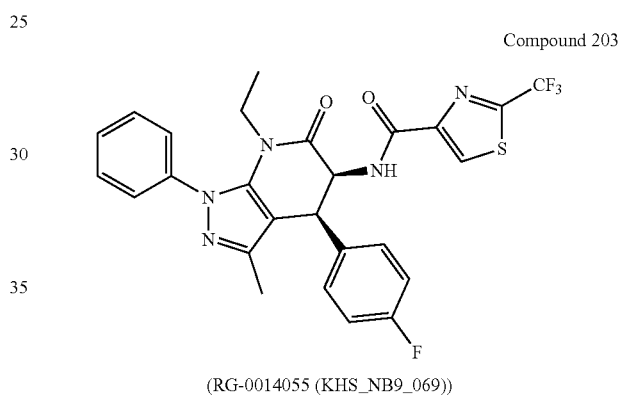

(RG-0014055 (KHS_NB9_069))

¹H NMR (400 MHz, Chloroform-d) δ 8.39 (s, 1H), 7.96 (d, J=6.6 Hz, 1H), 7.58-7.39 (m, 5H), 7.02-6.79 (m, 4H), 5.24 (t, J=6.9 Hz, 1H), 4.67 (d, J=7.2 Hz, 1H), 3.98 (dq, J=14.4, 7.2 Hz, 1H), 3.16 (dq, J=14.0, 6.9 Hz, 1H), 2.14 (s, 3H), 0.98 (t, J=7.1 Hz, 3H). HRMS (ESI+) m/z calcd for $C_{26}H_{22}F_4N_5O_2S^+$ [M+H]⁺ 544.1425, found 544.1421.

Compound 204

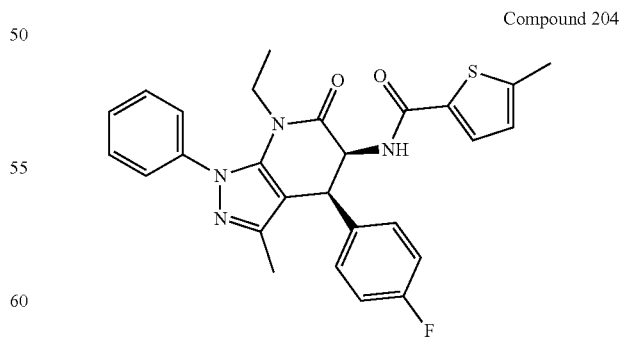

(RG-0014062 (KHS_NB9_078))

¹H NMR (400 MHz, Chloroform-d) δ 7.59-7.39 (m, 5H), 7.28 (d, J=3.7 Hz, 1H), 6.99-6.83 (m, 4H), 6.77-6.66 (m, 2H), 5.17 (dd, J=7.2, 5.8 Hz, 1H), 4.70 (d, J=7.2 Hz, 1H), 3.95 (dq, J=14.3, 7.2 Hz, 1H), 3.15 (dq, J=14.0, 6.9 Hz, 1H), 2.51 (s, 3H), 2.13 (s, 3H), 0.97 (t, J=7.1 Hz, 3H). HRMS (ESI+) m/z calcd for $C_{27}H_{26}FN_4O_2S^+$ [M+H]$^+$ 489.1755, found 489.1733.

Compound 205

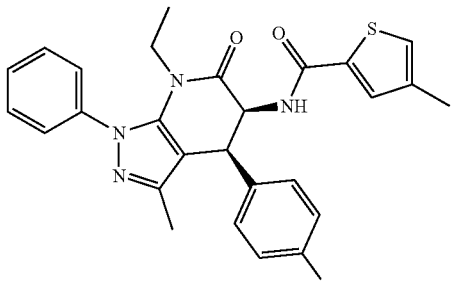

(RG-0014044 (KHS_NB8_079))

$^1$H NMR (400 MHz, Chloroform-d) δ 7.57-7.40 (m, 5H), 7.27 (s, 1H), 7.09 (s, 1H), 7.00-6.88 (m, 4H), 6.78 (d, J=5.7 Hz, 1H), 5.24-5.09 (m, 1H), 4.71 (d, J=7.2 Hz, 1H), 3.95 (dq, J=14.3, 7.1 Hz, 1H), 3.16 (dq, J=13.8, 6.9 Hz, 1H), 2.26 (s, 3H), 2.13 (s, 3H), 0.98 (t, J=7.1 Hz, 3H). HRMS (ESI+) m/z calcd for $C_{27}H_{26}FN_4O_2S^+$ [M+H]$^+$ 489.1755, found 489.1752.

Compound 206

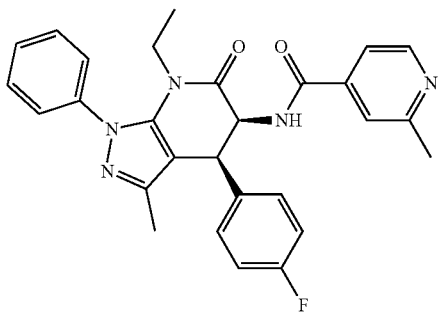

(RG-0014167 (KHS_NB10_035))

$^1$H NMR (400 MHz, Chloroform-d) δ 8.61 (d, J=5.1 Hz, 1H), 7.54-7.42 (m, 6H), 7.37-7.31 (m, 1H), 7.06 (d, J=5.7 Hz, 1H), 6.93 (d, J=6.9 Hz, 4H), 5.17 (dd, J=7.3, 5.6 Hz, 1H), 4.76 (d, J=7.3 Hz, 1H), 3.96 (dq, J=14.4, 7.2 Hz, 1H), 3.19 (dq, J=13.9, 6.9 Hz, 1H), 2.62 (s, 3H), 2.15 (s, 3H), 1.00 (t, J=7.1 Hz, 3H). HRMS (ESI+) m/z calcd for $C_{28}H_{27}FN_5O_2^+$ [M+H]$^+$ 484.2143, found 484.2163.

Compound 207

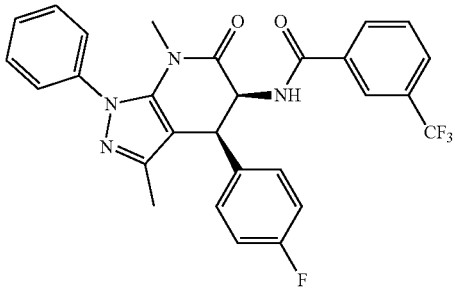

(RG-0008885 (KHS_NB6_022-1))

$^1$H NMR (400 MHz, Chloroform-d) δ 8.00 (s, 1H), 7.86-7.72 (m, 2H), 7.66-7.47 (m, 5H), 7.45-7.39 (m, 1H), 7.01-6.83 (m, 5H), 5.29-5.14 (m, 1H), 4.75 (d, J=7.4 Hz, 1H), 3.04 (s, 3H), 2.16 (s, 3H). HRMS (ESI+) m/z calcd for $C_{28}H_{23}F_4N_4O_2^+$ [M+H]$^+$ 523.1752, found 523.1754.

Compound 208

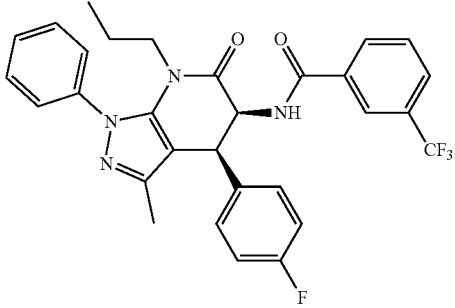

(RG-0013048 (KHS_NB6_077))

$^1$H NMR (400 MHz, Chloroform-d) δ 8.02 (s, 1H), 7.86 (d, J=7.7 Hz, 1H), 7.78 (d, J=7.6 Hz, 1H), 7.60-7.43 (m, 6H), 7.02 (d, J=5.6 Hz, 1H), 6.96-6.86 (m, 4H), 5.20 (dd, J=7.3, 5.5 Hz, 1H), 4.77 (d, J=7.3 Hz, 1H), 3.91-3.73 (m, 1H), 3.02-2.91 (m, 1H), 2.14 (s, 3H), 1.50-1.33 (m, 2H), 0.57 (t, J=7.3 Hz, 3H). HRMS (ESI+) m/z calcd for $C_{30}H_{27}F_4N_4O_2^+$ [M+H]$^+$ 551.2065, found 551.2054.

Compound 209

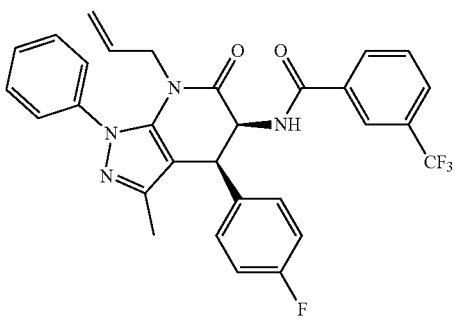

(RG-0014007 (KHS_NB9_029))

$^1$H NMR (400 MHz, Chloroform-d) δ 8.03 (s, 1H), 7.87 (d, J=7.9 Hz, 1H), 7.78 (d, J=7.9 Hz, 1H), 7.65-7.40 (m, 6H), 7.01 (d, J=5.7 Hz, 1H), 6.99-6.86 (m, 4H), 5.69-5.52 (m, 1H), 5.24 (dd, J=7.2, 5.7 Hz, 1H), 5.13 (d, J=10.1 Hz, 1H), 4.88 (d, J=17.1 Hz, 1H), 4.76 (d, J=7.3 Hz, 1H), 4.64-4.54 (m, 1H), 3.71 (dd, J=15.1, 7.7 Hz, 1H), 2.15 (s, 3H). HRMS (ESI+) m/z calcd for $C_{30}H_{25}F_4N_4O_2^+$ [M+H]$^+$ 549.1908, found 549.1918.

Compound 210

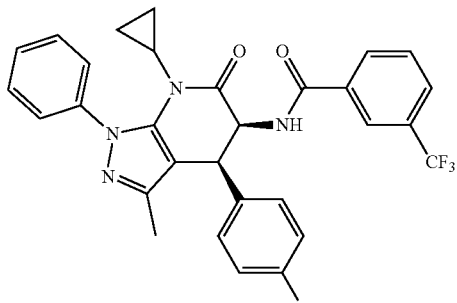

(RG-0013054 (KHS_NB6_091))

$^1$H NMR (400 MHz, Chloroform-d) δ 8.03 (s, 1H), 7.86 (d, J=7.8 Hz, 1H), 7.78 (d, J=7.9 Hz, 1H), 7.61-7.42 (m, 6H), 7.01 (d, J=5.5 Hz, 1H), 6.97-6.84 (m, 4H), 5.68-5.55 (m, 1H), 5.28-5.20 (m, 1H), 5.14 (d, J=10.1 Hz, 1H), 4.92-4.83 (m, 1H), 4.76 (d, J=7.2 Hz, 1H), 4.59 (dd, J=15.4, 5.4 Hz, 1H), 3.73-3.66 (m, 1H), 2.14 (s, 3H). HRMS (ESI+) m/z calcd for $C_{30}H_{25}F_4N_4O_2^+$ [M+H]$^+$ 549.1908, found 549.1924.

Compound 211

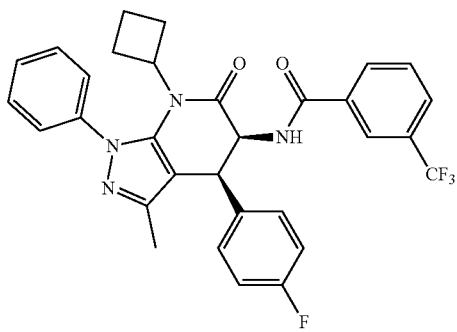

(RG-0013050 (KHS_NB6_079))

$^1$H NMR (400 MHz, Chloroform-d) δ 8.04 (s, 1H), 7.87 (d, J=7.7 Hz, 1H), 7.78 (d, J=7.8 Hz, 1H), 7.62-7.38 (m, 6H), 7.18-7.06 (m, 2H), 7.03 (d, J=5.7 Hz, 1H), 6.98-6.85 (m, 2H), 5.21 (dd, J=7.2, 5.5 Hz, 1H), 4.78 (d, J=7.2 Hz, 1H), 3.98-3.85 (m, 1H), 3.02-2.82 (m, 1H), 2.16 (s, 3H), 0.99-0.84 (m, 1H), 0.54-0.33 (m, 2H), 0.24-0.03 (m, 2H). HRMS (ESI+) m/z calcd for $C_{31}H_{27}F_4N_4O_2^+$ [M+H]$^+$ 563.2065, found 563.2064.

Compound 212

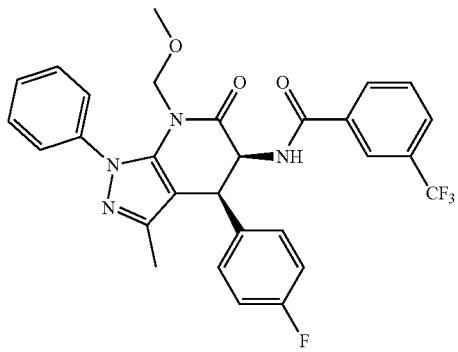

(RG-0013049 (KHS_NB6_078))

$^1$H NMR (400 MHz, Chloroform-d) δ 8.01 (s, 1H), 7.86-7.81 (m, 1H), 7.80-7.75 (m, 1H), 7.59-7.47 (m, 6H), 7.09-7.04 (m, 2H), 6.95-6.90 (m, 3H), 5.31-5.14 (m, 2H), 4.76 (dd, J=7.2, 4.4 Hz, 1H), 4.39 (d, J=7.5 Hz, 1H), 3.13 (s, 3H), 2.15 (s, 3H). HRMS (ESI+) m/z calcd for $C_{29}H_{25}F_4N_4O_3^+$ [M+H]$^+$ 553.1857, found 553.1851.

Compound 213

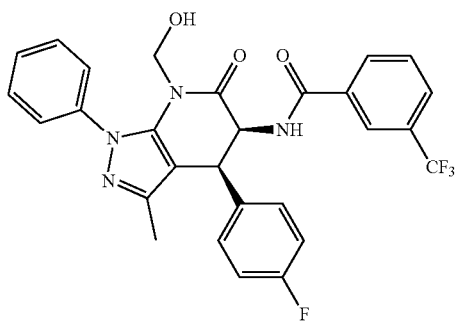

(RG-0013981 (KHS_NB8_077))

$^1$H NMR (400 MHz, Chloroform-d) δ 7.90 (s, 1H), 7.72 (d, J=7.2 Hz, 1H), 7.65 (s, 1H), 7.57-7.45 (m, 6H), 7.41-7.34 (m, 1H), 7.09-7.01 (m, 2H), 6.92-6.81 (m, 2H), 5.14 (s, 1H), 4.39-4.28 (m, 2H), 4.11-4.02 (m, 1H), 2.14 (s, 3H). HRMS (ESI+) m/z calcd for $C_{28}H_{23}F_4N_4O_3^+$ [M+H]$^+$ 539.1701, found 539.1699.

Compound 214

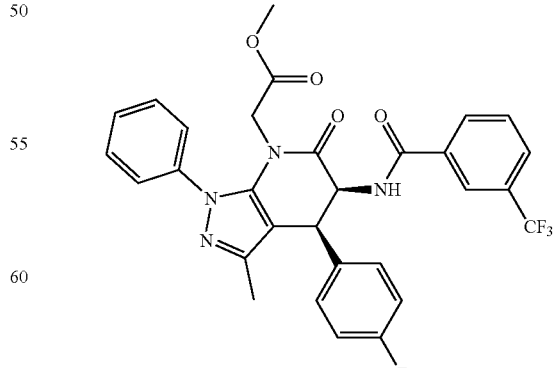

(RG-0013841 (KHS_NB8_043))

¹H NMR (400 MHz, Chloroform-d) δ 7.97 (s, 1H), 7.81 (d, J=7.8 Hz, 1H), 7.76 (d, J=7.8 Hz, 1H), 7.57-7.40 (m, 6H), 7.21-7.12 (m, 2H), 6.95 (t, J=8.6 Hz, 2H), 6.85 (d, J=5.7 Hz, 1H), 5.35 (t, J=6.8 Hz, 1H), 4.79 (d, J=7.7 Hz, 1H), 4.45 (d, J=17.7 Hz, 1H), 4.00 (d, J=17.7 Hz, 1H), 3.61 (s, 3H), 2.13 (s, 3H). HRMS (ESI+) m/z calcd for $C_{30}H_{25}F_4N_4O_4^+$ [M+H]⁺ 581.1806, found 581.1796.

Compound 215

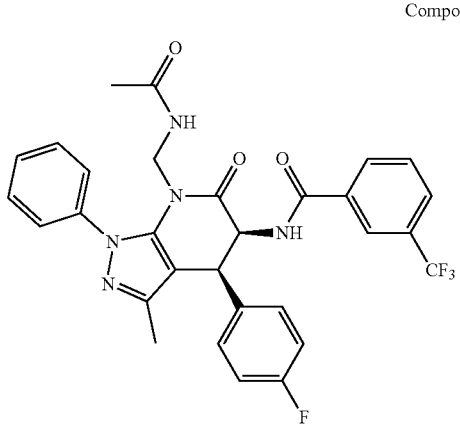

(RG-0013840 (KHS_NB8_041))

¹H NMR (400 MHz, Chloroform-d) δ 8.03 (s, 1H), 7.91 (d, J=7.8 Hz, 1H), 7.80 (d, J=7.8 Hz, 1H), 7.63-7.40 (m, 6H), 6.96-6.84 (m, 4H), 6.46-6.35 (m, 1H), 5.30-5.19 (m, 1H), 5.05-4.96 (m, 1H), 4.73 (d, J=7.1 Hz, 1H), 4.60 (d, J=13.7 Hz, 1H), 2.14 (s, 3H), 1.90 (s, 3H). HRMS (ESI+) m/z calcd for $C_{30}H_{26}F_4N_5O_3^+$ [M+H]⁺ 580.1966, found 580.1966.

Compound 216

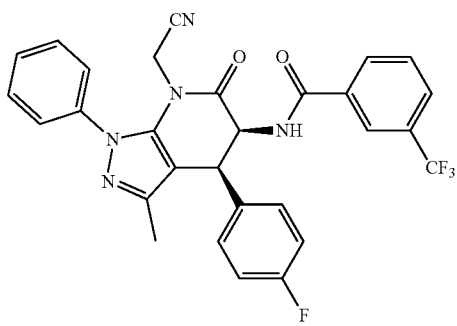

(RG-0013809 (KHS_NB8_032))

¹H NMR (400 MHz, Chloroform-d) δ 8.03 (s, 1H), 7.82 (dd, J=16.7, 7.8 Hz, 2H), 7.55 (m, J=14.5, 7.7 Hz, 6H), 7.02-6.89 (m, 4H), 6.81 (d, J=6.2 Hz, 1H), 5.38 (t, J=6.5 Hz, 1H), 4.84-4.73 (m, 2H), 3.93 (d, J=17.4 Hz, 1H), 2.17 (s, 3H). HRMS (ESI+) m/z calcd for $C_{29}H_{22}F_4N_5O_2^+$ [M+H]⁺ 548.1704, found 548.1698.

Compound 217

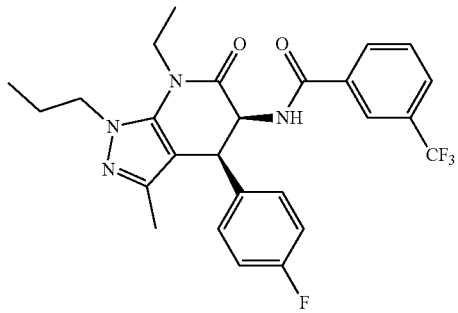

(RG-0013807 (KHS_NB7_046))

¹H NMR (400 MHz, Chloroform-d) δ 8.01 (s, 1H), 7.85 (d, J=8.0 Hz, 1H), 7.77 (d, J=8.0 Hz, 1H), 7.56 (t, J=8.3 Hz, 1H), 7.06-6.95 (m, 1H), 6.98-6.76 (m, 4H), 5.08-4.97 (m, 1H), 4.64 (d, J=7.3 Hz, 1H), 4.29-4.13 (m, 2H), 4.13-4.01 (m, 1H), 3.86-3.74 (m, 1H), 2.07 (s, 3H), 1.95-1.75 (m, 2H), 1.35 (t, J=7.1 Hz, 3H), 0.95 (t, J=7.3 Hz, 3H). HRMS (ESI+) m/z calcd for $C_{26}H_{27}F_4N_4O_2^+$ [M+H]⁺ 503.2065, found 503.2067.

Compound 218

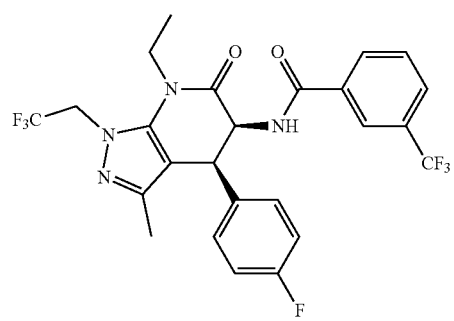

(RG-0009514 (KHS_NB6_063))

¹H NMR (400 MHz, Chloroform-d) δ 8.00 (s, 1H), 7.87-7.74 (m, 2H), 7.59-7.52 (m, 1H), 7.02-6.95 (m, 1H), 6.95-6.82 (m, 4H), 5.09-4.99 (m, 1H), 4.91-4.80 (m, 1H), 4.68 (d, J=7.0 Hz, 1H), 4.68-4.59 (m, 1H), 4.32-4.20 (m, 1H), 3.85-3.73 (m, 1H), 2.09 (s, 3H), 1.35 (t, J=7.5 Hz, 3H). HRMS (ESI+) m/z calcd for $C_{25}H_{22}F_7N_4O_2^+$ [M+H]⁺ 543.1625, found 543.1625.

Compound 219

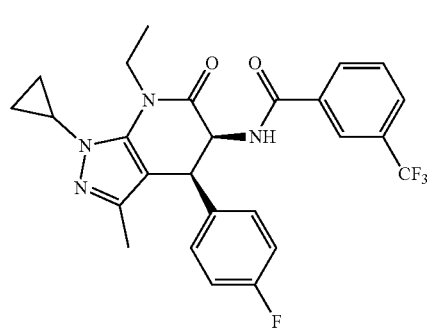

(RG-0013847 (KHS_NB8_061))

¹H NMR (400 MHz, Chloroform-d) δ 8.01 (s, 1H), 7.87-7.71 (m, 2H), 7.62-7.49 (m, 1H), 6.99 (m, 1H), 6.95-

6.78 (m, 4H), 5.05-4.89 (m, 1H), 4.62 (d, J=7.3 Hz, 1H), 4.47-4.34 (m, 1H), 4.30-4.14 (m, 1H), 3.54-3.39 (m, 1H), 2.04 (s, 3H), 1.38-1.30 (m, 2H), 1.29-1.15 (m, 1H), 1.11-1.02 (m, 1H). HRMS (ESI+) m/z calcd for $C_{26}H_{25}F_4N_4O_2^+$ [M+H]$^+$ 501.1908, found 501.1912.

Compound 220

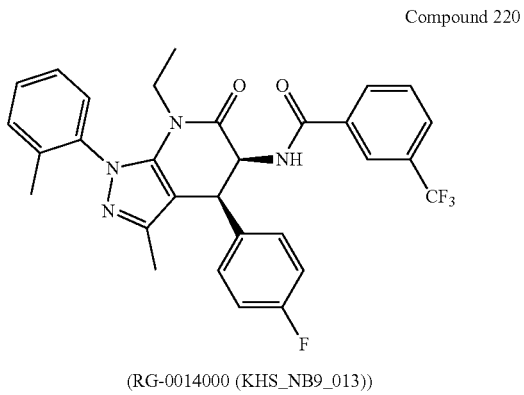 [SMILES: CCN1C(=O)[C@@H](NC(=O)c2cccc(C(F)(F)F)c2)[C@@H](c2ccc(F)cc2)c2c(C)nn(-c3ccccc3C)c21]

(RG-0014000 (KHS_NB9_013))

$^1$H NMR (400 MHz, Chloroform-d) δ 8.01 (s, 1H), 7.85 (d, J=7.8 Hz, 1H), 7.77 (d, J=7.8 Hz, 1H), 7.61-7.53 (m, 2H), 7.44-7.34 (m, 2H), 7.31-7.26 (m, 1H), 7.04-6.97 (m, 1H), 6.97-6.90 (m, 4H), 5.12 (dd, J=7.3, 5.5 Hz, 1H), 4.77 (d, J=7.3 Hz, 1H), 3.88 (dq, J=14.4, 7.2 Hz, 1H), 3.02 (dq, J=14.0, 7.0 Hz, 1H), 2.15 (s, 3H), 2.01 (s, 3H), 0.94 (t, J=7.3 Hz, 3H). HRMS (ESI+) m/z calcd for $C_{30}H_{27}F_4N_4O_2^+$ [M+H]$^+$ 551.2065, found 551.2056.

Compound 221 (RG-0014001 (KHS_NB9_014))

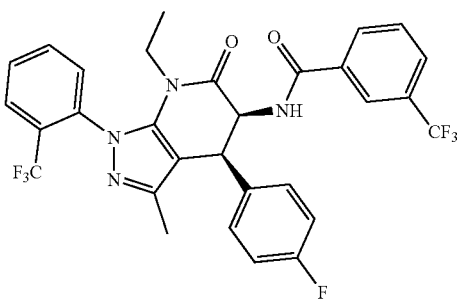

$^1$H NMR (400 MHz, Chloroform-d) δ 7.99 (s, 1H), 7.89-7.74 (m, 4H), 7.74-7.62 (m, 2H), 7.60-7.50 (m, 1H), 7.02 (d, J=5.2 Hz, 1H), 6.99-6.86 (m, 4H), 5.08 (dd, J=7.3, 5.2 Hz, 1H), 4.82 (d, J=7.3 Hz, 1H), 3.92 (dq, J=14.4, 7.2 Hz, 1H), 2.86 (dq, J=14.0, 6.9 Hz, 1H), 2.15 (s, 3H), 0.94 (t, J=6.9 Hz, 3H). HRMS (ESI+) m/z calcd for $C_{30}H_{24}F_7N_4O_2^+$ [M+H]$^+$ 605.1782, found 605.1791.

Compound 222 (RG-0014169 (KHS_NB10_045, KHS_NB11_032))

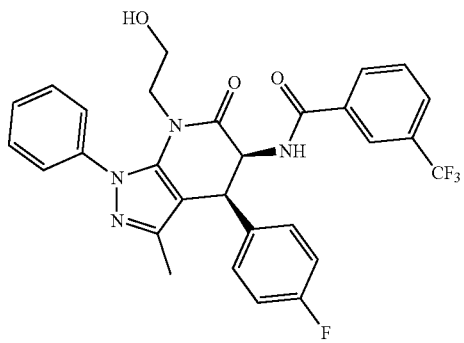

$^1$H NMR (400 MHz, Chloroform-d) δ 8.02 (s, 1H), 7.85 (d, J=7.8 Hz, 1H), 7.78 (d, J=7.7 Hz, 1H), 7.61-7.39 (m, 6H), 7.14-7.04 (m, 2H), 7.01-6.88 (m, 3H), 5.27 (dd, J=7.4, 5.8 Hz, 1H), 4.76 (d, J=7.4 Hz, 1H), 4.12-4.00 (m, 1H), 3.66-3.49 (m, 2H), 3.46-3.35 (m, 1H), 2.15 (s, 3H), 1.77-1.67 (m, 1H). HRMS (ESI+) m/z calcd for $C_{29}H_{25}F_4N_4O_3^+$ [M+H]$^+$ 553.1857, found 553.1874.

Compound 223 (RG-0014152 (KHS_NB10_022))

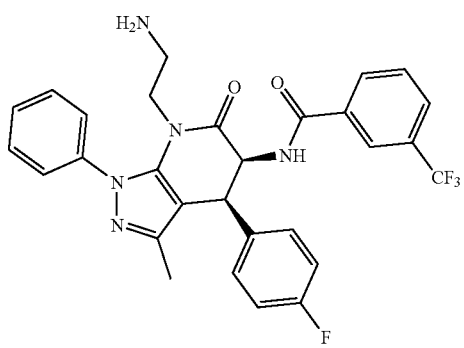

$^1$H NMR (400 MHz, Chloroform-d) δ 8.02 (s, 1H), 7.86 (d, J=7.9 Hz, 1H), 7.78 (d, J=7.9 Hz, 1H), 7.63-7.40 (m, 6H), 7.08-6.87 (m, 5H), 5.24 (dd, J=7.4, 5.6 Hz, 1H), 4.77 (d, J=7.4 Hz, 1H), 3.94-3.82 (m, 1H), 3.29-3.15 (m, 1H), 2.80-2.61 (m, 2H), 2.13 (s, 3H). HRMS (ESI+) m/z calcd for $C_{29}H_{26}F_4N_5O_2^+$ [M+H]$^+$ 552.2017, found 552.2036.

Compound 224 (RG-0014164 (KHS_NB10_032))

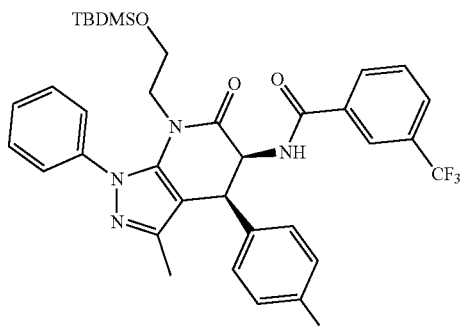

$^1$H NMR (400 MHz, Chloroform-d) δ 8.01 (s, 1H), 7.84 (d, J=7.9 Hz, 1H), 7.78 (d, J=7.9 Hz, 1H), 7.56 (t, J=7.8 Hz, 1H), 7.53-7.38 (m, 5H), 7.12-7.03 (m, 2H), 6.99-6.84 (m, 3H), 5.20 (dd, J=7.4, 5.7 Hz, 1H), 4.74 (d, J=7.4 Hz, 1H), 4.00-3.91 (m, 1H), 3.77-3.68 (m, 1H), 3.56-3.47 (m, 1H), 3.40-3.30 (m, 1H), 2.14 (s, 3H), 0.78 (s, 9H), −0.08 (s, 3H), −0.08 (s, 3H). HRMS (ESI+) m/z calcd for $C_{35}H_{39}F_4N_4O_3Si^+$ [M+H]+ 667.2722, found 667.2730.

Compound 225 (RG-0014162 (KHS_NB10_017))

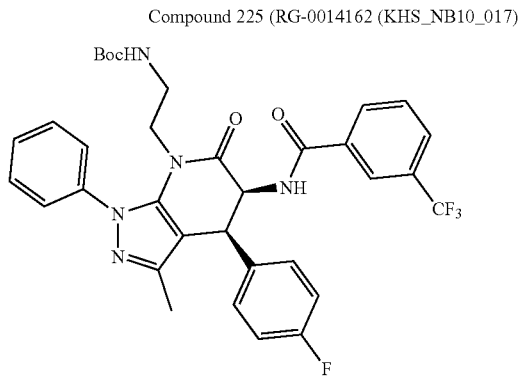

$^1$H NMR (400 MHz, Chloroform-d) δ 8.03 (s, 1H), 7.87 (d, J=7.7 Hz, 1H), 7.79 (d, J=7.8 Hz, 1H), 7.62-7.55 (m, 1H), 7.55-7.44 (m, 5H), 7.00 (d, J=5.6 Hz, 1H), 6.97-6.92 (m, 4H), 5.24 (dd, J=7.3, 5.6 Hz, 1H), 4.77 (d, J=7.3 Hz, 1H), 4.47 (s, 1H), 3.94-3.84 (m, 1H), 3.38-3.29 (m, 1H), 3.18-3.03 (m, 2H), 2.15 (s, 3H), 1.38 (s, 9H). HRMS (ESI+) m/z calcd for $C_{34}H_{34}F_4N_5O_4^+$ [M+H]+ 652.2541, found 652.2534.

Compound 226 (RG-0013987 (KHS_NB8_093))

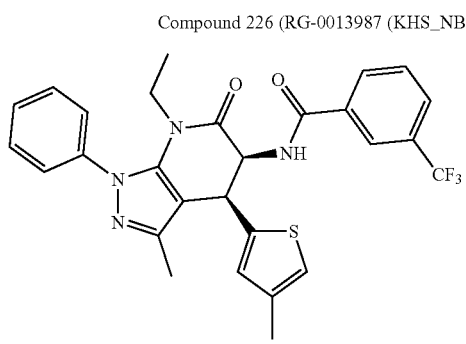

$^1$H NMR (400 MHz, Chloroform-d) δ 8.09 (s, 1H), 8.00 (d, J=7.8 Hz, 1H), 7.79 (d, J=8.0 Hz, 1H), 7.63-7.56 (m, 1H), 7.55-7.41 (m, 5H), 7.22 (d, J=6.0 Hz, 1H), 6.76-6.72 (m, 1H), 6.47 (s, 1H), 5.18 (dd, J=6.7, 5.9 Hz, 1H), 4.93 (d, J=6.8 Hz, 1H), 3.98 (dq, J=14.3, 7.3 Hz, 1H), 3.11 (dq, J=13.9, 6.9 Hz, 1H), 2.23 (s, 3H), 2.12 (s, 3H), 0.94 (t, J=7.1 Hz, 3H). HRMS (ESI+) m/z calcd for $C_{28}H_{26}F_3N_4O_2S^+$ [M+H]+ 539.1723, found 539.1725.

Compound 227 (RG-0014004 (KHS_NB9_025))

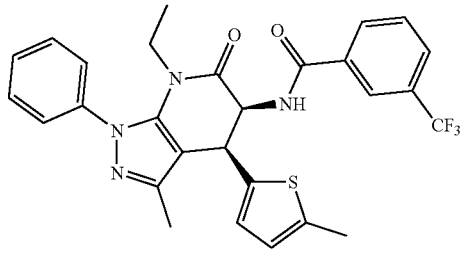

$^1$H NMR (400 MHz, Chloroform-d) δ 8.11 (s, 1H), 8.00 (d, J=7.0 Hz, 1H), 7.79 (d, J=7.5 Hz, 1H), 7.60 (t, J=7.7 Hz, 1H), 7.55-7.39 (m, 5H), 7.24-7.21 (m, 1H), 6.55-6.50 (m, 1H), 6.45 (d, J=3.4 Hz, 1H), 5.17 (dd, J=6.7, 6.0 Hz, 1H), 4.90 (d, J=6.7 Hz, 1H), 3.96 (dq, J=14.3, 7.2 Hz, 1H), 3.13 (dq, J=14.2, 7.1 Hz, 1H), 2.37 (s, 3H), 2.22 (s, 3H), 0.94 (t, J=7.1 Hz, 3H). HRMS (ESI+) m/z calcd for $C_{28}H_{26}F_3N_4O_2S^+$ [M+H]+ 539.1723, found 539.1728.

Compound 228 (RG-0013988 (KHS_NB8_094))

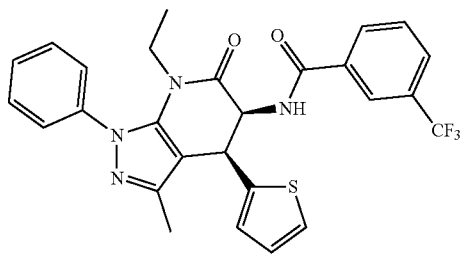

$^1$H NMR (400 MHz, Chloroform-d) δ 8.11 (s, 1H), 7.99 (d, J=7.7 Hz, 1H), 7.79 (d, J=8.0 Hz, 1H), 7.63-7.57 (m, 1H), 7.55-7.41 (m, 5H), 7.25 (s, 1H), 7.20-7.14 (m, 1H), 6.90 (dd, J=5.1, 3.5 Hz, 1H), 6.68 (d, J=3.5 Hz, 1H), 5.19 (dd, J=6.6, 5.8 Hz, 1H), 5.03 (d, J=6.8 Hz, 1H), 3.99 (dq, J=14.4, 7.2 Hz, 1H), 3.11 (dq, J=14.0, 7.0 Hz, 1H), 2.22 (s, 3H), 0.94 (t, J=7.1 Hz, 3H). HRMS (ESI+) m/z calcd for $C_{27}H_{24}F_3N_4O_2S^+$ [M+H]+ 525.1567, found 525.1564.

Compound 229 (RG-0014005 (KHS_NB9_026))

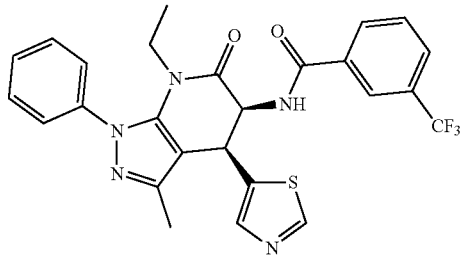

$^1$H NMR (400 MHz, Chloroform-d) δ 8.70 (s, 1H), 8.14 (s, 1H), 8.00 (d, J=7.8 Hz, 1H), 7.81 (d, J=7.5 Hz, 1H), 7.65-7.57 (m, 1H), 7.55-7.42 (m, 6H), 7.37-7.32 (m, 1H), 5.21-5.12 (m, 2H), 3.99 (dq, J=14.4, 7.3 Hz, 1H), 3.10 (dq, J=14.0, 7.0 Hz, 1H), 2.24 (s, 3H), 0.92 (t, J=7.1 Hz, 3H). HRMS (ESI+) m/z calcd for $C_{26}H_{23}F_3N_5O_2S^+$ [M+H]+ 526.1519, found 526.1523.

Compound 230 (RG-0014042 (KHS_NB9_049))

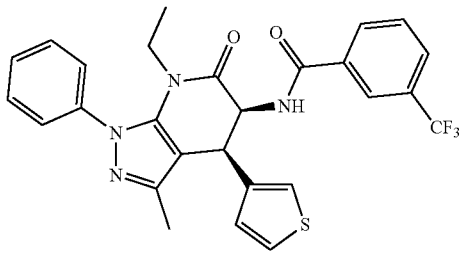

¹H NMR (400 MHz, Chloroform-d) δ 8.06 (s, 1H), 7.93 (d, J=7.9 Hz, 1H), 7.78 (d, J=7.7 Hz, 1H), 7.58 (t, J=7.8 Hz, 1H), 7.54-7.38 (m, 5H), 7.15 (d, J=5.7 Hz, 1H), 6.87-6.82 (m, 1H), 6.74 (dd, J=5.0, 1.4 Hz, 1H), 5.22-5.12 (m, 1H), 4.88 (d, J=7.2 Hz, 1H), 3.99 (dq, J=14.3, 7.2 Hz, 1H), 3.14 (dq, J=14.1, 6.9 Hz, 1H), 2.20 (s, 3H), 0.96 (t, J=7.1 Hz, 3H). HRMS (ESI+) m/z calcd for $C_{27}H_{24}F_3N_4O_2S^+$ [M+H]⁺ 525.1567, found 525.1557.

Compound 231 (RG-0013997 (KHS_NB9_008))

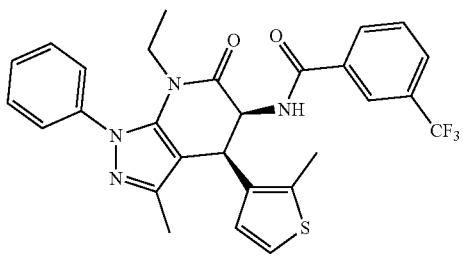

¹H NMR (400 MHz, Chloroform-d) δ 7.95 (s, 1H), 7.81 (d, J=8.7 Hz, 1H), 7.76 (d, J=8.8 Hz, 1H), 7.59-7.51 (m, 1H), 7.51-7.42 (m, 5H), 6.98 (d, J=5.3 Hz, 1H), 6.95 (d, J=6.1 Hz, 1H), 6.42 (d, J=5.2 Hz, 1H), 5.23 (dd, J=7.1, 6.2 Hz, 1H), 4.80 (d, J=7.7 Hz, 1H), 3.94 (dq, J=14.4, 7.1 Hz, 1H), 3.26 (dq, J=14.0, 6.9 Hz, 1H), 2.34 (s, 3H), 2.15 (s, 3H), 1.03 (t, J=7.1 Hz, 3H). HRMS (ESI+) m/z calcd for $C_{28}H_{26}F_3N_4O_2S^+$ [M+H]⁺ 539.1723, found 539.1729.

Compound 232 (RG-0014050 (KHS_NB9_058))

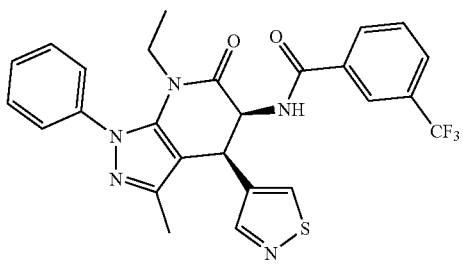

¹H NMR (400 MHz, Chloroform-d) δ 8.16 (d, J=10.0 Hz, 2H), 8.12 (s, 1H), 7.94 (d, J=7.8 Hz, 1H), 7.81 (d, J=7.8 Hz, 1H), 7.60 (t, J=7.8 Hz, 1H), 7.54-7.43 (m, 5H), 7.30 (d, J=4.9 Hz, 1H), 5.15 (dd, J=7.0, 4.8 Hz, 1H), 5.08 (d, J=6.9 Hz, 1H), 4.00 (dq, J=14.4, 7.3 Hz, 1H), 3.14 (dq, J=13.9, 6.9 Hz, 1H), 2.21 (s, 3H), 0.94 (t, J=7.1 Hz, 3H). HRMS (ESI+) m/z calcd for $C_{26}H_{23}F_3N_5O_2S^+$ [M+H]⁺ 526.1519, found 526.1504.

Compound 233 (RG-0014043 (KHS_NB9_050))

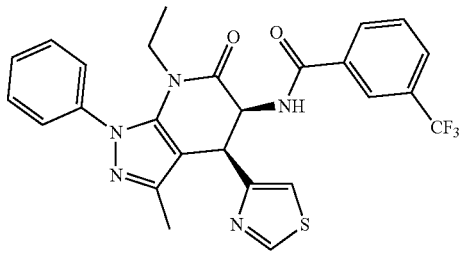

¹H NMR (400 MHz, Chloroform-d) δ 8.75 (s, 1H), 8.03 (s, 1H), 7.93 (d, J=8.1 Hz, 1H), 7.75 (d, J=7.9 Hz, 2H), 7.55 (t, J=7.8 Hz, 1H), 7.52-7.34 (m, 5H), 7.02 (s, 1H), 5.26 (t, J=6.7 Hz, 1H), 4.86 (d, J=6.6 Hz, 1H), 4.15-3.98 (m, 1H), 3.13-2.96 (m, 1H), 2.25 (s, 3H), 0.89 (t, J=7.1 Hz, 3H). HRMS (ESI+) m/z calcd for $C_{26}H_{23}F_3N_5O_2S^+$ [M+H]⁺ 526.1519, found 526.1509.

Compound 234 (RG-0013991 (KHS_NB8_098))

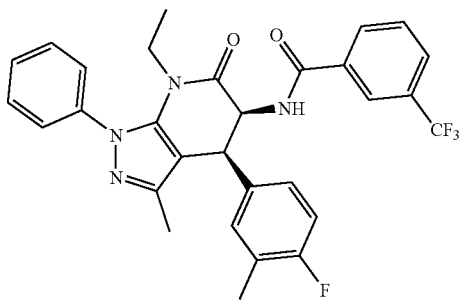

¹H NMR (400 MHz, Chloroform-d) δ 8.00 (s, 1H), 7.87 (d, J=7.8 Hz, 1H), 7.78 (d, J=7.9 Hz, 1H), 7.61-7.54 (m, 1H), 7.54-7.42 (m, 5H), 6.98 (d, J=5.8 Hz, 1H), 6.88-6.83 (m, 1H), 6.80-6.71 (m, 2H), 5.20 (dd, J=7.3, 5.8 Hz, 1H), 4.70 (d, J=7.3 Hz, 1H), 4.00 (dq, J=14.4, 7.2 Hz, 1H), 3.16 (dq, J=14.0, 6.9 Hz, 1H), 2.15 (s, 3H), 2.12 (s, 3H), 1.01 (t, J=7.1 Hz, 3H). HRMS (ESI+) m/z calcd for $C_{30}H_{27}F_4N_4O_2^+$ [M+H]⁺ 551.2065, found 551.2067.

Compound 235 (RG-0013990 (KHS_NB8_097))

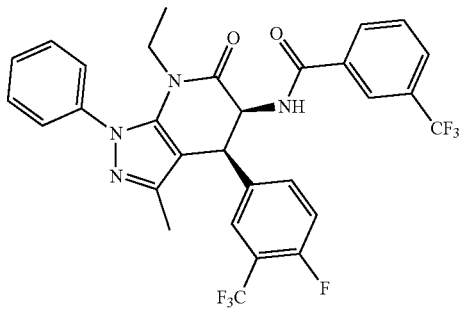

¹H NMR (400 MHz, Chloroform-d) δ 8.04 (s, 1H), 7.88 (d, J=7.8 Hz, 1H), 7.80 (d, J=8.1 Hz, 1H), 7.63-7.55 (m, 1H), 7.55-7.43 (m, 5H), 7.21-7.13 (m, 2H), 7.13-7.02 (m, 2H), 5.22-5.15 (m, 1H), 4.88 (d, J=7.3 Hz, 1H), 4.02 (dq, J=14.3, 7.2 Hz, 1H), 3.14 (dq, J=14.0, 7.0 Hz, 1H), 2.16 (s, 3H), 0.99

(t, J=7.1 Hz, 3H). HRMS (ESI+) m/z calcd for $C_{30}H_{24}F_7N_4O_2^+$ [M+H]$^+$ 605.1782, found 605.1780.

Compound 236

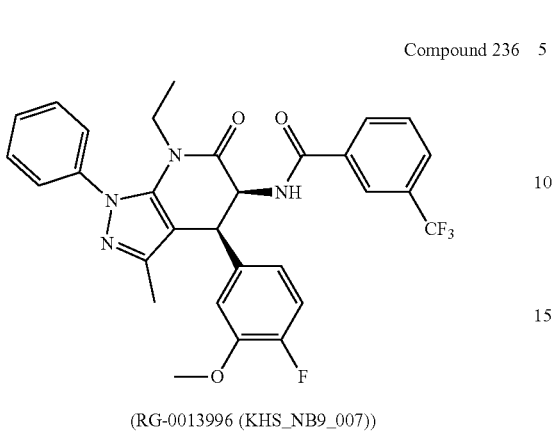

(RG-0013996 (KHS_NB9_007))

$^1$H NMR (400 MHz, Chloroform-d) δ 8.07 (s, 1H), 7.87 (d, J=7.8 Hz, 1H), 7.79 (d, J=7.8 Hz, 1H), 7.61-7.54 (m, 1H), 7.54-7.41 (m, 5H), 7.09 (d, J=5.6 Hz, 1H), 6.97-6.89 (m, 1H), 6.58 (dd, J=8.1, 2.1 Hz, 1H), 6.51-6.41 (m, 1H), 5.25-5.13 (m, 1H), 4.77 (d, J=7.4 Hz, 1H), 3.97 (dq, J=14.4, 7.2 Hz, 1H), 3.60 (s, 3H), 3.19 (dq, J=14.0, 7.0 Hz, 1H), 2.16 (s, 3H), 1.00 (t, J=7.0 Hz, 3H). HRMS (ESI+) m/z calcd for $C_{30}H_{27}F_4N_4O_3^+$ [M+H]$^+$ 567.2014, found 567.2025.

Compound 237

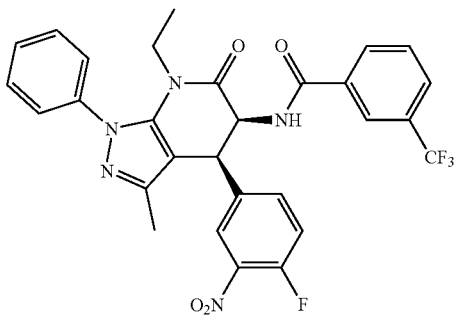

(RG-0013995 (KHS_NB9_006))

$^1$H NMR (400 MHz, Chloroform-d) δ 8.06 (s, 1H), 7.91 (d, J=7.9 Hz, 1H), 7.80 (d, J=7.6 Hz, 1H), 7.66-7.61 (m, 1H), 7.58 (d, J=7.8 Hz, 1H), 7.56-7.44 (m, 5H), 7.29 (dd, J=7.9, 4.2 Hz, 1H), 7.22-7.12 (m, 2H), 5.18 (dd, J=7.3, 4.8 Hz, 1H), 4.94 (d, J=7.3 Hz, 1H), 4.03 (dq, J=14.5, 7.2 Hz, 1H), 3.16 (dq, J=13.9, 6.9 Hz, 1H), 2.17 (s, 3H), 1.03 (t, J=7.1 Hz, 3H). HRMS (ESI+) m/z calcd for $C_{29}H_{24}F_4N_5O_4^+$ [M+H]$^+$ 582.1759, found 582.1773.

Compound 238

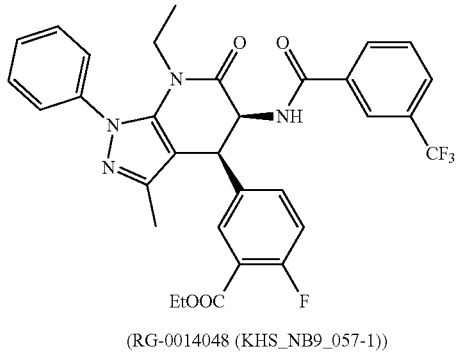

(RG-0014048 (KHS_NB9_057-1))

$^1$H NMR (400 MHz, Chloroform-d) δ 8.05 (s, 1H), 7.88 (d, J=7.7 Hz, 1H), 7.78 (d, J=7.6 Hz, 1H), 7.63-7.40 (m, 7H), 7.17-7.10 (m, 1H), 7.08 (d, J=5.3 Hz, 1H), 7.00 (dd, J=10.3, 8.5 Hz, 1H), 5.20 (dd, J=7.3, 5.3 Hz, 1H), 4.83 (d, J=7.3 Hz, 1H), 4.32-4.20 (m, 2H), 4.01 (dq, J=14.5, 7.2 Hz, 1H), 3.16 (dq, J=14.0, 7.0 Hz, 1H), 2.15 (s, 3H), 1.23 (t, J=7.1 Hz, 3H), 1.03 (t, J=7.1 Hz, 3H). HRMS (ESI+) m/z calcd for $C_{32}H_{29}F_4N_4O_4^+$ [M+H]$^+$ 609.2119, found 609.2120.

Compound 239

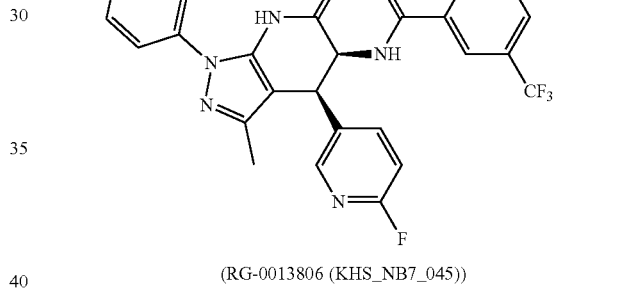

(RG-0013806 (KHS_NB7_045))

$^1$H NMR (400 MHz, Chloroform-d) δ 8.07 (s, 1H), 7.93-7.87 (m, 1H), 7.86-7.83 (m, 1H), 7.82-7.75 (m, 1H), 7.59 (t, J=7.8 Hz, 1H), 7.55-7.41 (m, 5H), 7.41-7.32 (m, 1H), 7.19 (d, J=4.9 Hz, 1H), 6.82 (dd, J=8.5, 3.0 Hz, 1H), 5.19 (dd, J=7.3, 4.9 Hz, 1H), 4.89 (d, J=7.2 Hz, 1H), 4.04-3.92 (m, 1H), 3.23-3.12 (m, 1H), 2.16 (s, 3H), 0.99 (t, J=7.1 Hz, 3H). HRMS (ESI+) m/z calcd for $C_{28}H_{24}F_4N_5O_2^+$ [M+H]$^+$ 538.1861, found 538.1861.

Compound 240

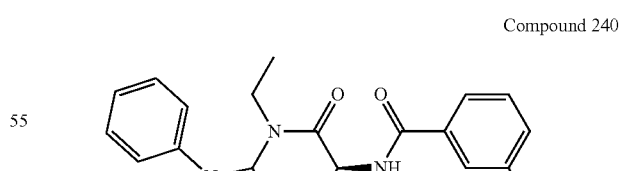

(RG-0014039 (KHS_NB9_043))

¹H NMR (400 MHz, Chloroform-d) δ 8.05 (s, 1H), 7.87 (d, J=8.0 Hz, 1H), 7.79 (d, J=7.9 Hz, 1H), 7.58 (t, J=7.8 Hz, 1H), 7.54-7.41 (m, 5H), 7.40-7.30 (m, 2H), 7.06 (d, J=5.4 Hz, 1H), 6.87-6.78 (m, 2H), 5.21 (dd, J=7.4, 5.4 Hz, 1H), 4.76 (d, J=7.2 Hz, 1H), 4.09-3.87 (m, 1H), 3.26-3.06 (m, 1H), 2.14 (s, 3H), 0.99 (t, J=7.1 Hz, 3H). HRMS (ESI+) m/z calcd for $C_{29}H_{25}BrF_3N_4O_2^+$ [M+H]⁺ 597.1107, found 597.1082.

Compound 241

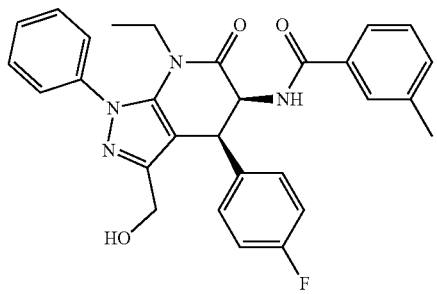

(RG-0008880 (KHS_NB6_041, 005))

¹H NMR (400 MHz, Chloroform-d) δ 7.58-7.45 (m, 7H), 7.35-7.27 (m, 2H), 6.99-6.87 (m, 5H), 5.24 (t, J=6.5 Hz, 1H), 4.90 (d, J=7.3 Hz, 1H), 4.61 (d, J=5.9 Hz, 2H), 3.97 (dq, J=14.3, 7.2 Hz, 1H), 3.16 (dq, J=13.9, 6.8 Hz, 1H), 2.38 (s, 3H), 1.84-1.74 (m, 1H), 0.99 (t, J=7.1 Hz, 3H). HRMS (ESI+) m/z calcd for $C_{29}H_{28}FN_4O_3^+$ [M+H]⁺ 499.2140, found 499.2137.

Compound 242

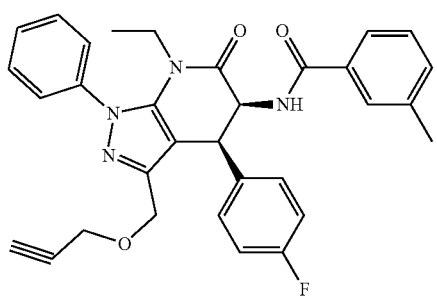

(RG-0013055 (KHS_NB6_094))

¹H NMR (400 MHz, Chloroform-d) δ 7.58-7.43 (m, 7H), 7.35-7.28 (m, 2H), 6.99-6.85 (m, 5H), 5.28-5.20 (m, 1H), 4.91 (d, J=7.5 Hz, 1H), 4.62-4.55 (m, 1H), 4.54-4.47 (m, 1H), 4.05-3.91 (m, 1H), 3.24-3.10 (m, 1H), 2.38 (s, 3H), 2.36-2.32 (m, 1H), 0.99 (t, J=7.1 Hz, 3H). HRMS (ESI+) m/z calcd for $C_{32}H_{30}FN_4O_3^+$ [M+H]⁺ 537.2296, found 537.2293.

Compound 243

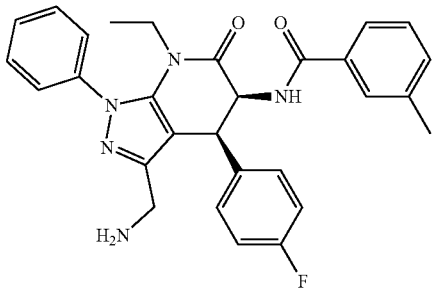

(RG-0009512 (KHS_NB6_054))

¹H NMR (400 MHz, Chloroform-d) δ 7.57-7.43 (m, 7H), 7.35-7.27 (m, 2H), 7.01-6.87 (m, 5H), 5.27-5.18 (m, 1H), 4.88 (d, J=7.0 Hz, 1H), 4.03-3.91 (m, 1H), 3.87-3.73 (m, 2H), 3.24-3.09 (m, 1H), 2.38 (s, 3H), 0.99 (t, J=7.1 Hz, 3H). HRMS (ESI+) m/z calcd for $C_{29}H_{29}FN_5O_2^+$ [M+H]⁺ 498.2300, found 498.2292.

Compound 244

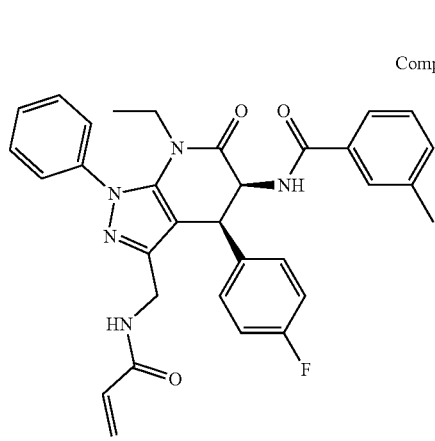

(RG-0013063 (KHS_NB7_013))

¹H NMR (400 MHz, Chloroform-d) δ 7.69-7.42 (m, 7H), 7.39-7.26 (m, 2H), 7.01-6.79 (m, 5H), 6.17-6.02 (m, 1H), 5.93-5.73 (m, 2H), 5.53-5.44 (m, 1H), 5.29-5.21 (m, 1H), 4.77 (d, J=7.4 Hz, 1H), 4.55-4.36 (m, 2H), 4.04-3.86 (m, 1H), 3.20-3.06 (m, 1H), 2.38 (s, 3H), 0.98 (t, J=7.3 Hz, 3H). HRMS (ESI+) m/z calcd for $C_{32}H_{31}FN_5O_3^+$ [M+H]⁺ 552.2405, found 552.2412.

Compound 245

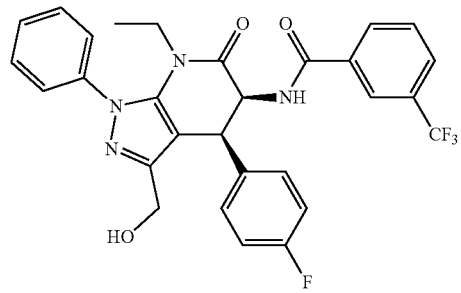

(RG-0013052 (KHS_NB6_085))

¹H NMR (400 MHz, Chloroform-d) δ 8.02 (s, 1H), 7.86 (d, J=7.9 Hz, 1H), 7.77 (s, 1H), 7.60-7.46 (m, 5H), 7.29-7.11 (m, 2H), 7.01-6.89 (m, 4H), 5.24 (dd, J=9.6, 6.0 Hz, 1H), 4.91 (d, J=7.4 Hz, 1H), 4.65-4.58 (m, 2H), 4.02-3.92 (m, 1H), 3.20-3.15 (m, 1H), 1.82-1.73 (m, 1H), 0.99 (t, J=7.3 Hz, 3H). HRMS (ESI+) m/z calcd for $C_{29}H_{25}F_4N_4O_3^+$ [M+H]⁺ 553.1857, found 553.1881.

Compound 246

(RG-0013838 (KHS_NB8_039-up-1))

¹H NMR (400 MHz, Chloroform-d) δ 8.04 (s, 1H), 7.87 (d, J=7.8 Hz, 1H), 7.77 (d, J=7.8 Hz, 1H), 7.59-7.43 (m, 6H), 6.98-6.86 (m, 5H), 5.23 (t, J=6.6 Hz, 1H), 4.92 (d, J=7.2 Hz, 1H), 4.72 (d, J=12.5 Hz, 1H), 4.59 (d, J=12.4 Hz, 1H), 3.95 (dq, J=14.4, 7.2 Hz, 1H), 3.18 (dq, J=14.1, 7.3 Hz, 1H), 0.99 (t, J=7.2 Hz, 3H), 0.72 (s, 9H), −0.10 (d, J=6.2 Hz, 6H). HRMS (ESI+) m/z calcd for $C_{35}H_{39}F_4N_4O_3Si^+$ [M+H]⁺ 667.2722, found 667.2694.

Compound 247

(RG-0013839 (KHS_NB8_039-up-2))

¹H NMR (400 MHz, Chloroform-d) δ 8.03 (s, 1H), 7.87 (d, J=7.9 Hz, 1H), 7.78 (d, J=7.9 Hz, 1H), 7.61-7.44 (m, 6H), 7.00-6.88 (m, 5H), 5.28-5.14 (m, 2H), 4.96 (d, J=13.0 Hz, 1H), 4.86 (d, J=7.3 Hz, 1H), 3.97 (dq, J=14.4, 7.4 Hz, 1H), 3.19 (dq, J=14.3, 6.9 Hz, 1H), 1.61 (s, 3H), 1.00 (t, J=7.1 Hz, 3H). HRMS (ESI+) m/z calcd for $C_{31}H_{27}F_4N_4O_4^+$ [M+H]⁺ 595.1963, found 595.1960.

Compound 248

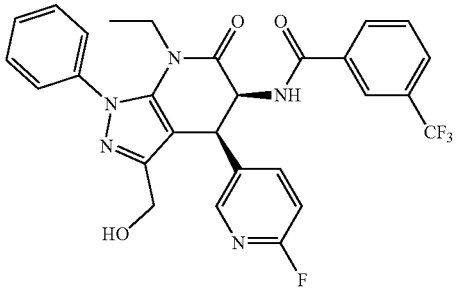

(RG-0013992 (KHS_NB8_099))

¹H NMR (400 MHz, Chloroform-d) δ 8.06 (s, 1H), 7.89 (d, J=7.8 Hz, 1H), 7.86-7.83 (m, 1H), 7.80 (d, J=8.4 Hz, 1H), 7.64-7.44 (m, 6H), 7.45-7.34 (m, 1H), 7.15 (d, J=5.0 Hz, 1H), 6.81 (dd, J=8.4, 3.0 Hz, 1H), 5.23 (dd, J=7.3, 5.0 Hz, 1H), 5.06 (d, J=7.3 Hz, 1H), 4.65 (dd, J=5.8, 2.4 Hz, 2H), 3.98 (dq, J=14.4, 7.2 Hz, 1H), 3.19 (dq, J=13.9, 7.0 Hz, 1H), 1.82 (t, J=5.8 Hz, 1H), 0.99 (t, J=7.1 Hz, 3H). HRMS (ESI+) m/z calcd for $C_{28}H_{24}F_4N_5O_3^+$ [M+H]⁺ 554.1810, found 554.1816.

Compound 249

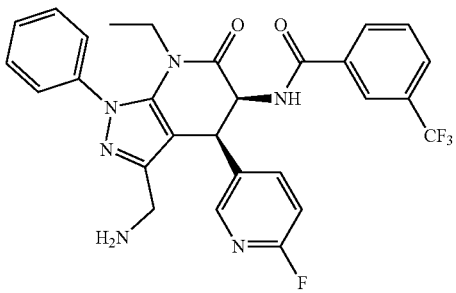

(RG-0014006 (KHS_NB9_027))

¹H NMR (400 MHz, Chloroform-d) δ 8.07 (s, 1H), 7.89 (d, J=7.9 Hz, 1H), 7.87-7.84 (m, 1H), 7.80 (d, J=7.7 Hz, 1H), 7.63-7.45 (m, 6H), 7.39 (td, J=8.0, 2.5 Hz, 1H), 7.17 (d, J=4.9 Hz, 1H), 6.81 (dd, J=8.4, 2.9 Hz, 1H), 5.22 (dd, J=7.1, 4.9 Hz, 1H), 5.04 (d, J=7.2 Hz, 1H), 3.98 (dq, J=14.3, 7.2 Hz, 1H), 3.88-3.73 (m, 2H), 3.17 (dt, J=13.8, 7.0 Hz, 1H), 0.99 (t, J=7.1 Hz, 3H). ¹³C NMR (101 MHz, Chloroform-d) δ 167.2, 165.8, 164.4, 162.1, 147.5, 147.3, 141.0, 140.9, 139.1, 138.9, 134.1, 131.5 (q, J=32.8 Hz), 130.0, 129.7, 129.4, 129.3, 128.8 (q, J=3.1 Hz), 125.5, 124.4 (q, J=4.0 Hz), 123.6 (q, J=273.0 Hz), 109.7, 109.4, 103.6, 55.7, 39.3, 38.7, 34.1, 12.8. HRMS (ESI+) m/z calcd for $C_{28}H_{25}F_4N_6O_2^+$ [M+H]⁺ 553.1970, found 553.1967.

Compound 250

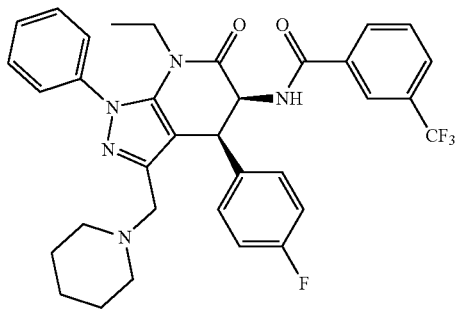

(RG-0014060 (KHS_NB9_075))

Compound 252

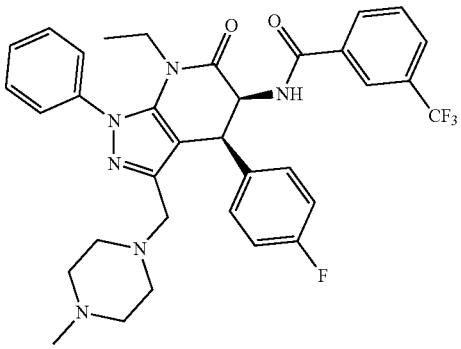

(RG-0014058 (KHS_NB9_073))

$^1$H NMR (400 MHz, Chloroform-d) δ 8.03 (s, 1H), 7.85 (d, J=7.8 Hz, 1H), 7.77 (d, J=7.7 Hz, 1H), 7.60-7.41 (m, 6H), 6.99-6.86 (m, 5H), 5.25-5.17 (m, 1H), 4.96 (d, J=7.2 Hz, 1H), 3.94 (dq, J=14.3, 7.2 Hz, 1H), 3.52 (d, J=13.8 Hz, 1H), 3.31 (d, J=13.7 Hz, 1H), 3.21 (dq, J=14.0, 6.9 Hz, 1H), 2.34-2.10 (m, 4H), 1.33-1.18 (m, 4H), 1.13-1.04 (m, 2H), 1.01 (t, J=7.1 Hz, 3H). $^{13}$C NMR (126 MHz, Chloroform-d) δ 170.7, 168.4, 165.8, 163.9, 151.5, 147.6, 141.9, 141.8, 137.5, 135.8 (q, J=3.7 Hz), 134.0 (q, J=33.4 Hz), 132.7, 132.5, 132.4, 132.2, 132.0, 131.7, 131.1 (d, J=3.8 Hz), 128.2, 128.4 (q, J=273.5 Hz), 127.0 (q, J=3.8 Hz), 118.0, 117.9, 108.9, 58.8, 58.5 (2C), 57.3, 42.1, 39.7, 28.1 (2C), 26.7, 15.4. HRMS (ESI+) m/z calcd for $C_{34}H_{34}F_4N_5O_2^+$ [M+H]$^+$ 620.2643, found 620.2637.

$^1$H NMR (400 MHz, Chloroform-d) δ 8.03 (s, 1H), 7.85 (d, J=7.8 Hz, 1H), 7.78 (d, J=7.8 Hz, 1H), 7.61-7.37 (m, 6H), 6.98 (d, J=5.5 Hz, 1H), 6.95-6.85 (m, 4H), 5.22-5.13 (m, 1H), 4.94 (d, J=7.2 Hz, 1H), 3.94 (dq, J=14.3, 7.0 Hz, 1H), 3.65 (d, J=13.9 Hz, 1H), 3.44 (d, J=13.7 Hz, 1H), 3.22 (dq, J=13.9, 6.9 Hz, 1H), 2.76-2.06 (m, 8H), 1.02 (t, J=7.1 Hz, 3H). HRMS (ESI+) m/z calcd for $C_{34}H_{35}F_4N_6O_2^+$ [M+H]$^+$ 635.2752, found 635.2747.

Compound 253

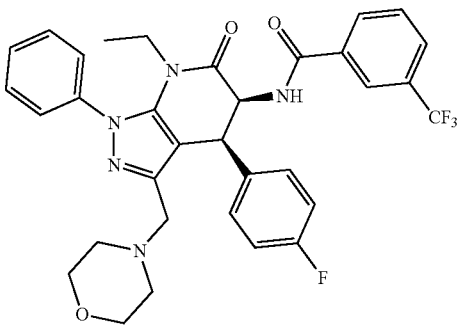

(RG-0014057 (KHS_NB9_072))

Compound 250

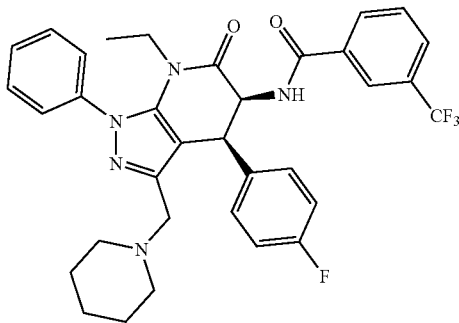

(RG-0014060 (KHS_NB9_075))

$^1$H NMR (400 MHz, Chloroform-d) δ 8.02 (s, 1H), 7.85 (d, J=7.9 Hz, 1H), 7.78 (d, J=7.9 Hz, 1H), 7.58-7.45 (m, 6H), 7.00-6.88 (m, 5H), 5.24-5.14 (m, 1H), 4.95 (d, J=7.2 Hz, 1H), 3.94 (dq, J=14.3, 7.1 Hz, 1H), 3.61 (d, J=13.7 Hz, 1H), 3.39-3.32 (m, 1H), 3.27-3.19 (m, 1H), 3.17-3.04 (m, 2H), 2.94-2.82 (m, 2H), 2.30-2.23 (m, 2H), 2.23-2.13 (m, 2H), 1.40 (s, 9H), 1.02 (t, J=6.9 Hz, 3H). HRMS (ESI+) m/z calcd for $C_{38}H_{41}F_4N_6O_4^+$ [M+H]$^+$ 721.3120, found 721.3108.

$^1$H NMR (400 MHz, Chloroform-d) δ 8.03 (s, 1H), 7.86 (d, J=7.9 Hz, 1H), 7.78 (d, J=8.0 Hz, 1H), 7.61-7.43 (m, 6H), 7.01-6.87 (m, 5H), 5.20 (dd, J=7.1, 5.7 Hz, 1H), 4.95 (d, J=7.2 Hz, 1H), 3.94 (dq, J=14.4, 7.2 Hz, 1H), 3.62 (d, J=13.7 Hz, 1H), 3.40-3.34 (m, 3H), 3.27-3.07 (m, 3H), 2.38-2.19 (m, 4H), 1.02 (t, J=7.1 Hz, 3H). HRMS (ESI+) m/z calcd for $C_{33}H_{32}F_4N_5O_3^+$ [M+H]$^+$ 622.2436, found 622.2428.

Compound 254

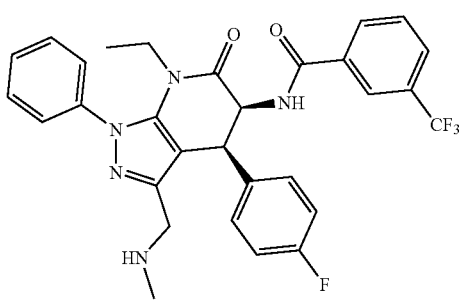

(RG-0014056 (KHS_NB9_071))

$^{1}$H NMR (400 MHz, Chloroform-d) δ 8.00 (s, 1H), 7.84 (d, J=7.8 Hz, 1H), 7.77 (d, J=7.6 Hz, 1H), 7.59-7.41 (m, 6H), 7.03-6.87 (m, 5H), 5.28-5.21 (m, 1H), 4.92 (d, J=7.2 Hz, 1H), 4.02-3.91 (m, 1H), 3.86 (d, J=14.2 Hz, 1H), 3.74 (d, J=14.2 Hz, 1H), 3.18 (dq, J=13.7, 6.9 Hz, 1H), 2.43 (s, 3H), 0.99 (t, J=6.9 Hz, 3H). HRMS (ESI+) m/z calcd for $C_{30}H_{28}F_4N_5O_2^+$ [M+H]$^+$ 566.2174, found 566.2158.

Compound 255

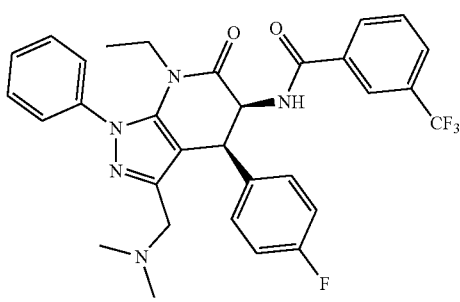

(RG-0014053 (KHS_NB9_064))

$^{1}$H NMR (400 MHz, Chloroform-d) δ 8.02 (s, 1H), 7.84 (d, J=7.8 Hz, 1H), 7.77 (d, J=7.8 Hz, 1H), 7.61-7.42 (m, 6H), 7.00-6.87 (m, 5H), 5.22 (dd, J=7.2, 5.8 Hz, 1H), 4.94 (d, J=7.2 Hz, 1H), 3.95 (dq, J=14.3, 7.2 Hz, 1H), 3.38 (s, 2H), 3.22 (dq, J=13.8, 6.9 Hz, 1H), 2.10 (s, 6H), 1.01 (t, J=7.1 Hz, 3H). HRMS (ESI+) m/z calcd for $C_{31}H_{30}F_4N_5O_2^+$ [M+H]$^+$ 580.2330, found 580.2326.

Compound 256

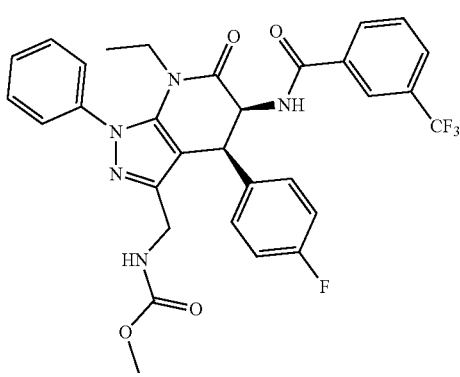

(RG-0014054 (KHS_NB9_065))

$^{1}$H NMR (400 MHz, Chloroform-d) δ 8.02 (s, 1H), 7.86 (d, J=7.9 Hz, 1H), 7.78 (d, J=7.9 Hz, 1H), 7.64-7.40 (m, 6H), 7.01-6.77 (m, 5H), 5.25 (t, J=6.6 Hz, 1H), 4.95 (s, 1H), 4.82 (d, J=7.3 Hz, 1H), 4.43-4.21 (m, 2H), 3.96 (dq, J=14.4, 7.2 Hz, 1H), 3.50 (s, 3H), 3.17 (dq, J=13.9, 6.9 Hz, 1H), 0.99 (t, J=7.1 Hz, 3H). HRMS (ESI+) m/z calcd for $C_{31}H_{28}F_4N_5O_4^+$ [M+H]$^+$ 610.2072, found 610.2062.

Compound 257

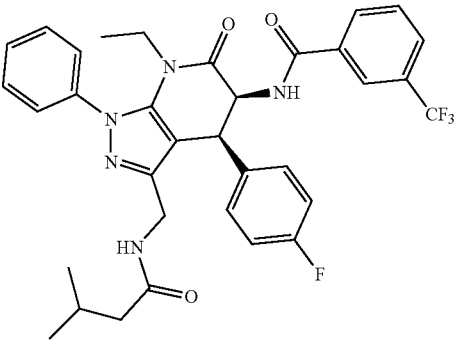

(RG-0014052 (KHS_NB9_061))

$^{1}$H NMR (400 MHz, Chloroform-d) δ 8.01 (s, 1H), 7.86 (d, J=7.8 Hz, 1H), 7.78 (d, J=7.9 Hz, 1H), 7.60-7.47 (m, 6H), 6.94 (d, J=6.8 Hz, 4H), 6.89 (d, J=6.0 Hz, 1H), 5.73 (s, 1H), 5.25 (dd, J=7.3, 6.0 Hz, 1H), 4.78 (d, J=7.3 Hz, 1H), 4.44-4.31 (m, 2H), 3.96 (dq, J=14.3, 7.2 Hz, 1H), 3.17 (dq, J=13.9, 7.0 Hz, 1H), 2.02-1.90 (m, 1H), 1.78 (dd, J=7.2, 2.2 Hz, 2H), 0.99 (t, J=7.1 Hz, 3H), 0.85 (t, J=6.6 Hz, 6H). HRMS (ESI+) m/z calcd for $C_{34}H_{34}F_4N_5O_3^+$ [M+H]$^+$ 636.2592, found 636.2580.

Compound 258

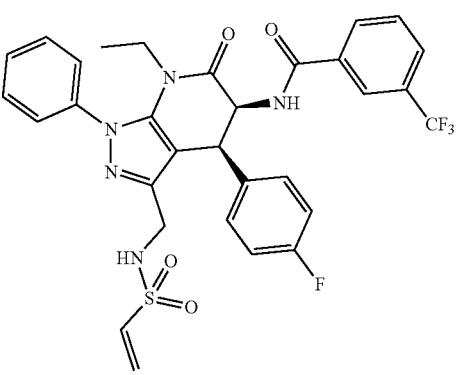

(RG-0014051 (KHS_NB9_059))

$^{1}$H NMR (400 MHz, Chloroform-d) δ 8.01 (s, 1H), 7.86 (d, J=7.8 Hz, 1H), 7.78 (d, J=7.9 Hz, 1H), 7.65-7.41 (m, 6H), 7.02-6.85 (m, 5H), 6.40 (dd, J=16.5, 9.8 Hz, 1H), 6.21 (d, J=16.5 Hz, 1H), 5.89 (d, J=9.8 Hz, 1H), 5.21 (dd, J=7.2, 5.8 Hz, 1H), 4.85-4.69 (m, 2H), 4.21-4.01 (m, 2H), 3.96 (dq, J=14.3, 7.2 Hz, 1H), 3.18 (dq, J=13.8, 6.9 Hz, 1H), 0.99 (t, J=7.1 Hz, 3H). HRMS (ESI+) m/z calcd for $C_{31}H_{28}F_4N_5O_4S^+$ [M+H]$^+$ 642.1793, found 642.1789.

Compound 259

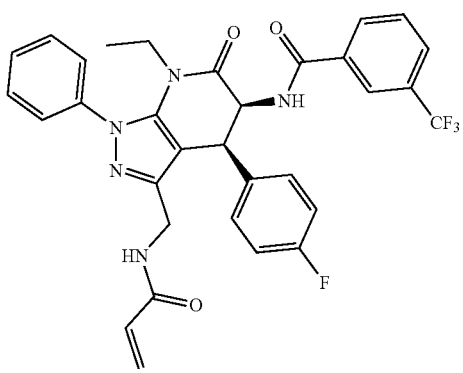

(RG-0014047 (KHS_NB9_056))

$^1$H NMR (400 MHz, Chloroform-d) δ 8.01 (s, 1H), 7.86 (d, J=7.8 Hz, 1H), 7.77 (d, J=8.0 Hz, 1H), 7.61-7.46 (m, 6H), 6.96-6.83 (m, 5H), 6.10 (dd, J=16.9, 1.4 Hz, 1H), 5.88-5.76 (m, 2H), 5.50 (dd, J=10.4, 1.3 Hz, 1H), 5.26 (dd, J=7.3, 6.0 Hz, 1H), 4.79 (d, J=7.3 Hz, 1H), 4.52 (dd, J=15.9, 5.8 Hz, 1H), 4.41 (dd, J=15.8, 4.6 Hz, 1H), 3.97 (dq, J=14.4, 7.2 Hz, 1H), 3.17 (dq, J=13.9, 6.8 Hz, 1H), 1.00 (t, J=7.1 Hz, 3H). HRMS (ESI+) m/z calcd for $C_{32}H_{28}F_4N_5O_3^+$ [M+H]$^+$ 606.2123, found 606.2109.

Compound 260

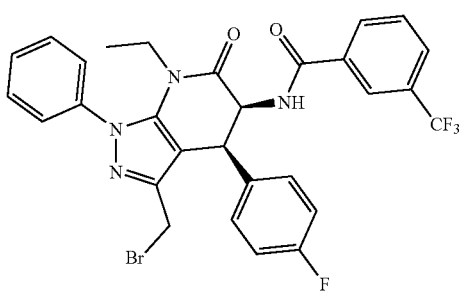

(RG-0014144 (KHS_NB9_099))

$^1$H NMR (500 MHz, Chloroform-d) δ 8.05 (s, 1H), 7.89 (d, J=7.8 Hz, 1H), 7.80 (d, J=8.0 Hz, 1H), 7.63-7.56 (m, 1H), 7.56-7.48 (m, 5H), 7.02-6.91 (m, 5H), 5.26 (dd, J=7.3, 5.9 Hz, 1H), 4.96 (d, J=7.3 Hz, 1H), 4.42 (d, J=11.2 Hz, 1H), 4.31 (d, J=11.1 Hz, 1H), 3.97 (dq, J=14.3, 7.1 Hz, 1H), 3.21 (dq, J=14.3, 7.0 Hz, 1H), 1.02 (t, J=7.1 Hz, 3H).

Compound 261

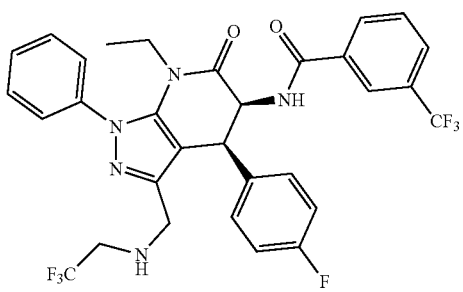

(RG-0014145 (KHS_NB10_002))

$^1$H NMR (400 MHz, Chloroform-d) δ 8.02 (s, 1H), 7.85 (d, J=7.8 Hz, 1H), 7.78 (d, J=7.8 Hz, 1H), 7.63-7.34 (m, 6H), 7.03-6.82 (m, 5H), 5.22 (dd, J=7.3, 5.7 Hz, 1H), 4.88 (d, J=7.3 Hz, 1H), 3.96 (dq, J=14.3, 7.2 Hz, 1H), 3.84 (s, 2H), 3.20 (dq, J=14.0, 7.0 Hz, 1H), 3.14-2.94 (m, 2H), 0.99 (t, J=7.1 Hz, 3H). HRMS (ESI+) m/z calcd for $C_{31}H_{27}F_7N_5O_2^+$ [M+H]$^+$ 634.2047, found 634.2060.

Compound 262

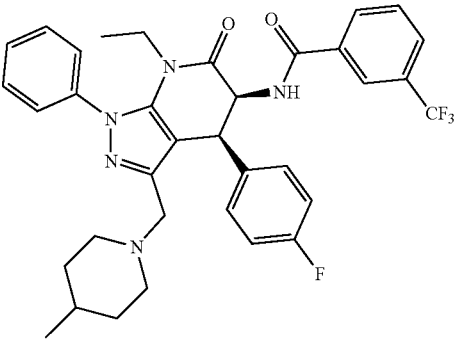

(RG-0014143 (KHS_NB9_098))

$^1$H NMR (400 MHz, Chloroform-d) δ 8.03 (s, 1H), 7.85 (d, J=8.0 Hz, 1H), 7.77 (d, J=8.1 Hz, 1H), 7.61-7.41 (m, 6H), 6.99-6.86 (m, 5H), 5.21 (dd, J=7.2, 5.9 Hz, 1H), 4.91 (d, J=7.2 Hz, 1H), 3.94 (dq, J=14.4, 7.2 Hz, 1H), 3.56 (d, J=13.7 Hz, 1H), 3.31 (d, J=13.7 Hz, 1H), 3.22 (dd, J=14.1, 7.0 Hz, 1H), 2.78 (d, J=11.0 Hz, 1H), 2.46 (d, J=10.8 Hz, 1H), 1.89 (t, J=11.5 Hz, 1H), 1.73 (t, J=11.4 Hz, 1H), 1.41 (d, J=12.6 Hz, 1H), 1.27-1.08 (m, 2H), 1.02 (t, J=7.1 Hz, 3H), 0.98-0.92 (m, 1H), 0.73 (d, J=6.2 Hz, 3H), 0.37-0.16 (m, 1H). HRMS (ESI+) m/z calcd for $C_{35}H_{36}F_4N_5O_2^+$ [M+H]$^+$ 634.2810, found 634.2818.

Compound 263

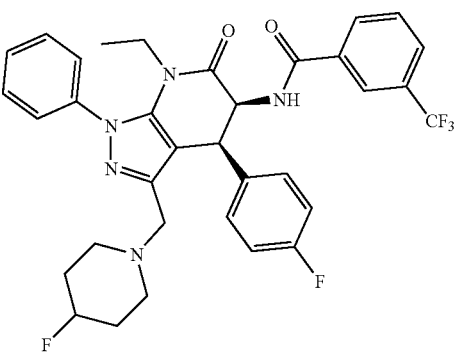

(RG-0014147 (KHS_NB10_004))

$^1$H NMR (400 MHz, Chloroform-d) δ 8.03 (s, 1H), 7.85 (d, J=7.9 Hz, 1H), 7.78 (d, J=8.0 Hz, 1H), 7.69-7.42 (m, 6H), 7.11-6.80 (m, 5H), 5.27-5.12 (m, 1H), 4.95 (d, J=7.0 Hz, 1H), 4.58-4.33 (m, 1H), 3.94 (qd, J=12.7, 7.8 Hz, 1H), 3.61 (d, J=13.9 Hz, 1H), 3.36 (d, J=14.0 Hz, 1H), 3.22 (qd, J=12.1, 6.0 Hz, 1H), 2.53-2.02 (m, 5H), 1.44-1.14 (m, 3H), 1.02 (t, J=7.2 Hz, 3H). HRMS (ESI+) m/z calcd for $C_{34}H_{33}F_5N_5O_2^+$ [M+H]$^+$ 638.2549, found 638.2564.

Compound 264

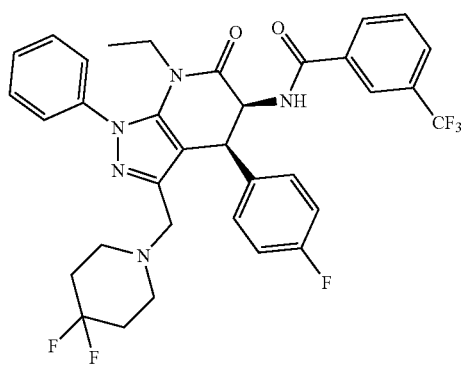

(RG-0014146 (KHS_NB10_003))

¹H NMR (400 MHz, Chloroform-d) δ 8.03 (s, 1H), 7.85 (d, J=7.7 Hz, 1H), 7.78 (d, J=6.8 Hz, 1H), 7.63-7.44 (m, 6H), 7.03-6.86 (m, 5H), 5.26-5.13 (m, 1H), 4.93 (d, J=7.8 Hz, 1H), 3.99-3.87 (m, 1H), 3.68 (d, J=13.7 Hz, 1H), 3.40 (d, J=13.8 Hz, 1H), 3.30-3.14 (m, 1H), 2.49-2.29 (m, 4H), 1.71-1.59 (m, 2H), 1.45-1.22 (m, 2H), 1.03 (d, J=7.2 Hz, 3H). HRMS (ESI+) m/z calcd for $C_{34}H_{32}F_6N_5O_2^+$ [M+H]⁺ 656.2455, found 656.2467.

Compound 265

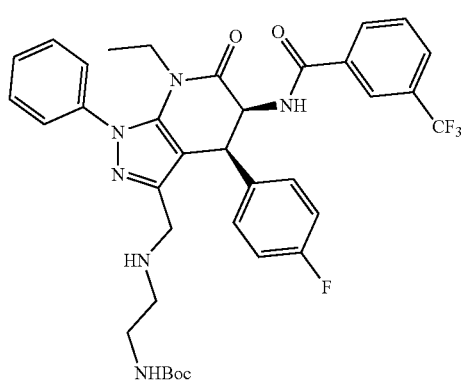

(RG-0014142 (KHS_NB9_095))

¹H NMR (400 MHz, Chloroform-d) δ 8.04 (s, 1H), 7.87 (d, J=7.8 Hz, 1H), 7.78 (d, J=7.7 Hz, 1H), 7.65-7.38 (m, 6H), 7.02 (d, J=5.6 Hz, 1H), 6.99-6.86 (m, 4H), 5.22 (t, J=6.4 Hz, 1H), 5.02-4.94 (m, 1H), 4.94 (d, J=7.4 Hz, 1H), 3.97 (dq, J=14.4, 7.5 Hz, 1H), 3.74 (s, 2H), 3.19 (dq, J=14.2, 7.2 Hz, 1H), 3.13-2.96 (m, 2H), 2.72-2.54 (m, 2H), 1.37 (s, 9H), 1.00 (t, J=7.0 Hz, 3H). HRMS (ESI+) m/z calcd for $C_{36}H_{39}F_4N_6O_4^+$ [M+H]⁺ 695.2963, found 695.2957.

Compound 266

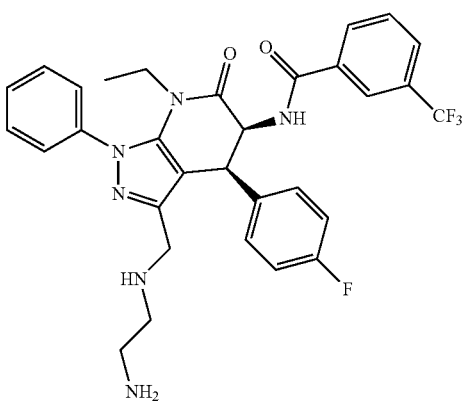

(RG-0014149 (KHS_NB10_006))

¹H NMR (400 MHz, Chloroform-d) δ 7.97 (s, 1H), 7.84 (d, J=7.8 Hz, 1H), 7.76 (d, J=7.8 Hz, 1H), 7.62-7.41 (m, 6H), 7.05 (d, J=5.4 Hz, 1H), 6.93 (d, J=6.9 Hz, 4H), 5.29 (t, J=6.4 Hz, 1H), 4.90 (d, J=7.2 Hz, 1H), 3.97-3.87 (m, 1H), 3.84 (d, J=14.5 Hz, 1H), 3.64 (d, J=14.3 Hz, 1H), 3.21-3.11 (m, 1H), 2.93-2.79 (m, 4H), 0.98 (t, J=7.0 Hz, 3H). HRMS (ESI+) m/z calcd for $C_{31}H_{31}F_4N_6O_2^+$ [M+H]⁺ 595.2439, found 595.2460.

Compound 267

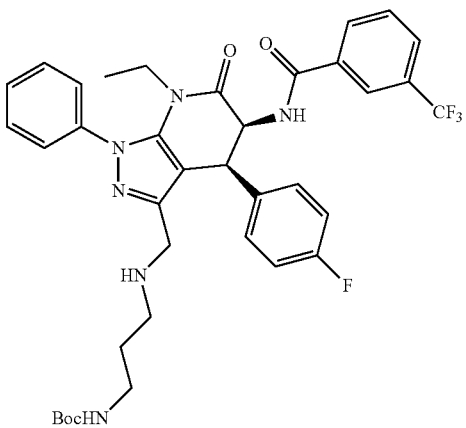

(RG-0014163 (KHS_NB10_023))

¹H NMR (400 MHz, Chloroform-d) δ 8.03 (s, 1H), 7.86 (d, J=7.8 Hz, 1H), 7.78 (d, J=7.8 Hz, 1H), 7.64-7.38 (m, 6H), 7.04-6.82 (m, 5H), 5.22 (dd, J=7.3, 5.7 Hz, 1H), 4.92 (d, J=7.3 Hz, 1H), 4.88-4.77 (m, 1H), 3.95 (dq, J=14.1, 6.9 Hz, 1H), 3.82-3.68 (m, 2H), 3.20 (dq, J=13.9, 6.8 Hz, 1H), 3.12-2.94 (m, 2H), 2.64-2.46 (m, 2H), 1.39 (s, 9H), 1.00 (t, J=7.1 Hz, 3H). HRMS (ESI+) m/z calcd for $C_{37}H_{41}F_4N_6O_4^+$ [M+H]⁺ 709.3120, found 709.3116.

Compound 268

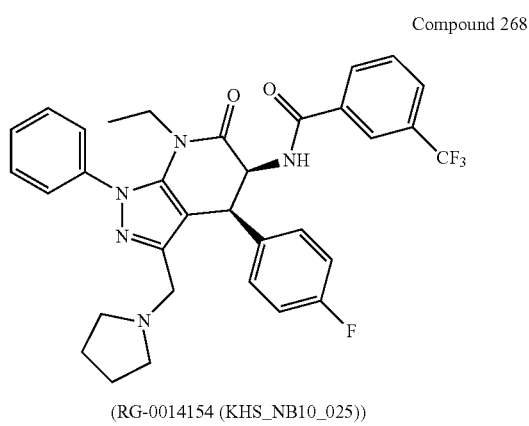 [SMILES: CCN1C(=O)[C@@H](NC(=O)c2cccc(C(F)(F)F)c2)[C@@H](c2ccc(F)cc2)c2c(CN3CCCC3)nn(-c3ccccc3)c21]

(RG-0014154 (KHS_NB10_025))

¹H NMR (400 MHz, Chloroform-d) δ 8.02 (s, 1H), 7.85 (d, J=7.9 Hz, 1H), 7.77 (d, J=7.7 Hz, 1H), 7.63-7.41 (m, 6H), 7.04-6.80 (m, 5H), 5.21 (dd, J=7.2, 5.8 Hz, 1H), 4.93 (d, J=7.2 Hz, 1H), 3.95 (dq, J=14.2, 7.1 Hz, 1H), 3.77-3.41 (m, 2H), 3.22 (dq, J=13.8, 6.8 Hz, 1H), 2.68-2.08 (m, 4H), 1.52-1.36 (m, 4H), 1.01 (t, J=7.1 Hz, 3H). HRMS (ESI+) m/z calcd for $C_{33}H_{32}F_4N_5O_2^+$ [M+H]⁺ 606.2487, found 606.2512.

Compound 269

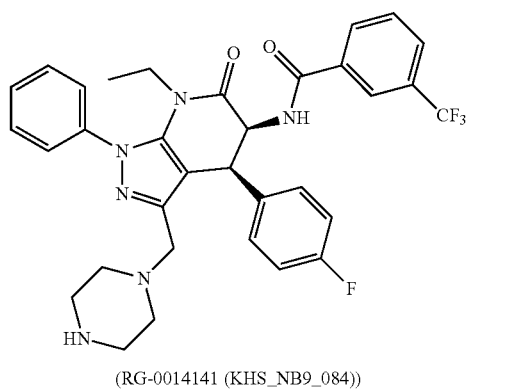

(RG-0014141 (KHS_NB9_084))

¹H NMR (400 MHz, Chloroform-d) δ 8.02 (s, 1H), 7.86 (d, J=7.7 Hz, 1H), 7.78 (d, J=7.8 Hz, 1H), 7.63-7.39 (m, 6H), 7.02-6.83 (m, 5H), 5.17 (t, J=6.4 Hz, 1H), 4.90 (d, J=7.3 Hz, 1H), 3.93 (dq, J=14.3, 7.1 Hz, 1H), 3.79-3.73 (m, 1H), 3.70-3.58 (m, 2H), 3.46 (d, J=14.0 Hz, 1H), 3.22 (dq, J=14.4, 7.2 Hz, 1H), 2.91-2.80 (m, 2H), 2.64-2.44 (m, 5H), 1.01 (t, J=7.0 Hz, 3H). HRMS (ESI+) m/z calcd for $C_{33}H_{33}F_4N_6O_2^+$ [M+H]⁺ 621.2596, found 621.2606.

Compound 270

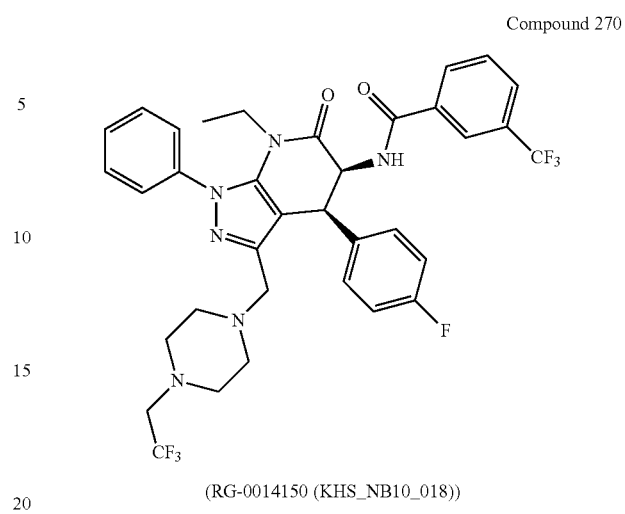

(RG-0014150 (KHS_NB10_018))

¹H NMR (400 MHz, Chloroform-d) δ 8.03 (s, 1H), 7.85 (d, J=7.7 Hz, 1H), 7.78 (d, J=7.8 Hz, 1H), 7.62-7.41 (m, 6H), 7.03-6.83 (m, 5H), 5.19 (t, J=6.5 Hz, 1H), 4.92 (d, J=7.2 Hz, 1H), 3.95 (dq, J=14.2, 7.2 Hz, 1H), 3.62 (d, J=13.7 Hz, 1H), 3.36 (d, J=13.8 Hz, 1H), 3.22 (dq, J=13.8, 6.8 Hz, 1H), 2.83-2.70 (m, 2H), 2.48-2.21 (m, 6H), 2.18-2.04 (m, 2H), 1.02 (t, J=7.2 Hz, 3H). HRMS (ESI+) m/z calcd for $C_{35}H_{34}F_7N_6O_2^+$ [M+H]⁺ 703.2626, found 703.2644.

Compound 271

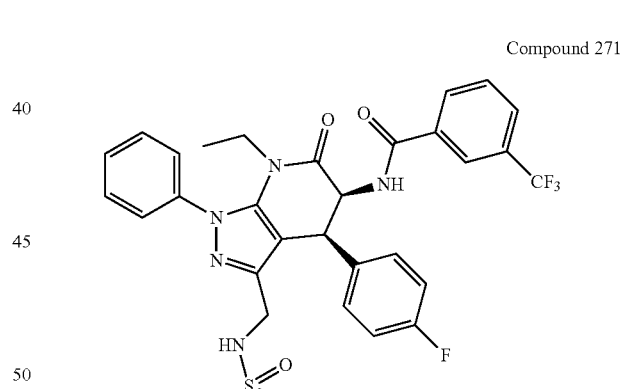

(RG-0014140 (KHS_NB9_082))

¹H NMR (400 MHz, Chloroform-d) δ 8.01 (s, 1H), 7.86 (d, J=7.6 Hz, 1H), 7.78 (d, J=7.6 Hz, 1H), 7.63-7.41 (m, 6H), 7.05-6.87 (m, 5H), 5.28-5.17 (m, 1H), 4.83 (d, J=7.2 Hz, 1H), 4.74 (s, 1H), 4.37-4.24 (m, 1H), 4.23-4.12 (m, 1H), 4.03-3.91 (m, 1H), 3.26-3.15 (m, 1H), 2.88 (s, 3H), 1.00 (t, J=7.0 Hz, 3H). HRMS (ESI+) m/z calcd for $C_{30}H_{28}F_4N_5O_4S^+$ [M+H]⁺ 630.1793, found 630.1785.

Compound 272

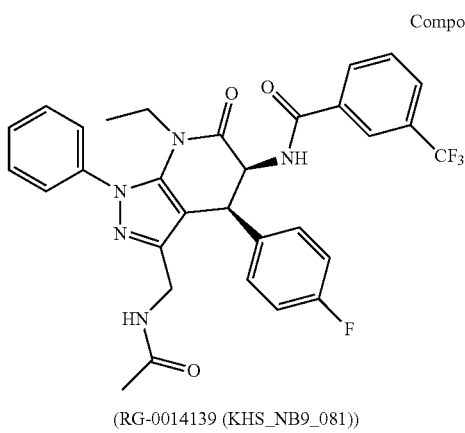

(RG-0014139 (KHS_NB9_081))

¹H NMR (400 MHz, Chloroform-d) δ 8.01 (s, 1H), 7.86 (d, J=8.0 Hz, 1H), 7.78 (d, J=8.0 Hz, 1H), 7.66-7.40 (m, 6H), 7.06-6.80 (m, 5H), 5.75 (s, 1H), 5.25 (t, J=7.5, 6.8 Hz, 1H), 4.78 (d, J=7.4 Hz, 1H), 4.56-4.37 (m, 1H), 4.37-4.25 (m, 1H), 4.05-3.91 (m, 1H), 3.26-3.01 (m, 1H), 1.71 (s, 3H), 1.00 (t, J=7.2 Hz, 3H). HRMS (ESI+) m/z calcd for $C_{31}H_{28}F_4N_5O_3^+$ [M+H]⁺ 594.2123, found 594.2136.

Compound 273

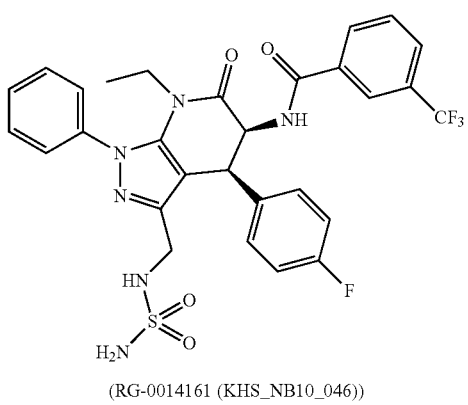

(RG-0014161 (KHS_NB10_046))

¹H NMR (400 MHz, Chloroform-d) δ 8.00 (s, 1H), 7.85 (d, J=7.8 Hz, 1H), 7.79 (d, J=7.5 Hz, 1H), 7.64-7.45 (m, 6H), 7.02 (d, J=5.6 Hz, 1H), 6.99-6.89 (m, 4H), 5.20 (dd, J=7.2, 5.5 Hz, 1H), 4.99-4.81 (m, 4H), 4.35-4.12 (m, 2H), 3.96 (dq, J=14.3, 7.1 Hz, 1H), 3.18 (dq, J=13.9, 6.8 Hz, 1H), 0.99 (t, J=7.1 Hz, 3H). HRMS (ESI+) m/z calcd for $C_{29}H_{27}F_4N_6O_4S^+$ [M+H]⁺ 631.1745, found 631.1750.

Compound 274

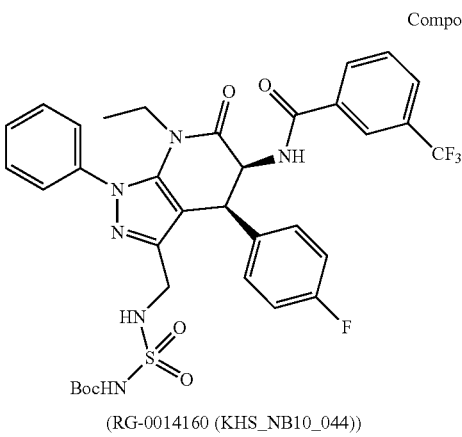

(RG-0014160 (KHS_NB10_044))

¹H NMR (400 MHz, Chloroform-d) δ 8.96 (s, 1H), 8.05 (s, 1H), 7.92 (d, J=7.8 Hz, 1H), 7.79 (d, J=7.6 Hz, 1H), 7.64-7.35 (m, 6H), 7.19-7.08 (m, 1H), 7.01-6.81 (m, 4H), 5.43 (s, 1H), 5.28-5.18 (m, 1H), 5.11-4.95 (m, 1H), 4.30 (d, J=15.4 Hz, 1H), 4.15 (d, J=15.8 Hz, 1H), 3.95 (dq, J=14.2, 7.2 Hz, 1H), 3.21 (dq, J=14.0, 7.1 Hz, 1H), 1.35 (s, 9H), 0.99 (t, J=7.1 Hz, 3H). HRMS (ESI+) m/z calcd for $C_{34}H_{35}F_4N_6O_6S$ [M+H]⁺ 731.2269, found 731.2264.

Compound 275

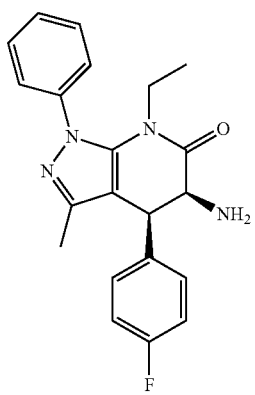

(RG-0013837 (KHS_NB8_038))

¹H NMR (400 MHz, Chloroform-d) δ 7.56-7.33 (m, 5H), 7.12-6.98 (m, 2H), 6.99-6.88 (m, 2H), 4.15 (d, J=6.6 Hz, 1H), 4.07-3.87 (m, 2H), 3.19-3.00 (m, 1H), 2.10 (s, 3H), 0.94 (t, J=6.9 Hz, 3H). LRMS (ESI+) m/z calcd for $C_{21}H_{22}FN_4O^+$ [M+H]⁺ 365.4, found 365.4.

Compound 276
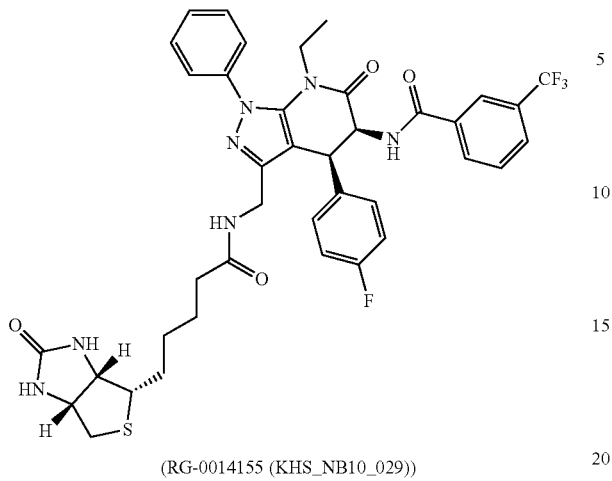
(RG-0014155 (KHS_NB10_029))
¹H NMR (400 MHz, Chloroform-d) δ 8.00 (s, 1H), 7.85 (d, J=7.8 Hz, 1H), 7.77 (d, J=7.9 Hz, 1H), 7.63-7.46 (m, 6H), 7.00-6.82 (m, 5H), 6.81-6.56 (m, 1H), 6.12 (d, J=57.4 Hz, 1H), 5.34-5.20 (m, 2H), 4.87 (dd, J=30.7, 7.3 Hz, 1H), 4.39 (dd, J=15.8, 5.5 Hz, 1H), 4.36-4.26 (m, 1H), 4.25-4.11 (m, 2H), 3.95 (dq, J=14.2, 7.1 Hz, 1H), 3.15 (dq, J=13.8, 6.8 Hz, 1H), 3.07-2.97 (m, 1H), 2.73 (dt, J=12.8, 5.4 Hz, 1H), 2.48 (t, J=12.9 Hz, 1H), 2.08-1.90 (m, 2H), 1.58-1.44 (m, 4H), 1.35 (p, J=7.7 Hz, 2H), 0.98 (t, J=7.1 Hz, 3H). HRMS (ESI+) m/z calcd for $C_{39}H_{40}F_4N_7O_4S^+$ [M+H]⁺ 778.2793, found 778.2805.
Compound 277
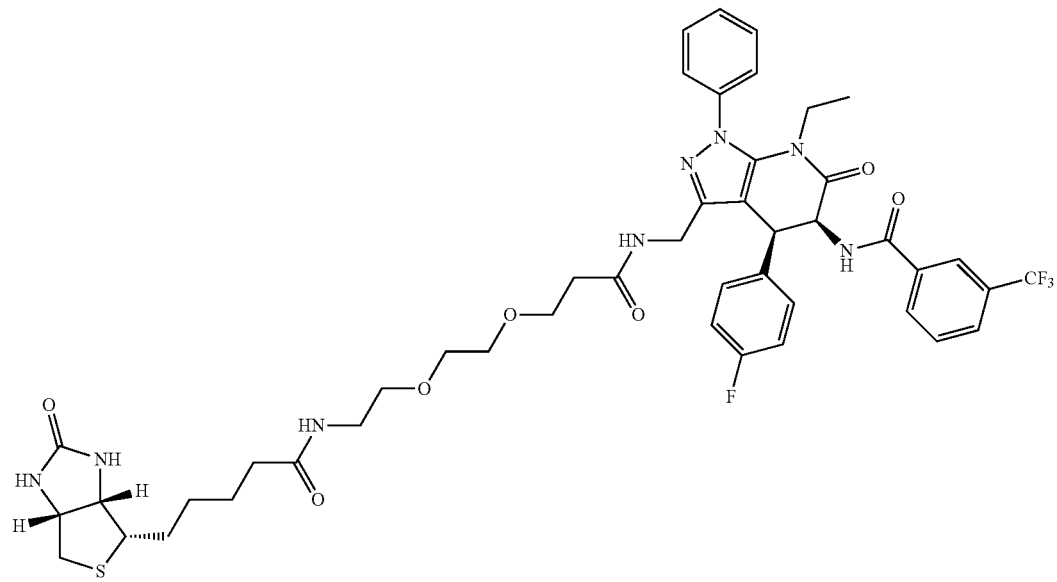
(RG-0014159 (KHS_NB10_042))

$^1$H NMR (400 MHz, Chloroform-d) δ 8.00 (s, 1H), 7.85 (d, J=7.8 Hz, 1H), 7.78 (d, J=7.9 Hz, 1H), 7.61-7.45 (m, 6H), 7.14-7.04 (m, 1H), 7.00-6.87 (m, 5H), 6.80-6.59 (m, 1H), 5.55 (d, J=64.3 Hz, 1H), 5.34-5.20 (m, 1H), 4.98 (d, J=6.1 Hz, 1H), 4.86 (d, J=7.2 Hz, 1H), 4.50-4.28 (m, 3H), 4.27-4.18 (m, 1H), 4.00-3.88 (m, 1H), 3.68-3.41 (m, 8H), 3.40-3.27 (m, 2H), 3.23-2.99 (m, 3H), 2.88-2.77 (m, 1H), 2.73-2.51 (m, 2H), 2.32-2.18 (m, 2H), 2.18-2.01 (m, 3H), 1.48-1.31 (m, 3H), 0.98 (t, J=7.1 Hz, 3H). HRMS (ESI+) m/z calcd for $C_{46}H_{53}F_4N_8O_7S^+$ [M+H]$^+$ 937.3689, found 937.3699.

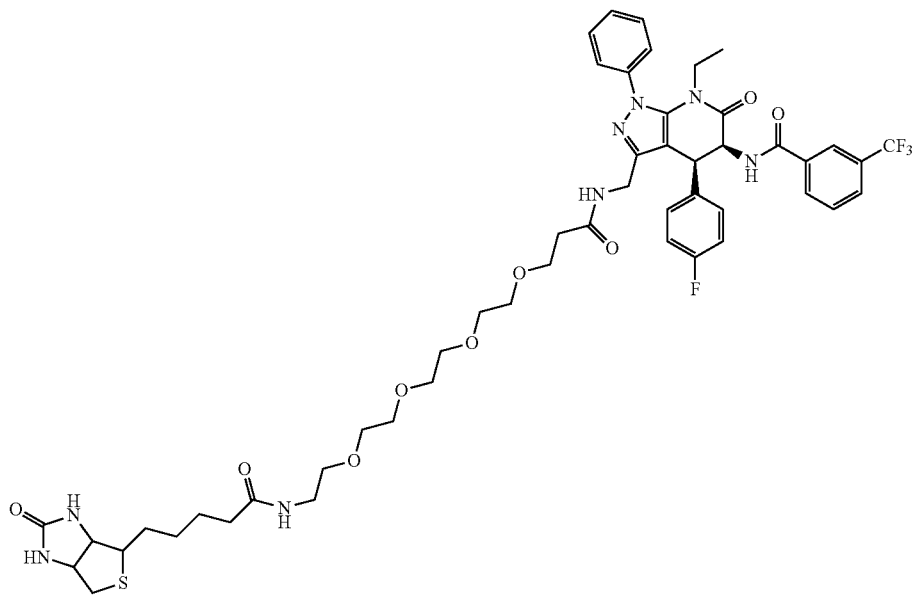

Compound 278

(RG-0014148 (KHS_NB10_005))

$^1$H NMR (400 MHz, Chloroform-d) δ 8.01 (s, 1H), 7.85 (d, J=7.8 Hz, 1H), 7.78 (d, J=7.9 Hz, 1H), 7.61-7.43 (m, 6H), 7.23-7.10 (m, 1H), 7.03-6.89 (m, 4H), 6.70-6.51 (m, 1H), 5.62-5.47 (m, 1H), 5.27 (q, J=6.7 Hz, 1H), 5.13-5.00 (m, 1H), 4.87 (dd, J=17.0, 7.2 Hz, 1H), 4.49-4.33 (m, 3H), 4.30-4.19 (m, 1H), 3.99-3.88 (m, 1H), 3.81-3.72 (m, 1H), 3.64-3.48 (m, 14H), 3.44-3.35 (m, 2H), 3.25-3.04 (m, 3H), 2.89-2.77 (m, 1H), 2.59 (dd, J=62.2, 12.8 Hz, 1H), 2.35-1.93 (m, 6H), 1.55-1.30 (m, 4H), 0.98 (t, J=7.0 Hz, 3H). HRMS (ESI+) m/z calcd for $C_{50}H_{61}F_4N_8O_9S^+$ [M+H]$^+$ 1025.4213, found 1025.4261.

All publications, patents, and patent applications mentioned in this specification are herein incorporated by reference to the same extent as if each individual publication, patent, or patent application was specifically and individually indicated to be incorporated by reference, including the references set forth in the following list.

REFERENCES

1. Deshaies, R. J.; Joazeiro, C. A., RING domain E3 ubiquitin ligases. *Annu. Rev. Biochem.* 2009, 78, 399-434.
2. Petroski, M. D.; Deshaies, R. J., Function and regulation of cullin-RING ubiquitin ligases. *Nat. Rev. Mol. Cell Biol.* 2005, 6 (1), 9-20.
3. Dubiel, W.; Dubiel, D.; Wolf, D. A.; Naumann, M., Cullin 3-Based Ubiquitin Ligases as Master Regulators of Mammalian Cell Differentiation. *Trends in biochemical sciences* 2018, 43 (2), 95-107.
4. Strand, N. S.; Allen, J. M.; Ghulam, M.; Taylor, M. R.; Munday, R. K.; Carrillo, M.; Movsesyan, A.; Zayas, R. M., Dissecting the function of Cullin-RING ubiquitin ligase complex genes in planarian regeneration. *Developmental Biology* 2018, 433 (2), 210-217.
5. Zheng, N.; Shabek, N., Ubiquitin Ligases: Structure, Function, and Regulation. *Annual review of biochemistry* 2017, 86 (1), 129-157.
6. Lu, A.; Pfeffer, S. R., A CULLINary ride across the secretory pathway: more than just secretion. *Trends Cell Biol.* 2014, 24 (7), 389-399.
7. Cui, D.; Xiong, X.; Zhao, Y., Cullin-RING ligases in regulation of autophagy. *Cell Div.* 2016, 11, 8.
8. Bulatov, E.; Ciulli, A., Targeting Cullin-RING E3 ubiquitin ligases for drug discovery: structure, assembly and small-molecule modulation. *Biochem. J.* 2015, 467 (3), 365-386.
9. Zhou, L.; Zhang, W.; Sun, Y.; Jia, L., Protein neddylation and its alterations in human cancers for targeted therapy. *Cellular signalling* 2018, 44, 92-102.
10. Ying, J.; Zhang, M.; Qiu, X.; Lu, Y., Targeting the neddylation pathway in cells as a potential therapeutic approach for diseases. *Cancer Chemother Pharmacol* 2018, 81 (5), 797-808.
11. Bielskiene, K.; Bagdoniene, L.; Mozuraitiene, J.; Kazbariene, B.; Janulionis, E., E3 ubiquitin ligases as drug targets and prognostic biomarkers in melanoma. *Medicina (Kaunas)* 2015, 51 (1), 1-9.
12. Huang, X.; Dixit, V. M., Drugging the undruggables: exploring the ubiquitin system for drug development. *Cell Res.* 2016, 26 (4), 484-498.
13. Weathington, N. M.; Mallampalli, R. K., Emerging therapies targeting the ubiquitin proteasome system in cancer. *J Clin. Invest.* 2014, 124 (1), 6-12.
14. MLN4924 Clinical Trials. http://www.cancer.gov/clinicaltrials/search/results?protocolsearchid=7656926.
15. Schlierf, A.; Altmann, E.; Quancard, J.; Jefferson, A. B.; Assenberg, R.; Renatus, M.; Jones, M.; Hassiepen, U.;

Schaefer, M.; Kiffe, M.; Weiss, A.; Wiesmann, C.; Sedrani, R.; Eder, J.; Martoglio, B., Targeted inhibition of the COP9 signalosome for treatment of cancer. *Nat. Commun.* 2016, 7, 13166.

16. Hammill, J. T.; Bhasin, D.; Scott, D. C.; Min, J.; Chen, Y.; Lu, Y.; Yang, L.; Kim, H. S.; Connelly, M. C.; Hammill, C.; Holbrook, G.; Jeffries, C.; Singh, B.; Schulman, B. A.; Guy, R. K., Discovery of an Orally Bioavailable Inhibitor of Defective in Cullin Neddylation 1 (DCN1)-Mediated Cullin Neddylation. *J Med Chem* 2018, 61 (7), 2694-2706.

17. Hammill, J. T.; Scott, D. C.; Min, J.; Connelly, M. C.; Holbrook, G.; Zhu, F.; Matheny, A.; Yang, L.; Singh, B.; Schulman, B. A.; Guy, R. K., Piperidinyl Ureas Chemically Control Defective in Cullin Neddylation 1 (DCN1)-Mediated Cullin Neddylation. *J Med Chem* 2018, 61 (7), 2680-2693.

18. Zhou, H.; Lu, J.; Liu, L.; Bernard, D.; Yang, C. Y.; Fernandez-Salas, E.; Chinnaswamy, K.; Layton, S.; Stuckey, J.; Yu, Q.; Zhou, W.; Pan, Z.; Sun, Y.; Wang, S., A potent small-molecule inhibitor of the DCN1-UBC12 interaction that selectively blocks cullin 3 neddylation. *Nat. Commun.* 2017, 8 (1), 1150.

19. Zhou, H.; Zhou, W.; Zhou, B.; Liu, L.; Chern, T. R.; Chinnaswamy, K.; Lu, J.; Bernard, D.; Yang, C. Y.; Li, S.; Wang, M.; Stuckey, J.; Sun, Y.; Wang, S., High-Affinity Peptidomimetic Inhibitors of the DCN1-UBC12 Protein-Protein Interaction. *J Med Chem* 2018, 61 (5), 1934-1950.

20. Scott, D. C.; Sviderskiy, V. O.; Monda, J. K.; Lydeard, J. R.; Cho, S. E.; Harper, J. W.; Schulman, B. A., Structure of a RING E3 trapped in action reveals ligation mechanism for the ubiquitin-like protein NEDD8. *Cell* 2014, 157 (7), 1671-1684.

21. Monda, J. K.; Scott, D. C.; Miller, D. J.; Lydeard, J.; King, D.; Harper, J. W.; Bennett, E. J.; Schulman, B. A., Structural conservation of distinctive N-terminal acetylation-dependent interactions across a family of mammalian NEDD8 ligation enzymes. *Structure* 2013, 21 (1), 42-53.

22. Kurz, T.; Ozlu, N.; Rudolf, F.; O'Rourke, S. M.; Luke, B.; Hofmann, K.; Hyman, A. A.; Bowerman, B.; Peter, M., The conserved protein DCN-1/Dcn1p is required for cullin neddylation in C. elegans and S. cerevisiae. *Nature* 2005, 435 (7046), 1257-1261.

23. Keuss, M. J.; Thomas, Y.; McArthur, R.; Wood, N. T.; Knebel, A.; Kurz, T., Characterization of the mammalian family of DCN-type NEDD8 E3 ligases. *J Cell Sci.* 2016, 129 (7), 1441-1454.

24. Scott, D. C.; Monda, J. K.; Bennett, E. J.; Harper, J. W.; Schulman, B. A., N-terminal acetylation acts as an avidity enhancer within an interconnected multiprotein complex. *Science* 2011, 334 (6056), 674-678.

25. Fu, W.; Sun, J.; Huang, G.; Liu, J. C.; Kaufman, A.; Ryan, R. J.; Ramanathan, S. Y.; Venkatesh, T.; Singh, B., Squamous Cell Carcinoma-related Oncogene (SCCRO) Family Members Regulate Cell Growth and Proliferation through Their Cooperative and Antagonistic Effects on Cullin Neddylation. *The Journal of biological chemistry* 2016, 291 (12), 6200-17.

26. Sarkaria, I.; P, O. c.; Talbot, S. G.; Reddy, P. G.; Ngai, I.; Maghami, E.; Patel, K. N.; Lee, B.; Yonekawa, Y.; Dudas, M.; Kaufman, A.; Ryan, R.; Ghossein, R.; Rao, P. H.; Stoffel, A.; Ramanathan, Y.; Singh, B., Squamous cell carcinoma related oncogene/DCUN1D1 is highly conserved and activated by amplification in squamous cell carcinomas. *Cancer Res* 2006, 66 (19), 9437-44.

27. Kim, A. Y.; Bommelje, C. C.; Lee, B. E.; Yonekawa, Y.; Choi, L.; Morris, L. G.; Huang, G.; Kaufman, A.; Ryan, R. J.; Hao, B.; Ramanathan, Y.; Singh, B., SCCRO (DCUN1D1) is an essential component of the E3 complex for neddylation. *J. Biol. Chem.* 2008, 283 (48), 33211-33220.

28. Sarkaria, I. S.; Pham, D.; Ghossein, R. A.; Talbot, S. G.; Hezel, M.; Dudas, M. E.; Ebright, M. I.; Chuai, S.; Memoli, N.; Venkatraman, E. S.; Miller, V. A.; Kris, M. G.; Zakowski, M. F.; Rusch, V. W.; Singh, B., SCCRO expression correlates with invasive progression in bronchioloalveolar carcinoma. *The Annals of thoracic surgery* 2004, 78 (5), 1734-41.

29. Sarkaria, I.; P, O. c.; Talbot, S. G.; Reddy, P. G.; Ngai, I.; Maghami, E.; Patel, K. N.; Lee, B.; Yonekawa, Y.; Dudas, M.; Kaufman, A.; Ryan, R.; Ghossein, R.; Rao, P. H.; Stoffel, A.; Ramanathan, Y.; Singh, B., Squamous cell carcinoma related oncogene/DCUN1D1 is highly conserved and activated by amplification in squamous cell carcinomas. *Cancer Res.* 2006, 66 (19), 9437-9444.

30. Estilo, C. L.; P, O. C.; Ngai, I.; Patel, S. G.; Reddy, P. G.; Dao, S.; Shaha, A. R.; Kraus, D. H.; Boyle, J. O.; Wong, R. J.; Pfister, D. G.; Huryn, J. M.; Zlotolow, I. M.; Shah, J. P.; Singh, B., The role of novel oncogenes squamous cell carcinoma-related oncogene and phosphatidylinositol 3-kinase p110alpha in squamous cell carcinoma of the oral tongue. *Clinical cancer research: an official journal of the American Association for Cancer Research* 2003, 9 (6), 2300-6.

31. P, O. c.; Sarkaria, I.; Talbot, S. G.; Reddy, P.; Dao, S.; Ngai, I.; Shaha, A.; Kraus, D.; Shah, J.; Rusch, V.; Ramanathan, Y.; Singh, B., SCCRO (DCUN1D1) induces extracellular matrix invasion by activating matrix metalloproteinase 2. *Clinical cancer research: an official journal of the American Association for Cancer Research* 2008, 14 (21), 6780-9.

32. Talbot, S. G.; P, O. c.; Sarkaria, I S.; Ghossein, R.; Reddy, P.; Ngai, I.; Cordeiro, C. N.; Wong, R. J.; Kris, M. G.; Rusch, V. W.; Singh, B., Squamous cell carcinoma related oncogene regulates angiogenesis through vascular endothelial growth factor —A. *Ann. Surg. Oncol.* 2004, 11 (5), 530-534.

33. Shemorry, A.; Hwang, C. S.; Varshavsky, A., Control of protein quality and stoichiometries by N-terminal acetylation and the N-end rule pathway. *Molecular cell* 2013, 50 (4), 540-51.

34. Chen, Y.; McGee, J.; Chen, X.; Doman, T. N.; Gong, X.; Zhang, Y.; Hamm, N.; Ma, X.; Higgs, R. E.; Bhagwat, S. V.; Buchanan, S.; Peng, S. B.; Staschke, K. A.; Yadav, V.; Yue, Y.; Kouros-Mehr, H., Identification of druggable cancer driver genes amplified across TCGA datasets. *PloS one* 2014, 9 (5), e98293.

35. Huang, G.; Singh, B., Coamplification and cooperation: toward identifying biologically relevant oncogenes. *Clin. Cancer Res.* 2013, 19 (20), 5549-5551.

36. Estilo, C. L.; P, O. C.; Ngai, I.; Patel, S. G.; Reddy, P. G.; Dao, S.; Shaha, A. R.; Kraus, D. H.; Boyle, J. O.; Wong, R. J.; Pfister, D. G.; Huryn, J. M.; Zlotolow, I. M.; Shah, J. P.; Singh, B., The role of novel oncogenes squamous cell carcinoma-related oncogene and phosphatidylinositol 3-kinase p110alpha in squamous cell carcinoma of the oral tongue. *Clin Cancer Res* 2003, 9 (6), 2300-6.

37. Zhang, Z. H.; Li, J.; Luo, F.; Wang, Y. S., Clinical significance of SCCRO (DCUN1D1) in prostate cancer and its proliferation-inhibiting effect on Lncap cells. *Eur Rev Med Pharmacol Sci* 2017, 21 (19), 4283-4291.

38. Jiang, Y.; Hou, R.; Li, S.; Li, S.; Dang, G., MicroRNA-302 inhibits cell migration and invasion in cervical cancer by targeting DCUN1D1. *Exp Ther Med* 2018, 16 (2), 1000-1008.
39. Keuss, M. J.; Thomas, Y.; McArthur, R.; Wood, N. T.; Knebel, A.; Kurz, T., Characterization of the mammalian family of DCN-type NEDD8 E3 ligases. *J Cell Sci* 2016, 129 (7), 1441-54.
40. Zhang, Z.; Li, J.; Luo, F.; Wang, Y., Clinical significance of SCCRO (DCUN1D1) in prostate cancer and its proliferation-inhibiting effect on Lncap cells. *European review for medical and pharmacological sciences* 2017, 21 (19), 4283-4291.
41. Scott, D. C.; Hammill, J. T.; Min, J.; Rhee, D. Y.; Connelly, M.; Sviderskiy, V. O.; Bhasin, D.; Chen, Y.; Ong, S. S.; Chai, S. C.; Goktug, A. N.; Huang, G.; Monda, J. K.; Low, J.; Kim, H. S.; Paulo, J. A.; Cannon, J. R.; Shelat, A. A.; Chen, T.; Kelsall, I R.; Alpi, A. F.; Pagala, V.; Wang, X.; Peng, J.; Singh, B.; Harper, J. W.; Schulman, B. A.; Guy, R. K., Blocking an N-terminal acetylation-dependent protein interaction inhibits an E3 ligase. *Nat. Chem. Biol.* 2017, 13 (8), 850-857.
42. Ritchie, T. J.; Macdonald, S. J., The impact of aromatic ring count on compound developability—are too many aromatic rings a liability in drug design? Drug discovery today 2009, 14 (21-22), 1011-20.
43. Izumi, S.; Kobayashi, Y.; Takemoto, Y., Catalytic Asymmetric Synthesis of anti-alpha, beta-Diamino Acid Derivatives. *Org Lett* 2016, 18 (4), 696-9.
44. Shi, F.; Zhang, J.; Tu, S.; Jia, R.; Zhang, Y.; Jiang, B.; Jiang, H., An efficient synthesis of new class of pyrazolo [3,4-b] pyridine-6-one derivatives by a novel cascade reaction. *Journal of Heterocyclic Chemistry* 2007, 44 (5), 1013-1017.
45. Martinez Molina, D.; Jafari, R.; Ignatushchenko, M.; Seki, T.; Larsson, E. A.; Dan, C.; Sreekumar, L.; Cao, Y.; Nordlund, P., Monitoring drug target engagement in cells and tissues using the cellular thermal shift assay. *Science* 2013, 341 (6141), 84-7.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

What is claimed is:

1. A DCN1/2-mediated cullin neddylation modulator according to Formula I:

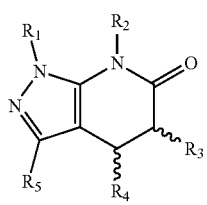

wherein;

$R_1$ is alkyl, haloalkyl, heteroalkyl, cycloalkyl, heterocycloalkyl, alkenyl, alkynyl, acyl, aryl, heteroaryl, haloaryl, alkyl ester, alkyl carboxylic acid, alkyl amide, or cyanomethyl;

$R_2$ is alkyl, haloalkyl, cycloalkyl, heterocycloalkyl, alkenyl, alkynyl, acyl, aryl, heteroaryl, haloaryl, or cyanomethyl;

$R_3$ is selected from —NHC(=O)—$R_6$, —NHC(=O)—NH—$R_6$, —NHSO$_2$—$R_6$, —C(=O)—NH—$R_6$, or —CH$_2$C(=O)—$R_6$;

$R_4$ is selected from alkyl, acyl, aryl, or heteroaryl;

$R_5$ is selected from alkyl, cycloalkyl, heterocycloalkyl, aryl, heteroaryl, carboxylic acid, nitrile, or —(CH$_2$)$_n$—X—$R_7$, $R_6$ is selected from alkyl, alkenyl, acyl, aryl, or heteroaryl;

$R_7$ is selected from H, alkyl, haloalkyl, heteroalkyl, cycloalkyl, heterocycle, heterocycloalkyl, alkenyl, alkynyl, acyl, aryl, heteroaryl, alkyl ester, alkyl carboxylic acid, alkyl amide, cyanomethyl, or —Y—Z—Y—$R_8$;

$R_8$ is H or biotin;

X is selected from O, NH, S, or Linker;

each Y is independently selected from CH$_2$, NH, O, or S;

Z is —(OCH$_2$CH$_2$)$_n$—, alkyl linker, or aminoalkyl linker;

Linker is selected from —(OCH$_2$CH$_2$)$_n$—(PEG), alkyl linker, or aminoalkyl linker; and each n is independently an integer from 0 to 20.

2. The modulator of claim 1, wherein $R_1$, $R_2$, and $R_4$ are not the same.
3. The modulator of claim 1, wherein at least two of $R_1$, $R_2$, and $R_4$ are the same.
4. The modulator of claim 1, wherein each of $R_1$, $R_2$, and $R_4$ are the same.
5. The modulator of claim 1, wherein $R_1$ is an aryl.
6. The modulator of claim 1, wherein $R_2$ is an alkyl.
7. The modulator of claim 1, wherein $R_4$ is a haloaryl.
8. The modulator of claim 1, wherein $R_3$ and $R_4$ comprise a cis geometry.
9. The modulator of claim 1, wherein $R_1$ is an aryl and $R_4$ is a haloaryl.
10. The modulator of claim 1, wherein $R_1$ is an aryl, $R_2$ is an alkyl, and $R_4$ is a haloaryl.
11. The modulator of claim 1, wherein $R_5$ is —(CH$_2$)$_n$—X—$R_7$.
12. The modulator of claim 1, wherein $R_5$ is —(CH$_2$)$_n$—X—$R_7$; $R_7$ is —Y—Z—Y—$R_8$; and $R_8$ is biotin.
13. The modulator of claim 12, wherein $R_3$ and $R_4$ comprise a cis geometry.
14. The modulator of claim 12, wherein $R_1$ is an aryl.
15. The modulator of claim 12, wherein $R_2$ is an alkyl.
16. The modulator of claim 12, wherein $R_4$ is a haloaryl.
17. The modulator of claim 12, wherein $R_1$ is an aryl, $R_2$ is an alkyl, and $R_4$ is a haloaryl.
18. A pharmaceutical composition comprising a therapeutically effective amount of a compound of claim 1, or a pharmaceutically acceptable salt thereof, and a pharmaceutically acceptable carrier.
19. A method for ameliorating disorders associated with dysfunctional DCN1 and/or UBC12, Alzheimer's disease, ether neurodegenerative diseases, bacterial infections, or viral infections, the method comprising the step of administering to a mammal a therapeutically effective amount of a compound of claim 1.
20. A method for ameliorating cancers, the method comprising the step of administering to a mammal a therapeutically effective amount of a compound of claim 1.

* * * * *